(12) United States Patent
Al-awar et al.

(10) Patent No.: US 11,576,981 B2
(45) Date of Patent: Feb. 14, 2023

(54) ACYL HYDRAZONE LINKERS, METHODS AND USES THEREOF

(71) Applicant: Ontario Institute for Cancer Research (OICR), Toronto (CA)

(72) Inventors: Rima Al-awar, Toronto (CA); Andrew Zhang, Fremont, CA (US); Ahmed Mamai, Mississauga (CA)

(73) Assignee: ONTARIO INSTITUTE FOR CANCER RESEARCH (OICR), Toronto (CA)

( * ) Notice: Subject to any disclaimer, the term of this patent is extended or adjusted under 35 U.S.C. 154(b) by 282 days.

(21) Appl. No.: 16/770,273

(22) PCT Filed: Dec. 6, 2018

(86) PCT No.: PCT/CA2018/051561
§ 371 (c)(1),
(2) Date: Jun. 5, 2020

(87) PCT Pub. No.: WO2019/109188
PCT Pub. Date: Jun. 13, 2019

(65) Prior Publication Data
US 2020/0397916 A1    Dec. 24, 2020

Related U.S. Application Data

(60) Provisional application No. 62/595,342, filed on Dec. 6, 2017.

(51) Int. Cl.
*A61K 47/68* (2017.01)
*A61K 45/06* (2006.01)
(Continued)

(52) U.S. Cl.
CPC .......... *A61K 47/6849* (2017.08); *A61K 45/06* (2013.01); *A61K 47/6803* (2017.08);
(Continued)

(58) Field of Classification Search
CPC ............ A61K 47/6849; A61K 47/6851; A61K 47/6803; A61K 47/6817; A61K 45/06;
(Continued)

(56) References Cited

U.S. PATENT DOCUMENTS

2005/0009751 A1    1/2005    Senter et al.
2007/0197455 A1    8/2007    Moran et al.
(Continued)

FOREIGN PATENT DOCUMENTS

CA    2977032 A1    1/2014
CA    2891280 A1 *  5/2014    ............. A61K 31/10
(Continued)

OTHER PUBLICATIONS

International Search Report and Written Opinion of corresponding International Application No. PCT/CA2018/051561 dated Mar. 5, 2019, 19 pages.
(Continued)

*Primary Examiner* — Kristin A Vajda
(74) *Attorney, Agent, or Firm* — Bereskin & Parr LLP/S.E.N.C.R.L., s.r.l.; Patricia Folkins; Shuo Xing

(57) ABSTRACT

The present application is directed to compounds of Formula (I)-(VIII):

(Continued)

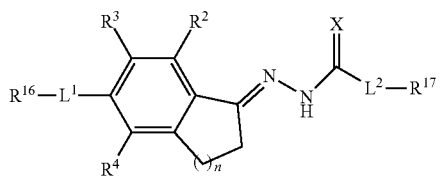

and

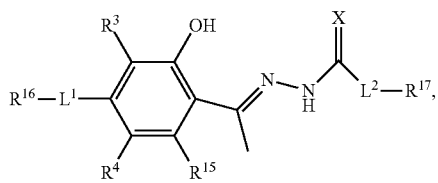

compositions comprising these compounds and their uses, for example as medicaments and/or diagnostics.

20 Claims, 1 Drawing Sheet

(51) Int. Cl.
　　*A61P 35/00*　　　(2006.01)
　　*C07C 323/60*　　　(2006.01)
　　*C07D 207/46*　　　(2006.01)
(52) U.S. Cl.
　　CPC ...... *A61K 47/6817* (2017.08); *A61K 47/6851* (2017.08); *A61P 35/00* (2018.01); *C07C 323/60* (2013.01); *C07D 207/46* (2013.01); *C07C 2602/08* (2017.05); *C07C 2602/10* (2017.05); *C07C 2602/12* (2017.05)
(58) Field of Classification Search
　　CPC ... A61P 35/00; C07C 323/60; C07C 2602/10; C07C 2602/12; C07C 2602/08; C07D 207/46
　　USPC ...................................................... 424/181.1
　　See application file for complete search history.

(56) References Cited

U.S. PATENT DOCUMENTS

| | | | |
|---|---|---|---|
| 2009/0076076 | A1 | 3/2009 | Siles et al. |
| 2021/0106694 | A1 | 4/2021 | Al-awar et al. |

FOREIGN PATENT DOCUMENTS

| | | |
|---|---|---|
| CA | 2642273 C | 9/2016 |
| CA | 2987322 A1 | 2/2017 |
| CA | 2891280 C | 3/2018 |
| CN | 101434595 A | 5/2009 |
| CN | 103739589 A | 4/2014 |
| CN | 105985265 A | 10/2016 |
| CN | 105985265 A | 11/2018 |
| DE | 102005060813 A1 | 6/2007 |
| WO | 2002096910 A1 | 12/2002 |
| WO | 2005005378 A2 | 1/2005 |
| WO | 2011019882 A1 | 2/2011 |
| WO | 2014031784 A1 | 2/2014 |
| WO | 2014068443 A1 | 5/2014 |
| WO | 2016196280 A1 | 12/2016 |
| WO | 2017004519 A1 | 1/2017 |
| WO | 2018175622 A | 9/2018 |
| WO | 2018175622 A1 | 9/2018 |
| WO | 2019119141 A1 | 6/2019 |
| WO | 2020248065 A1 | 12/2020 |

OTHER PUBLICATIONS

Hamman, P.R. et al., Gemtuzumab Ozogamicin, A Potent and Selective Anti-CD33 Antibody-Calicheamicin Conjugate for Treatment of Acute Myeloid, Leukemia, Bioconjugate Chemistry, Dec. 19, 2001, vol. 13(1), pp. 47-58.
Extended European Search Report of corresponding European Patent Application No. 18885812.0 dated Sep. 30, 2021, 11 pages.
Kovtun, Y. V.; et al Antibody-drug conjugates designed to eradicate tumors with homogeneous and heterogeneous expression of the target antigen. Cancer Res. 2006, 66, 3214-3221.
Bulter, T. et al., "Chemoenymatic Synthesis of Biotinylated Nucleotide Sugars as Substrates for Glycosyltransferases", ChemBioChem., Nov. 26, 2001, vol. 2(12), pp. 884-894.
Merten H. et al., "Antibody-Drug Conjugates for Tumor Targeting Novel Conjugation Chemistries and the Promise of non-IgG Binding Proteins", Bioconjugate Chemistry, Jun. 18, 2015, vol. 26, pp. 2176-2185.
Hamann, P.R. et al., "Gemtuzumab Ozogamicin, A Potent and Selective Anti-CD33 Antibody-Calicheamicin Conjugate for Treatment of Acute Myeloid Leukemia", Bioconjucate Chemistry, Dec. 19, 2001, vol. 13(1), pp. 47-58.
Dascalu, A.E. et al., "Design, Synthesis and Evaluation of Hydrazine and Acyl Hydrazone", Boorganic & Medicinal Chemistry Letters, Apr. 28, 2020, vol. 30, pp. 1-4.
Alley, S. C. et al., "Antibody-drug conjugates: targeted drug delivery for cancer", Curr. Opin. Chem. Biol. 2010, 14, 529-537.
Ducry, L. et al., "Antibody-drug conjugates: linking cytotoxic payloads to monoclonal antibodies", Bioconjug. Chem. 2010, 21, 5-13.
Casi, G. et al., "Antibody-drug conjugates: basic concepts, examples and future perspectives", J. Control. Release 2012, 161, 422-428.
Adair, J. R. et al., "Antibody-drug conjugates—a perfect synergy", Expert Opin. Biol. Ther. 2012, 12, 1191-1206.
Carter, P. J., "Potent antibody therapeutics by design", Nat. Rev. Immunol. 2006, 6, 343-357.
Doronina, S. O. et al., "Development of potent monoclonal antibody auristatin conjugates for cancer therapy", Nat. Biotechnol. 2003, 21, 778-784.
Widdison, W. C. et al., "Semisynthetic maytansine analogues for the targeted treatment of cancer", J. Med. Chem. 2006, 49, 4392-4408.
Hartley, J. A. et al., "The development of pyrrolobenzodiazepines as antitumour agents", Expert Opin. Investig. Drugs 2011, 20, 733-744.
Doronina, S. O. et al., "Enhanced activity of monomethylauristatin F through monoclonal antibody delivery: effects of linker technology on efficacy and toxicity", Bioconjug. Chem. 2006, 17, 114-124.
Dosio, F. et al., "Immunotoxins and Anticancer Drug Conjugate Assemblies: The Role of the Linkage between Components", Toxins (Basel) 2011, 3, 848-883.
Wu, A. M. et al., "Arming antibodies: prospects and challenges for immunoconjugates", Nat. Biotechnol. 2005, 23, 1137-1146.
Hutter, M. L. et al., "Gemtuzumab ozogamicin in non-acute promyelocytic acute myeloid leukemia", Expert Opin. Biol. Ther. 2011, 11, 1369-1380.
Hamann, P. R. et al., "An anti-CD33 antibody-calicheamicin conjugate for treatment of acute myeloid leukemia. Choice of linker", Bioconjug. Chem. 2002, 13, 40-46.
Van Der Velden, V. H. et al., "Targeting of the CD33-calicheamicin immunoconjugate Mylotarg (CMA-676) in acute myeloid leukemia: in vivo and in vitro saturation and internalization by leukemic and normal myeloid cells", Blood 2001, 97, 3197-3204.
Siegel, M.M. et al., Calicheamicin Derivatives Conjugated to Monoclonal Antibodies: Determination of Loading Values and Distributions by Infrared and UV Matrix-Assisted Laser Desorption/Ionization Mass Spectrometry and Electrospray Ionization Mass Spectrometry, Anal. Chem, Jul. 15, 1997, vol. 69(14), pp. 2716-2726.
Howard, P.W., Antibody-drug Conjugates (ADCs), Protein Therapeutics, Aug. 14, 2017, Ed. 1, Chapter 9, pp. 271-309.

(56) References Cited

OTHER PUBLICATIONS

Chang, M. et al., "Smart Linkers in Polymer-drug Conjugates for Tumor-targeted Delivery", Journal of Drug Targeting, Nov. 11, 2015, vol. 24(6), pp. 475-491.

Kovtun, Y. V.; Audette, C. A.; Ye, Y.; Xie, H.; Ruberti, M. F.; Phinney, S. J.; Leece, B. A.; Chittenden, T.; Blattler, W. A.; Goldmacher, V. S. Antibody-drug conjugates designed to eradicate tumors with homogeneous and heterogeneous expression of the target antigen. Cancer Res. 2006, 66, 3214-3221.

Toki, B. E.; Cerveny, C. G.; Wahl, A. F.; Senter, P. D. Protease-mediated fragmentation of p-amidobenzyl ethers: a new strategy for the activation of anticancer prodrugs, J. Org. Chem. 2002, 67, 1866-1872.

Song, J. et al., "Small-molecule inhibitors of cathespin L incorporating functionalized ring-fused molecular frameworks", Bioorganic & Medicinal Chemistry Letters, vol. 23, 2013, pp. 2801-2807.

Song et al., "Synthesis and Biochemical Evaluation of Thiochromanone Thiosemicarbazone Analogues as Inhibitors of Cathepsin L", ACS Medicinal Chemistry Letters, vol. 3, 2012, pp. 450-453.

Song et al., "Synthesis and Antifungal Activity of Some Thiazole Derivatives", Asian Journal of Chemistry, vol. 25, 2013, pp. 1849-1852.

Wang G, "Preparation of carboxamide compounds as antiviral agents for the treatment of paramoxyvirus viral infections", vol. 160, 2014, pp. 1-3.

Naylor et al. Journal of Chemical Society (1958) 1190-3.

Bennett Celsa and Jane Andres, USPTO, "Making a Prima Facie Case (e.g. In Polymorph Cases)", Jun. 12, 2013.

Arbuzov et al. Zhurnal Obshchei Khimii (1952), 22, 1645-7.

Soraires Santacruz Maria C et al "Synthesis, antiviral evaluation and molecular docking studies of N-aryl substituted/unsubstituted thiosemicarbazones derived from 1-indanones as potent anti-bovine viral diarrhea virus agents", Bioorganic & Medicinal Chemistry, Elseveir, Amsterdam, NL, vol. 25, No. 15, May 27, 2017, pp. 4055-4063.

International search report of the corresponding PCT/CA2018/051561 application dated Mar. 5, 2019.

\* cited by examiner

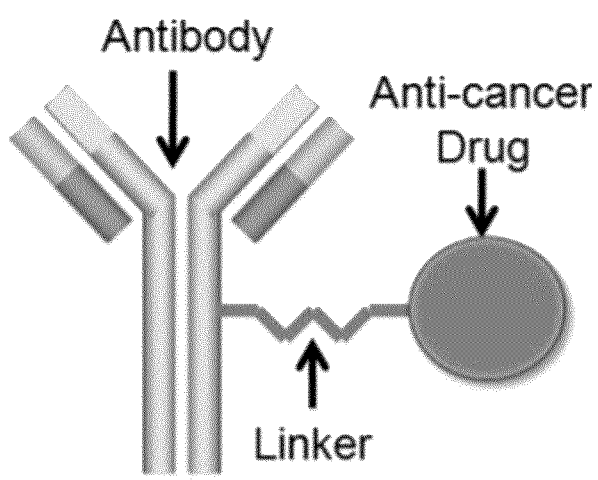

ACYL HYDRAZONE LINKERS, METHODS AND USES THEREOF

This application is a National Stage of co-pending International Application No. PCT/CA2018/051561 filed on Dec. 6, 2018 which claims the benefit of priority from U.S. Provisional Patent Application Ser. No. 62/595,342 filed on Dec. 6, 2017, the contents of both of which are incorporated herein by reference in their entirety.

FIELD

The present application relates to novel linker groups, to processes for their preparation, and for their use to link two chemical entities together, as well as to linked compounds comprising the linker groups and compositions comprising these linked compounds and to their use for example in the treatment or diagnosis of diseases and conditions, including, but not limited to, cancer.

BACKGROUND

Chemotherapy, which targets rapidly dividing cancer cells, has proven to be one of the primary weapons in the arsenal to fight cancer. However, this approach is limited by the fact that it also affects healthy cells, typically resulting in moderate to severe side effects.[1-2] Targeted therapies have the potential to greatly enhance the state of cancer therapeutics by selectively targeting cancerous cells while not harming healthy cells.[3-7] Biologics such as monoclonal antibodies have emerged as options for cancer therapy due to their inherent specificity for cancer associated targets and their potential to have fewer off-target effects.[8-10] In addition to carrying out the immune modulating functions of antibodies,[11] monoclonal antibodies have been used as a means of delivering cytotoxic drugs to cancer cells with high specificity, giving way to a type of therapeutic known as antibody-drug conjugates (ADC).[12-16] ADCs have gained significant attention as a means of targeted delivery of cytotoxic agents to cancer cells. ADCs consist of a cytotoxic drug chemically attached to an antibody through a linker, and upon target cell binding and internalization, the drug is released. While this idea has limitless potential, its application is limited by the variable in vivo stability of the linker, which will lead to lower efficacy and higher off-target effects.

ADCs (FIG. 1) contain three distinct entities: (1) an antibody designed to target a tumour-associated antigen,[17-18] (2) cytotoxic drugs,[19-21] and (3) linkers that connect the drugs to the antibody.[22-23] It is desirable that the ADC be stable, but upon antibody binding to the target cell and internalization, the drug is ideally released from the antibody to exert its actions.[16] The efficacy and toxicity of ADCs depend heavily on the linker between the drug and the antibody and is affected by two factors: stability in plasma and drug to antibody ratio (DAR) and conjugation sites.[24] Currently, over 60 ADCs are in clinical trials, with 4 clinically approved. In fact, Adcetris™ (Brentuximab vedotin) targeting CD30 for anaplastic large cell lymphoma and Hodgkin's lymphoma was approved in 2011, Kadcyla™ (Trastuzumab emtansine) which was approved in 2013 for Her2+ metastatic breast cancer, Mylotarg™ (Gemtuzumab ozogamicin) targeting CD33 for acute myeloid leukemia, which was withdrawn from the market in 2010 due to excessive toxicity, has been approved in 2017 under a different dosing regimen and very recently, Besponsa (Inotuzumab ozogamicin) has been approved for the treatment of refractory acute lymphoblastic leukemia.[27-28]

There are currently two major classes of linkers used in ADCs: cleavable linkers such as acyl hydrazones,[12,27,37-38] disulfides,[20,39-42] and peptides,[22,43-46] and non-cleavable linkers.[22,40-41] ADCs with acyl hydrazones as linkers are cleaved by the acidic environments of the lysosome. Disulfides and peptidic linkers are cleaved in thiol rich environments and by lysosomal peptidases but may have reduced potency, in part due to a greater difficulty of cleavage.[37,47] Noncleavable linkers will only break apart upon proteolytic degradation of the antibody post-internalization. While this linkage is very stable, internalization is essential, which may reduce its range of targets.[48] Taken together it is clear that the structure of the linker has a great impact on the stability, efficacy and safety of ADCs.

SUMMARY

The present application relates to the design and optimization of novel acyl hydrazone linkers. Different substitution patterns have been identified that allow for modulation and tuning of conjugate stability in different media mimicking biological environments.

Known clinical or marketed ADCs possess diverse linkers that have a wide range of intracellular cleavage rates. Ranging from the intracellularly readily cleavable linkers such as the acyl hydrazones to the relatively stable non-cleavable linkers, having the ability to tune the rate of release of the payload and to improve plasma stability provides opportunities not only to target a greater variety of diseased cells, but also to design agents tailored to achieve a better therapeutic window. Towards the goal of developing enhanced control of ADC linker stability, several model cyclic acyl hydrazones whose lability is modulated either by steric or stereoelectronic effects have been prepared. Exemplary acyl hydrazones containing a substituted phenyl group adjacent to the imine carbon have been synthesized. Starting with the acyl hydrazone structure (D) present in Mylotarg the adjacent steric and electronic environments were varied and the half-life tested in a simulated lysosomal environment (pH 4.5) and in human plasma.

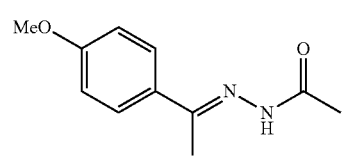

D

When the imine carbon atom of the linker group is part of a cyclic structure (as in most of the compounds of the application), about a 2-fold increase in half-life was observed compared to D. Incorporation of a hydroxy group ortho to the acyl hydrazone resulted in over an order of magnitude increase in the acid half-life. On the other hand, incorporation of a methoxy group ortho to the acyl hydrazone significantly reduced the half-life of the cyclic hydrazone. In addition, when the imine carbon atom of the linker group is part of a cyclic structure (as in most of the compounds of the application) a dramatic increase in human plasma stability was observed with 87% of the compound remaining at the end of the assay for a representative cyclic linker of the application as compared to 37% for model compound D. Introduction of a hydroxy group in the ortho position rendered the cyclic linker compound labile in plasma while incorporation of an acetamide group at the same position rendered the cyclic linker compound very stable in plasma with 92% remaining at the end of the assay. These results suggest that the adjacent steric and electronic environment can affect the stability of acyl hydrazones. Analogues of the model linkers have been incorporated into actual linker molecules as described in greater detail herein below.

Therefore, in one aspect, the present application includes a compound of Formula (I):

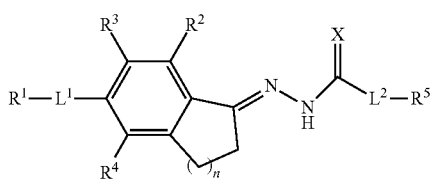
(I)

or a pharmaceutically acceptable salt and/or solvate thereof, wherein:
$R^1$ and $R^5$ are independently, a reactive functional group;
$R^2$ is selected from H, halo, $C_{1-6}$alkyl, $C_{1-6}$fluoroalkyl, $OR^6$, CN, $SR^6$ and $NR^6R^7$;
$R^3$ and $R^4$ are independently selected from H, CN, $NO_2$, halo, $C_{1-6}$alkyl, $C_{1-6}$fluoroalkyl, $OR^8$, $SR^8$ and $NR^8R^9$;
X is selected from O, S and $NR^{10}$;
$R^6$, $R^7$, $R^8$, $R^9$ and $R^{10}$ are independently selected from H, $C_{1-6}$alkyl and $C_{1-6}$fluoroalkyl;
$L^1$ and $L^2$ are independently a linker moiety; and
n is 0, 1, 2 or 3.

In another aspect, the present application includes a compound of Formula (II):

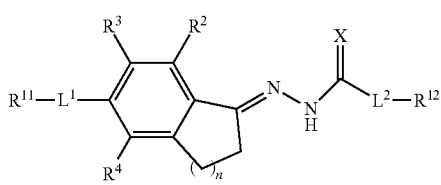
(II)

or a pharmaceutically acceptable salt and/or solvate thereof, wherein:
$R^2$ is selected from H, halo, $C_{1-6}$alkyl, $C_{1-6}$fluoroalkyl, $OR^6$, CN, $SR^6$ and $NR^6R^7$;
$R^3$ and $R^4$ are independently selected from H, CN, $NO_2$, halo, $C_{1-6}$alkyl, $C_{1-6}$fluoroalkyl, $OR^8$, $SR^8$ and $NR^8R^9$;
$R^{11}$ and $R^{12}$ are different and are selected from compounds to be linked together;
X is selected from O, S and $NR^{10}$;
$R^6$, $R^7$, $R^8$, $R^9$, and $R^{10}$ are independently selected from H, $C_{1-6}$alkyl and $C_{1-6}$fluoroalkyl,
$L^1$ and $L^2$ are independently a linker moiety; and
n is 0, 1, 2 or 3.

In some embodiments, the compounds to be linked together are selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support In a further aspect, the present application includes an antibody-drug conjugate comprising an antibody covalently attached by a linker to one or more drugs, the conjugate having a Formula (III):

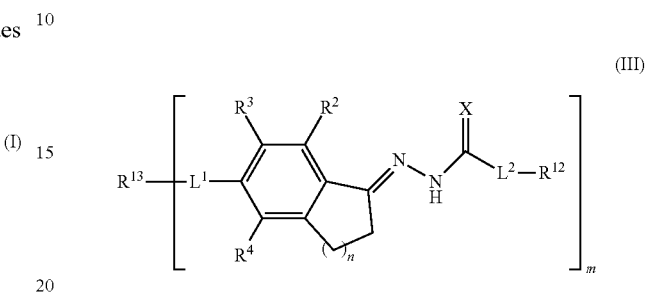
(III)

or a pharmaceutically acceptable salt and/or solvate thereof, wherein
$R^{13}$ is an antibody;
$R^{14}$ is a drug;
$L^1$, $L^2$, $R^2$, $R^3$, $R^4$ and n are as defined as above; and
m is an integer from 1 to 20.

In a further aspect the present application also includes a compound of the Formula IV:

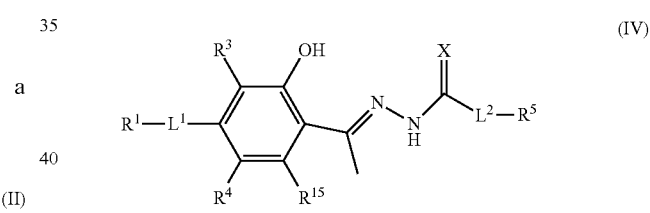
(IV)

or a pharmaceutically acceptable salt and/or solvate thereof, wherein $R^1$, $R^3$, $R^4$, $R^5$, X, $L^1$ and $L^2$ are as defined above and $R^{15}$ is selected from H, CN, $NO_2$, halo, $C_{1-6}$alkyl, $C_{1-6}$fluoroalkyl, $OR^6$, $SR^6$ and $NR^6R^7$.

In a further aspect, the present application also includes a compound of the Formula V:

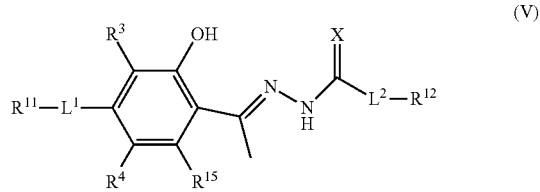
(V)

or a pharmaceutically acceptable salt and/or solvate thereof, wherein $R^3$, $R^4$, $R^{11}$, $R^{12}$, X, $L^1$ and $L^2$ are as defined above and $R^{15}$ is selected from H, CN, $NO_2$, halo, $C_{1-6}$alkyl, $C_{1-6}$fluoroalkyl, $OR^6$, $SR^6$ and $NR^6R^7$.

In a further aspect the present application also includes a compound of the Formula VI:

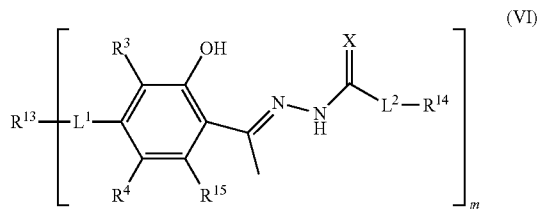

(VI)

or a pharmaceutically acceptable salt and/or solvate thereof, wherein $R^3$, $R^4$, $R^{13}$, $R^{14}$, X, $L^1$, $L^2$ and m are as defined above and $R^{15}$ is selected from H, CN, $NO_2$, halo, $C_{1-6}$alkyl, $C_{1-6}$fluoroalkyl, $OR^6$, $SR^6$ and $NR^6R^7$.

In a further aspect, the present application also includes a compound of Formula VII:

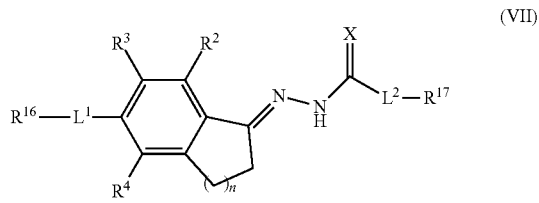

(VII)

or a pharmaceutically acceptable salt and/or solvate thereof, wherein one of $R^{16}$ and $R^{17}$ is a reactive functional group; and the other of $R^{16}$ and $R^{17}$ is a compound to be linked to another same or different compound; and
$R^2$, $R^3$, $R^4$, X, $L^1$, $L^2$ and m are as defined above.

In a further aspect, the present application also includes a compound of Formula VIII:

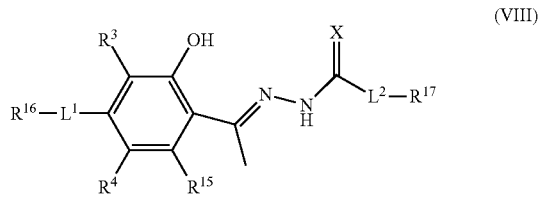

(VIII)

or a pharmaceutically acceptable salt and/or solvate thereof, wherein one of $R^{16}$ and $R^{17}$ is a reactive functional group; and the other of $R^{16}$ and $R^{17}$ is a compound to be linked to another same or different compound; $R^3$, $R^4$, $R^{15}$, X, $L^1$, $L^2$ and m are as defined above.

The present application includes a composition comprising one or more compounds of the application and a carrier. In an embodiment, the composition is a pharmaceutical composition comprising one or more compounds of Formula II or III and a pharmaceutically acceptable carrier.

The present application also includes a method of treating and/or diagnosing one or more diseases, disorders or conditions by administering an effective amount of one or more compounds of Formula (II), (III), (V) or (VI), or a pharmaceutically acceptable salt and/or solvate thereof, to a subject in need thereof. In an embodiment of the present application, the disease, disorder or condition is cancer.

In another aspect, the present application includes a method of synthesizing one or more compounds of Formula (II) as defined above, or a pharmaceutically acceptable salt and/or solvate thereof, wherein the method comprises reacting one or more compounds of Formula (I) as defined above with a first compound, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, and then a second, different compound, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support.

In another aspect, the present application includes a method of synthesizing one or more compounds of Formula (V) as defined above, or a pharmaceutically acceptable salt and/or solvate thereof, wherein the method comprises reacting one or more compounds of Formula (IV) as defined above with a first compound, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, and then a second, different compound, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support.

In another aspect the present application includes a method of preparing an ADC of Formula (III) as defined above comprising:
(a) reacting a compound of Formula (I) with a drug to provide a Formula (I)-drug conjugate;
(b) reacting the Formula (I)-drug conjugate with an antibody to provide the ADC of Formula (III), and optionally
(c) purifying the ADC of Formula (III).

In another aspect the present application includes a method of preparing an ADC of Formula (VI) comprising:
(a) reacting a compound of Formula (IV) with a drug to provide a Formula (IV)-drug conjugate;
(b) reacting the Formula (IV)-drug conjugate with an antibody to provide the ADC of Formula (VI); and optionally
(c) purifying the ADC of Formula (VI).

In another aspect, the present application includes a method of preparing an ADC of Formula (III) as defined above comprising:
(a) reacting a compound of Formula (VII) as defined above with an antibody to provide the ADC of Formula (III), and optionally
(b) purifying the ADC of Formula (III).

In another aspect, the present application includes a method of preparing an ADC of Formula (VI) as defined above comprising:
(a) reacting a compound of Formula (VIII) as defined above with an antibody to provide the ADC of Formula (VI); and optionally
(b) purifying the ADC of Formula (VI).

In another aspect of the present application is a use of one or more compounds Formula (II), (III), (V) and (VI), as defined above, or a pharmaceutically acceptable salt and/or solvate thereof, as a medicament and/or a diagnostic agent.

The novel acyl hydrazone linkers of this present application have been demonstrated in an exemplary embodiment as linkers for ADCs. Therefore, compounds of Formula (II), (III), (V) and (VI) may be useful for treating diseases, disorders or conditions treatable by ADCs. In a further aspect, the present application includes a method of administering an antibody or a drug to a subject comprising administering a compound of Formula (II), (III), (V) or (VI), or a pharmaceutically acceptable salt and/or solvate thereof, to the subject.

In a further aspect of the application there is provided a use of one or more compounds of Formula (II), (III), (V) and (VI) as defined above, or a pharmaceutically acceptable salt and/or solvate thereof, to treat and/or diagnose cancer.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 is a schematic showing the general structure of an antibody-drug conjugate.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "compound(s) of the application" or "compound(s) of the present application" and the like as used herein refers to a compound of Formula (I), (II), (III), (IV), (V), (VI), (VII) or (VIII) and/or salts and/or solvates thereof.

The term "composition of the application" or "composition of the present application" and the like as used herein refers to a composition comprising one or more compounds of the application.

The term "and/or" as used herein means that the listed items are present, or used, individually or in combination. In effect, this term means that "at least one of" or "one or more" of the listed items is used or present. The term "and/or" with respect to salts and/or solvates thereof means that the compounds of the application exist as individual salts or hydrates, as well as a combination of, for example, a salt of a solvate of a compound of the application or a solvate of a salt of a compound of the application.

As used in the present application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers are racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may exist as mixtures of E and Z isomers or cis and trans isomers and it is intended that any above mentioned isomer, as well as mixtures thereof, are included within the scope of the present application.

The compounds of the present application may further exist in varying polymorphic forms and it is contemplated that any polymorphs, or mixtures thereof, which form are included within the scope of the present application.

The compounds of the present application may further be radiolabeled and accordingly all radiolabeled versions of the compounds of the application are included within the scope of the present application. There the compounds of the application also include those in which one or more radioactive atoms are incorporated within their structure.

The compounds of the present application also include those in which one or more hydrogen atoms are replaced with deuterium.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The present description refers to a number of chemical terms and abbreviations used by those skilled in the art. Nevertheless, definitions of selected terms are provided for clarity and consistency.

The term "linker moiety" as used herein refers to any molecular structure that joins two or more other molecular structures together.

The term "small molecule" as used herein refers to a molecule having a low molecular weight and with a size, for example, on the order of about 10 nm.

The term "reactive functional group" as used herein refers to a group of atoms or a single atom that will react with another group of atoms or a single atom (so called "complementary functional group") to form a chemical interaction between the two groups or atoms.

The term "chemical interaction" as used herein refers to the formation of either a covalent or ionic bond between the reactive functional groups. The chemical interaction is one that is strong enough to append the acyl hydrazone linkers of the present application to compounds to be linked together.

The term "reacts with" as used herein generally means that there is a flow of electrons or a transfer of electrostatic charge resulting in the formation of a chemical interaction.

The term "conjugating" as used herein means to bind two molecules together via a chemical interaction.

The term "binding moiety" as used herein refers to any moiety that binds to a receptor or active site in a biological molecule. In an embodiment, the binding is specific binding, that is, the binding moiety will bind to one receptor or active site preferentially over other receptors or active sites.

The term "labelling agent" as used herein refers to any agent that is used for detection of molecules. Different types of labelling agents are known in the art depending on the form of detection to be used. For example, the labelling agent is selected from a radiolabel, a fluorescent label, a spin label, isotope label, a positron emission topography (PET) and a single-photon emission computer tomography label.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-6}$alkyl means an alkyl group having 1, 2, 3, 4, 5 or 6 carbon atoms. All alkyl groups are optionally fluorosubstituted unless otherwise indicated.

The term "alkylene" as used herein, whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{1-6}$alkylene means an alkylene group having 1, 2, 3, 4, 5 or 6 carbon atoms. All alkylene groups are optionally fluorosubstituted.

The term "alkenylene" as used herein, whether it is used alone or as part of another group, means a straight or branched chain, unsaturated alkylene group, that is, an unsaturated carbon chain that contains substituents on two of its ends and at least one double bond. The number of carbon atoms that are possible in the referenced alkenylene group are indicated by the prefix "$C_{n1-n2}$". For example, the term $C_{2-6}$alkenylene means an alkenylene group having 2, 3, 4, 5 or 6 carbon atoms. All alkenylene groups are optionally fluorosubstituted, unless otherwise indicated.

The term "alkynylene" as used herein, whether it is used alone or as part of another group, means a straight or branched chain, unsaturated alkylene group, that is, an unsaturated carbon chain that contains substituents on two of its ends and at least one triple bond. The number of carbon atoms that are possible in the referenced alkynylene group are indicated by the prefix "$C_{n1-n2}$". For example, the term $C_{2-6}$alkynylene means an alkynylene group having 2, 3, 4, 5 or 6 carbon atoms. All alkynylene groups are optionally fluorosubstituted, unless otherwise indicated.

The term "optionally substituted" refers to groups, structures, or molecules that are either unsubstituted or are substituted with one or more substituents.

The term "fluorosubstituted" refers to the substitution of one or more, including all, hydrogens in a referenced group with fluorine.

The term "halo" or "halogen" as used herein, whether it is used along or as part of another group, refers to a halogen atom and includes fluoro, chloro, bromo and iodo.

The term "cell" as used herein refers to a single cell or a plurality of cells and includes a cell either in a cell culture or in a subject.

The term "subject" as used herein includes all members of the animal kingdom including mammals, and suitably refers to humans. Thus the methods of the present application are applicable to both human therapy and veterinary applications.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful, for example, so that an ester functionality, if any, elsewhere in a compound is not hydrolyzed. The selection criteria for the appropriate salt will be known to one skilled in the art.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "atm" as used herein refers to atmosphere.

The term "MS" as used herein refers to mass spectrometry.

The term "aq." As used herein refers to aqueous.

DCM as used herein refers to dichloromethane.

DIPEA as used herein refers to N,N-diisopropyl ethylamine

DMF as used herein refers to dimethylformamide.

THF as used herein refers to tetrahydrofuran.

DMSO as used herein refers to dimethylsulfoxide.

EtOAc as used herein refers to ethyl acetate.

MeOH as used herein refers to methanol.

MeCN as used herein refers to acetonitrile.

HCl as used herein refers to hydrochloric acid.

TFA as used herein refers to trifluoroacetic acid.

CV as used herein refers to column volume.

Hex as used herein refers to hexanes.

PBS as used herein refers to phosphate-based buffer.

Epi as used herein refers to Eppendorf tubes.

MW as used herein refers to molecular weight.

HPLC as used herein refers to high performance liquid chromatography.

LCMS as used herein refers to liquid chromatography-mass spectrometry.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J.F.W. Ed., Plenum Press, 1973, in Greene, T. W. and Wuts, P.G.M., "Protective Groups in Organic Synthesis", John Wiley & Sons, $3^{rd}$ Edition, 1999 and in Kocienski, P. Protecting Groups, $3^{rd}$ Edition, 2003, Georg Thieme Verlag (The Americas).

The term "treating" or "treatment" as used herein and as is well understood in the art, means an approach for obtaining beneficial or desired results, including clinical results. In some embodiments, beneficial or desired clinical results may include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" may also mean prolonging survival as compared to expected survival if not receiving treatment. "Treating" and "treatment" as used herein may also include prophylactic treatment. For example, a subject with early cancer may be treated to prevent progression, or alternatively a subject in remission may be treated to prevent recurrence. Treatment methods comprise administering to a subject a therapeutically effective amount of one or more of the compounds and optionally consist of a single administration, or alternatively comprise a series of administrations. For example, compounds may be administered at least once a week. However, in another embodiment, the compounds may be administered to the subject from about one time per two weeks, three weeks or one month. In another embodiment, the compounds may be administered about one time per week to about once daily. In another embodiment, the compounds may be administered 2, 3, 4, 5 or 6 times daily. The length of the treatment period depends on a variety of factors, such as the severity of the disease, disorder or condition, the age of the subject, the concentration and/or the activity of the compounds, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds may be administered to the subject in an amount and for duration sufficient to treat the subject.

As used herein, the term "effective amount" or "therapeutically effective amount" means an amount of one or more compounds that is effective, at dosages and for periods of time necessary to achieve the desired result. For example in the context of a treatment for a disease, disorder of condition, an effective amount is an amount that, for example, increases said treatment compared to the treatment without administration of the one or more compounds. In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of one or more compounds or compositions to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

The term "cancer" as used herein refers to cellular-proliferative disease states.

The term "antibody" as used herein refers to a full-length antibody molecule or an immunologically active portion of a full-length antibody molecule, i.e., a molecule that contains an antigen binding site that immunospecifically binds antigen of a target of interest or part thereof, such targets including but not limited to, cancer cells that produce specific identifiable antigens. The term "antibody" also refers to monoclonal antibodies, polyclonal antibodies, multispecific antibodies (e.g., bispecific antibodies), and antibody fragments. Antibodies may be murine, human humanized, chimeric, or derived from other species.

The term "monoclonal antibody" as used herein refers to an antibody obtained from a population of substantially homogenous antibodies, i.e., the individual antibodies comprising the population are identical except for possible naturally occurring mutations that may be present in minor amounts. Monoclonal antibodies are highly specific, being directed towards a single antigenic site. In contrast to polyclonal antibody preparations which include different antibodies directed against different determinants (epitopes), each monoclonal antibody is directed against a single determinant on the antigen. In addition to their specificity, the monoclonal antibodies are advantageous as they can be synthesized uncontaminated by other antibodies. The modifier "monoclonal" indicates the character of the antibody as being obtained from a substantially homogenous population of antibodies, and is not to be construed as requiring production of the antibody by any particular method.

The term "ErbB" as used herein is a receptor protein tyrosine kinase which belongs to the ErbB receptor family responsible for mediating cell growth, differentiation and survival. The ErbB receptor family includes four distinct members including epidermal growth factor receptor (EGFR, ErbB1, HER1), HER2 (ErbB2 or $p185^{neu}$), HER3 (ErbB3) and HER4 (ErbB4 or tyro2).

The terms "epidermal growth factor receptor" or "EGFR", includes naturally occurring and mutant forms thereof (e.g., a deletion mutant EGFR).

The term "ErbB-expressing cancer" is a cancer characterized by comprising cells which have ErbB protein present at least at their cell surface. In an embodiment, the ErbB protein is the EGFR protein which is produced at sufficient levels at the surface of the cells such that an anti-EGFR antibody can bind thereto and have a therapeutic and/or diagnostic effect with respect to the cancer.

A "chemotherapeutic agent" or "anticancer agent" are terms that refer to a chemical compound useful in the treatment of a neoplastic disorder or cancer.

The term "drug" as used herein, is intended to refer to any compound or mixture of compounds which is capable of exerting a effective pharmacological effect.

The term DM1 as used herein refers to a compound of the formula

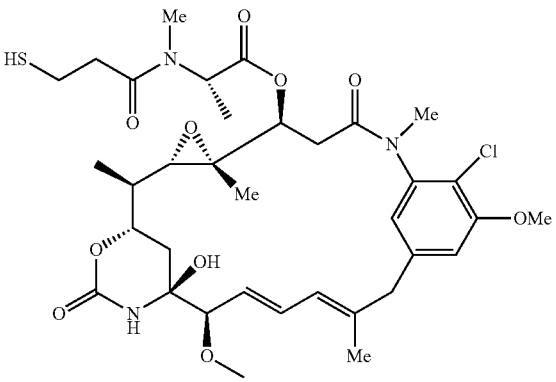 [SMILES: COc1cc2cc(c1Cl)N(C)C(=O)C[C@H](OC(=O)[C@H](C)N(C)C(=O)CCS)[C@]1(C)O[C@H]1[C@H](C)[C@@H]1C[C@@](O)(NC(=O)O1)[C@H](OC)/C=C/C=C(\C)C2]

including pharmaceutically acceptable salts and/or solvates thereof. DM1 is also known as mertansine, and in some of its forms, emtansine.

The term "monomethyl auristatin E" or "MMAE" as used herein refers to a compound of the formula

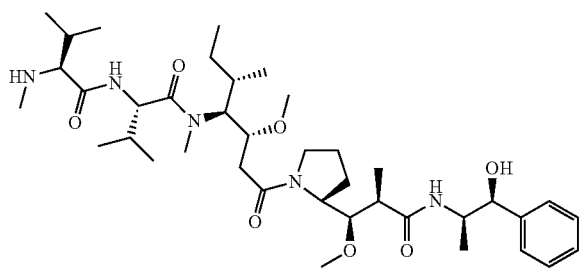 [SMILES: CC[C@H](C)[C@@H]([C@@H](CC(=O)N1CCC[C@@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

including pharmaceutically acceptable salts and/or solvates thereof.

II. Compounds of the Application

The present application includes the design and optimization of acyl hydrazone linkers that can generally be used with a wide variety of molecular classes and tolerate many different functional groups.

Accordingly, the present application includes a compound of Formula (I):

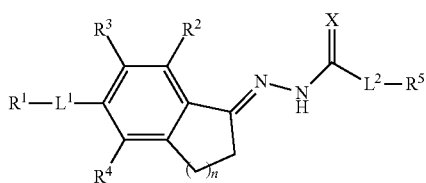

or a pharmaceutically acceptable salt and/or solvate thereof, wherein:

$R^1$ and $R^5$ are independently a reactive functional group;
$R^2$ is selected from H, halo, $C_{1-6}$alkyl, $C_{1-6}$fluoroalkyl, $OR^6$, CN, $SR^6$ and $NR^6R^7$;
$R^3$ and $R^4$ are independently selected from H, CN, $NO_2$, halo, $C_{1-6}$alkyl, $C_{1-6}$fluoroalkyl, $OR^8$, $SR^8$ and $NR^8R^9$;
X is selected from O, S and $NR^{10}$;
$R^6$, $R^7$, $R^8$, $R^9$ and $R^{10}$ are independently selected from H, $C_{1-6}$alkyl and $C_{1-6}$fluoroalkyl;
$L^1$ and $L^2$ are independently a linker moiety; and
n is 0, 1, 2 or 3.

In some embodiments, $L^1$ and $L^2$ independently comprise at least one ester, carbonate, carbamate or amide linkage although a person skilled in the art would appreciate that other linker moieties, such as ethers, sulfones, sulfoxides, thioethers, thioamides, thioesters and/or amines can additionally, or alternatively, be present. In some embodiments, $L^1$ and $L^2$ independently also comprise one or more $C_1$-$C_{20}$alkylene groups, $C_2$-$C_{20}$alkenylene groups and $C_2$-$C_{20}$alkynylene groups.

In some embodiments, $L^1$ and $L^2$ are independently selected from a direct bond, Z, $R^a$, Z—$R^a$, $R^a$—Z, $R^a$—Z—$R^b$ and Z—$R^a$—$Z^a$, wherein Z and $Z^a$ are independently selected from O, S, S(O), $SO_2$, NH, N($C_{1-6}$alkyl), C(Q), C(Q)Y, YC(Q), YC(Q)$Y^a$, ($C_{1-6}$alkyleneY)$_p$ and Y—($C_{1-6}$alkyleneY)$_p$, wherein $R^a$ and $R^b$ are independently selected from $C_{1-10}$alkylene, $C_{2-10}$alkenylene and $C_{2-10}$alkynylene; Q, Y and $Y^a$ are independently selected from O, S, NH and N($C_{1-6}$alkyl); and p is selected from 1, 2, 3, 4, 5 and 6.

In some embodiments, $R^a$ and $R^b$ are independently selected from $C_{1-6}$alkylene, $C_{2-6}$alkenylene and $C_{2-6}$alkynylene. In some embodiments, $R^a$ and $R^b$ are independently selected from $C_{1-6}$alkylene.

In some embodiments, Q, Y and $Y^a$ are independently selected from O, S, NH and N(CH$_3$).

In some embodiments Z and $Z^a$ are independently selected from O, S, S(O), $SO_2$, NH, N(CH$_3$), C(O), C(O)NH, NHC(O), NHC(O)O, OC(O)O, NHC(O)NH, OC(O)NH, NHC(NH)NH, ($C_{1-6}$alkyleneO)$_p$ and O—($C_{1-6}$alkyleneO)$_p$. In some embodiments, Z and $Z^a$ are independently selected from O, NH, C(O)NH and NHC(O).

In some embodiments $L^1$ is selected from OC(O)$C_{1-10}$alkyleneO, NHC(O)$C_{1-10}$alkyleneO, $C_{1-6}$alkyleneO, OC(O)$C_{1-10}$alkyleneNH, NHC(O)$C_{1-10}$alkyleneNH, $C_{1-6}$alkyleneNH, C(O)$C_{1-10}$alkyleneO and C(O)$C_{1-10}$alkyleneNH. In some embodiments $L^1$ is selected from OC(O)$C_{1-10}$alkyleneO, NHC(O)$C_{1-10}$alkyleneO, $C_{1-6}$alkyleneO, OC(O)$C_{1-10}$alkyleneNH, NHC(O)$C_{1-10}$alkyleneNH, $C_{1-6}$alkyleneNH, C(O)$C_{1-10}$alkyleneO, C(O)$C_{1-10}$alkyleneNH, NHC(O)$C_{1-10}$alkyleneC(O)NH and NHC$_{1-10}$alkyleneC(O)NH. In some embodiments, $L^1$ is selected from $C_{1-10}$alkyleneC(O)NH, $C_{1-10}$alkyleneO, $C_{1-10}$alkyleneC(O)NH and $C_{1-10}$alkyleneO.

In some embodiments, $L^2$ is selected from $C_{1-10}$alkyleneS and $C_{1-10}$alkylene.

In some embodiments, the reactive functional groups of $R^1$ and $R^5$ are nucleophilic and are reactive to a complementary electrophilic group present on the compound to be attached. Useful electrophilic groups on the compound include, but are not limited to, aldehyde, olefin, acetylene, carboxylic acid, ester and ketone functional groups. In some embodiments, the reactive functional groups of $R^1$ and $R^5$ are electrophilic and are reactive to a complementary nucleophilic group present on the compound to be attached. Useful nucleophilic groups on the compound include, but are not limited to, hydrazide, oxime, amino, thiol, hydrazine, thiosemicarbazone, hydrazine carboxylate and aryl hydrazide. In some embodiments, the nucleophilic group is selected from amino and thiol groups provided by reactive lysine and cysteine amino acid groups, respectively.

In some embodiments, the nucleophilic and electrophilic reactive functional groups of $R^1$ and $R^5$ include, but are not limited to, Michael addition acceptors, olefins, acetylenes, alcohols, phenols, ethers, oxides, halides, aldehydes, ketones, carboxylic acids, esters, amines, thiols, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, ortho esters, N-hydroxysuccinimide esters, maleimide, sulfites, enamines, ureas, semicarbazides, carbodiimides, carbamates, imines, azides, azo compounds and nitroso compounds.

In some embodiments, the reactive functional groups of $R^1$ and $R^5$ are independently selected from a nucleophilic group and an electrophilic group. In some embodiments, the reactive functional groups of $R^1$ and $R^5$ are selected from Michael addition acceptors, N-hydroxysuccinimide esters, amines, maleimide and thiols.

To attach different entities on each side of the linkers of the application it is desirable that each of the reactive functional groups in $R^1$ and $R^5$ have different reactivities so that one of $R^1$ and $R^5$ can functionalized by reaction with a complementary functional group in the presence of the other of $R^1$ and $R^5$, and without the other of $R^1$ and $R^5$ participating in the reaction. In some embodiments, one of $R^1$ and $R^5$ is masked or in protected form (i.e. comprising a protecting group) to prevent it from reacting while the other of $R^1$ and $R^5$ is being functionalized and the masking or protecting group is removed after the first reaction and functionalization is complete.

In some embodiments, $R^3$ and $R^4$ are independently selected from H, CN, $NO_2$, halo, $C_{1-6}$alkyl, $C_{1-6}$fluoroalkyl, $OR^8$ and $SR^8$. In some embodiments, $R^3$ and $R^4$ are independently selected from H, CN, halo, $C_{1-6}$alkyl and $C_{1-6}$fluoroalkyl. In some embodiments, $R^3$ and $R^4$ are independently selected from H, CN, halo and $C_{1-6}$alkyl. In some embodiments, $R^3$ and $R^4$ are independently selected from H, halo and $C_{1-6}$alkyl.

In some embodiments, $R^2$ is selected from H, Cl, F, CH$_3$, CF$_3$, CN and $OR^6$. In some embodiments, $R^2$ is $OR^6$.

In some embodiments, $R^6$, $R^7$, $R^8$, $R^9$, and $R^{19}$ are independently selected from H, $C_{1-4}$alkyl and $C_{1-4}$fluoroalkyl. In some embodiments, $R^6$ and $R^7$ are independently selected from H and $C_{1-4}$alkyl. In some embodiments, $R^6$ is H. In some embodiments, $R^6$ is selected from methyl, ethyl, propyl, isopropyl, sec-butyl, n-butyl and t-butyl. In some embodiments, $R^6$ is H or methyl. In some embodiments, $R^7$ is H.

In some embodiments, n is 0, 1 or 2. In some embodiments, n is 1. In some embodiments, n is 2.

In some embodiments, the compound of Formula I has the following structure:

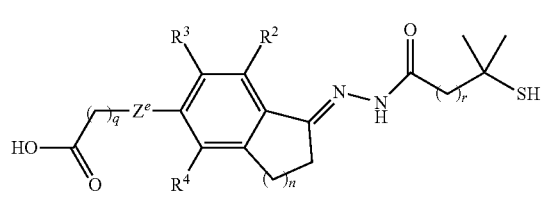
(I)

or a pharmaceutically acceptable salt and/or solvate thereof, wherein
$R^2$, $R^3$ and $R^4$ are as defined above;
$Z^e$ is selected from C(O)NH and O;
n is 0, 1, 2 or 3; and
q and r are independently 1, 2, 3, 4, 5, 6, 7 or 8.

In some embodiments, the compound of Formula I has the following structure:

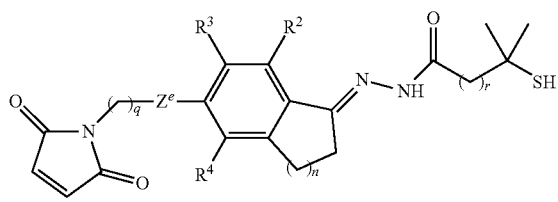
(I)

or a pharmaceutically acceptable salt and/or solvate thereof, wherein
$R^2$, $R^3$ and $R^4$ are as defined above;
$Z^e$ is selected from C(O)NH and O;
n is 0, 1, 2 or 3; and
q and r are independently 1, 2, 3, 4, 5, 6, 7 or 8.

In some embodiments, the compound of Formula I has the following structure:

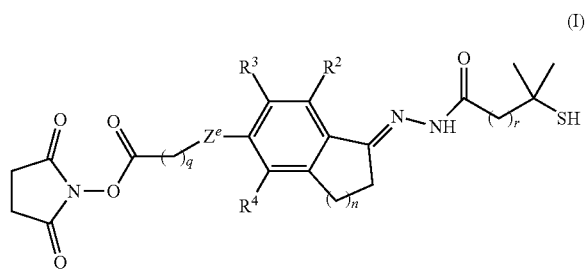
(I)

or a pharmaceutically acceptable salt and/or solvate thereof, wherein
$R^2$, $R^3$ and $R^4$ are as defined above;
$Z^e$ is selected from C(O)NH and O;
n is 0, 1, 2 or 3; and
q and r are independently 1, 2, 3, 4, 5, 6, 7 or 8.

In some embodiments, q is 2, 3 or 4. In some embodiments, q is 3. In some embodiments, r is 1 or 2. In some embodiments, r is 1. In some embodiments, $R^3$ and $R^4$ are both H.

In some embodiments Z is O. In some embodiments Z is C(O)NH.

In some embodiments, the compound of Formula I is selected from:

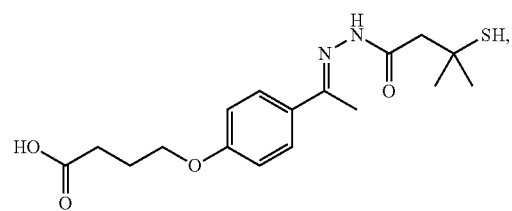
Ia

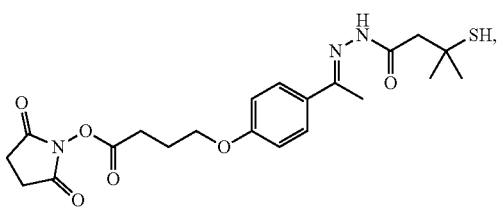
Ia-1

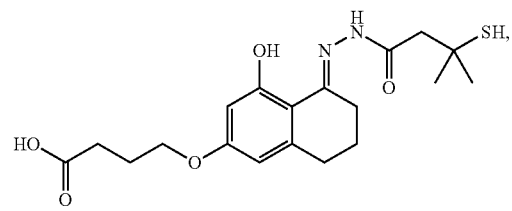
Ib

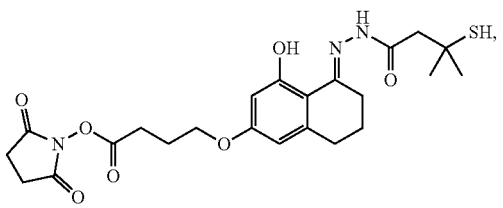
Ib-1

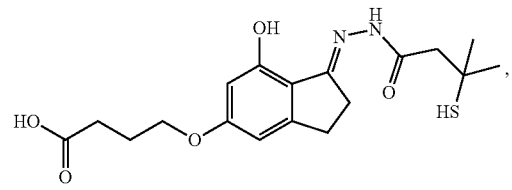
Ic

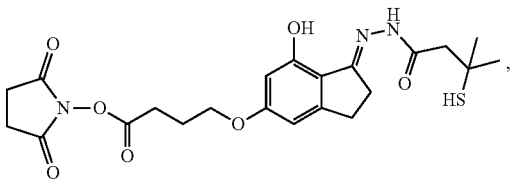
Ic-1

-continued
Id
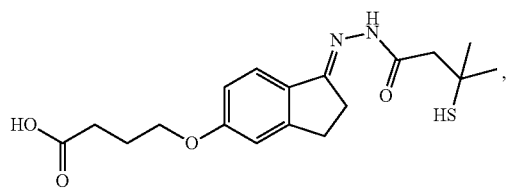
Id-1
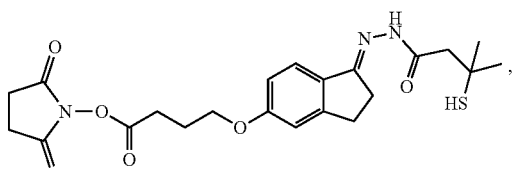
Ie
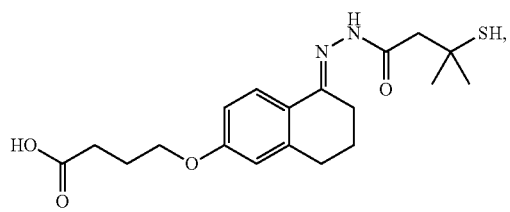
Ie-1
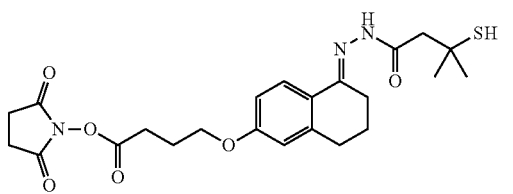
If
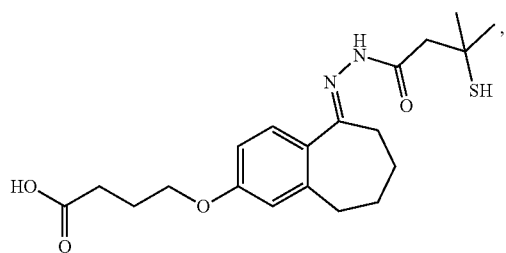
If-1
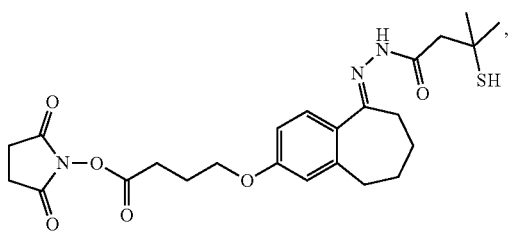
Ig
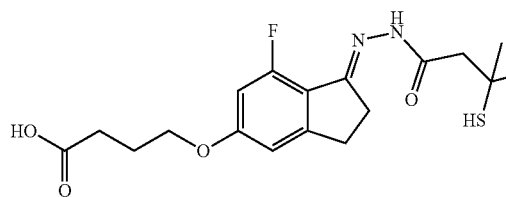
Ig-1
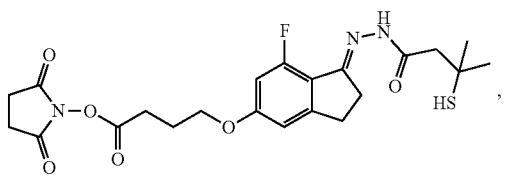
Ih
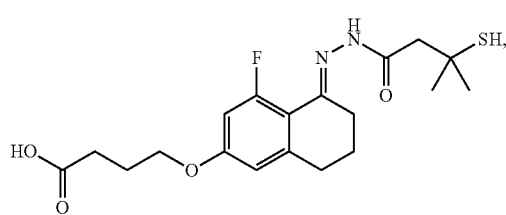
Ih-1
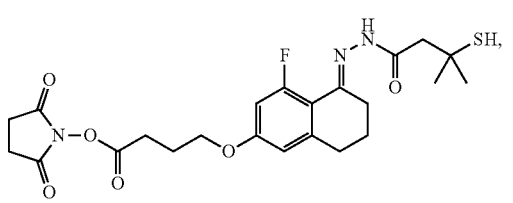
Ii
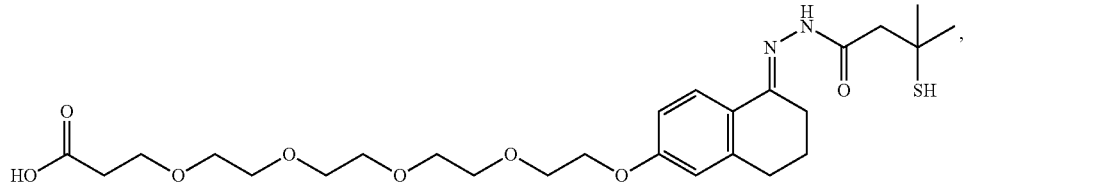
Ii-1
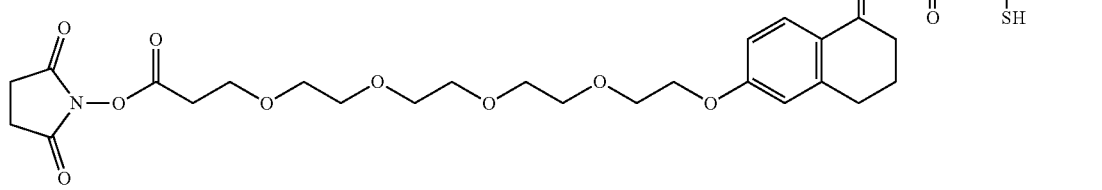

-continued

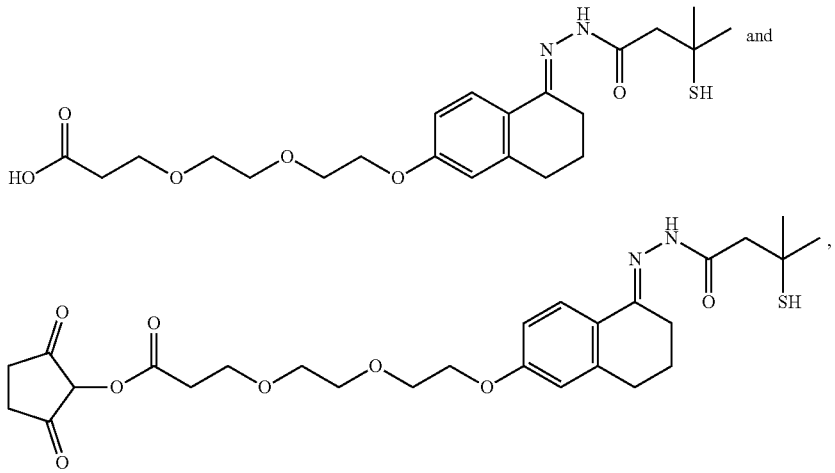

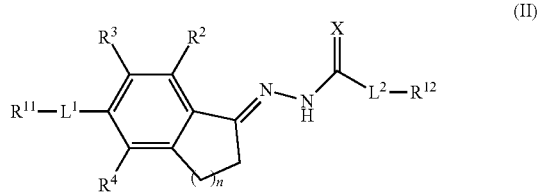

or a pharmaceutically acceptable salt and/or solvate thereof.

The present application also includes a compound of Formula (II):

(II)

or a pharmaceutically acceptable salt and/or solvate thereof, wherein:

$R^{11}$ and $R^{12}$ are different and are selected from compounds to be linked together; and $L^1$, $L^2$, $R^2$, $R^3$, $R^4$, X and n are as defined above.

In some embodiments, $R^{11}$ and $R^{12}$ are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support. In some embodiments, $R^{11}$ and $R^{12}$ are independently selected from a fluorescent dye, drug, small molecule, antibody, lipid, carbohydrate, nucleic acid, peptide, radiolabel, PET label, nanoparticle, polymer, macrocycle and metal complex.

In some embodiments, $R^{11}$ and $R^{12}$ are independently selected from an antibody and drug. In some embodiments, $R^{11}$ is an antibody and $R^{12}$ is a drug.

In some embodiments, the compound of Formula (II) is for targeting a binding moiety, a labelling agent and/or a therapeutic agent to a specific site in the body of a subject. Accordingly, in some embodiments, $R^{11}$ and $R^{12}$ are complementary or dependent on the identity of each other. For example, if $R^{12}$ is a pay load such as a drug or a label, then $R^{11}$ is a complementary group such as a binding moiety targeting a specific site in the body (a ligand specific for a receptor or an antibody specific for an antigen) which can deliver the payload to that specific site in the body.

In some embodiments, one of $R^{11}$ and $R^{12}$ is an antibody and the other of $R^{11}$ and $R^{12}$ is a drug. In some embodiments, $R^{11}$ is an antibody and $R^{12}$ is a drug. In some embodiments, the antibody binds to one or more tumor-associated antigens. In some embodiments, the antibody binds to one or more tumor-associated cell-surface receptors and the drug is a drug for treating cancer.

In some embodiments, the antibody is any antibody of therapeutic value. In some embodiments, the antibody is a wild type antibody amenable to cysteine or lysine conjugation. In some embodiments, the antibody is bio-engineered for site specific conjugation to enable a more controlled DAR ratio.

In some embodiments, the antibody is of the immunoglobulin (Ig) type. The immunoglobulin can be of any type (e.g., IgG, IgE, IgM, IgD and IgA), class (e.g., IgG1, IgG2, IgG3, IgG4, IgA1 and IgA2) or subclass of immunoglobulin molecule.

In some embodiments, the antibody specifically binds to a receptor encoded by an ErbB gene. In some embodiments, the antibody specifically binds to an ErbB receptor selected from EGFR, HER2, HER3 and HER4. In some embodiments, the tumor-associated cell-surface receptor is an ErbB receptor. In some embodiments, the antibody specifically binds to the EGFR receptor.

In some embodiments, the antibody is a monoclonal antibody of the IgG isotype. In some embodiments, the antibody is a chimeric antibody. In some embodiments, the antibody is selected from zalutumumab, nimotuzumab, matuzumab and cetuximab. In some embodiments, the antibody is cetuximab. In some embodiments, the antibody is trastuzumab.

In some embodiments, the drug is a drug for treating cancer. In some embodiments, the drug is selected from a protein kinase inhibitor, proteasome inhibitor, topoisomerase inhibitor, aromatase inhibitor, anthracycline, tubulin inhibitor, DNA binding molecule and an alkylating agent. In some embodiments, the drug is a tubulin inhibitor. In some embodiments, the drug is monomethyl auristatin E (MMAE). In some embodiments, the drug is a macrolide. In some embodiments, the drug is a maytansinoid. In some embodiments, the drug is DM1. In some embodiments, the drug is a DNA binding agent from the pyrrolobenzodiazepine family.

In some embodiments, the drug is an anticancer drug. In some embodiments, the anticancer drug is a thiol-containing anticancer drug or a calicheamicin derivative. In some embodiments, the thiol containing anticancer drug is a maytansinoid, such as DM1. In some embodiments the drug is a DNA binding agent selected from the pyrrolobenzodiazepine family. In some embodiments, the anticancer drug is a tubulin polymerization inhibitor. In some embodiments, the drug is MMAE.

In some embodiments, the compound of Formula II has the following structure:

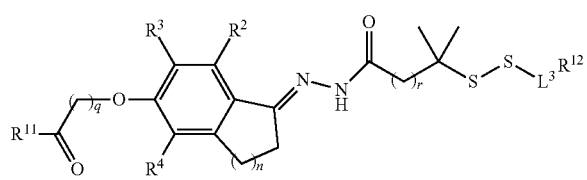

(II)

or a pharmaceutically acceptable salt and/or solvate thereof, wherein
$R^2$, $R^3$ and $R^4$ are as defined above;
$R^{11}$ and $R^{12}$ are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;
$L^3$ is a linker moiety;
n is 0, 1, 2 or 3;
q is 1, 2, 3, 4, 5, 6, 7 or 8; and
r is 1, 2, 3, 4, 5, 6, 7 or 8.

In some embodiments, the compound of Formula II has the following structure:

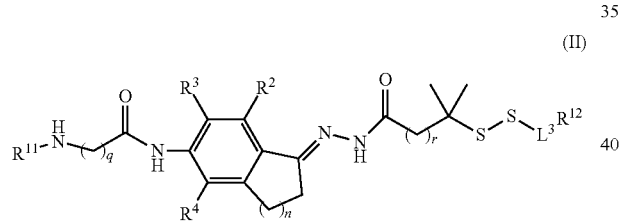

(II)

or a pharmaceutically acceptable salt and/or solvate thereof, wherein
$R^2$, $R^3$ and $R^4$ are as defined above;
$R^{11}$ and $R^{12}$ are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;
$L^3$ is a linker moiety;
n is 0, 1, 2 or 3;
q is 1, 2, 3, 4, 5, 6, 7 or 8; and
r is 1, 2, 3, 4, 5, 6, 7 or 8.

In some embodiments q is 2, 3 or 4. In some embodiments q is 3. In some embodiments, r is 1 or 2. In some embodiments, r is 1. In some embodiments, $R^3$ and $R^4$ are both H.

In some embodiments $L^3$ is selected from a direct bond, $Z^b$—$R^c$, $Z^b$—$R^c$, $R^c$—$Z^b$, $R^c$—$Z^b$—$R^d$ and $Z^b$—$R^c$—$Z^c$, wherein $Z^b$ and $Z^c$ are independently selected from O, S, S(O), SO$_2$, NH, N(C$_{1-6}$alkyl), C(Q$^a$), C(Q$^a$)Y$^b$, Y$^b$C(Q$^a$), Y$^b$C(Q$^a$)Y$^c$, (C$_{1-6}$alkyleneY$^b$)$_p$ and Y$^b$—(C$_{1-6}$alkyleneY$^b$)$_p$, wherein R$^c$ and R$^d$ are independently selected from C$_{1-10}$alkylene, C$_{2-10}$alkenylene and C$_{2-10}$alkynylene; Q$^a$, Y$^b$ and Y$^c$ are independently selected from O, S, NH and N(C$_{1-6}$alkyl), and p is selected from 1, 2, 3, 4, 5 and 6.

In some embodiments, $R^c$ and $R^d$ are independently selected from C$_{1-6}$alkylene, C$_{2-6}$alkenylene and C$_{2-6}$alkynylene. In some embodiments, $R^c$ and $R^d$ are independently selected from C$_{1-6}$alkylene.

In some embodiments, Q$^a$, Y$^b$ and Y$^c$ are independently selected from O, S, NH and N(CH$_3$).

In some embodiments $Z^b$ and $Z^c$ are independently selected from O, S, S(O), SO$_2$, NH, N(CH$_3$), C(O), C(O)NH, NHC(O), NHC(O)O, OC(O)O, NHC(O)NH, OC(O)NH, NHC(NH)NH, (C$_{1-6}$alkyleneO)$_p$ and O—(C$_{1-6}$alkyleneO)$_p$.

In some embodiments $L^3$ is selected from OC(O)C$_{1-10}$alkyleneO, NHC(O)C$_{1-10}$alkyleneO, C$_{1-6}$alkyleneO, OC(O)C$_{1-10}$alkyleneNH, NHC(O)C$_{1-10}$alkyleneNH, C$_{1-6}$alkyleneNH, C(O)C$_{1-10}$alkyleneO and C(O)C$_{1-10}$alkyleneNH.

In some embodiments, the half-life of the compounds of Formula II is controlled by the substituent selection for $R^2$, $R^3$ and/or $R^4$. In some embodiments, to increase the acidic half-life in lysosomal environments of the compounds of Formula II, $R^2$ is OH or $R^3$ is halo, such as F. In some embodiments, to decrease acidic half-life in lysosomal environments of the compounds of Formula III, $R^2$ is OMe.

In a further aspect the present application also includes a compound of the Formula IV:

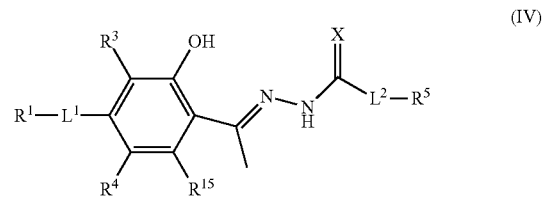

(IV)

or a pharmaceutically acceptable salt and/or solvate thereof, wherein $R^1$, $R^3$, $R^4$, $R^5$, X, $L^1$ and $L^2$ are as defined above for Formula I and $R^{15}$ is selected from H, CN, NO$_2$, halo, C$_{1-6}$alkyl, C$_{1-6}$fluoroalkyl, OR$^6$, SR$^6$ and NR$^6$R$^7$. In some embodiments, $R^{15}$ is H or CH$_3$.

In some embodiments, the compound of Formula (IV) has the following structure:

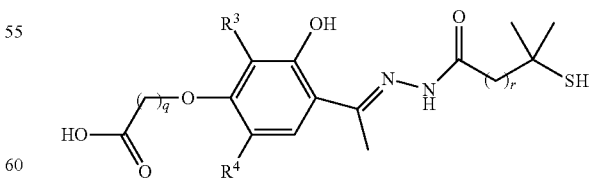

wherein $R^3$, $R^4$, q and r are as defined above for Formula I, or a pharmaceutically acceptable salt and/or solvate thereof.

In some embodiment, the compound of Formula IV is selected from:

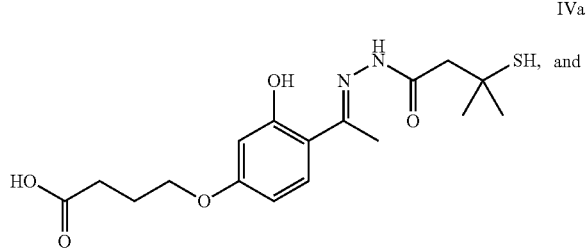

IVa

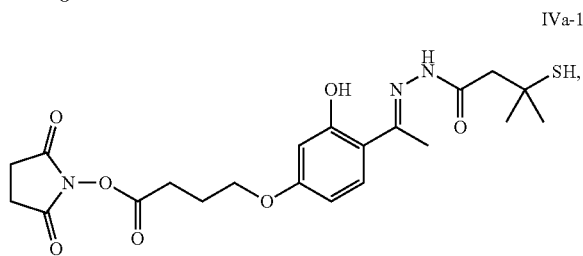

IVa-1 or a pharmaceutically acceptable salt and/or solvate thereof.

In a further aspect, the present application also includes a compound of the Formula V:

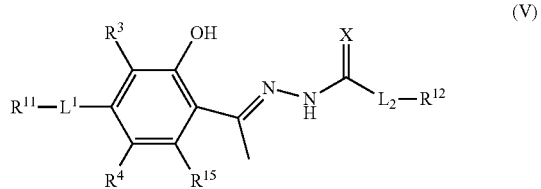

(V)

or a pharmaceutically acceptable salt and/or solvate thereof, wherein $R^3$, $R^4$, $R^{11}$, $R^{12}$, X, $L^1$ and $L^2$ are as defined above for Formula II and $R^{15}$ is selected from H, CN, $NO_2$, halo, $C_{1-6}$alkyl, $C_{1-6}$fluoroalkyl, $OR^6$, $SR^6$ and $NR^6R^7$. In some embodiments, $R^{15}$ is H or $CH_3$ In some embodiments, the compound of Formula V has the following structure:

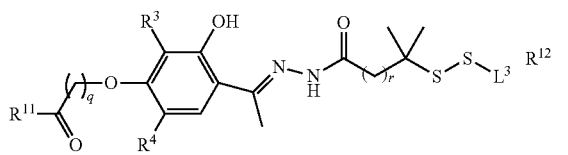

(V)

wherein $R^3$, $R^4$, $R^{11}$, $R^{12}$, q, q, r and $L^3$ are as defined above for Formula II,
or a pharmaceutically acceptable salt and/or solvate thereof.

In a further aspect, the present application also includes a compound of Formula VII:

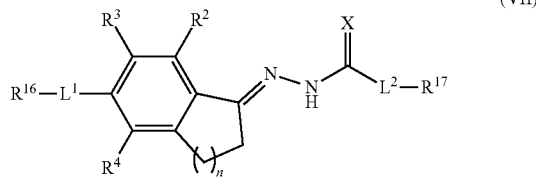

(VII)

or a pharmaceutically acceptable salt and/or solvate thereof, wherein one of $R^{16}$ and $R^{17}$ is a reactive functional group; and the other of $R^{16}$ and $R^{17}$ is a compound to be linked to another same or different compound; and $R^2$, $R^3$, $R^4$, X, $L^1$, $L^2$ and m are as defined above.

In some embodiments, the compound of Formula (VII) has the following structure:

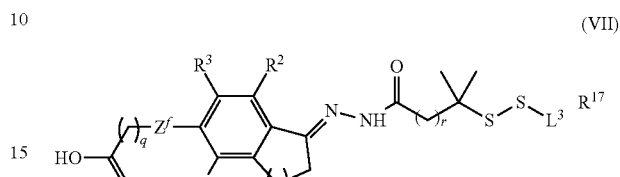

(VII)

wherein $R^{17}$ is a compound to be linked to another same or different compound;

$Z^f$ is C(O)NH or O; and $R^2$, $R^3$, $R^4$, $L^3$, q, r and n are as defined above, or a pharmaceutically acceptable salt and/or solvate thereof.

In some embodiments, the compound of Formula VII is a compound of the following structure:

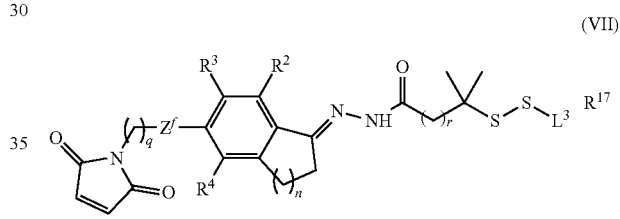

(VII)

wherein $R^{17}$ is a compound to be linked to another same or different compound;

$R^2$, $R^3$, $R^4$, $L^3$, q, r and n are as defined above; and $Z^f$ is C(O)NH or O;

or a pharmaceutically acceptable salt and/or solvate thereof.

In some embodiments, the compound of Formula VII is a compound of the following structure;

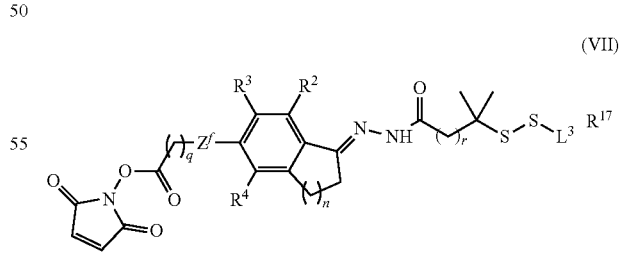

(VII)

wherein $R^{17}$ is a compound to be linked to another same or different compound as defined in Formula $R^2$, $R^3$, $R^4$, $L^3$, q, r and n are as defined above; and $Z^f$ is C(O)NH or O;

or a pharmaceutically acceptable salt and/or solvate thereof.

In some embodiments, the compound of Formula VII is selected from:
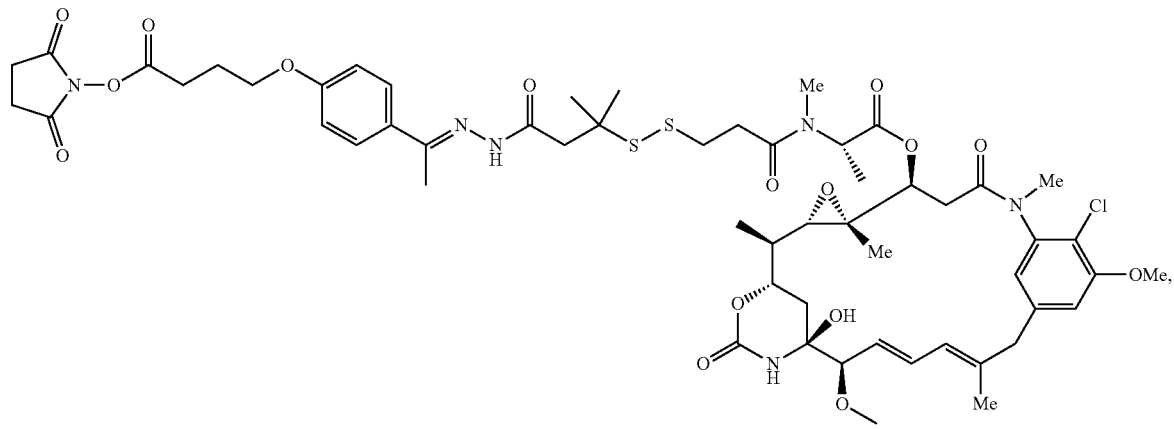
VIIa
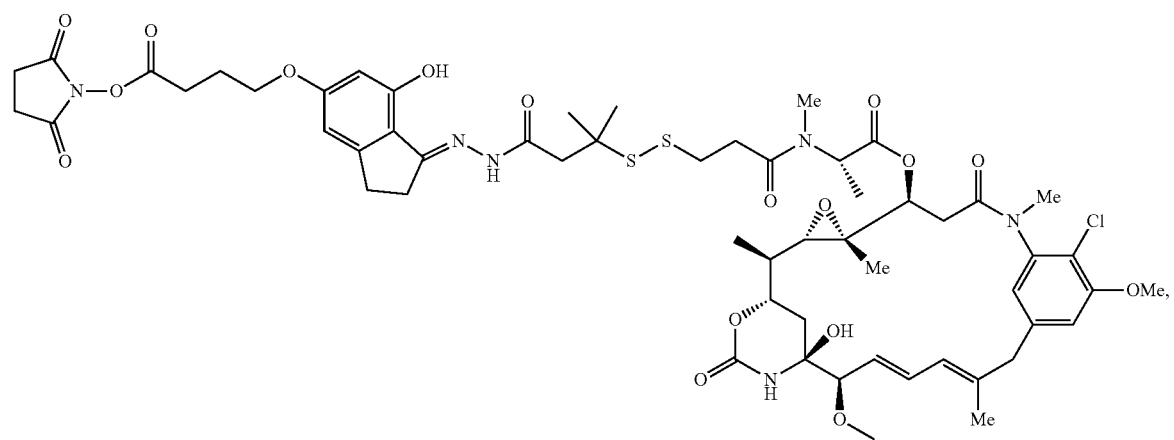
VIIc
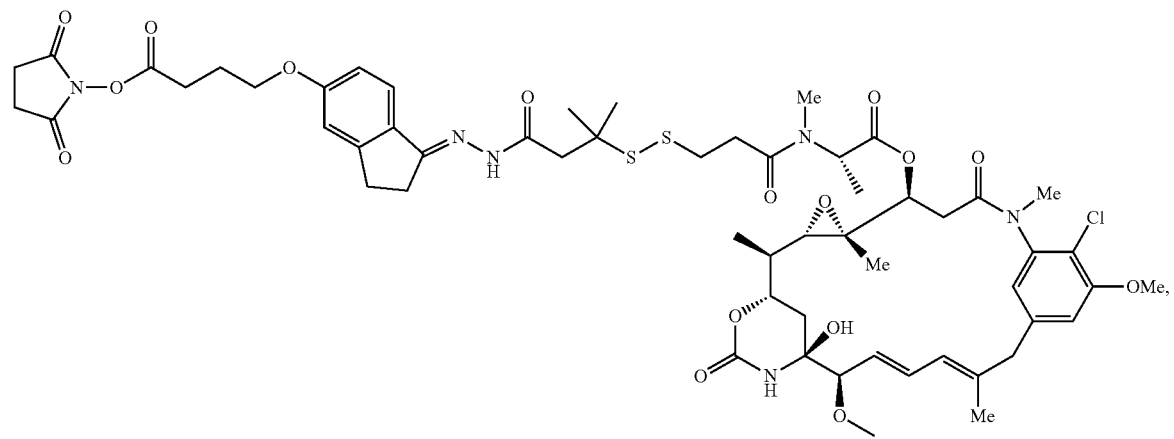
VIId -continued
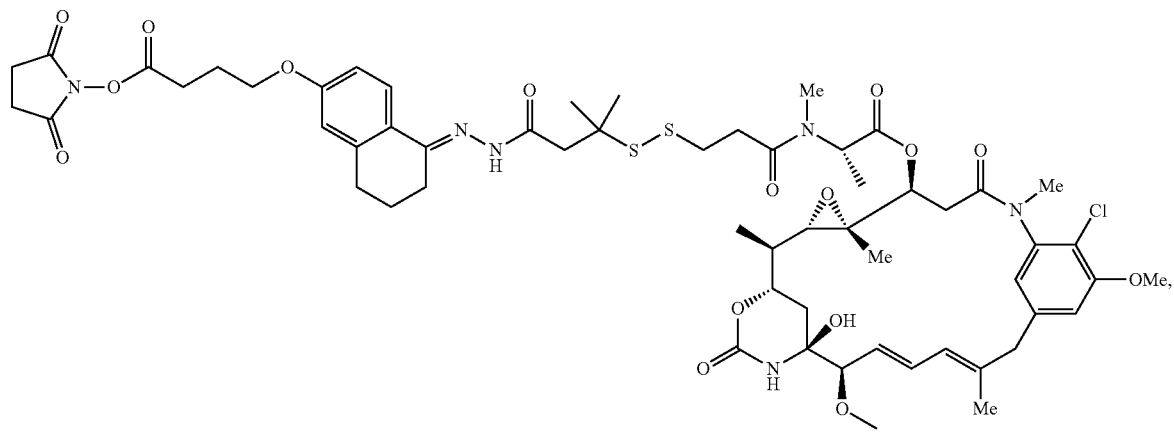
VIIe
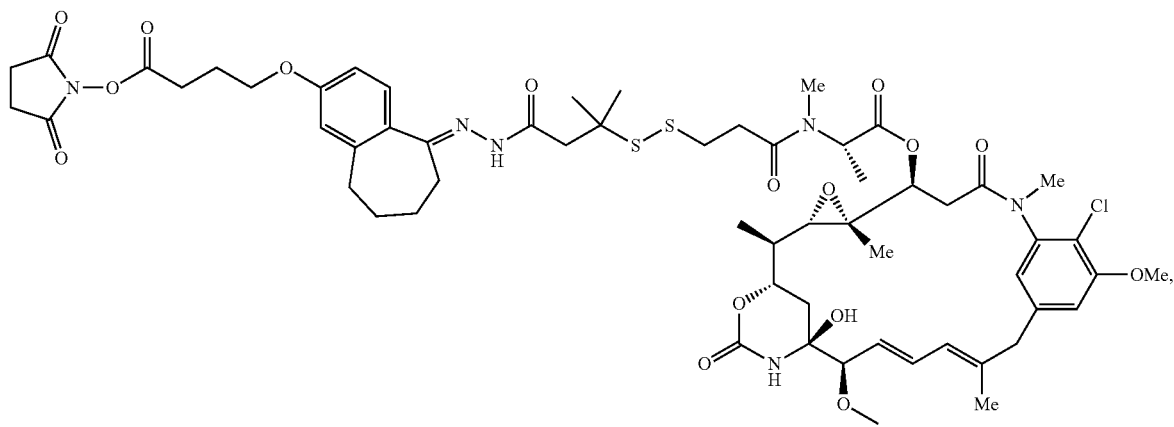
VIIf
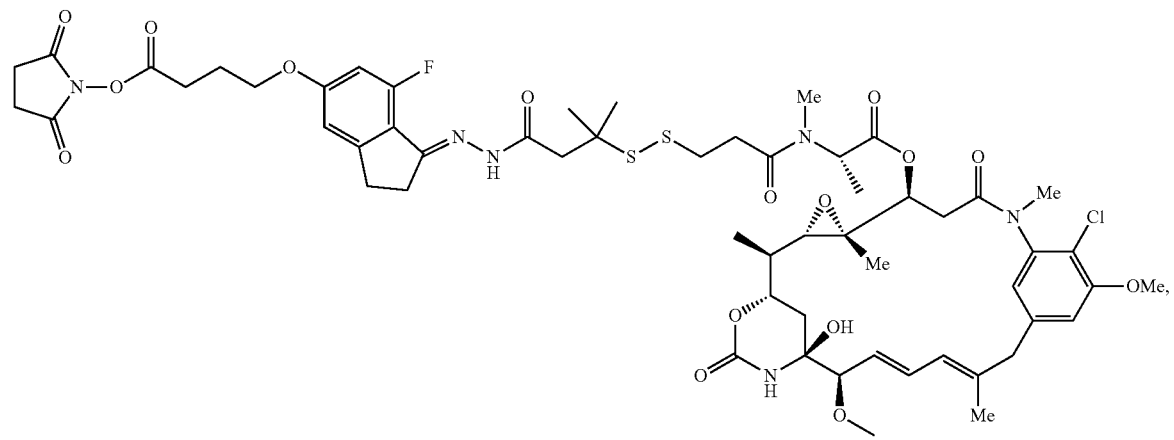
VIIg -continued
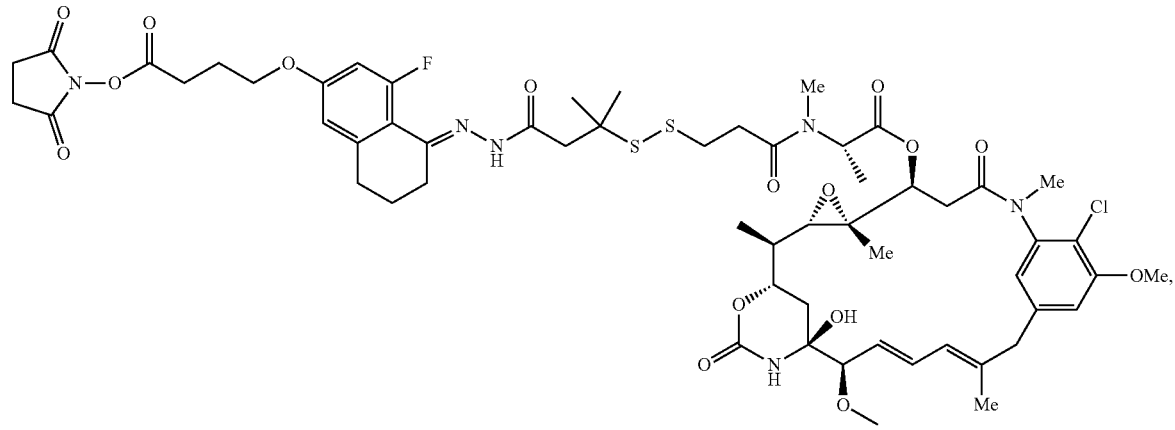
VIIh
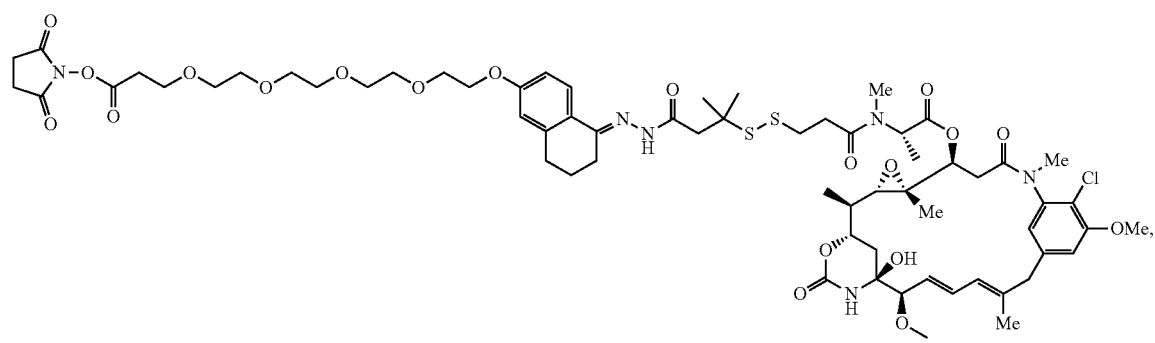
VIIi
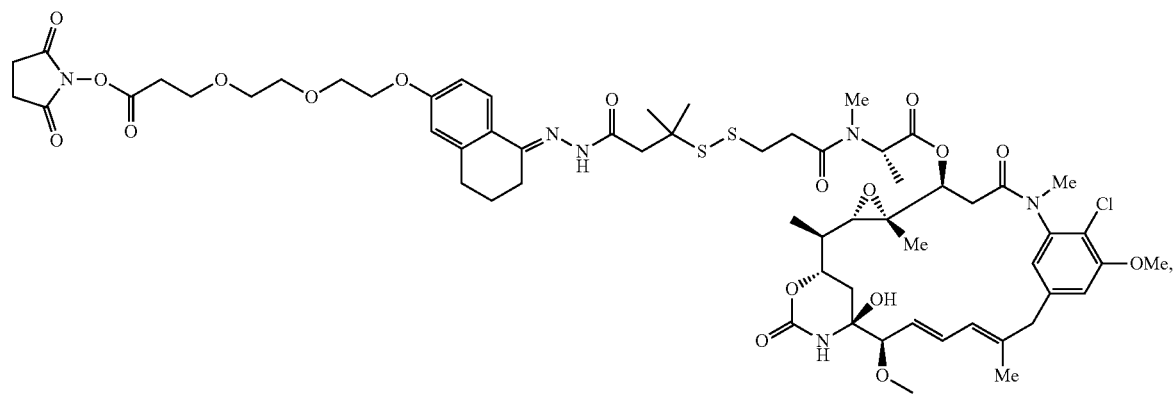
VIIj
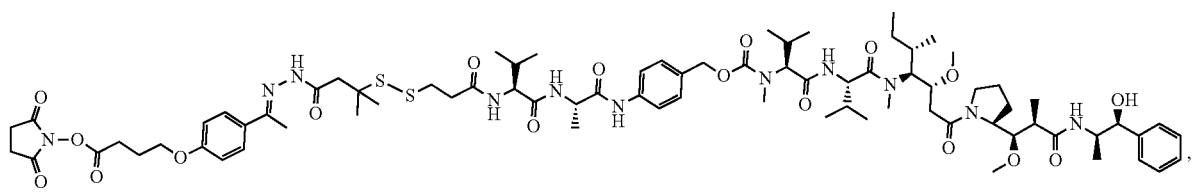
VIIk
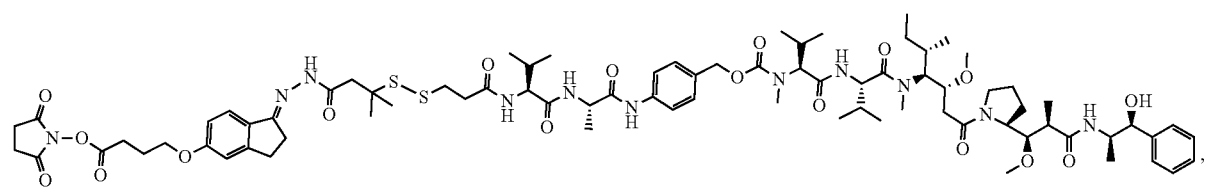
VIIL VIIm
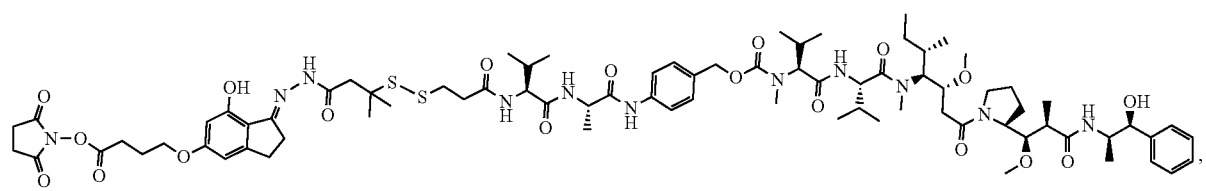
VIIn
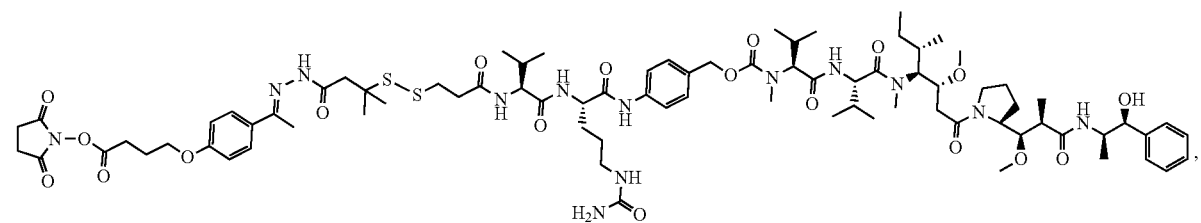
VIIp
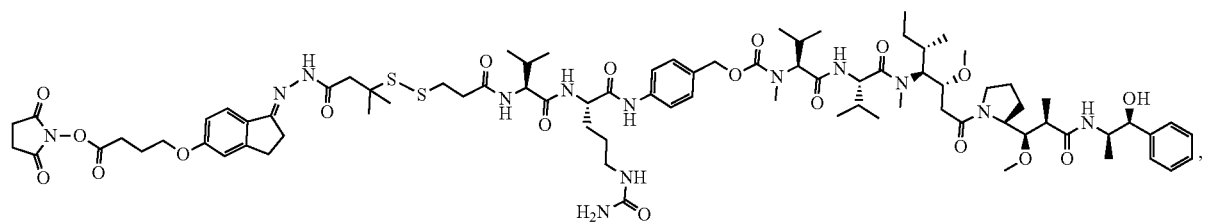
VIIq
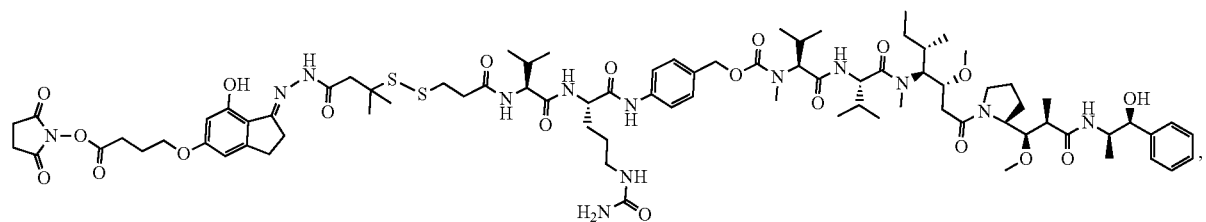
VIIr
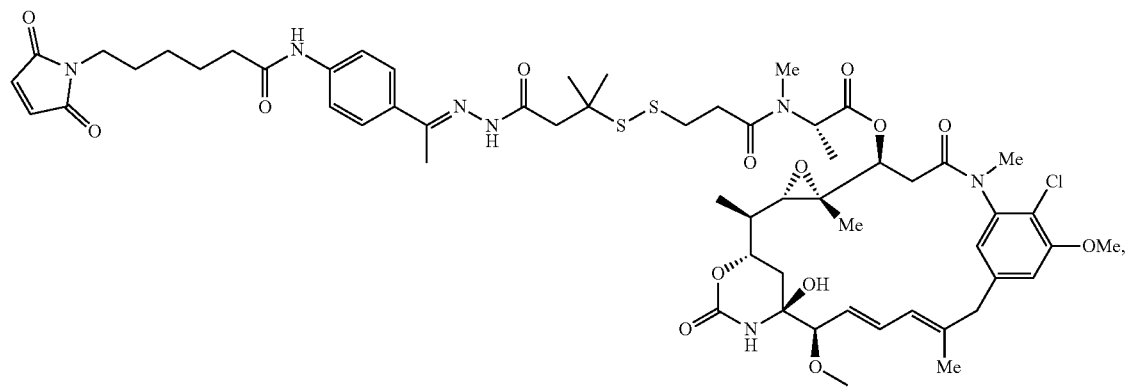

-continued
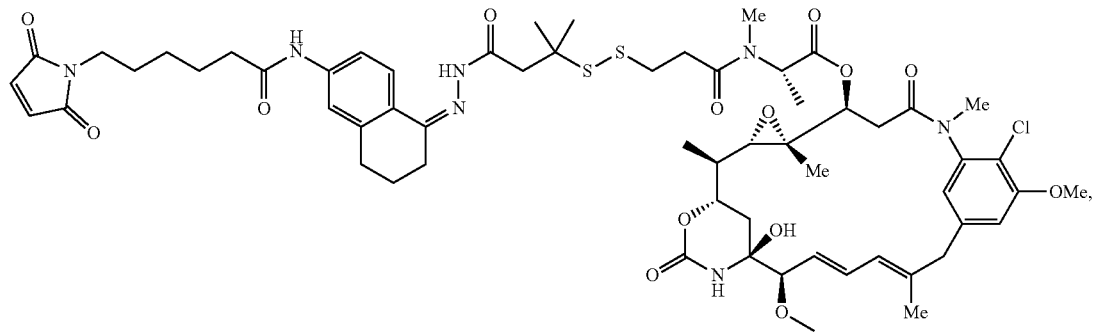
VIIs
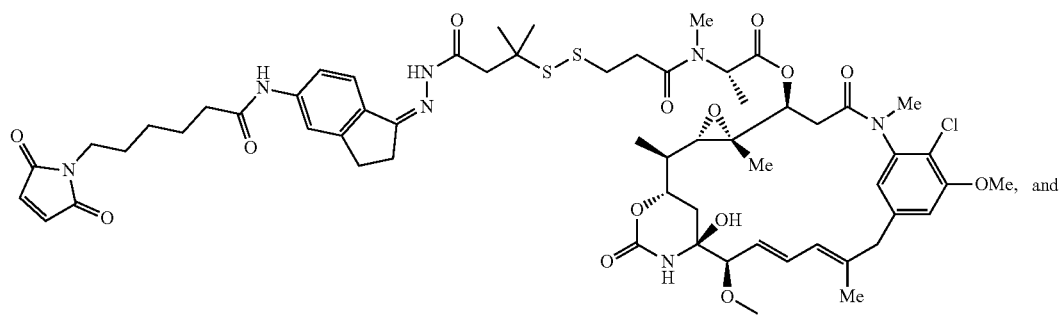
VIIt
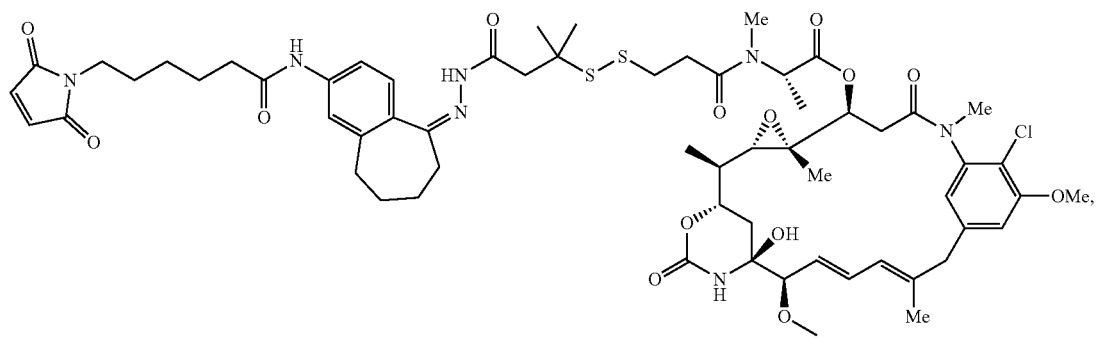
VIIu
or a pharmaceutically acceptable salt and/or solvate thereof.

In a further aspect, the present application also includes a compound of Formula VIII:

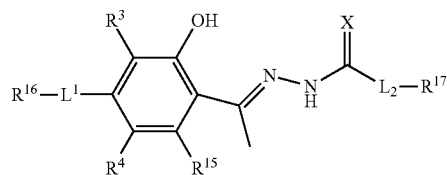
(VIII)

or a pharmaceutically acceptable salt and/or solvate thereof, wherein one of $R^{16}$ and $R^{17}$ is a reactive functional group; and the other of $R^{16}$ and $R^{17}$ is a compound to be linked to another same or different compound; $R^3$, $R^4$, $R^{15}$, X, $L^1$, $L^2$ and m are as defined above.

In some embodiments, the compound of Formula VIII is selected from:

III. Antibody-Drug Conjugates of the Application

The present application includes an antibody-drug conjugate (ADC) comprising an antibody covalently attached by a linker to one or more drugs, the conjugate having a Formula (III):

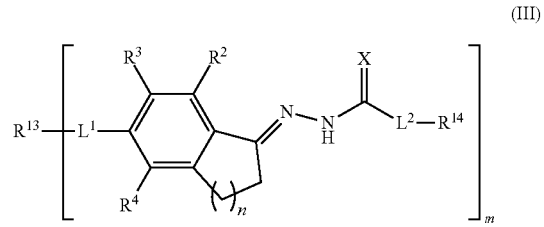
(III)

or a pharmaceutically acceptable salt and/or solvate thereof, wherein

VIIIb

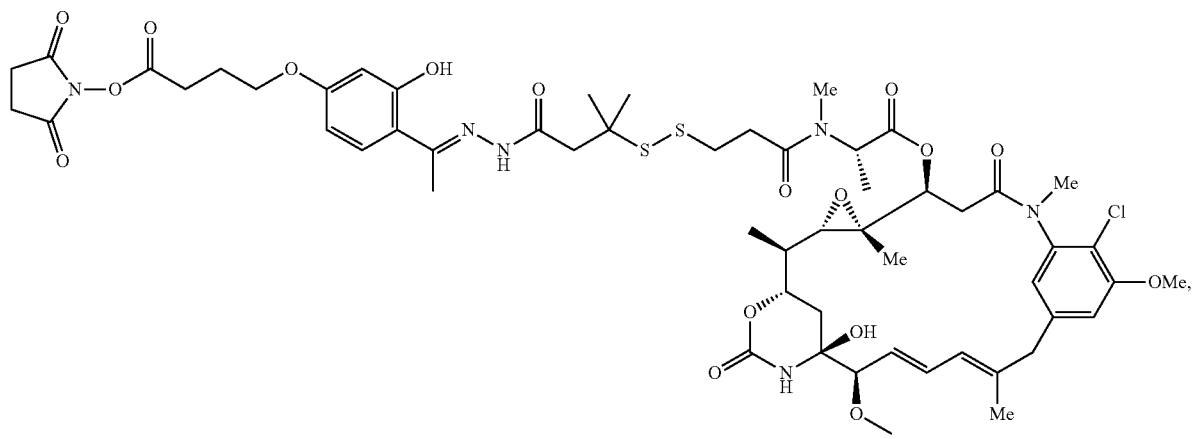

VIIIb

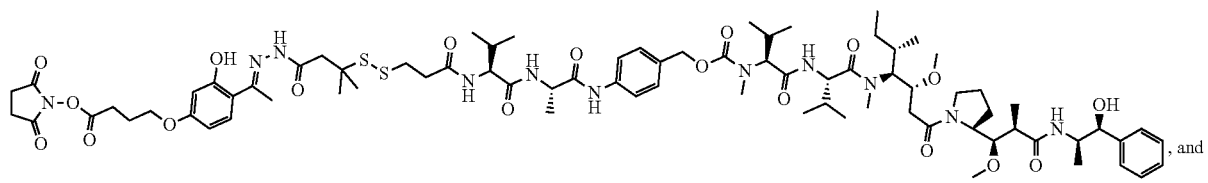
, and

VIIIc

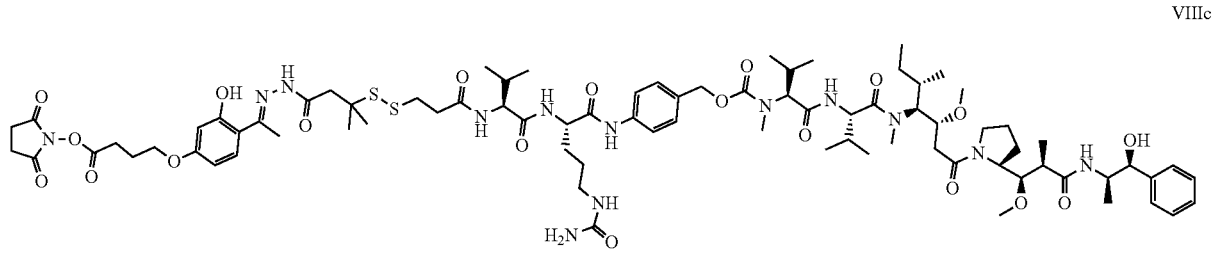

or a pharmaceutically acceptable salt and/or solvate thereof.

$R^{13}$ is an antibody;
$R^{14}$ is a drug;
$L^1$, $L^2$, $R^2$, $R^3$, $R^4$ and n are as defined as above; and
m is an integer from 1 to 20.

In some embodiments, the compound of Formula III has the following structure:

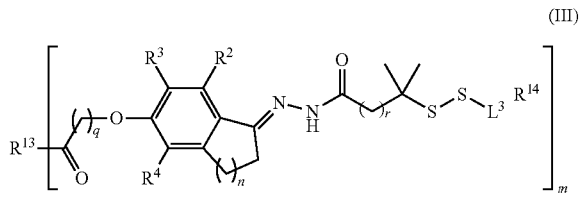

wherein
$R^2$, $R^3$ and $R^4$ are as defined above;
$R^{13}$ is an antibody;
$R^{14}$ is a drug;
$L^1$, $L^2$, $R^2$, $R^3$, $R^4$ and n are as defined as above;
$L^3$ is a linker moiety;
q is 1, 2, 3, 4, 5, 6, 7 or 8;
r is 1, 2, 3, 4, 5, 6, 7 or 8; and
m is an integer from 1 to 20,
or a pharmaceutically acceptable salt and/or solvate thereof.

In some embodiments q in the compounds of Formula III is 2, 3 or 4. In some embodiments q in the compounds of Formula III is 3. In some embodiments, r in the compounds of Formula III is 1 or 2. In some embodiments, r in the compounds of Formula III is 1. In some embodiments, $R^3$ and $R^4$ are both H.

In some embodiments in the compounds of Formula III $L^3$ is selected from a direct bond, $Z^b$ $R^c$, $Z^b$—$R^c$, $R^c$—$Z^b$, $R^c$—$Z^b$—$R^d$ and $Z^b$—$R^c$—$Z^c$, wherein $Z^b$ and $Z^c$ are independently selected from O, S, S(O), $SO_2$, NH, N($C_{1-6}$alkyl), $C(Q^a)$, $C(Q^a)Y^b$, $Y^bC(Q^a)$, $Y^bC(Q^a)Y^c$, $(C_{1-6}\text{alkylene}Y^b)_p$ and $Y^b$—$(C_{1-6}\text{alkylene}Y^b)_p$, wherein $R^c$ and $R^d$ are independently selected from $C_{1-10}$alkylene, $C_{2-10}$ alkenylene and $C_{2-10}$alkynylene; $Q^a$, $Y^b$ and $Y^c$ are independently selected from O, S, NH and N($C_{1-6}$alkyl), and p is selected from 1, 2, 3, 4, 5 and 6.

In some embodiments in the compounds of Formula III $R^c$ and $R^d$ are independently selected from $C_{1-6}$alkylene, $C_{2-6}$alkenylene and $C_{2-6}$alkynylene. In some embodiments, $R^c$ and $R^d$ are independently selected from $C_{1-6}$alkylene.

In some embodiment in the compounds of Formula III $Q^a$, $Y^b$ and $Y^c$ are independently selected from O, S, NH and $N(CH_3)$.

In some embodiments in the compounds of Formula III $Z^b$ and $Z^c$ are independently selected from O, S, S(O), $SO_2$, NH, $N(CH_3)$, C(O), C(O)NH, NHC(O), NHC(O)O, OC(O)O, NHC(O)NH, OC(O)NH, NHC(NH)NH, $(C_{1-6}\text{alkyleneO})_p$ and O—$(C_{1-6}\text{alkyleneO})_p$, In some embodiments, the antibody binds to one or more tumor-associated antigens. In some embodiments, the antibody binds to one or more tumor-associated cell-surface receptors. In some embodiments, the antibody specifically binds to a receptor encoded by an ErbB gene. In some embodiments, the tumor-associated cell-surface receptor is an ErbB receptor.

In some embodiments, the antibody specifically binds to an ErbB receptor selected from EGFR, HER2, HER3 and HER4. In some embodiments, the antibody specifically binds to the EGFR receptor. In some embodiments, the antibody is a monoclonal antibody. In some embodiments, the antibody is a chimeric antibody. In some embodiments, the antibody is selected from zalutumumab, nimotuzumab, matuzumab and cetuximab. In some embodiments, the antibody is cetuximab. In some embodiments, the antibody is trastuzumab.

In some embodiments, the drug is a drug for targeting cancer. In some embodiments, the drug is selected from a protein kinase inhibitor, proteasome inhibitor, topoisomerase inhibitor, aromatase inhibitor, anthracycline, tubulin inhibitor, DNA binding molecule and an alkylating agent. In some embodiments, the drug is a tubulin inhibitor. In some embodiments, the drug is a macrolide. In some embodiments, the drug is a maytansinoid. In some embodiments, the one or more drug moieties is DM1. In some embodiments, the drug is a DNA binding agent from the pyrrolobenzodiazepine family.

In some embodiments, the drug is an anticancer drug. In some embodiments, the anticancer drug is a thiol-containing anticancer drug or a calicheamicin derivative. In some embodiments, the thiol containing anticancer drug is a maytansinoid, such as DM1. In some embodiments, the drug is a DNA binding agent from the pyrrolobenzodiazepine family. In some embodiments, the anticancer drug is a tubulin polymerization inhibitor. In some embodiments, the drug is MMAE.

The drug loading of ADCs is represented by the integer m, which indicates the average number of drugs conjugated per antibody in the conjugate of Formula (III). The drug to antibody (DAR) ratio is relevant for the preparation of ADC's, as higher drug loading, e.g. m>5, may cause aggregation, insolubility, toxicity or loss of cellular permeability. Further, the DAR ratio is dependent upon the number of reactive sites present on the antibody. For example, where the attachment point is a cysteine thiol or lysine amine, as in the exemplary embodiments of the present application, an antibody may have only one or few number of these reactive groups through which a linker maybe attached. Additionally, the antibody may be subjected to denaturing conditions to reveal reactive nucleophilic groups such as lysine and cysteine. In some embodiments, the DAR ratio of the compounds of Formula (IIb) ranges from 1 to 20 drugs per antibody.

In some embodiments, m is an integer from 1 to 10. In some embodiments, m is an integer from 1 to 5.

Known antibodies for the treatment and prevention of cancer can be conjugated as ADCs. Antibodies immunospecific for a cancer cell antigen are obtained commercially or produced by any method known to a person skilled in the art, including, e.g., chemical syntheses or by recombinant expression techniques. In some embodiments, the nucleotide sequence encoding antibodies immunospecific for a cancer cell antigens is obtained, for example, from the GenBank database or a similar nucleotide sequence database, literature publications, or through routine cloning and sequencing.

In some embodiments, the ADCs of the present application selectively deliver an effective dose of a cytotoxic agent, such as a drug, to tumor tissue with greater selectivity, i.e., a lower effective dose is achieved, than upon delivery of the same dose of drug not conjugated to an antibody.

In some embodiments, the drug of the compound of Formula III is not cleaved from the antibody until the compound enters a cell with a cell-surface receptor specific for the antibody of the compound, at which time the drug is cleaved from the antibody. In some embodiments, the drug is intracellularly cleaved from the antibody of the compound of Formula III through enzymatic action, hydrolysis, oxidation or pH conditions. In some embodiments, the acidic half-life in lysosomal environments of the compounds of Formula III is controlled by the substituent selection for $R^2$, $R^3$ and/or $R^4$. In some embodiments, to increase the acidic half-life in lysosomal environments of the compounds of Formula III, $R^2$ is OH or $R^3$ is halo, such as F. In some embodiments, to decrease the acidic half-life in lysosomal environments of the compounds of Formula III, $R^2$ is OMe.

In a further aspect the present application also includes a compound of the Formula VI:

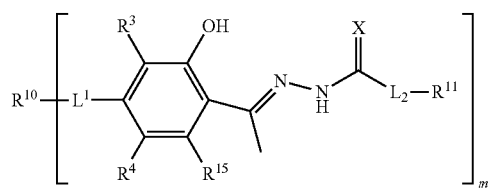

(VI)

wherein $R^3$, $R^4$, $R^{10}$, $R^{11}$, X, $L^1$, $L^2$ and m are as defined above for Formula III and $R^{15}$ is selected from H, CN, $NO_2$, halo, $C_{1-6}$alkyl, $C_{1-6}$fluoroalkyl, $OR^6$, $SR^6$ and $NR^6R^7$, or a pharmaceutically acceptable salt and/or solvate thereof.
In some embodiments, $R^{15}$ is H or $CH_3$.

In some embodiments, the compound of Formula (VI) has the following structure:

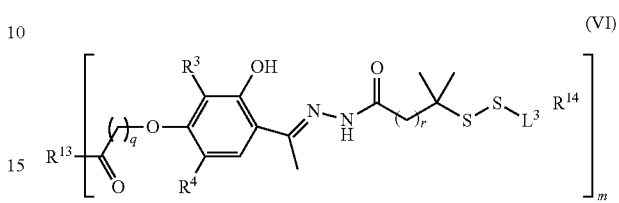

(VI)

wherein $R^3$, $R^4$, $R^{13}$, $R^{14}$, $L^3$, q, r and m are as defined above for Formula III,
or a pharmaceutically acceptable salt and/or solvate thereof.
In some embodiments, the compound of Formulae III and VI are each selected from:

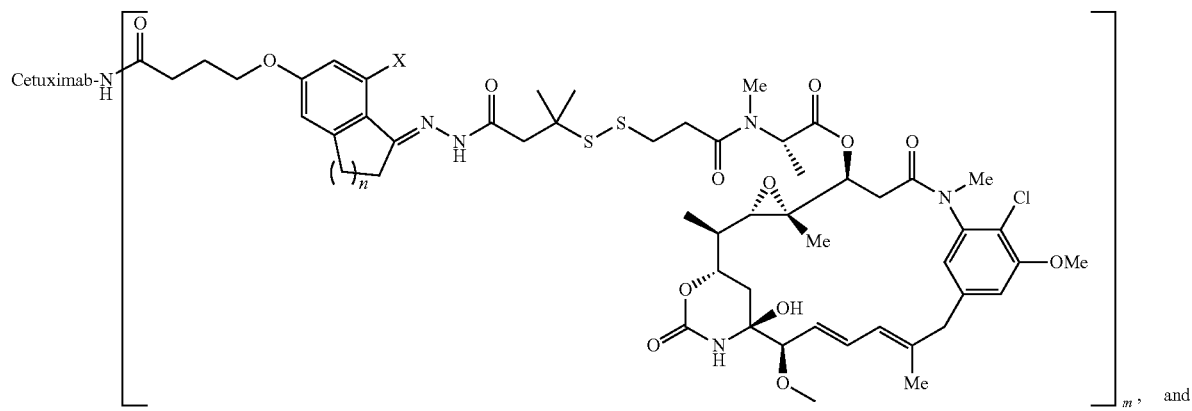

, and

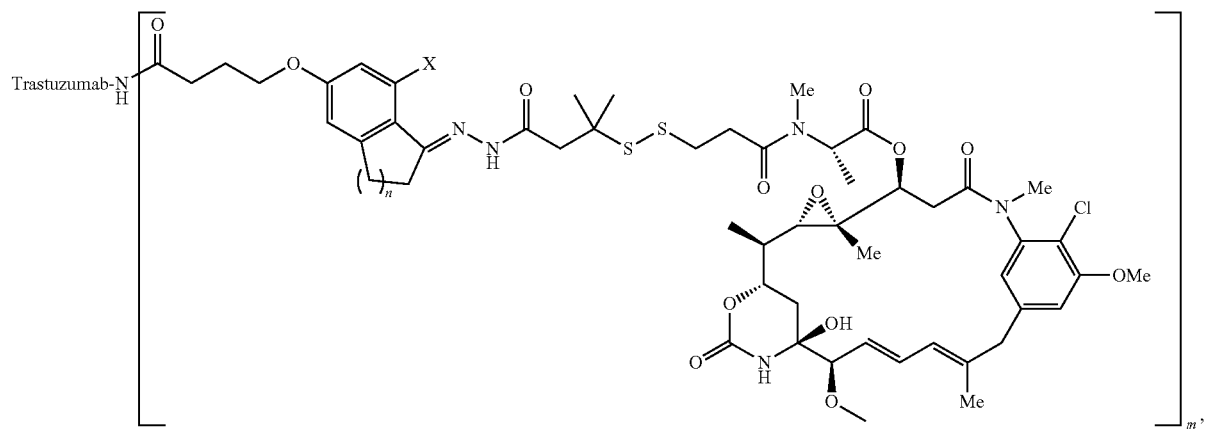

wherein X is $R^2$ as defined above, n=0, 1, or 2, and m=1 to 20, or a pharmaceutically acceptable salt and/or solvate thereof.

IV. Methods of Preparing Compounds of the Application

Scheme 1 illustrates one embodiment of a route to compounds of the application in which a functionalized hydrazide is formed from commercially available compounds A, wherein $R^5$ is a reactive functional group or a protected form thereof and X and $L^2$ is as defined in Formula I to afford intermediates B. The subsequent coupling of B with aromatic compounds C, wherein $R^1$-$R^4$, $L^1$ and n are as defined in Formula I and in which $R^1$ may be in protected form, provides compounds of the application.

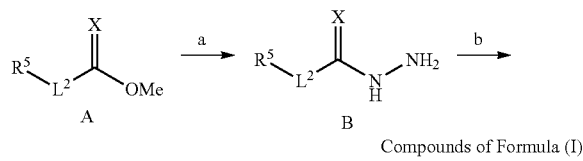

Compounds of Formula (I)

Scheme 1
a) $NH_2NH_2 \cdot H_2O$/alcohol solvent;
b)

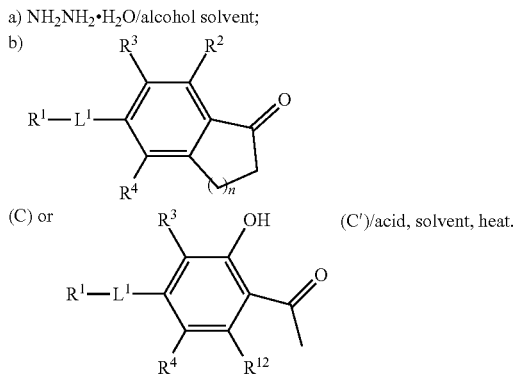

(C')/acid, solvent, heat.

Compounds of Formula C and C' are either commercially available or are synthesized from commercially available compounds using methods known in the art, for example starting from compounds of Formula D:

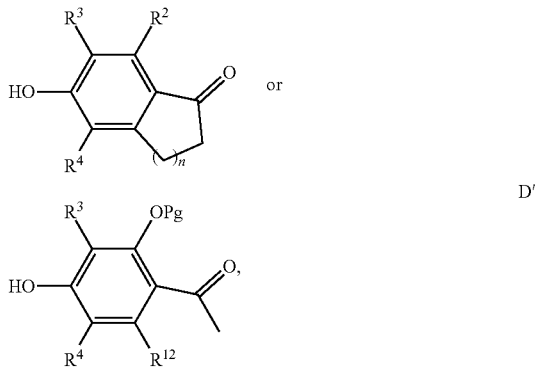

wherein $R^2$-$R^4$ are as defined in Formula (I) and Pg is a suitable protecting group.

In some embodiments, the reactive functional groups $R^1$ and $R^5$ of the compounds of Formula (I), (IV), (VII) or (VIII) are subsequently conjugated to a complementary reactive functional group of compounds to be linked, for example, a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, to produce the compounds of Formula (II), (III), (V) or (VI) of the present application.

Accordingly, in another aspect, the present application includes a method of synthesizing one or more compounds of Formula (II), (III), (V) or (VI) as defined above, or a pharmaceutically acceptable salt and/or solvate thereof, wherein the method comprises reacting one or more compounds of Formula (I) or (IV) as defined above with a first compound to be linked, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, and then a second, different compound to be linked, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support.

To attach different entities on each side of the hydrazine linkers of the application it is desirable that each of the reactive functional groups in $R^1$ and $R^5$ have different reactivities so that one of $R^1$ and $R^5$ can be functionalized by reaction with a complementary functional group in the presence of the other of $R^1$ and $R^5$, and without the other of $R^1$ and $R^5$ participating in the reaction. In some embodiments, one of $R^1$ and $R^5$ is masked or in protected form (i.e. comprises a protecting group) to prevent it from reacting while the other of $R^1$ and $R^5$ is being functionalized and the masking or protecting group is removed after the first reaction and functionalization is complete.

For preparing ADC compounds of Formula (III) or (VI) of the application, in some embodiments, a compound of Formula (I)-drug conjugate or Formula (IV)-drug conjugate is first prepared. Methods for conjugating a Formula (I)-drug conjugate or Formula (IV)-drug conjugate to an antibody and purifying the ADCs are known to those skilled in the art.

Accordingly, in another aspect the present application includes a method of preparing an ADC of Formula (III) or (VI) comprising:
(a) reacting a compound of Formula (I) or (IV) with a drug to provide a Formula (I)-drug conjugate or Formula (IV)-drug conjugate, respectively;
(b) reacting the Formula (I)-drug conjugate or Formula (IV)-drug conjugate with an antibody to provide the ADC of Formula (III) or (VI), respectively; and optionally
(c) purifying the ADC of Formula (III) or (IV).

In another aspect, the present application includes a method of preparing an ADC of Formula (III) comprising:
(a) reacting a compound of Formula (VII) as defined above with an antibody to provide the ADC of Formula (III), and optionally
(b) purifying the ADC of Formula (III).

In another aspect, the present application includes a method of preparing an ADC of Formula (VI) comprising:

(a) reacting a compound of Formula (VIII) as defined above with an antibody to provide the ADC of Formula (VI); and optionally
(b) purifying the ADC of Formula (VI).

The present application also includes a use of a compound of Formula (I), (IV), (VII) or (VIII) to prepare an ADC.

In some embodiments, the resulting ADC products are isolated or purified using known methods, such as for example, lyophilization, chromatography, precipitation, filtration, microfluidic and/or liquid chromatography separation methods.

In some embodiments, the drug is an anticancer drug. In some embodiments, the anticancer drug is a thiol-containing anticancer drug or a calicheamicin derivative. In some embodiments, the thiol containing anticancer drug is a maytansinoid, such as DM1. In some embodiments, the drug is a DNA binding agent from the pyrrolobenzodiazepine family.

V. Compositions of the Application

The compounds of the application are suitably formulated in a conventional manner into compositions using one or more carriers. Accordingly, the present application also includes a composition comprising one or more compounds of the application and a carrier. The compounds of Formula (II), (III), (V) and/or (VI) or pharmaceutically acceptable salts and/or solvates thereof, are suitably formulated into pharmaceutical compositions for administration to subjects in a biologically compatible form suitable for administration in vivo. Accordingly, the present application further includes a pharmaceutical composition comprising one or more compounds of Formula (II), (III), (V) and/or (VI), or pharmaceutically acceptable salts and/or solvates thereof, and a pharmaceutically acceptable carrier. In embodiments of the application the pharmaceutical compositions are used in the treatment and/or diagnosis of any of the diseases, disorders or conditions described herein.

The compounds of Formula (II), (III), (V) and/or (VI), or pharmaceutically acceptable salts and/or solvates thereof, are administered to a subject in a variety of forms depending on the selected route of administration, as will be understood by those skilled in the art. For example, compounds Formula (II), (III), (V) and/or (VI), or pharmaceutically acceptable salts and/or solvates thereof, are administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, compounds of Formula (II), (III), (V) and/or (VI), or pharmaceutically acceptable salts and/or solvates thereof, are orally administered, for example, with an inert diluent or with an assimilable edible carrier, or are enclosed in hard or soft shell gelatin capsules, or are compressed into tablets, or are incorporated directly with the food of the diet. In some embodiments, the compounds are incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compounds are protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compounds of Formula (II), (III), (V) and/or (VI), or pharmaceutically acceptable salts and/or solvates thereof, are suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of Formula (II), (III), (V) and/or (VI), or pharmaceutically acceptable salts and/or solvates thereof, and use the lyophilizates obtained, for example, for the preparation of products for injection.

In some embodiments, the compounds of Formula (II), (III), (V) and/or (VI), or pharmaceutically acceptable salts and/or solvates thereof, are administered parenterally. For example, solutions of compounds of Formula (II), (III), (V) and/or (VI) or pharmaceutically acceptable salts and/or solvates thereof, are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of Formula (II), (III), (V) and/or (VI), or pharmaceutically acceptable salts and/or solvates thereof, are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, compounds of Formula (II), (III), (V) and/or (VI), or pharmaceutically acceptable salts and/or solvates thereof, are formulated for parenteral administration by injection, including using conventional catheterization techniques or infusion. Formulations for injection are, for example, presented in unit dosage form, e.g., in ampoules or in multidose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of Formula (II), (III), (V) and/or (VI) or pharmaceutically acceptable salts and/or solvates thereof, are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of compounds of Formula (II), (III), (V) and/or (VI), or pharmaceutically acceptable salts and/or solvates thereof, and a suitable powder base such as lactose or starch. The aerosol dosage forms can also take the form of a pump-atomizer.

Compositions suitable for buccal or sublingual administration include tablets, lozenges, and pastilles, wherein compounds of Formula (II) and/or (III), or pharmaceutically acceptable salts and/or solvates thereof, are formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of Formula (II), (III), (V) and/or (VI), or pharmaceutically acceptable salts and/or solvates thereof, are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

In some embodiments compounds of Formula (II), (III), (V) and/or (VI), or pharmaceutically acceptable salts and/or solvates thereof, are coupled with soluble polymers as targetable drug carriers. Such polymers include, for example, polyvinylpyrrolidone, pyran copolymer, polyhydroxypropylmethacrylamide-phenol, polyhydroxy-ethyl-aspartamide-phenol, or polyethyleneoxide-polylysine substituted with palmitoyl residues. Furthermore, in some embodiments, compounds of Formula (II) and/or (III), or pharmaceutically acceptable salts and/or solvates thereof, are coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of Formula (II), (III), (V) and/or (VI), or pharmaceutically acceptable salts and/or solvates thereof, are suitably used on their own but will generally be administered in the form of a pharmaceutical composition in which the one or more compounds of Formula (II), (III), (V) and/or (VI), or pharmaceutically acceptable salts and/or solvates thereof, (the active ingredient) are in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

The compounds of Formula (II), (III), (V) and/or (VI), or pharmaceutically acceptable salts and/or solvates thereof, are either used alone or in combination with other known agents useful for treatment and/or imaging. When used in combination with other agents useful in treatment and/or imaging, it is an embodiment that compounds of Formula (II), (III), (V) and/or (VI), or pharmaceutically acceptable salts and/or solvates thereof, are administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, compounds of Formula (II), (III), (V) and/or (VI), or pharmaceutically acceptable salts and/or solvates thereof, are administered with another therapeutic agent simultaneously or sequentially in separate unit dosage forms or together in a single unit dosage form. Accordingly, the present application provides a single unit dosage form comprising one or more compounds of Formula (II), (III), (V) and/or (VI), or pharmaceutically acceptable salts and/or solvates thereof, an additional therapeutic agent, and a pharmaceutically acceptable carrier.

In some embodiments, the additional therapeutic agent is a chemotherapeutic agent. In some embodiments, the chemotherapeutic agent is selected from the classes of alkylating agents, anthracyclines, cytoskeletal disruptors, epothilones, histone deacetylase inhibitors, topoisomerase inhibitors, kinase inhibitors, nucleotide analogs, peptide antibiotics, platinum-based agents, retinoids, Vinca alkaloids, epigenetic modifiers and immuno-modulators.

VI. Methods and Uses of the Application

Compounds of Formula (II), (III), (V) and/or (VI), or pharmaceutically acceptable salts and/or solvates thereof, comprise a wide variety of active compounds which have possibilities of treating and/or diagnosing a variety of diseases, disorders or conditions.

Accordingly, the present application includes a method of treating and/or diagnosing one or more diseases, disorders or conditions by administering an effective amount of one or more compounds of Formula (II), (III), (V) and/or (VI), or pharmaceutically acceptable salts and/or solvates thereof, to a subject in need thereof. In some embodiments, the disease, disorder or condition depends on the identity of the compounds being conjugated as would be understood by a person skilled in the art.

In some embodiments, the disease, disorder or condition is a neoplastic disorder. Accordingly, the present application also includes a method of treating and/or diagnosing a neoplastic disorder comprising administering a therapeutically effective amount of one or more compounds of Formula (II), (III), (V) and/or (VI), or pharmaceutically acceptable salts and/or solvates thereof, to a subject in need thereof. The present application also includes a use of one or more compounds of Formula (II), (III), (V) and/or (VI), or pharmaceutically acceptable salts and/or solvates thereof, for treatment of and/or diagnosing a neoplastic disorder as well as a use of one or more compounds of Formula (II), (III), (V) and/or (VI), or pharmaceutically acceptable salts and/or solvates thereof, for the preparation of a medicament for treatment of and/or diagnosing a neoplastic disorder. The application further includes one or more compounds of Formula (II), (III), (V) and/or (VI), or pharmaceutically acceptable salts and/or solvates thereof, for use in treating and/or diagnosing a neoplastic disorder. In an embodiment, the treatment is in an amount effective to ameliorate at least one symptom of the neoplastic disorder, for example, reduced cell proliferation or reduced tumor mass, among others, in a subject in need of such treatment.

In some embodiments, the present application includes a method of treating and/or diagnosing one or more diseases, disorders or conditions mediated by ErbB comprising administering a therapeutically effective amount of one or more compounds of Formula (II), (III), (V) and/or (VI), or pharmaceutically acceptable salts and/or solvates thereof, to a subject in need thereof. The present application also includes a use of one or more compounds of Formula (II), (III), (V) and/or (VI), or pharmaceutically acceptable salts and/or solvates thereof, for treatment of and/or diagnosing one or more diseases, disorders or conditions mediated by ErbB as well as a use of one or more compounds of Formula (II), (III), (V) and/or (VI), or pharmaceutically acceptable salts and/or solvates thereof, for the preparation of a medicament for treatment of and/or diagnosing one or more diseases, disorders or conditions mediated by ErbB.

In some embodiments, the disease, disorder or condition is cancer. Accordingly, the present application also includes a method of treating and/or diagnosing cancer comprising administering a therapeutically effective amount of one or more compounds of Formula (II), (III), (V) and/or (VI), or pharmaceutically acceptable salts and/or solvates thereof, to a subject in need thereof. The present application also includes a use of one or more compounds of Formula (II), (III), (V) and/or (VI), or pharmaceutically acceptable salts and/or solvates thereof, for treatment of and/or diagnosing cancer as well as a use of one or more compounds of Formula (II), (III), (V) and/or (VI), or pharmaceutically acceptable salts and/or solvates thereof, for the preparation of a medicament for treatment of and/or diagnosing cancer. The application further includes one or more compounds of Formula (II), (III), (V) and/or (VI), or pharmaceutically acceptable salts and/or solvates thereof, for use in treating cancer. In an embodiment, the compound is administered for the prevention of cancer in a subject such as a mammal having a predisposition for cancer. In some embodiments, the cancer is an ErbB-expressing cancer. In some embodiments, the subject is human.

In some embodiments, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In some embodiments, the cancer is selected from ErbB-expressing cancer. In some embodiments, the cancer is selected from breast cancer, skin cancer, prostate cancer, head and neck cancer, colorectal cancer, pancreatic cancer, kidney cancer, lung cancer and brain cancer. In some embodiments of the present application, the cancer is selected from breast cancer, prostate cancer, head and neck cancer, colorectal cancer, pancreatic cancer, kidney cancer, lung cancer and brain cancer.

In a further embodiment, the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

In some embodiments, when the methods and uses are related to diagnostics, one compound to be linked comprises a binding moiety and the other compound to be linked comprises a labelling agent.

EXAMPLES

The following non-limiting examples are illustrative of the present application:

A. General Methods

Exemplary compounds of the application were synthesized using the methods described herein, or other methods, which are known in the art. Unless otherwise noted, reagents and solvents were obtained from commercial suppliers (e.g. Aldrich, Enamine, Alfa Aesar, Combi-Blocks, Bepharm, J&W PharmLab).

The compounds and/or intermediates were characterized by high performance liquid chromatography (HPLC) using a Waters ACQUITY UPLC system with a SQ (single quadrupole) MS and a photodiode array (PDA) detector (Milford, Mass.). The analytical columns were reversed phase Acquity UPLC BEH C18 (2.1×50 mm, 1.7 μm). A gradient elution was used (flow 0.4 mL/min), typically starting with mobile phase 0.1% formic acid in water (solvent A) and 0.1% formic acid in acetonitrile (solvent B). A gradient starting at 95% solvent A going to 5% in 1.8 min., holding for 0.5 min., going back to 95% in 0.5 min. and equilibrating the column for 0.5 min. Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel IB2-F flexible sheets. TLC results were readily detected visually under ultraviolet light, or by employing well-known iodine vapor and other various staining techniques.

The compounds and/or intermediates were characterized by LCMS. General conditions are as follows. Low and High resolution Mass spectra were acquired on LC/MS systems using electrospray ionization methods from a range of instruments of the following configurations: Low resolution—Waters ACQUITY UPLC system with a SQ (single quadrupole) MS; Waters ACQUITY UPLC H-Class system with a 3100 (single quadrupole) MS. High resolution—Waters ACQUITY UPLC II system equipped with a Synapt Xevo QTof and Waters ACQUITY UPLC II system equipped with a Synapt G2S QTof mass spectrometer with an atmospheric pressure ionization source. [M+H] refers to the protonated molecular ion of the chemical species.

Nuclear magnetic resonance (NMR) analysis was performed on a Bruker 500 MHz NMR spectrometer using ICON-NMR, under TopSpin program control. Spectra were measured at 298K, unless indicated otherwise and were referenced relative to the solvent chemical shift.

B. Model Experiments

Towards the goal developing enhanced control of ADC linker stability, several model cyclic acyl hydrazones whose lability is modulated either by steric or stereoelectronic effects have been prepared. Exemplary acyl hydrazones containing a substituted phenyl group adjacent to the imine carbon have been synthesized. Starting with the acyl hydrazone structure (D) present in Mylotarg, the adjacent steric and electronic environments in model linker compounds were varied and their half-life tested in a simulated lysosomal environment (pH 4.5), as shown in Table 1. When the imine carbon is part of cyclic structure (as in F), about a 2-fold increase in half-life was observed compared to D. Incorporation of a hydroxy group ortho to the acyl hydrazone (as in E) resulted in over an order of magnitude increase in the acid half-life. On the other hand, incorporation of a methoxy group in the same position (as in G) rendered the cyclic hydrazone very labile with a half-life of only 2 min.

In addition, for an ADC to have a better therapeutic window, ideally it should be stable in plasma and having the payload released only upon entry to the target cells. Thus targeted cytotoxicity would be mostly confined to the diseased cells of interest. Starting with the acyl hydrazone structure (D) present in Mylotarg, the adjacent steric and electronic environments were varied in model linker compounds and their stability was tested in plasma. Upon a 6-day incubation in human plasma, the amount of remaining parent acyl hydrazone was measured as shown in Table 2. Reference compound (D) showed a moderate stability with 37% remaining. When a hydroxy group is introduced in the ortho position (as in E), the compound became labile since only 1.4% was remaining after 5 days. The stability is rescued when the imine carbon is part of cyclic structure (as in L) with 50% remaining after 6 days. Increasing the size of the ring and removing the hydroxy group, improved even better the plasma stability (as in F) with 87% remaining. Introducing an acetamide group in the ortho position (as in M), gave a model compound with the best plasma stability profile with 92% remaining after 6 days incubation. These results suggest that the adjacent steric and electronic environments can also affect the stability of acyl hydrazones in human plasma. Analogues of the compounds in Tables 1 & 2 have been incorporated into linkers, using a similar strategy as employed in the linker synthesis in Mylotarg, as described in greater detail herein below

TABLE 1

Effects of sterics and electronics on stability of acyl hydrazones

| Compound | Structure | Acidic (pH 4.5) Half life (min) |
|---|---|---|
| D | MeO-phenyl-C(=N-NH-C(=O)-CH3) | 15 |

TABLE 1-continued

Effects of sterics and electronics on stability of acyl hydrazones

| Compound | Structure | Acidic (pH 4.5) Half life (min) |
|---|---|---|
| E | [structure: 4-methoxy-2-hydroxyacetophenone acetyl hydrazone] | 169 |
| F | [structure: 6-methoxy-tetralone acetyl hydrazone] | 41 |
| G | [structure: 8-methoxy-6-hydroxy-tetralone acetyl hydrazone] | 2 |
| Ia | [structure: 4-(carboxypropoxy)phenyl methyl ketone with mercapto-dimethyl acyl hydrazone] | 15 |
| Ie | [structure: 6-(carboxypropoxy)tetralone mercapto-dimethyl acyl hydrazone] | 31 |
| Ib | [structure: 6-(carboxypropoxy)-8-hydroxy-tetralone mercapto-dimethyl acyl hydrazone] | 234 |
| K | [structure: 7-fluoro-tetralone acetyl hydrazone] | 88 |

TABLE 1-continued

Effects of sterics and electronics on stability of acyl hydrazones

| Compound | Structure | Acidic (pH 4.5) Half life (min) |
|---|---|---|
| L | 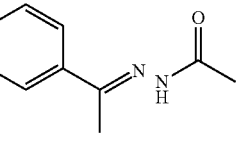 | 185 |

TABLE 2

Effects of sterics and electronics on stability of acyl hydrazones after 6 days incubation in human plasma

| Compound | Structure | % remaining after 6 days |
|---|---|---|
| D | 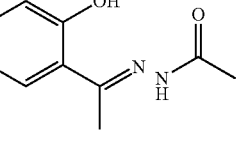 | 37 |
| E* | 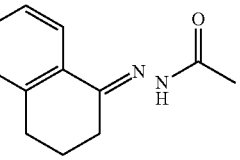 | 1.4* |
| F | 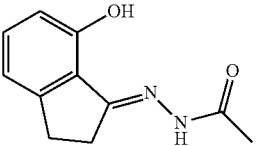 | 87 |
| L | 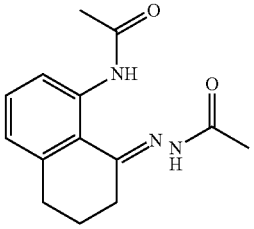 | 50 |
| M | 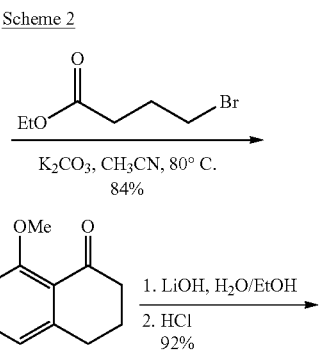 | 92 |

*compound E was incubated for 5 days instead of 6.

C. Synthesis of Compounds of the Application

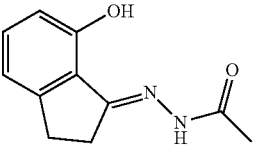

Scheme 2

Ethyl 4-((4-methoxy-5-oxo-5,6,7,8-tetrahydronaphthalen-2-yl)oxy)butanoate (1b-1)

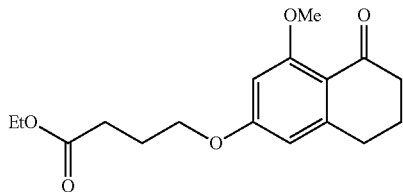

To a 100 ml round bottom flask was added a solution of 6-hydroxy-8-methoxy-2,3,4-trihydronaphthalen-1-one (2 g, 10.41 mmol) in acetonitrile (30 ml). Ethyl-4-bromobutyrate (2.23 g, 11.45 mmol) and potassium carbonate (1.58 g, 11.45 mmol) were added, and the mixture was heated to reflux at 80° C. for 7 hours, after which full conversion was observed. The solvent was evaporated under reduced pressure. The residue was purified using Biotage™ (100 g silica column; eluent EtOAc/Hexanes 0-100%). The fractions containing the product were collected and concentrated under reduced pressure to give the title compound 1b-1 as a green oil (2.76 g, 84% yield). $^1$H NMR (500 MHz, CDCl$_3$) δ=6.33 (s, 1H), 6.31 (s, 1H), 4.15 (q, J=7.2 Hz, 2H), 4.06 (t, J=6.2 Hz, 2H), 3.91 (s, 3H), 2.86 (t, J=6.2 Hz, 3H), 2.58 (t, J=6.2 Hz, 2H), 2.51 (t, J=7.2, 2H), 2.14-2.09 (m, 2H), 2.04-1.99 (m, 2H), 1.26 (t, J=7.2 Hz, 3H); LCMS [M+H]$^+$ 307.

4-((4-Methoxy-5-oxo-5,6,7,8-tetrahydronaphthalen-2-yl)oxy)butanoic acid (1b-2)

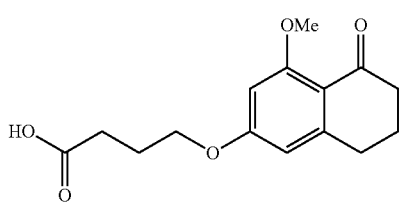

To a 250 ml round bottom flask was added a solution of compound 1b-1 (1.38 g, 4.50 mmol) in ethanol (90 ml). A 1.0 M solution of lithium hydroxide (4.5 mmol) in H$_2$O was added. The reaction was stirred at room temperature for 3 h, after which more LiOH was added (3.0 mmol). The reaction was allowed to proceed for another hour, after which a precipitate has formed. It was quenched with 1.0 M HCl (150 ml). The aqueous layer was extracted with ethyl acetate (4×125 ml). The combined organic layers were washed with brine (150 ml), dried over MgSO$_4$ and concentrated down to yield the title compound 1b-2 as a white powder (1.17 g, 92% yield). $^1$H NMR (500 MHz, MeOD) δ=6.47 (d, J=2.2 Hz, 1H), 6.45 (d, J=2.2 Hz, 1H), 4.11 (t, J=6.3 Hz, 2H), 3.83 (s, 3H), 2.91 (t, J=6.1 Hz, 2H), 2.55 (t, J=6.4 Hz, 2H), 2.49 (t, J=7.2 Hz, 2H), 2.11-2.05 (m, 2H), 2.03-1.98 (m, 2H); LCMS [M+H]$^+$ 279.

4-((4-Hydroxy-5-oxo-5,6,7,8-tetrahydronaphthalen-2-yl)oxy)butanoic acid (1 b-3)

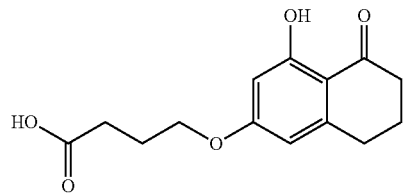

To a 100 ml round bottom flask was added compound 1 b-2 (500 mg, 1.8 mmol) as a solution in 48% HBr in H$_2$O (2 ml). Acetic acid (3.5 ml) was added, and the solution was stirred at 90° C. for 7 h, after which it was quenched with 100 ml of deionized water. The solution was then extracted with ethyl acetate (4×100 ml). The combined organic layers were washed with brine (400 ml), dried over MgSO$_4$ and concentrated down. Residual acetic acid was removed by a steady stream of nitrogen to give the title compound 1b-3 as an orange powder (320 mg, 66% yield). $^1$H NMR (500 MHz, MeOD) δ=6.34 (t, J=1.2 Hz, 1H), 6.25 (d, J=2.4 Hz, 1H), 4.06 (t, J=6.2 Hz, 2H), 2.88 (t, J=6.2 Hz, 2H), 2.62 (t, J=6.2 Hz, 2H), 2.47 (t, J=7.2 Hz, 2H), 2.08-1.99 (m, 4H); LCMS [M+H]$^+$ 265.

Scheme 3

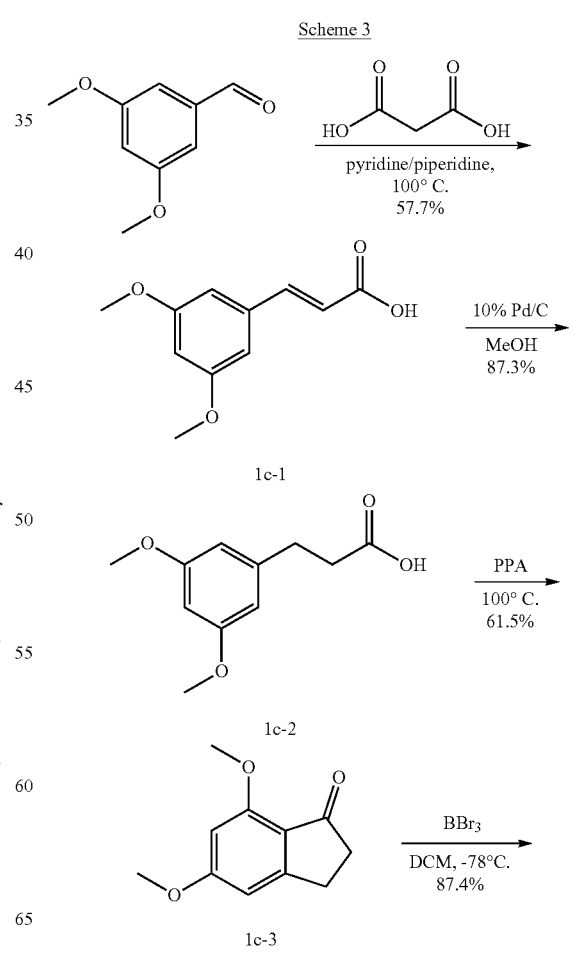

-continued

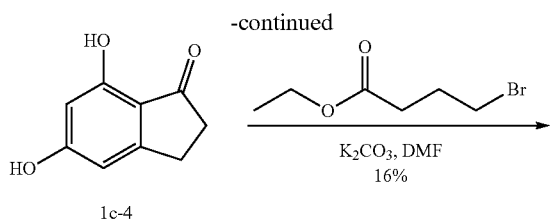

1c-4

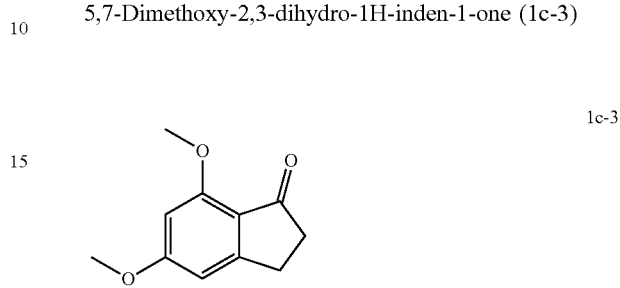

1c-5

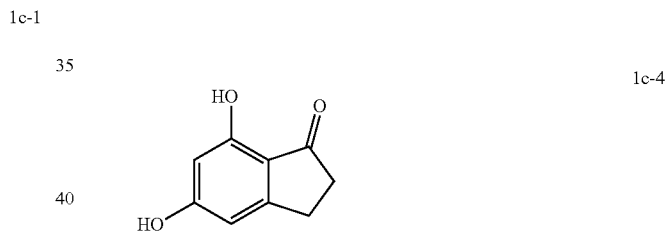

1c-6

(E)-3-(3,5-Dimethoxyphenyl)acrylic acid (1c-1)

1c-1

To a stirred solution of 3,5-dimethoxybenzaldehyde (15 g, 90.36 mmol) in pyridine (100 ml), malonic acid (14.2 g, 135.54 mmol) was added followed by piperidine (6 ml). The mixture was heated at 100° C. for 6 h under argon atmosphere. The solvent was concentrated down and the residue was poured into water (250 ml) then acidified to pH=3 by 2N HCl. The precipitate that has formed was dried to give the title compound 1c-1 as a white solid (10.9 g, 57.7% yield). LCMS [M+H]$^+$ 209.

3-(3,5-Dimethoxyphenyl)propanoic acid (1c-2)

1c-2

To a stirred solution of (E)-3-(3,5-dimethoxyphenyl) acrylic acid 1c-1 (17 g, 81.73 mmol) in methanol (250 ml), 10% Pd/C (5 g) was added then the mixture was stirred under hydrogen balloon pressure for 16 h. The reaction mixture was filtered through celite and washed with methanol. The combined filtrates were concentrated down to give the title compound 1c-2 as a white solid (15 g, 87.3% yield). LCMS [M+H]$^+$ 211.

5,7-Dimethoxy-2,3-dihydro-1H-inden-1-one (1c-3)

1c-3

A stirred solution of 3-(3,5-dimethoxyphenyl)propanoic acid 1c-2 (16 g, 76.19 mmol) in PPA (220 g) was heated at 100° C. for 16 h. The reaction mixture was cooled to rt, poured into ice cold water then extracted with EtOAc (2×500 ml). The combined organic layers were washed with a saturated sodium carbonate solution (500 ml), brine (200 ml) then dried over sodium sulphate. It was concentrated down to give the title compound 1c-3 as a pale orange solid (9 g, 61.5% yield). LCMS [M+H]$^+$ 193.

5,7-Dihydroxy-2,3-dihydro-1H-inden-1-one (1c-4)

1c-4

A solution of 5,7-dimethoxy-2,3-dihydro-1H-inden-1-one 1c-3 (9.1 g, 47.39 mmol) in DCM (100 ml) was cooled to −78° C. BBr$_3$ (470 ml, 473.9 mmol) was added then the reaction mixture was stirred under argon for 16 h. The reaction mixture was quenched with a saturated sodium bicarbonate solution (500 ml). The organic layer was concentrated down. The crude residue was washed with diethyl ether to give the title compound 1c-4 as an off-white solid (6.8 g, 87.4% yield). LCMS [M+H]$^+$ 165.

Ethyl 4-((7-hydroxy-1-oxo-2,3-dihydro-1H-inden-5-yl)oxy)butanoate (1c-5)

1c-5

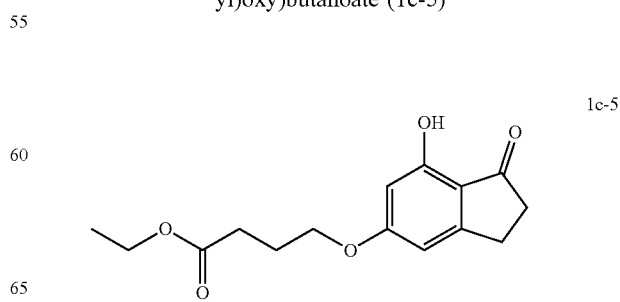

A stirred solution of 5,7-dihydroxy-2,3-dihydro-1H-inden-1-one 1c-4 (5.9 g, 36.19 mmol) in DMF (70 ml) was cooled to 0° C. then potassium carbonate (10 g, 72.38 mmol) was added followed by ethyl 4-bromobutanoate (6.2 ml, 43.2 mmol). The reaction mixture was stirred at rt for 16 h. It was diluted with water (200 ml), acidified with 2N HCl then extracted with EtOAc (2×500 ml). The combined organic layers were dried over $Na_2SO_4$ and concentrated under reduced pressure. The crude product was purified by column chromatography (silica gel 100-200 mesh) using 0-40% EtOAc in petroleum ether to give the title compound 1c-5 as an off-white solid (1.6 g, 16% yield). LCMS [M+H]+ 279.

4-((7-Hydroxy-1-oxo-2,3-dihydro-1H-inden-5-yl)oxy)butanoic acid (1c-6)

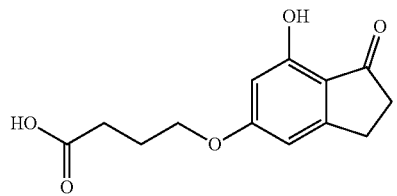

To a stirred solution of ethyl 4-((7-hydroxy-1-oxo-2,3-dihydro-1H-inden-5-yl)oxy)butanoate 1c-5 (2.9 g, 13.0 mmol) in THF/MeOH/$H_2O$ (30/10/20 ml) was added lithium hydroxide monohydrate (1.0 g, 26.0 mmol). The reaction mixture was stirred at rt for 16 h. It was concentrated down under reduced pressure. The resulting residue was acidified with 2N HCl (20 ml). The solid that has precipitated was filtered and washed with diethyl ether (50 ml) to give the title compound 1c-6 as an off-white solid (2.3 g, 70.7% yield). $^1$H NMR (300 MHz, DMSO-d6) δ=12.2 (br s, 1H), 9.88 (s, 1H), 6.51 (s, 1H), 6.24 (d, J=2.0 Hz, 1H), 4.02 (t, J=6.2 Hz, 2H), 2.94 (t, J=6.0 Hz, 2H), 2.54-2.48 (m, 2H), 2.37 (t, J=7.4 Hz, 2H), 1.93 (t, J=6.8 Hz, 2H). LCMS [M+H]+ 251.

Scheme 4

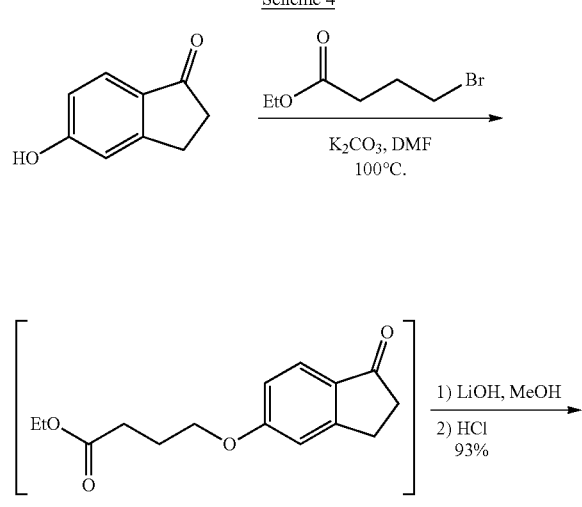

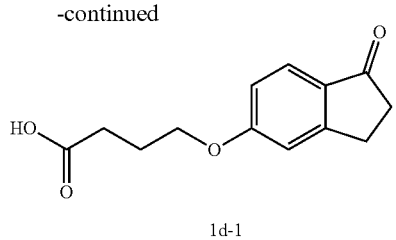

4-((1-Oxo-2,3-dihydro-1H-inden-5-yl)oxy)butanoic acid (1d-1)

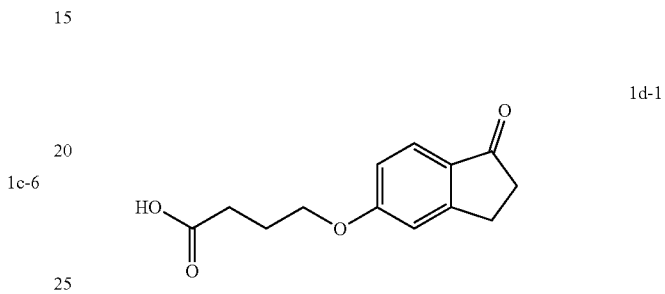

A 250 ml round bottom flask was charged with potassium carbonate (3.08 g, 22.27 mmol) and 5-hydroxy-1-indanone (3 g, 20.25 mmol) then N,N-dimethylformamide (20 ml) was added. To this mixture, ethyl 4-bromobutyrate (3.95 g, 20.25 mmol) was added via a syringe. The mixture was heated at 100° C. After 2 h at 100° C., LCMS showed about 94% completion. It was stirred overnight at room temperature, then some excess $K_2CO_3$ was added followed by 120 µl of ethyl 4-bromobutyrate. The mixture was heated at 100° C. for an additional 30 min upon which LCMS showed completion. The mixture was cooled down then a large volume of water was added followed by EtOAc. The organic layer was separated and washed several times with water to remove the DMF followed by brine/water then brine. It was dried over $Na_2SO_4$ then concentrated down. It was dried under high vacuum to afford the intermediate ethyl ester as a brown oil that crystallized in the fridge (m: 5.33 g). This product was dissolved in MeOH (20 ml), treated with a solution of lithium hydroxide monohydrate (1.67 g, 40.5 mmol) in water (10 ml) and stirred at room temperature. After about 3 hours, LCMS showed completion of the reaction. The volatiles were evaporated. The resulting residue was taken in water then the mixture was carefully acidified with HCl (1N) to pH (0-1). The beige solid that has formed was filtered and washed several times with water. It was dried under vacuum to afford the title compound 1d-1 as a beige powder (4.42 g, 93% yield). $^1$H NMR (500 MHz, DMSO-d6) δ=12.24 (br s, 1H), 7.61 (d, J=8.6 Hz, 1H), 7.15 (s, 1H), 7.01 (dd, J=2.0, 8.5 Hz, 1H), 4.16 (t, J=6.5 Hz, 2H), 3.12-3.07 (m, 2H), 2.66-2.62 (m, 2H), 2.45 (t, J=7.3 Hz, 2H), 2.03 (quin, J=6.8 Hz, 2H); LCMS [M+H]+ 235.

4-((5-Oxo-5,6,7,8-tetrahydronaphthalen-2-yl)oxy)butanoic acid (1e-1)

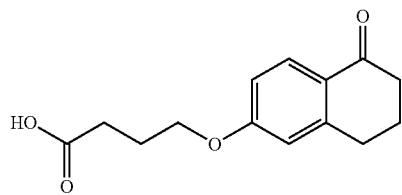

Compound 1e-1 was prepared following a similar procedure to compound 1d-1 (3.48 g, 89% yield). $^1$H NMR (500 MHz, DMSO-d6) δ=12.14 (s, 1H), 7.84-7.78 (m, 1H), 6.90-6.84 (m, 2H), 4.06 (t, J=6.5 Hz, 2H), 2.89 (t, J=6.1 Hz, 2H), 2.53-2.51 (m, 2H), 2.38 (t, J=7.2 Hz, 2H), 2.03-1.97 (m, 2H), 1.97-1.92 (m, 2H); LCMS [M+H]$^+$ 249.

Scheme 5

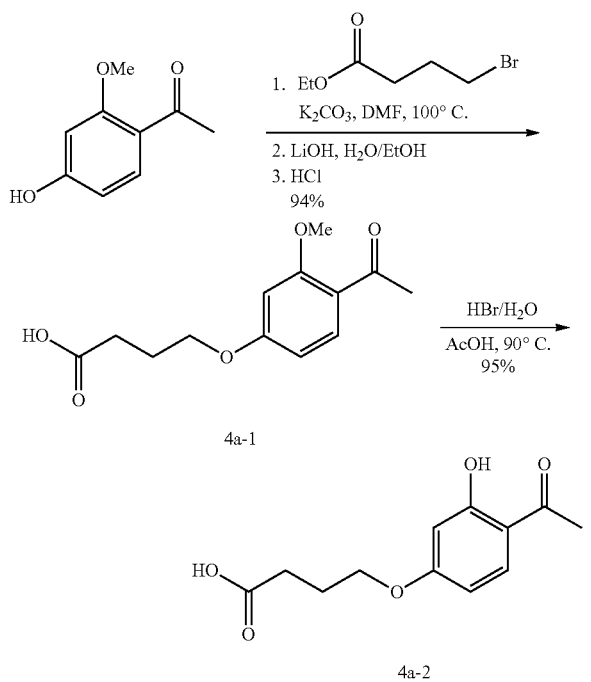

4-(4-Acetyl-3-methoxyphenoxy)butanoic acid (4a-1)

A 60 ml RB flask was charged with 4'-hydroxy-2'-methoxyacetophenone (1.2 g, 7.22 mmol) and potassium carbonate (1.497 g, 10.83 mmol) then DMF (15 ml) was added. To this mixture, ethyl 4-bromobutyrate (1.240 ml, 8.67 mmol) was added via a syringe. The mixture was heated at 100° C. for 2 h upon which LCMS showed completion. The mixture was cooled down then a large volume of water was added followed by EtOAc. The organic layer was washed with water (×3) then brine. It was dried over Na$_2$SO$_4$ then concentrated down. It was dried in the high vacuum to afford the intermediate ester product. This crude intermediate was dissolved in MeOH (15 ml) and treated with lithium hydroxide monohydrate (0.606 g, 14.44 mmol) in 7.5 ml water and stirred at rt. After 2 h, LCMS showed completion. The volatiles were evaporated. The residue was diluted with water then acidified with a solution of HCl (1N) to low pH. A beige precipitate was formed. It was filtered and washed several times with water. It was dried under high vacuum to afford the title compound 4a-1 as a beige powder (1.71 g, 94% yield). $^1$H NMR (500 MHz, DMSO-d6) δ=12.19 (br s, 1H), 7.65 (d, J=8.7 Hz, 1H), 6.68-6.64 (m, 1H), 6.60 (br d, J=8.7 Hz, 1H), 4.08 (br t, J=6.4 Hz, 2H), 3.33 (br s, 3H), 2.48 (s, 3H), 2.40 (br t, J=7.2 Hz, 2H), 1.96 (quin, J=6.8 Hz, 2H); LCMS [M+H]$^+$ 253.

4-(4-Acetyl-3-hydroxyphenoxy)butanoic acid (4a-2)

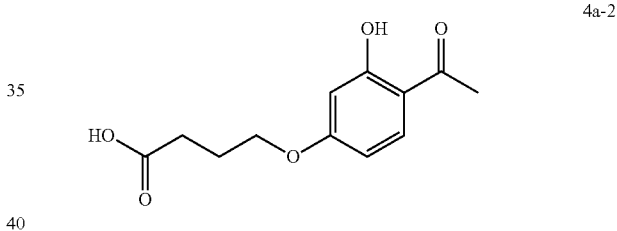

A 60 ml vial was charged 4-(4-acetyl-3-methoxyphenoxy)butanoic acid 4a-1 (1.695 g, 6.72 mmol) then 48% HBr in H$_2$O (6 ml) and acetic acid (6 ml) were added. The mixture was stirred at 90° C. for 4 h upon which LCMS showed completion. The mixture was cooled down, diluted with water and extracted several times with DCM and once with EtOAc. The organic layer was dried over Na$_2$SO$_4$ then concentrated down. It was dried under high vacuum to afford the title compound 4a-2 as a dark orange powder (1.52 g, 95% yield). $^1$H NMR (500 MHz, DMSO-d6) δ=12.62 (s, 1H), 12.16 (br s, 1H), 7.87-7.81 (m, 1H), 6.53 (br d, J=8.9 Hz, 1H), 6.46 (s, 1H), 4.07 (br t, J=6.2 Hz, 2H), 2.57 (s, 3H), 2.38 (br t, J=7.2 Hz, 2H), 1.95 (quin, J=6.7 Hz, 2H); LCMS [M+H]$^+$ 239.

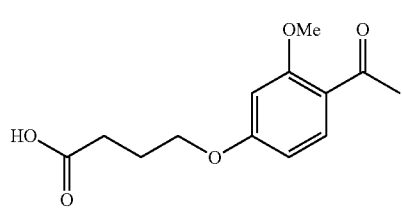

Scheme 6

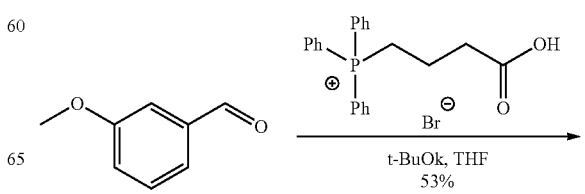

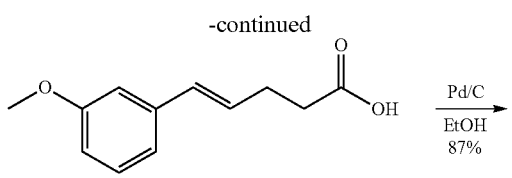

1f-1

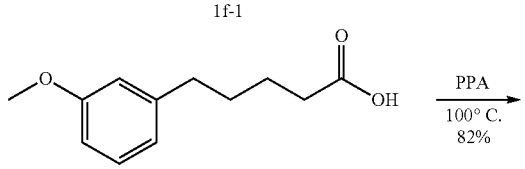

1f-2

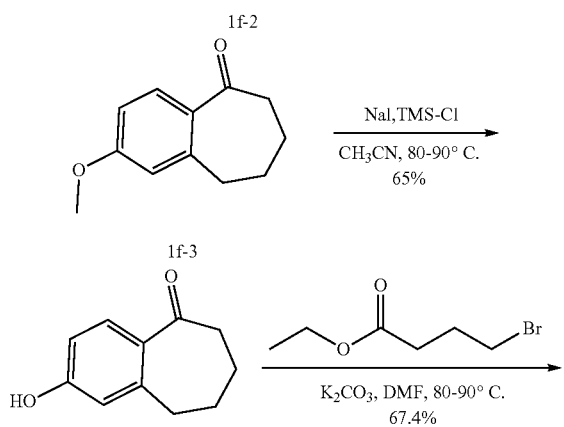

1f-3

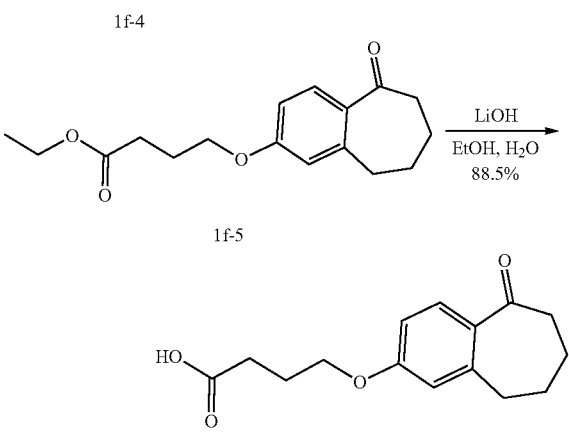

1f-5

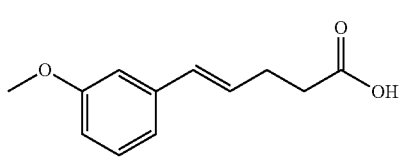

1f-6

(E)-5-(3-Methoxyphenyl)pent-4-enoic acid (1f-1)

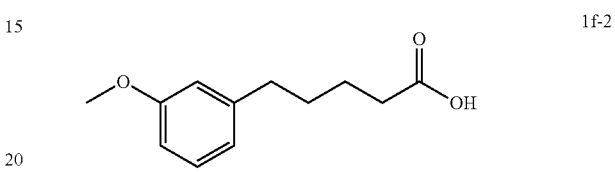

1f-1

A solution of (3-carboxypropyl)triphenylphosphonium bromide (31.47 g, 73.52 mmol) in THF (200 ml) was treated with potassium tert-butoxide (20.58 g, 18.37 mmol) and stirred at rt for 1 h under argon. 3-Methoxybenzaldehyde (10 g, 73.52 mmol) was added then the mixture was stirred at the same temperature for 16 h. The reaction mixture was cooled to 0° C., acidified to pH=2 by HCl (2 N) and extracted with EtOAc (2×500 ml). The combined organic layers were dried over Na$_2$SO$_4$ and concentrated under reduced pressure. The crude compound was purified by column chromatography (silica gel 100-200 mesh) using 0-70% EtOAc in petroleum ether as an eluent to give the title compound 1f-1 as a yellow gummy liquid (8 g, 53% yield). LCMS [M+H]$^+$ 207.

5-(3-Methoxyphenyl)pentanoic acid (1f-2)

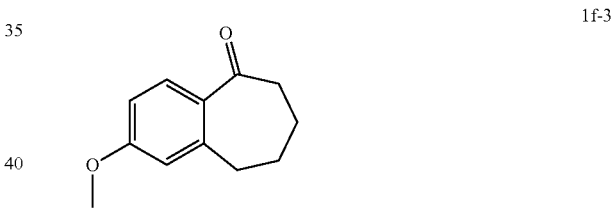

1f-2

To a stirred solution of (E)-5-(3-methoxyphenyl)pent-4-enoic acid 1f-1 (8 g, 38.83 mmol) in ethanol (80 ml) was added 10% Pd/C (2.5 g). The mixture was stirred at rt under hydrogen atmosphere for 24 h. It was filtered through celite and washed with methanol. The combined filtrates were concentrated down to give the title compound 1f-2 as a pale yellow solid (7 g, 87% yield). LCMS [M+H]$^+$ 209.

2-Methoxy-6,7,8,9-tetrahydro-5H-benzo[7]annulen-5-one (1f-3)

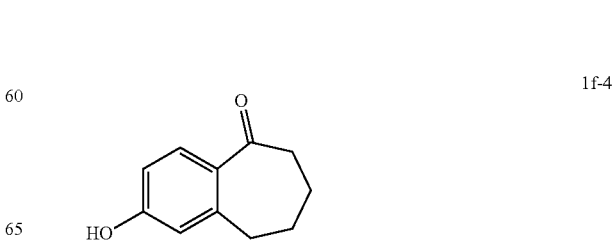

1f-3

To 5-(3-methoxyphenyl)pentanoic acid 1f-2 (4 g, 19.23 mmol) was added PPA (20 g). The reaction mixture was heated at 100° C. for 2 h. It was cooled to RT and poured into ice-cold water then extracted with Teac (2×500 ml). The combined organic layers were washed with a saturated sodium carbonate solution (500 ml) then brine (200 ml). It was dried over sodium sulphate and concentrated down. The crude compound was purified by column chromatography (silica gel 100-200 mesh) using 0-10% EtOAc in petroleum ether to give the title compound 1f-3 as a pale brown solid (3 g, 82% yield). LCMS [M+H]$^+$ 191.

2-Hydroxy-6,7,8,9-tetrahydro-5H-benzo[7]annulen-5-one (1 f-4)

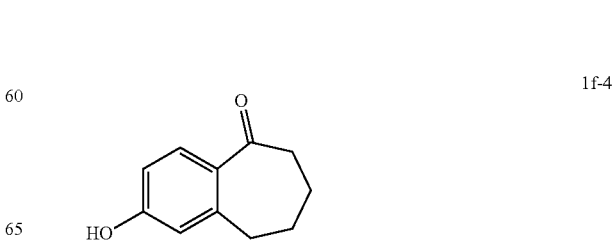

1f-4

A stirred solution of 2-methoxy-6,7,8,9-tetrahydro-5H-benzo[7]annulen-5-one 1f-3 (3 g, 15.78 mmol) in CH₃CN (30 ml) was treated with NaI (14.2 g, 94.79 mmol) followed by TMS-C₁ (12.1 ml, 94.79 mmol) at rt then heated at 80-90° C. for 24 h in a sealed tube. The reaction mixture was poured into water (100 ml) and extracted with EtOAc (2×200 ml). The organic layer was concentrated down. The crude product was purified by column chromatography (silica gel 100-200 mesh) using 0-50% EtOAc in petroleum ether to give the title compound if-4 as a pale brown solid (1.8 g, 65% yield). LCMS [M+H]⁺ 177.

Ethyl 4-((5-oxo-6,7,8,9-tetrahydro-5H-benzo[7]annulen-2-yl)oxy)butanoate (1 f-5)

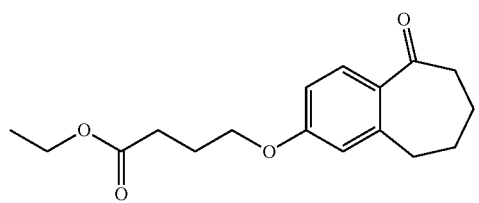

1f-5

A stirred solution 2-hydroxy-6,7,8,9-tetrahydro-5H-benzo[7]annulen-5-one if-4 (1.8 g, 10.22 mmol) in DMF (20 ml) was cooled to 0° C. then potassium carbonate (3.52 g, 25.56 mmol) followed by ethyl 4-bromobutanoate (2.38 g, 12.27 mmol) were added. The mixture was heated at 80-90° C. for 2 h. It was cooled down then poured into water (100 ml). This mixture was extracted with EtOAc (2×200 ml). The combined organic layers were concentrated down. The crude product was purified by column chromatography (silica gel 100-200 mesh) using 0-40% EtOAc in petroleum ether to give the title compound if-5 as a pale yellow solid (2 g, 67.4% yield). LCMS [M+H]⁺ 291.

4-((5-Oxo-6,7,8,9-tetrahydro-5H-benzo[7]annulen-2-yl)oxy)butanoic acid (1 f-6)

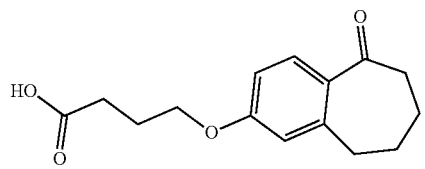

1f-6

To a stirred solution of ethyl 4-((5-oxo-6,7,8,9-tetrahydro-5H-benzo[7]annulen-2-yl)oxy)butanoate if-5 (2 g, 6.89 mmol) in EtOH/H₂O (20/10 ml) was added lithium hydroxide monohydrate (0.33 g, 13.79 mmol) then it was stirred at rt for 16 h. The reaction mixture was concentrated under reduced pressure then acidified with 2N HCl. The aqueous layer was extracted with EtOAc (2×100 ml). The combined organic layers were concentrated down. The crude product was washed with n-pentane to give the title compound if-6 as an off-white solid (1.6 g, 88.5% yield). ¹H NMR (300 MHz, DMSO-d6) δ=12.1 (br s, 1H), 7.61 (d, J=8.4 Hz, 1H), 6.9-6.83 (m, 2H), 4.04 (t, J=6.4 Hz, 2H), 2.90 (t, J=6.2 Hz, 2H), 2.64 (t, J=6.0 Hz, 2H), 2.38 (t, J=7.2 Hz, 2H), 2-1.90 (m, 2H), 1.81-1.72 (m, 2H), 1.72-1.63 (m, 2H); LCMS [M+H]⁺ 263.

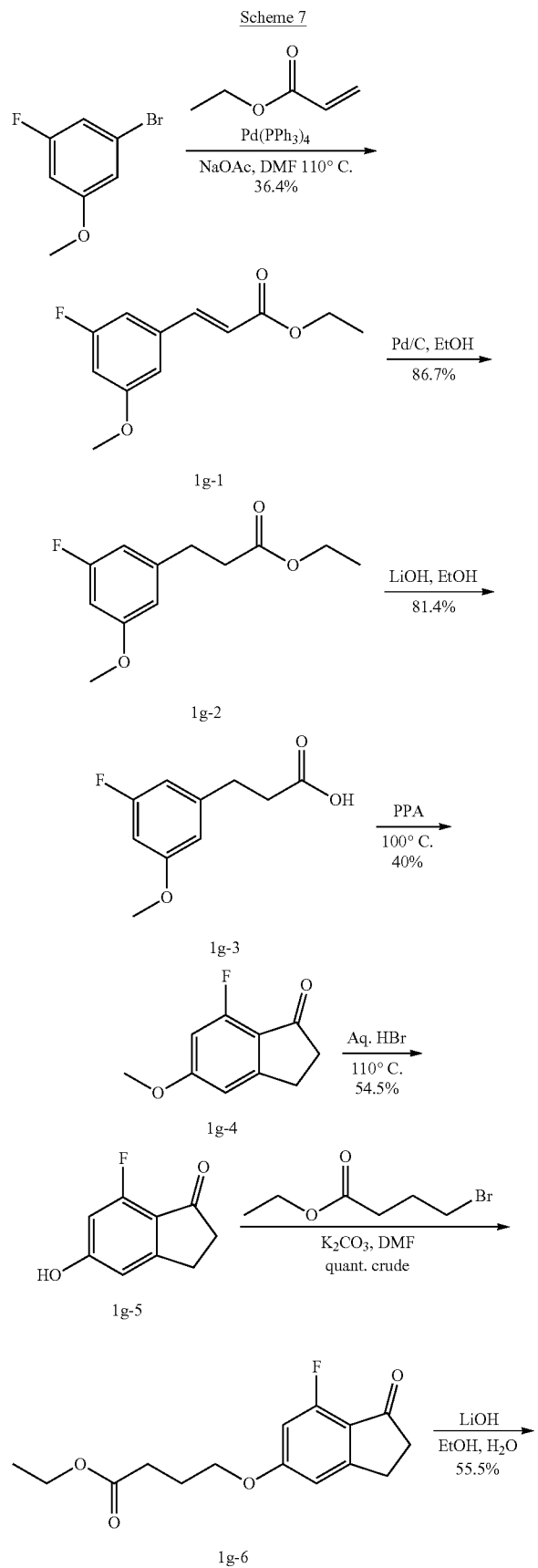

Scheme 7

-continued

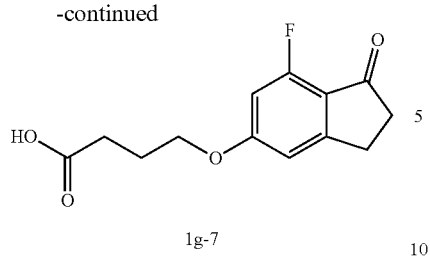

1g-7

Ethyl (E)-3-(3-fluoro-5-methoxyphenyl)acrylate (1g-1)

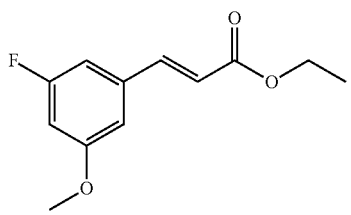

1g-1

A stirred solution of 1-bromo-3-fluoro-5-methoxybenzene (10 g, 49.01 mmol) in DMF (10 ml) was degassed with argon for 15 min. Ethyl acrylate (7.3 g, 73.17 mmol), NaOAc (10 g, 121.95 mmol) and Pd(PPh$_3$)$_4$ (1.4 g, 1.21 mmol) were added to this solution. The reaction mixture was heated at 110° C. for 16 h. It was filtered through a pad of celite and washed with ethyl acetate (3×500 ml). The filtrate was concentrated under vacuum. The crude product was purified by column chromatography (silica 100-200 mesh) using 0-5% EtOAc in petroleum ether to give the title compound 1g-1 as a brown liquid (4 g, 36.4% yield). LCMS [M+H]$^+$ 225.

Ethyl 3-(3-fluoro-5-methoxyphenyl)propanoate (1g-2)

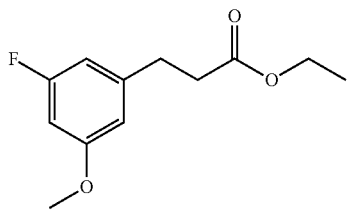

1g-2

To a solution of ethyl (E)-3-(3-fluoro-5-methoxyphenyl) acrylate 1g-1 (4 g, 17.85 mmol) in EtOH (40 ml) was added 10% Pd/C (2×0.5 g). It was stirred under a H$_2$ balloon for 16 h. The reaction mixture was filtered through a pad of celite and washed with methanol (3×50 ml). The filtrate was concentrated under vacuum to give the title compound 1g-2 as a yellow liquid (3.5 g, 86.7% yield). LCMS [M+H]$^+$ 227.

3-(3-Fluoro-5-methoxyphenyl)propanoic acid (1g-3)

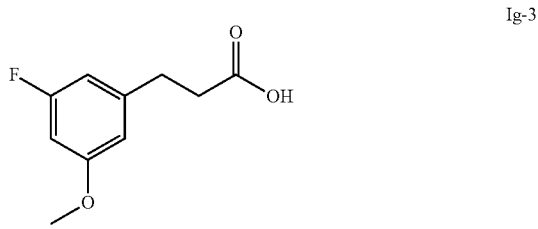

1g-3

To a stirred solution of ethyl 3-(3-fluoro-5-methoxyphenyl)propanoate 1g-2 (3.5 g, 15.5 mmol) in EtOH/H$_2$O (24/6 ml) was added lithium hydroxide monohydrate (0.952 g, 2.32 mmol). The reaction mixture was stirred at rt for 16 h. It was concentrated under reduced pressure then acidified with 2N HCl (20 ml). The solid that has precipitated was filtered and washed with diethyl ether (50 ml) to give the title compound 1g-3 as a yellow solid (2.5 g, 81.4% yield). LCMS [M−H]$^+$197.

7-Fluoro-5-methoxy-2,3-dihydro-1H-inden-1-one (1g-4)

1g-4

A stirred solution of 3-(3-fluoro-5-methoxyphenyl)propanoic acid 1g-3 (2.5 g, 1.26 mmol) in PPA (12.5 g) was heated at 100° C. for 1 h. The reaction mixture was cooled to rt and poured into ice cold water. It was then extracted with EtOAc (2×50 ml). The combined organic layers were washed with a saturated sodium carbonate solution (50 ml), brine (20 ml) then dried over sodium sulfate. It was concentrated down to give the title compound 1g-4 as a pale yellow solid (0.9 g, 40% yield). LCMS [M+H]$^+$ 181.

7-Fluoro-5-hydroxy-2,3-dihydro-1H-inden-1-one (1g-5)

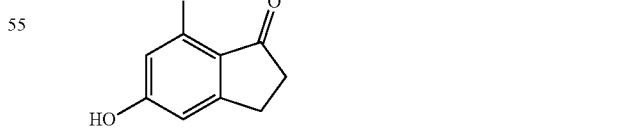

1g-5

A stirred solution of 7-fluoro-5-methoxy-2,3-dihydro-1H-inden-1-one 1g-4 (0.6 g, 3.33 mmol) in 48% aq.HBr (10 ml) was heated at 110° C. for 6 h. The reaction mixture was cooled to rt and poured into ice-cold water. It was extracted with EtOAc (2×300 ml). The combined organic layers were dried over sodium sulfate and concentrated down. The crude product was purified by column chromatography (silica gel 100-200 mesh) using 0-60% EtOAc in petroleum ether to give the title compound 1g-5 as a pale yellow solid (0.3 g, 54.5% yield). LCMS [M+H]⁺ 167.

Ethyl 4-((7-fluoro-1-oxo-2,3-dihydro-1H-inden-5-yl)oxy)butanoate (1g-6)

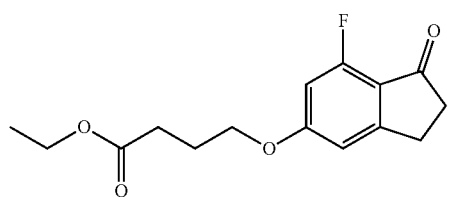

A stirred solution of 7-fluoro-5-hydroxy-2,3-dihydro-1H-inden-1-one 1g-5 (0.3 g, 1.81 mmol) in DMF (5 ml) was cooled to 0° C. Potassium carbonate (0.8 g, 5.42 mmol) and ethyl 4-bromobutanoate (0.3 ml, 2.16 mmol) were sequentially added. The reaction mixture was stirred at rt for 3 h. It was diluted with water (50 ml) and extracted with EtOAc (2×40 ml). The combined organic layers were dried over $Na_2SO_4$ and concentrated under reduced pressure to give the title compound 1g-6 as a pale yellow solid (0.6 g, quant. crude). LCMS [M+H]⁺ 281.

4-((7-Fluoro-1-oxo-2,3-dihydro-1H-inden-5-yl)oxy)butanoic acid (1g-7)

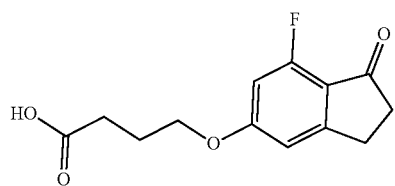

To a stirred solution of ethyl 4-((7-fluoro-1-oxo-2,3-dihydro-1H-inden-5-yl)oxy)butanoate 1g-6 (0.6 g, 2.14 mmol) in EtOH/H₂O (8/2 ml) was added lithium hydroxide monohydrate (0.15 g, 3.21 mmol). The reaction mixture was stirred at rt for 16 h. It was concentrated under reduced pressure then acidified with 2N HCl (20 ml). The solid that has precipitated was filtered and washed with diethyl ether (30 ml) to give the title compound 1g-7 as a pale yellow solid (0.3 g, 55.5% yield). ¹H NMR (400 MHz, DMSO) δ=ppm 12.18 (br s, 1H), 6.93 (s, 1H), 6.76 (dd, J=1.2 Hz, J=11.6 Hz 1H), 4.10 (t, J=6.4 Hz, 2H), 3.05 (t, J=6 Hz, 2H), 2.60 (t, J=3.1 Hz, 2H), 2.38 (t, J=7.2 Hz, 2H), 2.0-1.88 (m, 2H); LCMS [M+H]⁺ 253.

Scheme 8

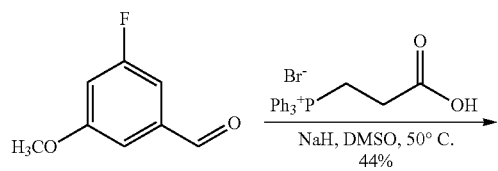

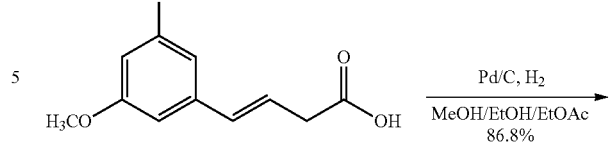

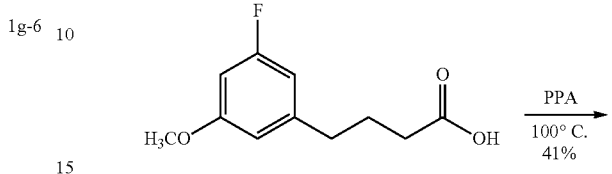

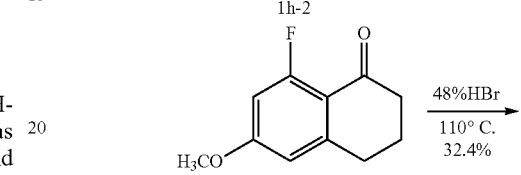

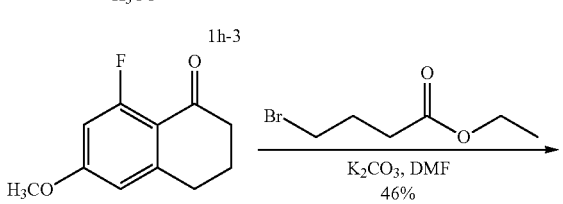

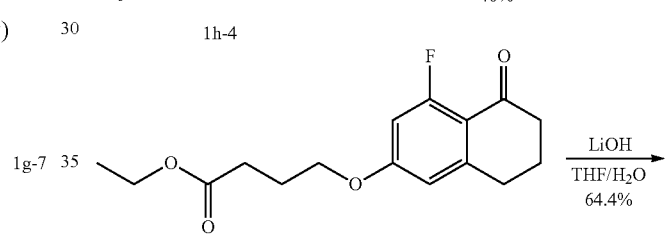

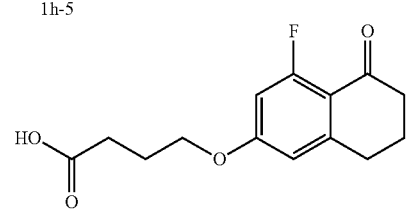

(E)-4-(3-Fluoro-5-methoxyphenyl)but-3-enoic acid (1h-1)

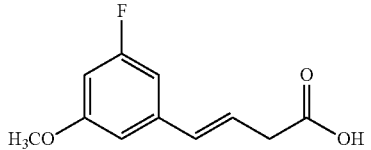

Dry DMSO (50 ml) was added to NaH (60% suspension in mineral oil, 3.8 g, 97.38 mmol) then the mixture was stirred at 0° C. A solution of (2-carboxyethyl)triphenylphosphonium bromide (14.8 g, 35.71 mmol) in DMSO (100 ml)

was added dropwise. To this stirring mixture, a solution of 3-fluoro-5-methoxybenzaldehyde (5 g, 32.46 mmol) in DMSO (25 ml) was added at 0° C. The mixture was heated to 50° C. and stirred at this temperature for 16 h under an argon atmosphere. The reaction mixture was diluted with water and washed with DCM (2×100 ml). The aqueous layer was acidified to pH=3 by 2N HCl then extracted with EtOAc (200 ml). The organic layer was washed with water (2×100 ml) and dried over Na$_2$SO$_4$. It was concentrated under reduced pressure to give the title compound 1h-1 as a brown liquid (3 g, 44% yield). LCMS [M+H]$^+$ 211.

4-(3-Fluoro-5-methoxyphenyl)butanoic acid (1h-2)

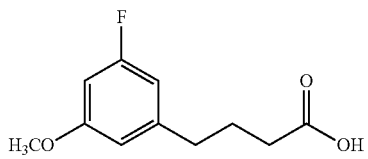

To a stirred solution of (E)-4-(3-fluoro-5-methoxyphenyl) but-3-enoic acid 1h-1 (8 g, 38.09 mmol) in methanol/ethanol/ethyl acetate (40/40/20 ml), 10% Pd/C (8 g) was added. This mixture was stirred under a hydrogen balloon atmosphere for 16 h. The crude reaction was filtered through celite and washed with methanol. The combined filtrates were concentrated down to give the title compound 1h-2 as a brown liquid (7 g, 86.6% yield). LCMS [M+H]$^+$ 213.

8-Fluoro-6-methoxy-3,4-dihydronaphthalen-1(2H)-one (1h-3)

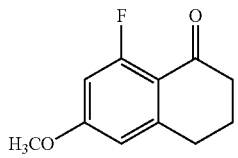

A solution of 4-(3-fluoro-5-methoxyphenyl)butanoic acid 1h-2 (8 g, 37.73 mmol) in PPA (40 g) was heated at 100° C. for 5 h. The reaction mixture was cooled to rt, poured into ice cold water then extracted with EtOAc (2×500 ml). The combined organic layers were washed with a saturated sodium carbonate solution (500 ml), brine (200 ml) then dried over sodium sulfate. It was concentrated down to give the title compound 1h-3 as a pale orange solid (3 g, 41% yield). LCMS [M+H]$^+$ 195.

8-Fluoro-6-hydroxy-3,4-dihydronaphthalen-1(2H)-one (1h-4)

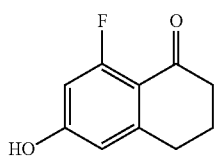

A solution of 8-fluoro-6-methoxy-3,4-dihydronaphthalen-1(2H)-one 1h-3 (2 g, 10.30 mmol) in 48% aq.HBr (20 ml) was heated at 110° C. for 16 h. The reaction mixture was poured into water (100 ml) and extracted with EtOAc (2×200 ml). The organic layer was concentrated down to give the title compound 1h-4 as a brown solid (600 mg, 32.4% yield). LCMS [M+H]$^+$ 181.

Ethyl 4-((4-fluoro-5-oxo-5,6,7,8-tetrahydronaphthalen-2-yl)oxy)butanoate (1h-5)

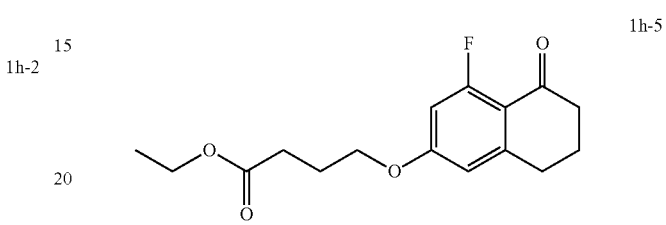

A stirred solution of 8-fluoro-6-hydroxy-3,4-dihydronaphthalen-1(2H)-one 1h-4 (1.2 g, 6.66 mmol) in DMF (20 ml) was cooled to 0° C. Potassium carbonate (1.83 g, 13.32 mmol) was added followed by ethyl 4-bromobutanoate (1.1 ml, 7.99 mmol). The reaction mixture was stirred at rt for 16 h. It was diluted with water (200 ml) and extracted with EtOAc (2×500 ml). The combined organic layers were dried over Na$_2$SO$_4$ and concentrated down. The crude product was purified by column chromatography (silica gel 100-200 mesh) using 0-40% EtOAc in petroleum ether to give the title compound 1h-5 as an off-white solid (900 mg, 46% yield). LCMS [M+H]$^+$ 295.

4-((4-Fluoro-5-oxo-5,6,7,8-tetrahydronaphthalen-2-yl)oxy)butanoic acid (1 h-6)

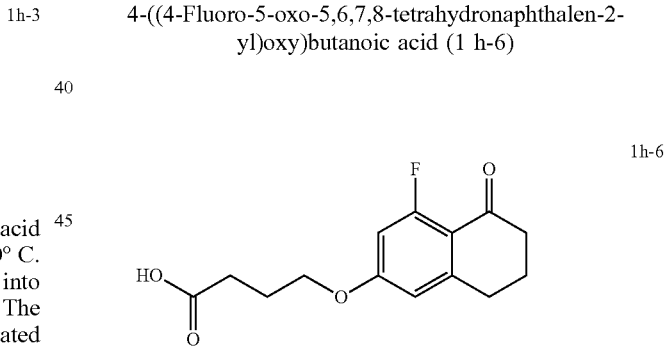

To a stirred solution of ethyl 4-((4-fluoro-5-oxo-5,6,7,8-tetrahydronaphthalen-2-yl)oxy)butanoate 1 h-5 (1.2 g, 4.08 mmol) in THF/H$_2$O (20/10 ml) was added lithium hydroxide monohydrate (342 mg, 8.16 mmol) then it was stirred at rt for 16 h. The reaction mixture was concentrated under reduced pressure then acidified with 2N HCl (20 ml). The solid that has precipitated was filtered and washed with diethyl ether (50 ml) to give the title compound 1 h-6 as an off-white solid (700 mg, 64.4% yield). $^1$H NMR (400 MHz, DMSO-d6) δ=12.2 (br s, 1H), 6.74-6.69 (m, 2H), 4.071 (t, J=6.4 Hz, 2H), 2.89 (t, J=6.0 Hz, 2H), 2.50-2.48 (m, 2H), 2.36 (t, J=7.6 Hz, 2H), 1.98-1.89 (m, 4H); LCMS [M+H]$^+$ 267.

The synthesis of 3-mercapto-3-methylbutanehydrazide (1-3) is described in Scheme (IX) using similar protocols to the ones described previously[49].

3-((4-Methoxybenzyl)thio)-3-methylbutanehydrazide (1-2)

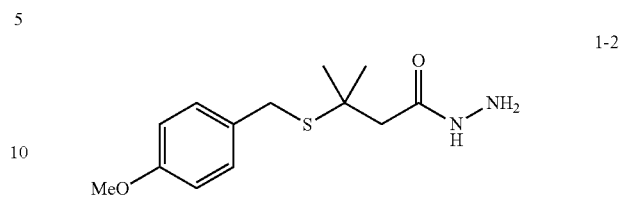

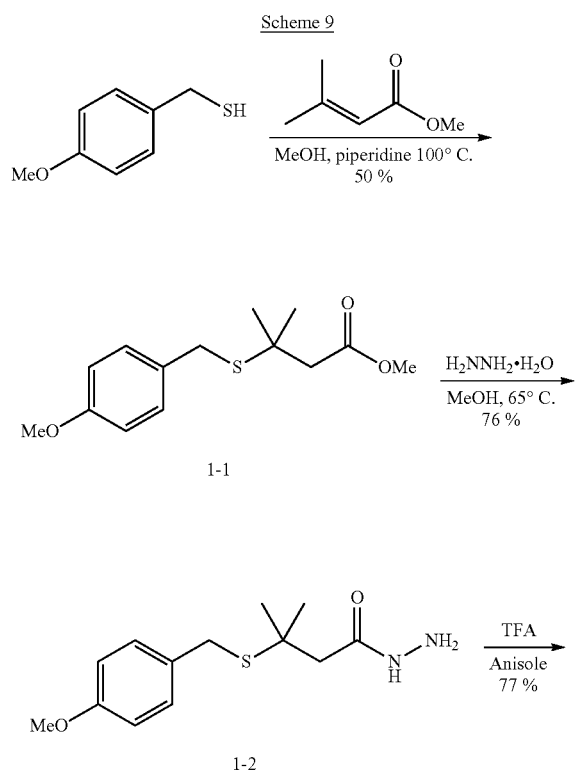

Scheme 9

Methyl 3-((4-methoxybenzyl)thio)-3-methylbutanoate (1-1):

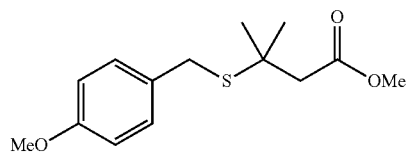

To a solution of methyl 3-methylbut-2-enoate (1.48 g, 13.0 mmol) in methanol (50 ml) was added 4-methoxy-a-toluenethiol (1 g, 6.5 mmol) and piperidine (55 mg, 0.65 mmol). The reaction was heated to reflux at 100° C. for 70 hours, after which it was concentrated under reduced pressure. The crude mixture was purified using Biotage™ (50 g silica column, eluent EtOAc/Hexanes from 0%-10% then 10%). The fractions containing the right product were collected and concentrated under reduced pressure to yield the title compound 1-1 as a clear oil (0.96 g, 50% yield). $^1$H NMR (500 MHz, DMSO-d6) δ=7.22 (d, J=8.7 Hz, 2H), 6.85 (d, J=8.7 Hz, 2H), 3.75 (s, 2H), 3.72 (s, 3H), 3.60 (s, 3H), 2.62 (s, 2H), 1.37 (s, 6H); LCMS [M+Na]$^+$ 291.

To a solution of compound 1-1 (1.76 g, 6.6 mmol) in methanol (4.5 ml) was added hydrazine monohydrate (1.64 g, 32.8 mmol). The reaction was heated to 65° C. for 20 hours, after which it was concentrated under reduced pressure. The crude mixture was purified using Biotage™ (25 g silica column, eluent EtOAc/Hexanes from 0%-100% then 100%). The fractions containing the right product were concentrated under reduced pressure to yield the title compound 1-2 as a white powder (1.4 g, 76% yield). $^1$H NMR (500 MHz, DMSO-d6) δ=9.02 (s, 1H), 7.23 (d, J=8.7 Hz, 2H), 6.85 (d, J=8.7 Hz, 2H), 4.20 (d, J=4.1 Hz, 2H), 3.74 (s, 2H), 3.72 (s, 3H), 2.34 (s, 2H), 1.36 (s, 6H); LCMS [M+H]$^+$ 269.

3-Mercapto-3-methylbutanehydrazide (1-3)

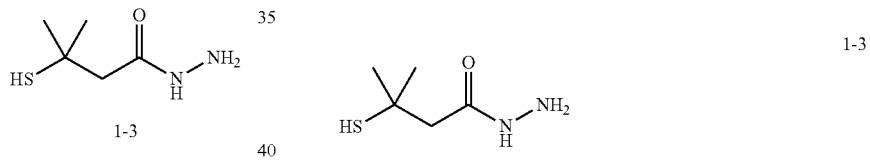

To a 100 ml round bottom flask was added a solution of compound 1-2 (250 mg, 0.93 mmol) in trifluoroacetic acid (8 ml). The reaction was cooled to 0° C. in an ice bath, after which anisole (0.15 ml, 1.40 mmol) was added. The reaction was then warmed to room temperature and allowed to stir for 24 hours, after which it was concentrated via steady stream of nitrogen. The crude residue was purified by anion exchange chromatography using a PoraPak Rxn CX 20 cc (2 g) cartridge. The column was first flushed with MeOH then the crude reaction mixture was loaded onto the resin using ethyl acetate. 50 ml of MeOH was flushed through the column, followed by 50 ml of a 95% MeOH/5% NH$_4$OH (28% in water) mixture. The fractions containing the right product were concentrated under reduced pressure, then dried via a steady stream of nitrogen to yield the title compound 1-3 as a clear oil that solidified upon standing (113 mg, 77% yield). $^1$H NMR (500 MHz, DMSO-d$_6$) δ=9.00 (s, 1H), 4.21 (s, 2H), 3.04 (s, 1H), 2.34 (s, 2H), 1.40 (s, 6H); LCMS [M+H]$^+$ 149.

Synthesis of the Activated Acyl Hydrazone Linkers

Scheme 10

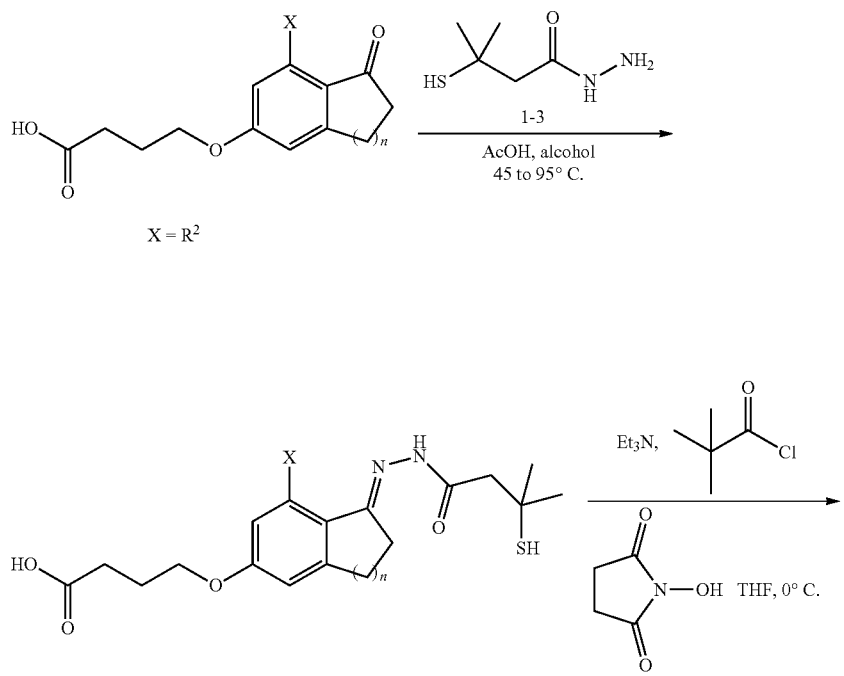

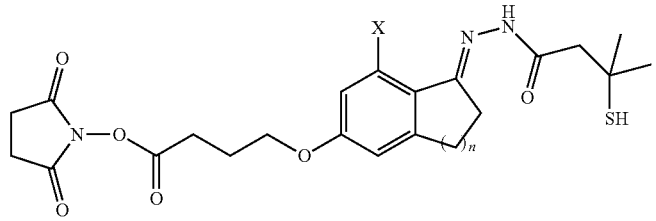

4-(4-(1-(2-(3-Mercapto methylbutanoyl) hydrazineylidene)ethyl)phenoxy) butanoic acid (Ia): Mylotarg Type Linker, Comparative Example)

2,5-Dioxopyrrolidin-1-yl-4-(4-(1-(2-(3-mercapto-3-methylbutanoyl) hydrazineylidene)ethyl)phenoxy) butanoate (Ia-1, Comparative Example)

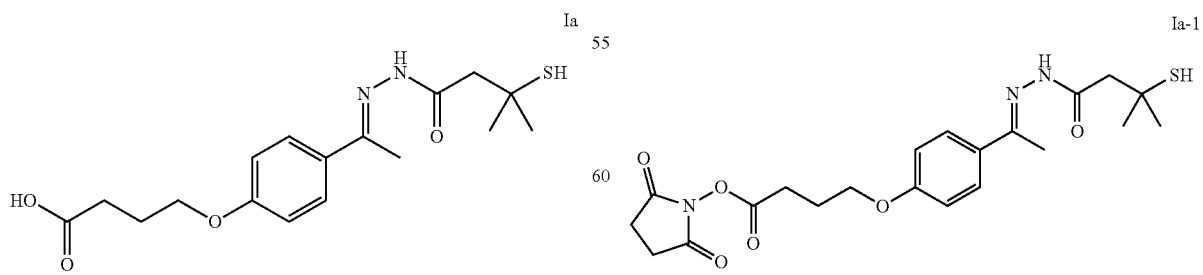

Compound Ia was prepared using similar protocols to the ones described previously[49].

Compound Ia-1 was prepared using similar protocols to the ones described previously[49].

(c) (4-((1-(2-(3-Mercapto-3-methylbutanoyl)hydrazineylidene)-2,3-dihydro-1H-inden-5-yl)oxy)butanoic acid (Id)

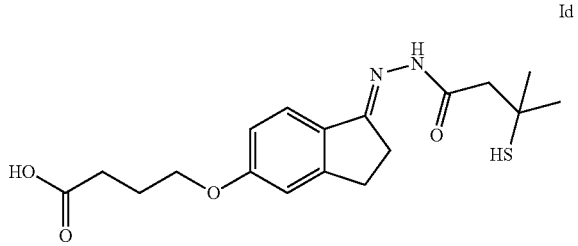 [SMILES: CC(C)(S)CC(=O)N/N=C1\CCc2cc(OCCCC(=O)O)ccc21]

A 30 ml glass vial was charged with 4-((1-oxo-2,3-dihydro-1H-inden-5-yl)oxy)butanoic acid 1d-1 (300 mg, 1.28 mmol), acetic acid (0.513 ml, 8.96 mmol) and 3-mercapto-3-methylbutanehydrazide 1-3 (190 mg, 1.28 mmol) then methanol (10 ml) was added. The mixture was heated at 45° C. for 2 days. LCMS showed there was still about 6% of starting material left. An additional 23 mg of 3-mercapto-3-methylbutanehydrazide 1-3 was added to the stirring solution. The heating was continued for another 2 days upon which LCMS showed there was still a small amount of starting material remaining. The reaction was stopped. It was loaded on elite and dried. The crude was purified by chromatography over Isco (12 g silica column; eluent: MeOH/DCM 0%, 0-5% then 5%) to give the title compound Id as a very light yellow powder (284 mg, 56.6% yield, 2 isomers). $^1$H NMR (500 MHz, DMSO-d6) δ=12.85-11.46 (m, 1H), 10.19 (s, 1H), 10.01 (s, 1H), 7.54 (dd, J=4.2, 8.5 Hz, 1H), 6.96-6.92 (m, 1H), 6.91-6.85 (m, 1H), 4.03 (q, J=6.3 Hz, 2H), 3.06-2.99 (m, 3H), 2.81-2.75 (m, 2H), 2.62 (s, 1H), 2.39 (t, J=7.3 Hz, 2H), 1.95 (quin, J=6.8 Hz, 2H), 1.49 (s, 3H), 1.47 (s, 3H); 1.40 (s, 6H); LCMS [M+H]$^+$ 365.

2,5-Dioxopyrrolidin-1-yl-4-((1-(2-(3-mercapto-3-methylbutanoyl)hydrazineylidene)-2,3-dihydro-1H-inden-5-yl)oxy)butanoate (Id-1)

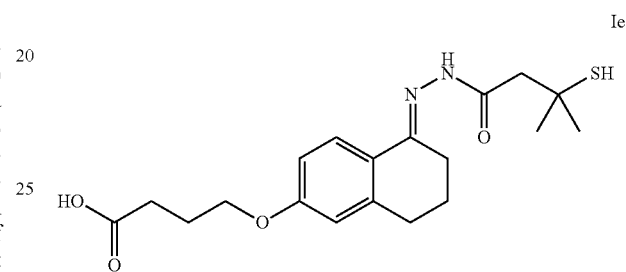

A 30 ml glass vial was charged with 4-((1-(2-(3-mercapto-3-methylbutanoyl)hydrazono)-2,3-dihydro-1H-inden-5-yl)oxy)butanoic acid Id (30.4 mg, 0.083 mmol) then THF (3 ml) was added. The solution was stirred at 0° C. upon which triethylamine (0.023 ml, 0.167 mmol) and trimethylacetyl chloride (0.011 ml, 0.092 mmol) were sequentially added. After 30 min, N-hydroxysuccinimide (10.56 mg, 0.092 mmol) was added as a solid. After 1 hour, the reaction was stopped. The Et$_3$N.HCl salt that has formed was filtered through a frit. The frit was washed several times with THF. The filtrate was concentrated down. The solid residue was taken in hexanes. It was sonicated however, it didn't break up. It was broken up with a spatula then it was vortexed quickly. The supernatant was pipetted out. This latter process was repeated twice then the resulting compound was dried under high vacuum to give the title compound Id-1 as an off-white powder (38.9 mg, quant. crude yield, 2 isomers). $^1$H NMR (500 MHz, DMSO-d6) δ=10.20 (s, 1H), 10.02 (s, 1H), 7.57-7.51 (m, 1H), 6.96 (br d, J=7.2 Hz, 1H), 6.91 (br d, J=8.3 Hz, 1H), 4.10 (q, J=5.9 Hz, 2H), 3.03 (br d, J=8.7 Hz, 4H), 2.86 (br t, J=7.2 Hz, 2H), 2.83 (br s, 4H), 2.81-2.76 (m, 2H), 2.63 (s, 1H), 2.60 (s, 1H), 2.13-2.04 (m, 2H), 1.49 (s, 3H), 1.47 (s, 3H); LCMS [M+H]$^+$ 462.

4-((5-(2-(3-Mercapto-3-methylbutanoyl)hydrazineylidene)-5,6,7,8-tetrahydronaphthalen-2-yl)oxy)butanoic acid (Ie)

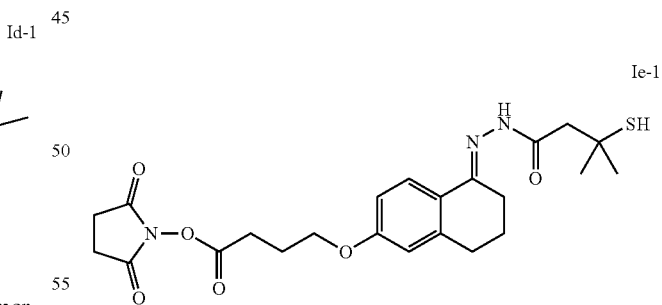

Compound Ie was prepared using a similar procedure to compound Id. It was collected as a light brown powder (651 mg, 68.8% yield, 2 isomers). $^1$H NMR (500 MHz, DMSO-d6) δ=12.27-11.90 (m, 1H), 10.28 (s, 1H), 10.13 (s, 1H), 7.92 (dd, J=8.8, 16.9 Hz, 1H), 6.82 (dt, J=2.6, 8.9 Hz, 1H), 6.74 (d, J=2.2 Hz, 1H), 4.00 (t, J=6.4 Hz, 2H), 3.09 (s, 1H), 3.04 (s, 1H), 3.02 (s, 1H), 2.75-2.67 (m, 2H), 2.64 (s, 1H), 2.58 (td, J=6.5, 10.1 Hz, 2H), 2.41-2.34 (m, 2H), 1.93 (quin, J=6.6 Hz, 2H), 1.85-1.73 (m, 2H), 1.48 (s, 3H), 1.46 (s, 3H); LCMS [M+H]$^+$ 379.

2,5-Dioxopyrrolidin-1-yl-4-((5-(2-(3-mercapto-3-methylbutanoyl)hydrazineylidene)-5,6,7,8-tetrahydronaphthalen-2-yl)oxy)butanoate (Ie-1)

Compound Ie-1 was prepared using a similar procedure to compound Id-1. It was collected as a light brown solid (26 mg, quant. crude yield, 2 isomers). $^1$H NMR (500 MHz, DMSO-d6) δ=12.45-11.55 (m, 1H), 10.38-10.22 (m, 1H), 10.15 (s, 1H), 7.94 (br dd, J=8.8, 15.8 Hz, 1H), 6.89-6.81 (m, 1H), 6.79-6.73 (m, 1H), 4.11-3.94 (m, 2H), 3.13-3.00 (m, 2H), 2.88-2.80 (m, 7H), 2.76-2.69 (m, 2H), 2.65 (s, 1H), 2.62-2.56 (m, 3H), 2.08 (quin, J=6.4 Hz, 2H), 1.81 (td, J=5.6, 15.7 Hz, 2H), 1.49 (s, 3H), 1.47 (s, 3H), 1.32 (s, 3H), 1.12 (s, 3H); LCMS [M+H]$^+$ 476.

4-((5-(2-(3-Mercapto-3-methylbutanoyl)hydrazineylidene)-6,7,8,9-tetrahydro-5H-benzo[7]annulen-2-yl)oxy)butanoic acid (If)

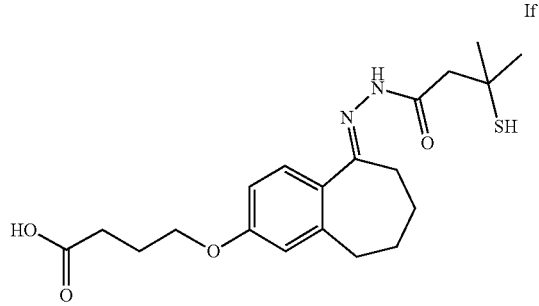 [SMILES: CC(C)(S)CC(=O)N/N=C1\CCCCc2cc(OCCCC(=O)O)ccc21]

Compound If was prepared using a similar procedure to compound Id. It was collected as an off-white foamy solid. (242 mg, 80% yield, 2 isomers). $^1$H NMR (500 MHz, DMSO-d6) δ=12.16 (br s, 1H), 10.30 (s, 1H), 10.13 (s, 1H), 7.35 (br d, J=8.3 Hz, 1H), 6.84-6.78 (m, 1H), 6.75 (br s, 1H), 4.00 (br t, J=6.2 Hz, 3H), 3.10-3.02 (m, 1H), 2.98 (s, 1H), 2.66 (br s, 4H), 2.39 (br t, J=7.2 Hz, 2H), 1.94 (br t, J=6.6 Hz, 2H), 1.74-1.66 (m, 2H), 1.59-1.50 (m, 2H), 1.47 (br s, 6H); LCMS [M+H]$^+$ 393.

2,5-Dioxopyrrolidin-1-yl-4-((5-(2-(3-mercapto-3-methylbutanoyl)hydrazineylidene)-6,7,8,9-tetrahydro-5H-benzo[7]annulen-2-yl)oxy)butanoate (If-1)

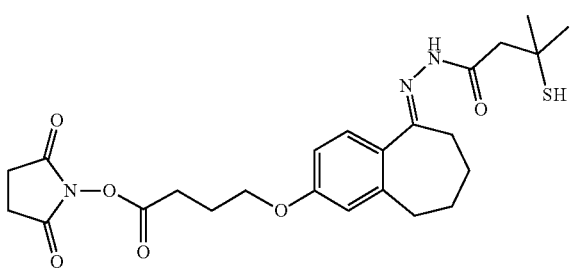

Compound Id was prepared using a similar procedure to compound Id-1. It was collected as a white sticky foamy solid (48 mg, quantitative crude yield, 2 isomers). $^1$H NMR (500 MHz, DMSO-d6) δ=10.31 (s, 1H), 10.14 (s, 1H), 7.35 (br d, J=7.5 Hz, 1H), 6.86-6.81 (m, 1H), 6.79-6.76 (m, 1H), 4.07 (br t, J=5.7 Hz, 2H), 3.08 (s, 1H), 2.98 (s, 1H), 2.86 (br s, 2H), 2.85-2.81 (m, 6H), 2.66 (br s, 5H), 2.60 (s, 1H), 2.59-2.54 (m, 2H), 2.12-2.04 (m, 2H), 1.69 (br d, J=4.4 Hz, 2H), 1.58-1.52 (m, 3H), 1.47 (br s, 6H), 1.37 (s, 1H), 1.31 (s, 2H), 1.01 (br t, J=7.1 Hz, 2H); LCMS [M+H]$^+$ 490.

4-(3-Hydroxy-4-(1-(2-(3-mercapto-3 methylbutanoyl)hydrazineylidene)ethyl)phenoxy)butanoic acid (IVa)

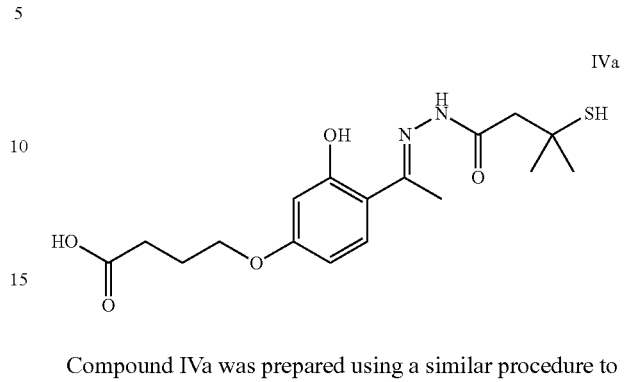

Compound IVa was prepared using a similar procedure to compound Id. It was collected as a tan foamy solid (125 mg, 40% yield, single isomer). $^1$H NMR (500 MHz, DMSO-d6) δ=13.50 (s, 1H), 12.14 (br s, 1H), 10.80 (s, 1H), 7.49 (d, J=8.9 Hz, 1H), 6.49-6.44 (m, 1H), 6.41 (s, 1H), 4.00 (br t, J=6.2 Hz, 2H), 3.02 (s, 1H), 2.70 (s, 2H), 2.38 (br t, J=7.2 Hz, 2H), 2.33 (s, 3H), 1.93 (quin, J=6.7 Hz, 2H), 1.48 (s, 6H); LCMS [M+H]$^+$ 369.

2,5-Dioxopyrrolidin-1-yl-4-(3-hydroxy-4-(1-(2-(3-mercapto-3-methylbutanoyl)hydrazineylidene)ethyl)phenoxy)butanoate (IVa-1)

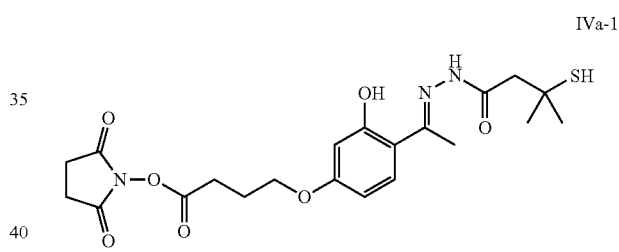

Compound IVa-1 was prepared using a similar procedure to compound Id-1. It was collected as a light brown gum (41 mg, quantitative crude yield). $^1$H NMR (500 MHz, DMSO-d6) δ=13.52-13.48 (m, 1H), 10.81 (br s, 1H), 7.50 (br d, J=8.8 Hz, 1H), 6.52-6.46 (m, 1H), 6.44 (br s, 1H), 4.08 (br t, J=5.9 Hz, 2H), 3.02 (br s, 1H), 2.89-2.79 (m, 7H), 2.70 (s, 2H), 2.60 (s, 1H), 2.33 (s, 3H), 2.11-2.01 (m, 2H), 1.48 (s, 4H), 1.12 (s, 6H); LCMS [M+H]$^+$ 466.

4-((7-Fluoro-1-(2-(3-mercapto-3-methylbutanoyl)hydrazineylidene)-2,3-dihydro-1H-inden-5-yl)oxy)butanoic acid (Ig)

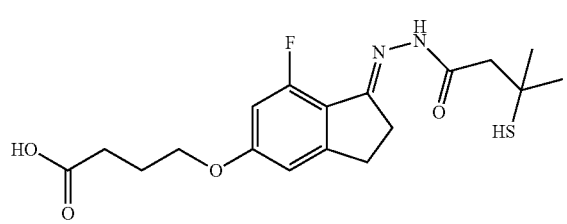

Compound Ig was prepared using a similar procedure to compound Ig. It was collected as a beige flaky powder (146 mg, 64% yield, 2 isomers). $^1$H NMR (500 MHz, DMSO-$d_6$) δ=12.50-11.87 (m, 1H), 10.25 (s, 1H), 10.00 (s, 1H), 6.80 (br d, J=7.1 Hz, 1H), 6.72 (br t, J=11.0 Hz, 1H), 4.07-4.00 (m, 2H), 3.08-3.01 (m, 3H), 2.99 (s, 1H), 2.80 (br d, J=5.5 Hz, 2H), 2.63 (s, 1H), 2.38 (br t, J=7.0 Hz, 2H), 1.94 (br t, J=6.5 Hz, 2H), 1.47 (br s, 6H); LCMS [M+H]$^+$ 383.

2,5-Dioxopyrrolidin-1-yl-4-((7-fluoro-1-(2-(3-mercapto-3-methylbutanoyl)hydrazineylidene)-2,3-dihydro-1H-inden-5-yl)oxy)butanoate (Ig-1)

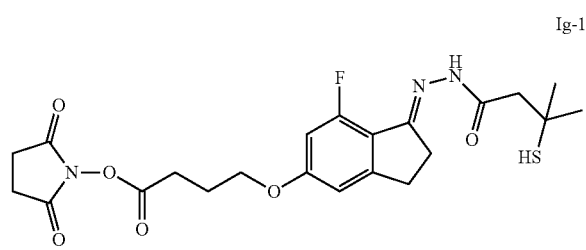 [SMILES: CC(C)(S)CC(=O)N/N=C1\CCc2cc(OCCCC(=O)ON3C(=O)CCC3=O)cc(F)c21]

Ig-1

Compound Ig-1 was prepared using a similar procedure to compound Id-1. It was collected as a beige semi-solid. (27.2 mg, 87% yield, 2 isomers). $^1$H NMR (500 MHz, DMSO-d6) δ=10.57-10.51 (m, 1H), 10.26 (s, 1H), 10.00 (br s, 1H), 6.83 (br d, J=8.3 Hz, 1H), 6.79-6.72 (m, 1H), 4.11 (q, J=5.7 Hz, 2H), 3.09-3.03 (m, 3H), 2.89-2.85 (m, 2H), 2.83 (br s, 6H), 2.64 (br d, J=6.8 Hz, 2H), 2.09 (br t, J=6.4 Hz, 2H), 1.50-1.43 (m, 6H); LCMS [M+H]$^+$ 480.

4-((7-Hydroxy-1-(2-(3-mercapto-3-methylbutanoyl)hydrazineylidene)-2,3-dihydro-1H-inden-5-yl)oxy)butanoic acid (Ic)

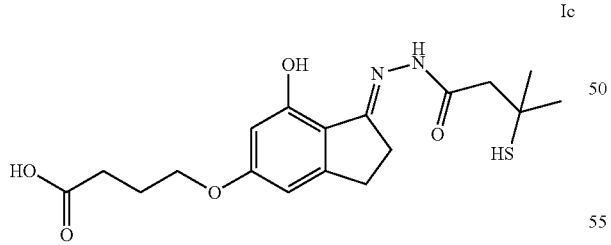

Ic

Compound Ic was prepared using a similar procedure to compound Id. It was collected as a pale yellow solid (250 mg, 66% yield, single isomer). $^1$H NMR (500 MHz, DMSO-d6) δ=10.48 (br s, 1H), 10.08 (br d, J=1.7 Hz, 1H), 9.73 (br d, J=14.9 Hz, 1H), 6.47 (s, 1H), 6.30 (s, 1H), 3.99 (br t, J=5.8 Hz, 2H), 3.03 (br s, 2H), 2.85 (br d, J=5.3 Hz, 2H), 2.62 (s, 2H), 2.36 (br t, J=7.3 Hz, 2H), 1.92 (br t, J=6.7 Hz, 2H), 1.39 (s, 6H); LCMS [M+H]$^+$ 381.

2,5-Dioxopyrrolidin-1-yl-4-((7-hydroxy-1-(2-(3-mercapto-3 methylbutanoyl)hydrazineylidene)-2,3-dihydro-1H-inden-5-yl)oxy)butanoate (Ic-1)

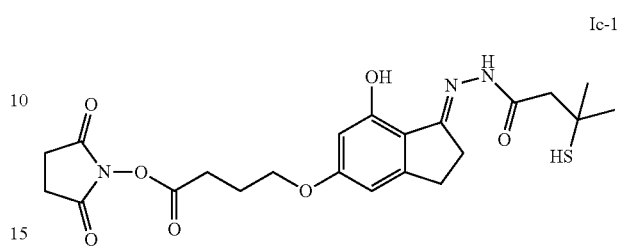

Ic-1

Compound Ic-1 was prepared using a similar procedure to compound Id-1. It was collected as a beige semi-solid. (562 mg, quantitative crude yield). LCMS [M+H]$^+$ 478.

4-((4-Fluoro-5-(2-(3-mercapto-3-methylbutanoyl)hydrazineylidene)-5,6,7,8-tetrahydronaphthalen-2-yl)oxy)butanoic acid (Ih)

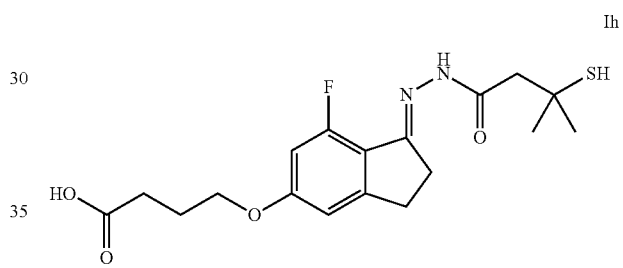

Ih

Compound Ih was prepared using a similar procedure to compound Id. It was collected as a light orange powder (161 mg, 71% yield, 2 isomers). $^1$H NMR (DMSO-d6, 500 MHz) δ=12.17 (br s, 1H), 10.32 (br s, 1H), 10.09 (br s, 1H), 6.72 (br d, 1H, J=13.8 Hz), 6.7-6.7 (m, 1H), 4.02 (br s, 2H), 3.0-3.1 (m, 2H), 2.67 (br d, 2H, J=8.1 Hz), 2.6-2.6 (m, 2H), 2.38 (br t, 2H, J=7.0 Hz), 1.93 (quin, 2H, J=6.4 Hz), 1.7-1.8 (m, 2H), 1.46 (s, 6H); LCMS [M+H]$^+$ 397.

2,5-Dioxopyrrolidin-1-yl-4-((4-fluoro-5-(2-(3-mercapto-3-methylbutanoyl)hydrazineylidene)-5,6,7,8-tetrahydronaphthalen-2-yl)oxy)butanoate (Ih-1)

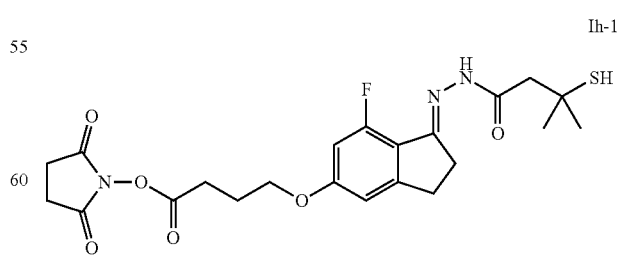

Ih-1

Compound Ih-1 was prepared using a similar procedure to compound Id-1. It was collected as a beige foamy solid (76 mg, 88% yield, 2 isomers). $^1$H NMR (DMSO-d6, 500 MHz)

δ=10.3-10.4 (m, 1H), 10.10 (br s, 1H), 6.73 (br s, 1H), 6.69 (br s, 1H), 4.1-4.1 (m, 2H), 3.0-3.0 (m, 1H), 2.8-2.9 (m, 5H), 2.7-2.7 (m, 2H), 2.6-2.6 (m, 2H), 2.0-2.1 (m, 2H), 1.75 (br d, 2H, J=5.3 Hz), 1.47 (s, 4H); LCMS [M+H]$^+$ 494.

4-((4-Hydroxy-5-(2-(3-mercapto-3-methylbutanoyl)hydrazono)-5,6,7,8-tetrahydronaphthalen-2-yl)oxy)butanoic acid (Ib)

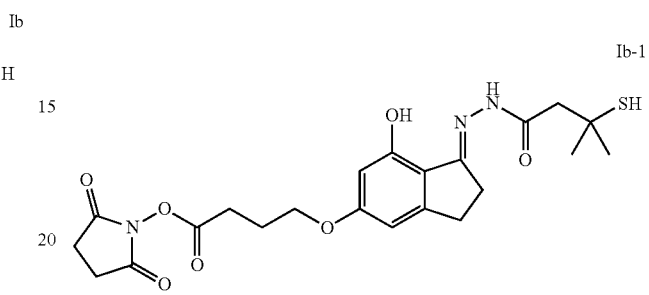

Compound Ib was prepared using a similar procedure to compound Id. It was collected as a yellow oil (193 mg, 64.6% yield, single isomer). $^1$H NMR (500 MHz, DMSO-d6) δ=ppm 13.56 (s, 1H) 10.69 (br s, 1H) 9.70-9.77 (m, 2H) 9.01 (br s, 1H) 6.27 (dd, J=16.14, 2.20 Hz, 2H) 3.98 (br t, J=6.36 Hz, 3H) 3.03-3.12 (m, 3H) 2.71-2.76 (m, 2H) 2.68 (s, 3H) 2.45 (s, 3H) 2.33-2.39 (m, 5H) 2.08 (s, 8H) 1.90-1.94 (m, 3H) 1.85 (s, 7H) 1.40-1.48 (m, 22H) LCMS [M+H]$^+$ 395.

2,5-Dioxopyrrolidin-1-yl-4-((4-hydroxy-5-(2-(3-mercapto-3-methylbutanoyl)hydrazono)-5,6,7,8-tetrahydronaphthalen-2-yl)oxy)butanoate (Ib-1)

Compound Ib-1 was prepared using a similar procedure to compound Id-1 as a crude residue around the vial (112 mg, 30% yield). LCMS [M+H]$^+$ 492.

Scheme 11

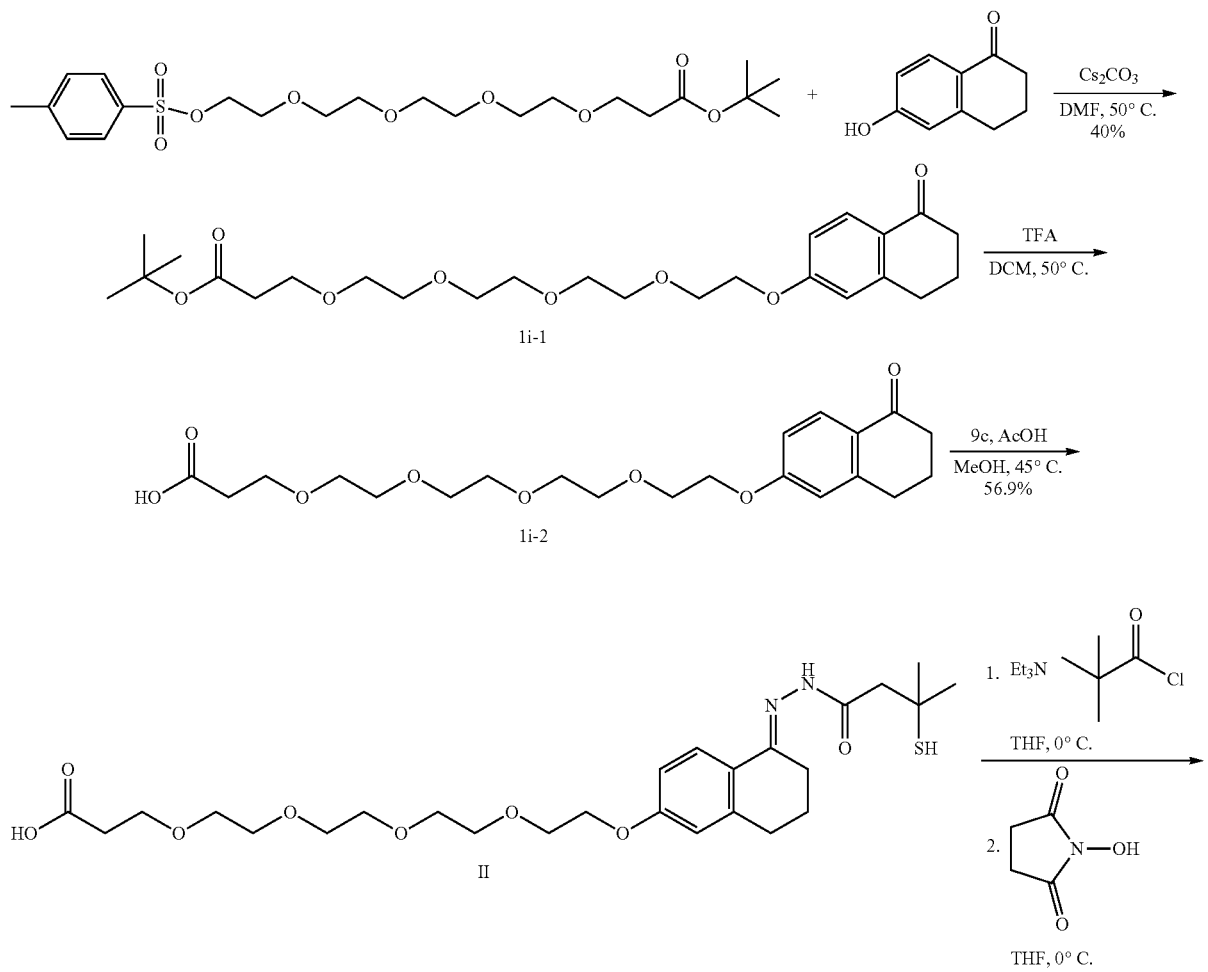

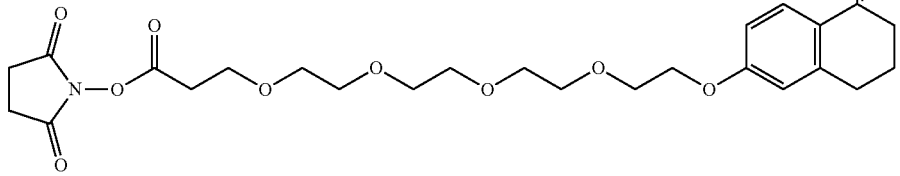

II-1 tert-Butyl 1-((5-oxo-5,6,7,8-tetrahydronaphthalen-2-yl)oxy)-3,6,9,12-tetraoxapentadecan-15-oate (1i-1)

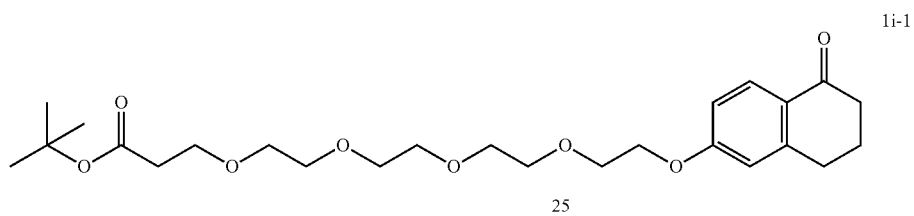

1i-1

A 30 ml vial was charged with 6-hydroxy-1-tetralone (65 mg, 0.401 mmol) and Tos-PEG5 t-butyl ester (210 mg, 0.441 mmol) then DMF (2 ml) was added. To this mixture, cesium carbonate (196 mg, 0.601 mmol) was added then it was heated at 50° C. After about 4 h, LCMS showed no more progress. Cesium carbonate (100 mg) and Tos-PEG5 t-butyl ester (94 mg) were added then the mixture was heated at 50° C. overnight upon which LCMS showed completion. Celite was added to the mixture and it was dried. It was purified using Isco (12 g silica column: eluent 0-50% then 50% EtOAc/Hexanes) to afford the title compound 1i-1 as a colorless thick oil (75 mg, 40% yield). $^1$H NMR (500 MHz, DMSO-d6) δ=7.84-7.80 (m, 1H), 6.91-6.87 (m, 2H), 4.18 (br s, 2H), 3.76 (br s, 2H), 3.61-3.56 (m, 4H), 3.54 (br s, 3H), 3.50 (br d, J=10.8 Hz, 8H), 2.91 (br t, J=5.3 Hz, 2H), 2.41 (br t, J=6.0 Hz, 2H), 2.06-1.96 (m, 2H), 1.39 (s, 9H); LCMS [M+H]$^+$ 467.

1-((5-Oxo-5,6,7,8-tetrahydronaphthalen-2-yl)oxy)-3,6,9,12-tetraoxapentadecan-15-oic acid (1i-2)

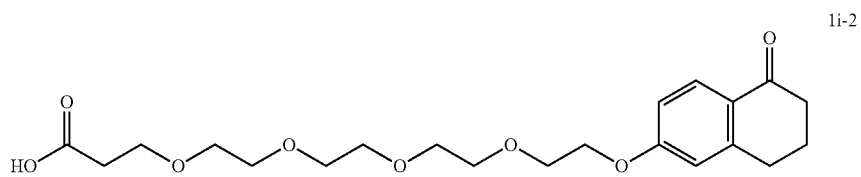 [SMILES: O=C(O)CCOCCOCCOCCOCCOc1ccc2c(c1)CCCC2=O]

1i-2

To a 30 ml vial containing tert-butyl 1-((5-oxo-5,6,7,8-tetrahydronaphthalen-2-yl)oxy)-3,6,9,12-tetraoxapentadecan-15-oate 1i-1 (73 mg, 0.156 mmol) was added DCM (2 ml) followed by TFA (2 ml) then it was heated at 50° C. After about 1 h LCMS showed completion. The reaction mixture was concentrated down. The residue was dried under high vacuum. The title compound 1i-2 was collected as a light brown thick oil (m: 89 mg, yield>100% due to residual TFA trapped in the product). $^1$H NMR (500 MHz, DMSO-d6) δ=7.85-7.75 (m, 1H), 6.93-6.84 (m, 2H), 4.18 (br s, 2H), 3.76 (br s, 2H), 3.62-3.57 (m, 4H), 3.54 (br d, J=4.6 Hz, 3H), 3.51 (br s, 4H), 3.49 (br s, 4H), 2.91 (br t, J=5.3 Hz, 2H), 2.44 (br t, J=6.1 Hz, 2H), 2.05-1.96 (m, 2H); LCMS [M+H]$^+$ 411.

1-((5-(2-(3-Methylbutanoyl)hydrazineylidene)-5,6,7,8-tetrahydronaphthalen-2-yl)oxy)-3,6,9,12-tetraoxa-pentadecan-15-oic acid (Ii)

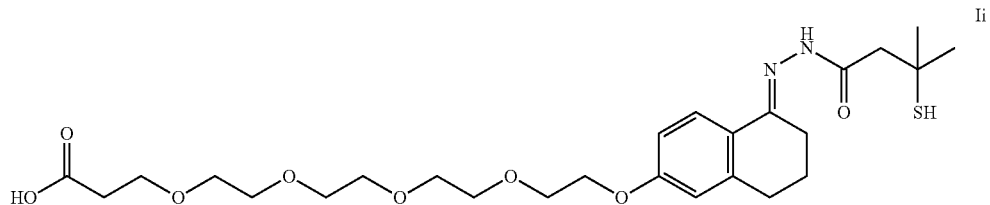 [SMILES: CC(C)(S)CC(=O)N/N=C1\CCCc2cc(OCCOCCOCCOCCOCCC(=O)O)ccc21]

A 30 ml vial was charged with 1-((5-oxo-5,6,7,8-tetrahydronaphthalen-2-yl)oxy)-3,6,9,12-tetraoxapentadecan-15-oic acid 1 i-2 (64 mg, 0.156 mmol) and 3-mercapto-3-methylbutanehydrazide 1-3 (25.4 mg, 0.172 mmol) then methanol (2 ml). Acetic Acid, glacial (0.063 ml, 1.092 mmol) was added then the mixture was heated at 50° C. After 90 min, the reaction mixture was cooled to room temperature and stirred overnight. It was heated to 50° C. for another hour upon which LCMS showed no more progress. 3-Mercapto-3-methylbutanehydrazide 1-3 (20 mg) was added then the heating was continued for 1 hour. LCMS showed only a very small amount of the starting material left. The reaction mixture was loaded on celite and dried. The crude was purified over Isco (12 g silica column: eluent MeOH/DCM 0, 0-5% then 5%). The title compound Ii was collected as a light brown powder (48 mg, 56.9% yield, 2 isomers). $^1$H NMR (500 MHz, DMSO-$d_6$) δ=10.30 (s, 1H), 10.15 (s, 1H), 9.99 (br s, 1H), 9.92 (br s, 1H), 9.81-9.66 (m, 1H), 7.93 (br dd, J=8.9, 15.0 Hz, 1H), 6.88-6.81 (m, 1H), 6.77 (br s, 1H), 4.11 (br s, 2H), 3.75 (br s, 2H), 3.59 (br d, J=5.5 Hz, 4H), 3.54 (br s, 2H), 3.51 (br s, 4H), 3.49 (br s, 4H), 3.18 (s, 1H), 3.14-3.11 (m, 1H), 3.08 (s, 1H), 3.05 (s, 1H), 3.03 (br d, J=4.0 Hz, 1H), 3.00 (s, 1H), 2.89 (s, 1H), 2.75-2.67 (m, 2H), 2.64 (s, 1H), 2.62-2.56 (m, 2H), 2.47-2.41 (m, 4H), 1.96-1.90 (m, 3H), 1.85 (br s, 4H), 1.81 (br dd, J=5.5, 9.9 Hz, 2H), 1.49 (s, 2H), 1.47 (s, 3H), 1.45 (br s, 2H), 1.43 (br s, 3H), 1.42 (br s, 3H); LCMS [M+H]$^+$ 541.

2,5-Dioxopyrrolidin-1-yl-1-((5-(2-(3-methylbutanoyl)hydrazineylidene)-5,6,7,8-tetrahydronaphthalen-2-yl)oxy)-3,6,9,12-tetraoxapentadecan-15-oate (Ii-1)

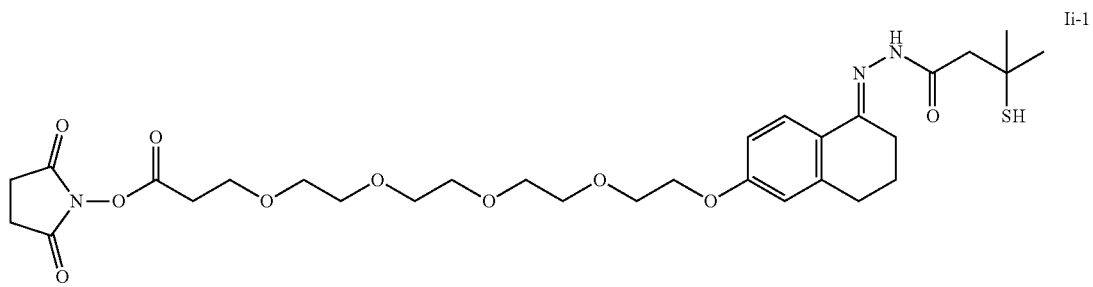 [SMILES: CC(C)(S)CC(=O)N/N=C1\CCCc2cc(OCCOCCOCCOCCOCCC(=O)ON3C(=O)CCC3=O)ccc21]

A 30 ml vial was charged with 1-((5-(2-(3-mercapto-3-methyl butanoyl)hydrazono)-5,6,7,8-tetrahydronaphthalen-2-yl)oxy)-3,6,9,12-tetraoxapentadecan-15-oic acid Ii (23 mg, 0.043 mmol) then THF (2 ml) was added. The solution was stirred at 0° C. upon which triethylamine (0.012 ml, 0.085 mmol) was added followed by trimethylacetyl chloride (5.76 µl, 0.047 mmol). After 30 min, N-hydroxysuccinimide (5.39 mg, 0.047 mmol) was added as a solid. The reaction was stirred for an additional 30 min and stopped. The Et$_3$N.HCl salt that has formed was filtered through a small frit. The frit was washed several times with THF. The filtrate was concentrated down. The residue was taken in hexanes. It was washed twice with hexanes. Since some of the product has dissolved in hexanes, all the organic washes were combined and evaporated down. The residue was dried under high vacuum to afford the crude product Ii-1 as a glassy thick gum (30.7 mg, quant. crude, 2 isomers). $^1$H NMR (500 MHz, DMSO-$d_6$) δ=10.65-10.45 (m, 1H), 10.30 (s, 1H), 10.15 (s, 1H), 9.58 (s, 1H), 9.36 (s, 1H), 7.93 (br dd, J=9.1, 14.4 Hz, 1H), 6.87-6.80 (m, 1H), 6.77 (br s, 1H), 4.11

(br s, 2H), 3.74 (br s, 3H), 3.59 (br s, 2H), 3.56-3.46 (m, 11H), 3.14 (s, 1H), 3.11 (s, 1H), 3.06-3.03 (m, 1H), 2.92 (br t, J=5.7 Hz, 2H), 2.81 (br s, 4H), 2.71 (br d, J=10.9 Hz, 3H), 2.64 (br s, 1H), 2.60 (s, 8H), 1.88-1.75 (m, 3H), 1.49 (s, 2H), 1.47 (s, 3H), 1.44 (br d, J=6.2 Hz, 6H), 1.31 (s, 1H), 1.14 (s, 6H), 1.11 (br d, J=6.7 Hz, 4H); LCMS [M+H]$^+$638.
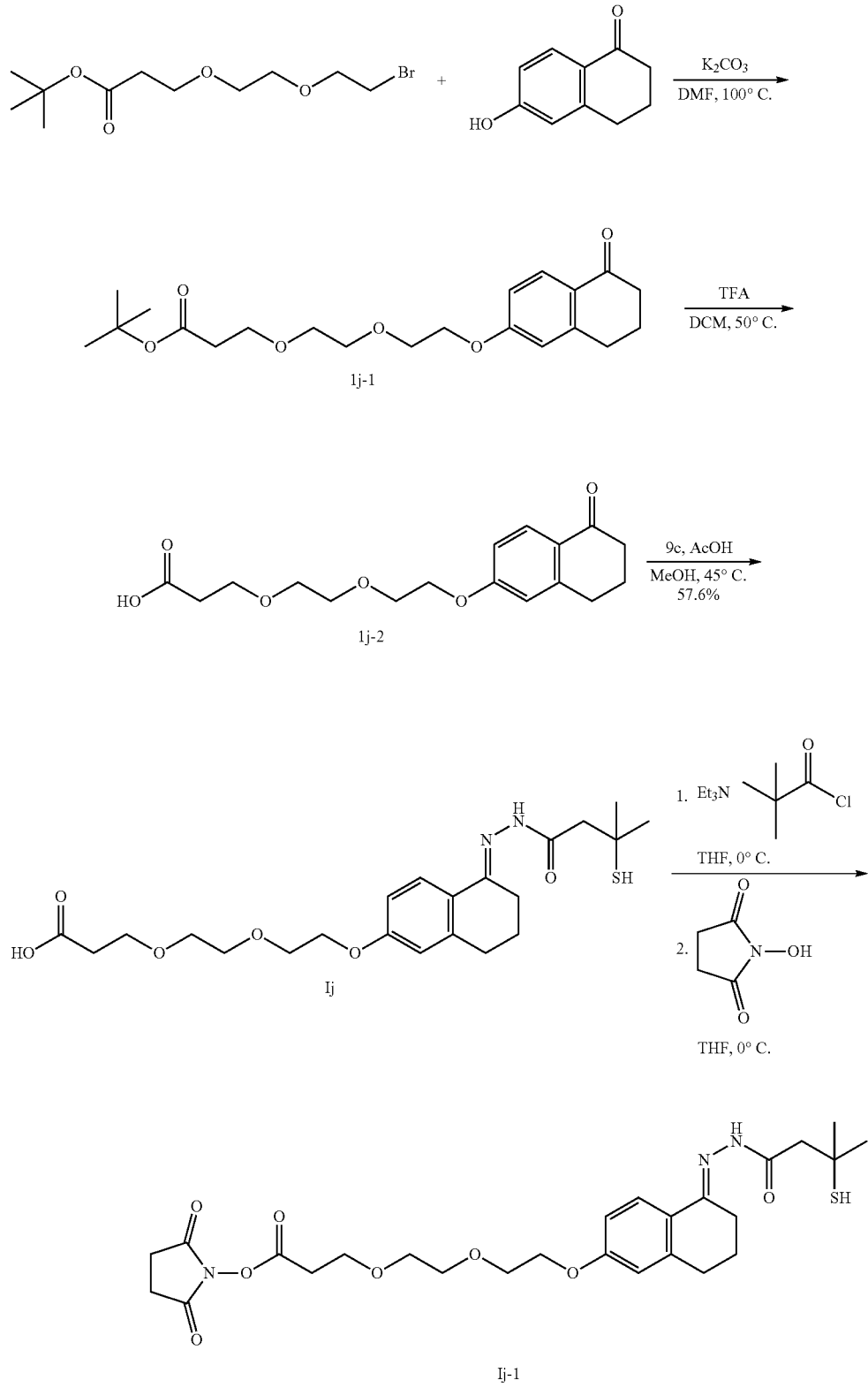

tert-Butyl3-(2-((5-oxo-5,6,7,8-tetrahydronaphthalen-2yl)oxy)ethoxy) propanoate (1j-1)

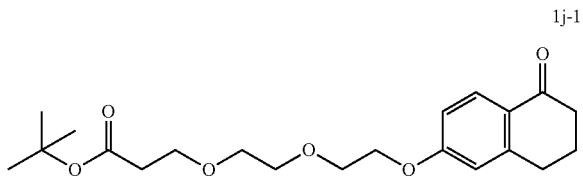 [SMILES: CC(C)(C)OC(=O)CCOCCOCCOc1ccc2c(c1)CCCC2=O]

A 30 ml vial was charged with 6-hydroxy-1-tetralone (100 mg, 0.617 mmol) and bromo-peg2-t-butyl ester (238 mg, 0.802 mmol) then N, N-dimethylformamide (3 ml) was added. To this mixture, potassium carbonate (111 mg, 0.802 mmol) was added. The reaction was heated at 100° C. for 2 h then stirred overnight at room temperature. $K_2CO_3$ (115 mg) was added followed by bromo-peg2-t-butyl ester (100 mg). The mixture was heated at 100° C. for 1 h upon which LCMS showed almost completion. The mixture was cooled down, loaded on celite then dried. It was purified over Isco (12 g silica column: eluent EtOAc/Hexanes: 0-60% then 60%) to afford the title compound 1j-1 as a yellow oil (249 mg, yield>100% because some of the excess bromo-peg2-t-butyl ester has co-eluted with the product). $^1$H NMR (500 MHz, DMSO-d6) δ=7.98-7.93 (m, 1H), 7.81 (br d, J=8.3 Hz, 1H), 6.92-6.86 (m, 2H), 4.17 (br s, 2H), 3.75 (br s, 2H), 3.62-3.56 (m, 4H), 3.52 (br d, J=2.9 Hz, 2H), 2.92-2.87 (m, 3H), 2.74 (s, 1H), 2.42 (br t, J=5.8 Hz, 2H), 2.05-1.94 (m, 2H), 1.39 (s, 9H); LCMS [M+H]$^+$ 379.

3-(2-(2-((5-Oxo-5,6,7,8-tetrahydronaphthalen-2-yl)oxy)ethoxy)ethoxy) propanoic acid (1j-2)

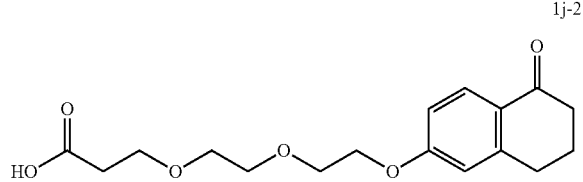 [SMILES: O=C(O)CCOCCOCCOc1ccc2c(c1)CCCC2=O]

tert-Butyl3-(2-(2-((5-oxo-5,6,7,8-tetrahydronaphthalen-2-yl)oxy)ethoxy)ethoxy) propanoate 1j-1 (245 mg, 0.647 mmol) was dissolved in DCM (2.5 ml), trifluoroacetic acid (2.5 ml) was added then the mixture was heated at 50° C. for 1 h upon which LCMS showed completion. The solvents were evaporated off. The residue was dried under vacuum. It was further dried with a strong stream of air to afford the title compound 1j-2 as a very light brown thick gum (214 mg, crude yield>100% due to some residual TFA trapped in the product). $^1$H NMR (500 MHz, DMSO-d6) δ=7.84-7.79 (m, 1H), 6.93-6.88 (m, 2H), 4.17 (br s, 2H), 3.75 (br s, 2H), 3.61 (br t, J=6.1 Hz, 3H), 3.59-3.56 (m, 2H), 3.52 (br d, J=3.3 Hz, 2H), 2.93-2.87 (m, 2H), 2.44 (br t, J=6.1 Hz, 2H), 2.04-1.97 (m, 2H); LCMS [M+H]$^+$ 323.

3-(2-(2-((5-(2-(3-Methylbutanoyl)hydrazineylidene)-5,6,7,8-tetrahydronaphthalen-2-yl)oxy)ethoxy)ethoxy)propanoic acid (Ij)

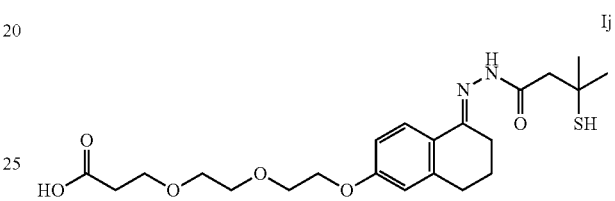

A 30 ml vial was charged with 3-(2-(2-((5-oxo-5,6,7,8-tetrahydronaphthalen-2-yl)oxy)ethoxy)ethoxy)propanoic acid 1j-2 (209 mg, 0.648 mmol) and 3-mercapto-3-methylbutanehydrazide 1-3 (106 mg, 0.713 mmol) then methanol (4 ml). Acetic Acid glacial (0.260 ml, 4.54 mmol) was added then the mixture was heated overnight at 50° C. LCMS showed only a small amount of the starting material was left. The crude reaction mixture was loaded on celite then dried. It was purified over Isco (12 g silica column: eluent MeOH/DCM 0, 0-5% then 5%). The title compound Ij was collected as a light yellow sticky gum (169 mg, 57.6% yield, 2 isomers). $^1$H NMR (500 MHz, DMSO-d6) δ=12.32-12.06 (m, 1H), 10.30 (s, 1H), 10.15 (s, 1H), 8.03-7.84 (m, 1H), 6.84 (br t, J=9.0 Hz, 1H), 6.77 (br s, 1H), 4.11 (br s, 2H), 3.74 (br s, 2H), 3.62 (br t, J=6.2 Hz, 2H), 3.58 (br s, 2H), 3.53 (br d, J=3.2 Hz, 2H), 3.11 (s, 1H), 3.06-3.01 (m, 1H), 2.76-2.68 (m, 2H), 2.65 (s, 1H), 2.62-2.54 (m, 2H), 2.45 (br t, J=6.2 Hz, 2H), 1.81 (td, J=5.7, 16.3 Hz, 2H), 1.49 (s, 3H), 1.47 (s, 3H); LCMS [M+H]$^+$ 453.

2,5-Dioxopyrrolidin-1-yl-3-(2-(2-((5-(2-(3-methylbutanoyl)hydrazineylidene)-5,6,7,8-tetrahydronaphthalen-2-yl)oxy)ethoxy)ethoxy)propanoate (Ij-1)

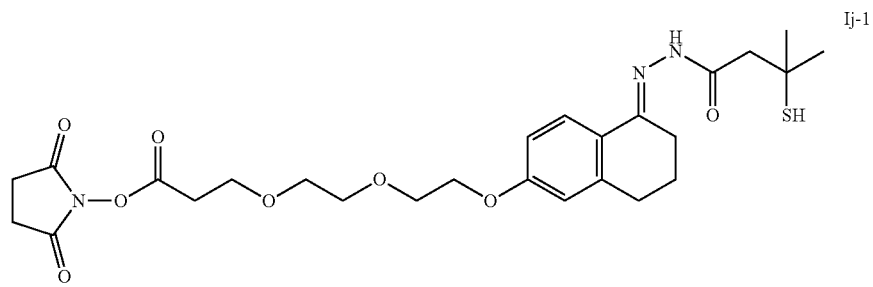 [SMILES: CC(C)(S)CC(=O)N/N=C1\CCCc2cc(OCCOCCOCCC(=O)ON3C(=O)CCC3=O)ccc21]

A 30 ml vial was charged with 3-(2-(2-((5-(2-(3-mercapto-3-methylbutanoyl) hydrazono)-5,6,7,8-tetrahydronaphthalen-2-yl)oxy)ethoxy)ethoxy)propanoic acid Ij (25 mg, 0.055 mmol) then THF (2 ml) was added. The solution was stirred at 0° C. upon which triethylamine (0.015 ml, 0.110 mmol) followed by trimethylacetyl chloride (7.5 μl, 0.061 mmol) were added. After 30 min, N-hydroxysuccinimide (7 mg, 0.061 mmol) was added as a solid. The reaction mixture was stirred for another 30 min then stopped. The Et$_3$N.HCl salt that has formed was filtered through a frit. The frit was washed several times with THF. The filtrate was concentrated down. The resulting residue was taken in hexanes. A sticky product was formed. The hexanes was taken out. Since some compound has dissolved in hexanes, all the organic washes were combined, evaporated then dried under high vacuum to afford the title compound Ij-1 as a sticky glassy gum (32.9 mg, quant. crude yield, 2 isomers). $^1$H NMR (500 MHz, DMSO-d6) δ=10.30 (s, 1H), 10.15 (s, 1H), 7.93 (br dd, J=8.9, 13.5 Hz, 1H), 6.84 (br t, J=8.9 Hz, 1H), 6.78-6.74 (m, 1H), 4.11 (br s, 2H), 3.78-3.71 (m, 4H), 3.59 (br d, J=5.5 Hz, 4H), 3.11 (s, 1H), 3.07-2.97 (m, 2H), 2.93 (br t, J=5.7 Hz, 2H), 2.81 (br s, 4H), 2.71 (br dd, J=5.8, 12.5 Hz, 2H), 2.64 (s, 1H), 2.58 (br dd, J=5.9, 10.1 Hz, 3H), 1.81 (td, J=5.8, 16.1 Hz, 2H), 1.49 (s, 3H), 1.47 (s, 3H); LCMS [M+H]$^+$ 550.

Synthesis of Linker-DM1 Constructs

Scheme 13

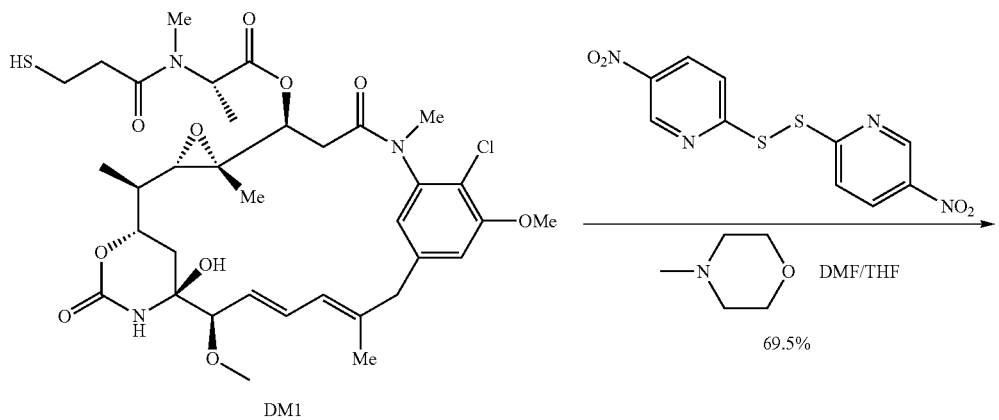

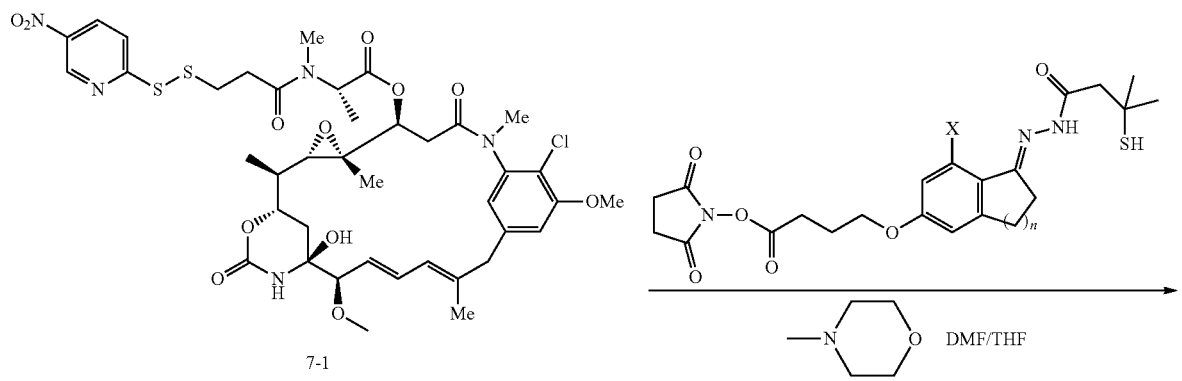

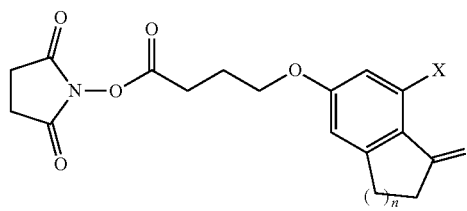

Linker DM1 constructs

The representative linkers are conjugated to DM1 via a disulfide bond formation reaction according to the synthetic procedures described in scheme (13). DM1 was reacted with 2,2'-dithiobis(5-nitropyridine) to form the DM1-thio(5-nitropyridine) compound 7-1. This intermediate was then reacted with thiol of linkers of formula I to form the disulfide bond between the linker and DM1 which gave the final DM1 constructs (VII) that are ready for antibody conjugation.

DM1-thio(5-nitropyridine) (7-1)

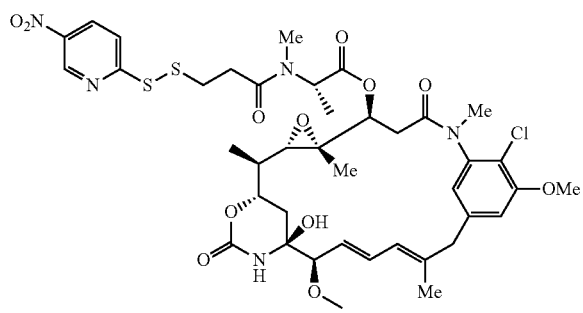

7-1

To a solution of 1,2-bis(5-nitropyridin-2-yl)disulfane (147 mg, 0.474 mmol) in THF (15 ml) was added 4-methylmorpholine (0.033 ml, 0.296 mmol). The mixture was stirred at room temperature then it was as added to a solution of DM1 (175 mg, 0.237 mmol) in N,N-dimethylformamide (7.50 ml). It was stirred at room temperature for 90 min. The reaction was stopped. Most of the THF was evaporated under reduced pressure. The resulting crude concentrate was diluted with EtOAc. The organic layer was washed with water (×3) then with brine. It was dried over $Na_2SO_4$ and concentrated down. It was purified by Isco (12 g silica column: eluent EtOAc/Hexanes 0-100% then 100%). The title compound 7-1 was collected as a light yellow powder (147 mg, 69.5% yield). $^1$H NMR (500 MHz, DMSO-d6) δ=9.11-9.09 (m, 1H), 8.45 (dd, J=2.4, 8.9 Hz, 1H), 7.88 (d, J=8.9 Hz, 1H), 7.00 (s, 1H), 6.88 (s, 1H), 6.58-6.49 (m, 2H), 6.37-6.35 (m, 1H), 5.93 (s, 1H), 5.57 (br dd, J=9.2, 13.7 Hz, 1H), 5.30 (q, J=6.7 Hz, 1H), 4.52 (br dd, J=2.0, 12.0 Hz, 1H), 4.09-4.00 (m, 2H), 3.87 (s, 3H), 3.48 (br d, J=8.9 Hz, 1H), 3.25 (s, 3H), 3.19-3.13 (m, 1H), 3.08 (s, 3H), 3.08-3.03 (m, 1H), 3.02-2.89 (m, 2H), 2.78 (br d, J=9.5 Hz, 1H), 2.70 (s, 3H), 2.46-2.39 (m, 1H), 2.03-1.97 (m, 2H), 1.54 (s, 3H), 1.49-1.41 (m, 2H), 1.24 (br d, J=13.0 Hz, 1H), 1.17 (br d, J=6.8 Hz, 3H), 1.12 (br d, J=6.2 Hz, 3H), 0.75 (s, 3H); LCMS [M+H]$^+$ 893.

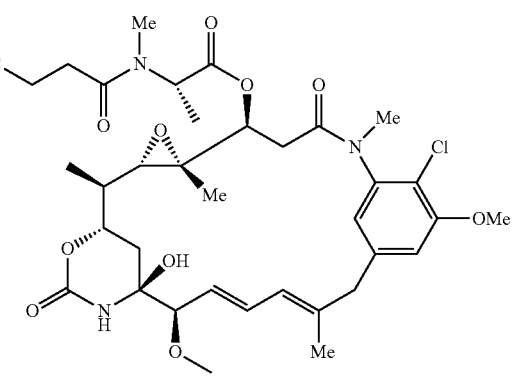

Acyclic Linker-DM1 Construct (VIIa)

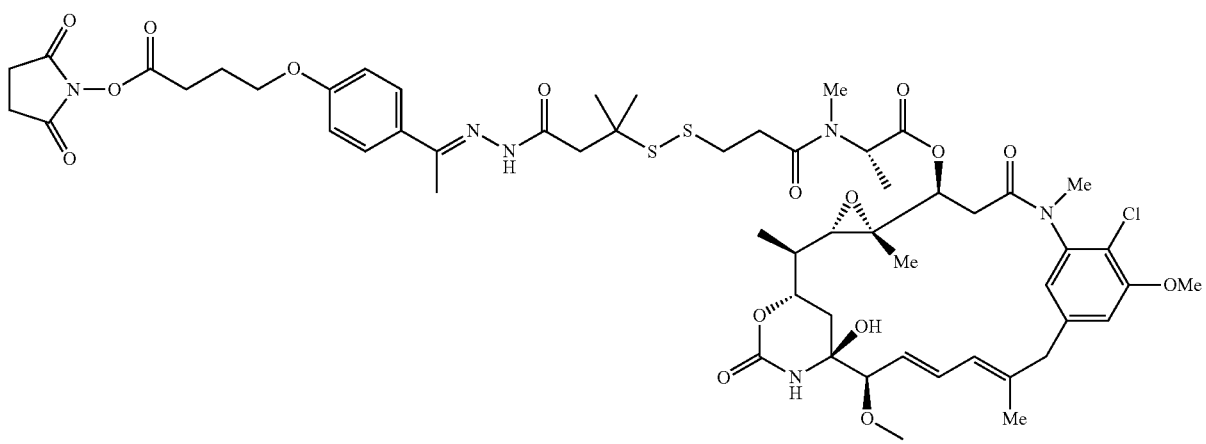

VIIa

In a small vial, compound 7-1 (15 mg, 0.017 mmol) was dissolved in DMF (1.5 ml) then 2,5-dioxopyrrolidin-1-yl 4-(4-(1-(2-(3-mercapto-3-methylbutanoyl)hydrazono)ethyl) phenoxy)butanoate Ia-1 (21.23 mg, 0.047 mmol) in THF (1.5 ml) was added. 4-Methylmorpholine (0.034 ml, 0.017 mmol) as a (0.5 M) solution in of DMF was added. The mixture was stirred at room temperature for 1 h upon which LCMS showed completion. The crude mixture was separated between water and EtOAc and shaken. The organic layer was washed with water (×3) then brine. It was dried over Na$_2$SO$_4$ and concentrated down. The crude was purified by chromatography over Isco (4 g silica column; eluent: EtOAc/Hexanes; 0-100% then 100% EtOAc). The product was taken into acetonitrile frozen then lyophilized. The title compound VIIa was collected as a white fluffy powder (16.92 mg, 85% yield, 2 isomers). $^1$H NMR (500 MHz, DMSO-d6) δ=10.39 (s, 1H), 10.23 (s, 1H), 7.78-7.71 (m, 2H), 7.18-7.11 (m, 1H), 7.03-6.95 (m, 2H), 6.89 (br d, J=6.1 Hz, 1H), 6.67-6.58 (m, 1H), 6.57-6.48 (m, 2H), 5.93 (br d, J=6.2 Hz, 1H), 5.76 (br s, 1H), 5.59-5.45 (m, 1H), 5.32 (br t, J=6.5 Hz, 1H), 4.56-4.48 (m, 1H), 4.12-4.03 (m, 4H), 3.91 (br d, J=5.6 Hz, 3H), 3.52-3.47 (m, 2H), 3.25 (br d, J=8.2 Hz, 3H), 3.17 (s, 1H), 3.13 (s, 2H), 2.96 (br d, J=13.3 Hz, 2H), 2.89-2.85 (m, 4H), 2.83 (br s, 4H), 2.71 (br d, J=18.0 Hz, 3H), 2.21 (br d, J=5.5 Hz, 3H), 2.13-2.02 (m, 4H), 1.58 (br d, J=14.4 Hz, 3H), 1.45 (br d, J=11.7 Hz, 4H), 1.24 (br s, 3H), 1.22 (br s, 3H), 1.17 (br t, J=6.4 Hz, 3H), 1.13 (br d, J=5.3 Hz, 3H), 0.79 (br d, J=4.3 Hz, 3H); LCMS [M+H]$^+$ 1186.

2,3-Dihydro-1H-indene Type Linker-DM1 Construct (VIId)

VIId

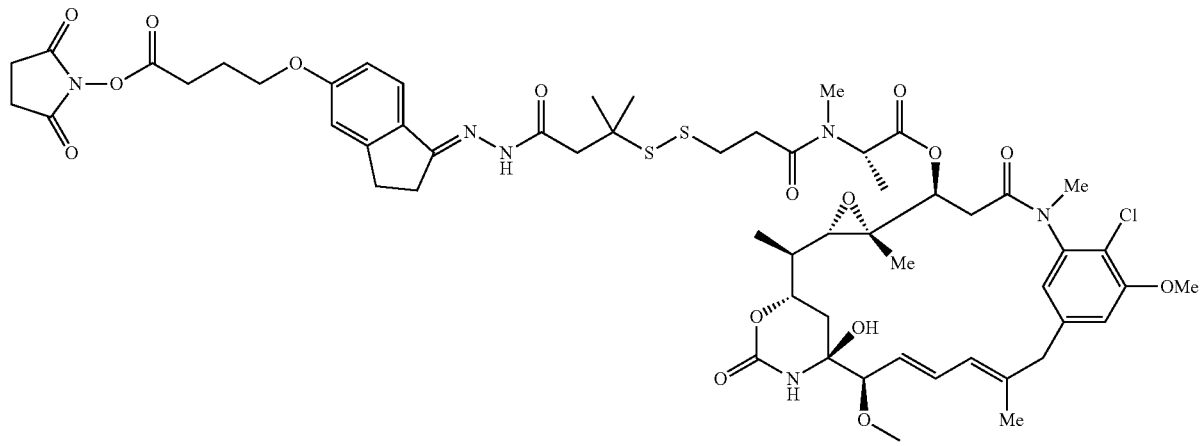

In a small vial, compound 7-1 (10 mg, 0.011 mmol) was dissolved in DMF (1 ml) then 2,5-dioxopyrrolidin-1-yl-4-((1-(2-(3-mercapto-3-methylbutanoyl)hydrazono)-2,3-dihydro-1H-inden-5-yl)oxybutanoate Id-1 (14.53 mg, 0.031 mmol) in THF (1 ml) was added. 4-Methylmorpholine (0.022 ml, 0.011 mmol) as a (0.5 M) solution in of DMF was added. The mixture was stirred at room temperature for 1 hour upon which LCMS showed completion. The crude mixture was separated between water and EtOAc and shaken. The organic layer was washed with water (×3) then brine. It was dried over Na$_2$SO$_4$ and concentrated down. The crude product was purified over Isco (4 g silica column; eluent: EtOAc/Hexanes; 0-100% then 100%). The product was taken into acetonitrile frozen then lyophilized. The title compound VIId was collected as a white fluffy powder (m: 11.67 mg, 87% yield, 2 isomers). $^1$H NMR (500 MHz, DMSO-d6) δ=10.25 (s, 1H), 10.09 (s, 1H), 7.60 (br dd, J=8.4, 15.8 Hz, 1H), 7.20 (br d, J=19.8 Hz, 1H), 7.01 (br d, J=9.7 Hz, 1H), 6.98-6.92 (m, 2H), 6.01-5.96 (m, 1H), 5.82 (br s, 1H), 5.59 (ddd, J=5.6, 8.8, 14.5 Hz, 1H), 5.41-5.33 (m, 1H), 4.61-4.55 (m, 1H), 4.19-4.10 (m, 3H), 3.97 (br d, J=7.1 Hz, 3H), 3.57-3.52 (m, 2H), 3.31 (br d, J=7.7 Hz, 3H), 3.21 (br d, J=11.5 Hz, 3H), 3.12-3.00 (m, 4H), 2.91 (br d, J=9.3 Hz, 4H), 2.88 (br s, 4H), 2.84 (br d, J=12.0 Hz, 3H), 2.77 (br d, J=9.4 Hz, 3H), 2.18-2.08 (m, 3H), 1.63 (br d, J=12.5 Hz, 3H), 1.50 (br d, J=11.4 Hz, 3H), 1.29 (br s, 9H), 1.23 (br d, J=5.6 Hz, 3H), 1.18 (br d, J=5.7 Hz, 3H), 0.85 (br s, 3H); LCMS [M+H]$^+$ 1198.

1,2,3,4-Tetrahydronaphthalene type linker-DM1 construct (VIIe)

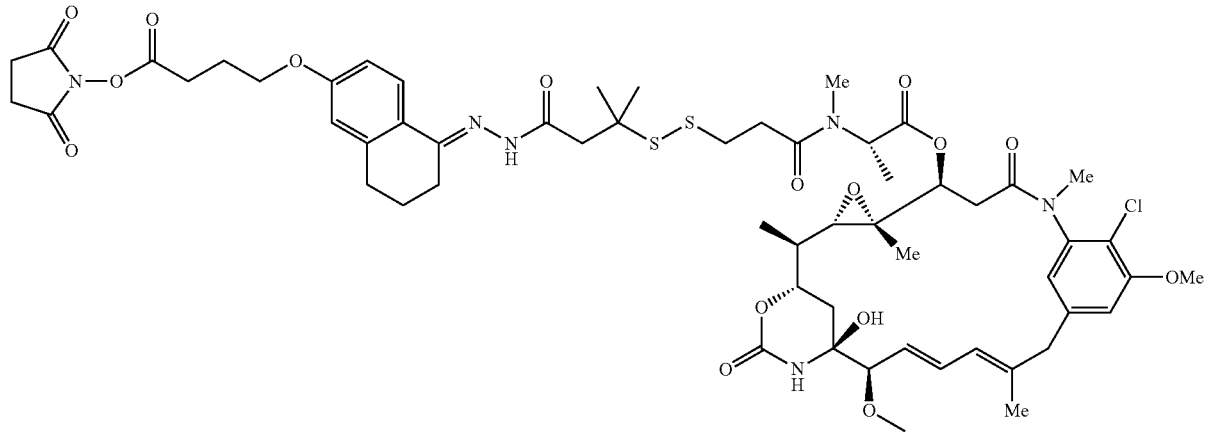

In a small vial, compound 7-1 (8 mg, 8.96 μmol) was dissolved in DMF (1 ml) then 2,5-dioxopyrrolidin-1-yl 4-((5-(2-(3-mercapto-3-methylbutanoyl)hydrazono)-5,6,7,8-tetrahydronaphthalen-2-yl)oxy)butanoate Ie-1 (11.98 mg, 0.025 mmol) in THF (1 ml) was added. 4-Methylmorpholine (0.018 ml, 8.96 μmol) as a (0.5 M) solution in DMF was added. The mixture was stirred at room temperature for 1 hour upon which LCMS showed completion. The crude mixture was separated between water and EtOAc and shaken. The organic layer was washed with water (×3) then brine. It was dried over $Na_2SO_4$ and concentrated down. The crude was purified over Isco (4 g silica column; eluent: EtOAc/Hexanes; 0-100% then 100% EtOAc). The product was taken into acetonitrile frozen then lyophilized. The title compound VIIe was collected as an off-white fluffy powder (6.72 mg, 61.9% yield, 2 isomers). 1H NMR (500 MHz, DMSO-d6) δ=10.25 (s, 1H), 10.09 (s, 1H), 7.97-7.77 (m, 1H), 7.11-7.01 (m, 1H), 6.87-6.75 (m, 2H), 6.73-6.66 (m, 1H), 6.59-6.51 (m, 1H), 6.50-6.43 (m, 1H), 5.86 (br d, J=6.2 Hz, 1H), 5.69 (br s, 1H), 5.50-5.40 (m, 1H), 5.28-5.18 (m, 1H), 4.49-4.39 (m, 1H), 4.04-3.95 (m, 3H), 3.84 (br d, J=7.0 Hz, 2H), 3.46-3.39 (m, 2H), 3.18 (br d, J=7.7 Hz, 2H), 3.09 (s, 1H), 3.06 (s, 1H), 2.90 (br d, J=13.7 Hz, 1H), 2.82-2.73 (m, 7H), 2.63 (br d, J=15.4 Hz, 4H), 2.05-1.94 (m, 3H), 1.73 (br dd, J=5.4, 11.2 Hz, 2H), 1.50 (br d, J=12.3 Hz, 2H), 1.45-1.32 (m, 4H), 1.16 (br d, J=1.8 Hz, 3H), 1.15 (br s, 3H), 1.10 (br t, J=5.9 Hz, 3H), 1.05 (br d, J=5.9 Hz, 2H), 0.71 (br d, J=4.0 Hz, 2H); LCMS $[M+H]^+$ 1212.

5,6,7,8-Tetrahydronaphthalen-1-ol type linker-DM1 construct (VIIb)

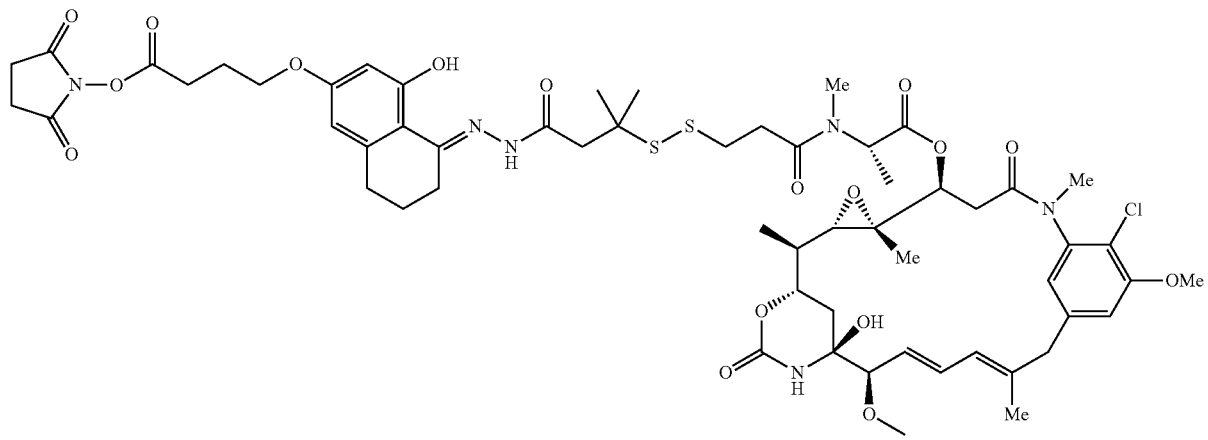

Linker-DM1 construct VIIb was prepared using a similar procedure to VIIa. It was collected as a white fluffy powder (2 mg, 9.8% yield, single isomer). 1H NMR (500 MHz, DMSO-d6) δ ppm 13.48 (br s, 1H) 10.64 (br s, 1H) 7.08 (s, 1H) 6.82 (s, 1H) 6.45-6.60 (m, 3H) 6.15-6.26 (m, 2H) 5.86 (s, 1H) 5.47 (br dd, J=14.79, 9.05 Hz, 1H) 5.25 (q, J=6.56 Hz, 1H) 4.45 (br dd, J=12.04, 1.90 Hz, 1H) 3.94-4.05 (m, 3H) 3.84 (s, 3H) 3.39-3.47 (m, 2H) 3.18 (s, 3H) 3.09 (s, 3H) 2.72-2.83 (m, 9H) 2.65 (s, 5H) 2.56-2.62 (m, 4H) 1.96-2.01 (m, 2H) 1.73-1.78 (m, 2H) 1.51 (s, 3 H) 1.46 (br d, J=13.45 Hz, 2H) 1.37 (br dd, J=14.00, 11.68 Hz, 3H) 1.16 (s, 6 H) 1.04-1.13 (m, 9H) 0.72 (s, 3H); LCMS $[M+H]^+$ 1228.

Acyclic Hydroxy-Phenyl Linker-DM1 Construct (VIIIb)

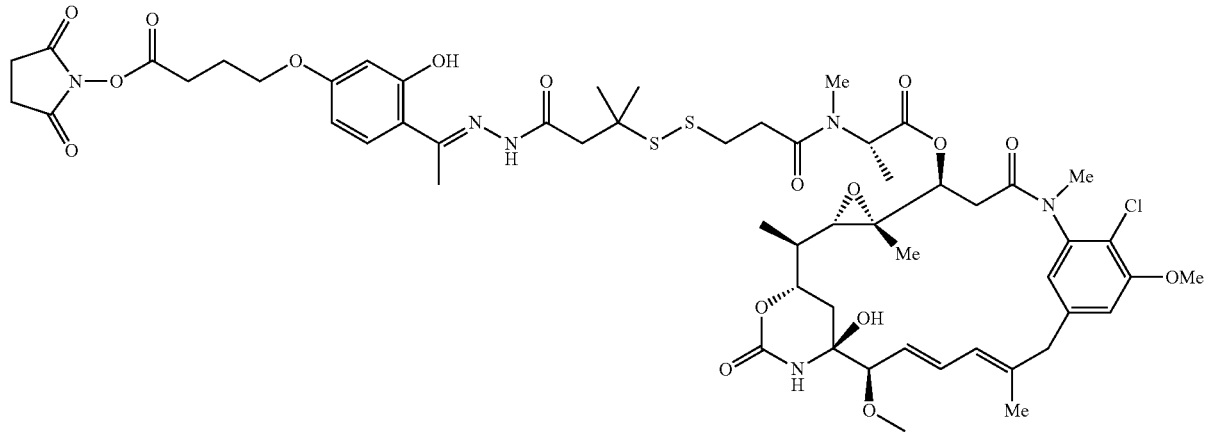

Linker-DM1 construct VIIIb was prepared using a similar procedure to VIIa. It was collected as a white fluffy powder (19 mg, 89% yield, single isomer). $^1$H NMR (500 MHz, DMSO-d6) δ=13.48 (br s, 1H), 10.82 (br s, 1H), 7.50 (br d, J=8.8 Hz, 1H), 7.15 (s, 1H), 6.92-6.85 (m, 1H), 6.67-6.52 (m, 3H), 6.49 (br d, J=8.1 Hz, 1H), 6.44 (br s, 1H), 5.93 (s, 1H), 5.76 (br d, J=2.2 Hz, 1H), 5.54 (br dd, J=9.4, 14.7 Hz, 1H), 5.32 (q, J=6.4 Hz, 1H), 4.53 (br d, J=11.6 Hz, 1H), 4.12-4.06 (m, 3H), 3.91 (s, 3H), 3.49 (br d, J=9.3 Hz, 2H), 3.26 (s, 3H), 3.17 (s, 3H), 2.89-2.80 (m, 10H), 2.72 (s, 3H), 2.32 (s, 4H), 2.11-2.01 (m, 4H), 1.59 (s, 3H), 1.51-1.41 (m, 4H), 1.24 (s, 6H), 1.18 (br d, J=6.6 Hz, 3H), 1.13 (br d, J=6.1 Hz, 3H), 0.79 (s, 3H); LCMS [M+H]$^+$ 1202.

Hydroxy-2,3-Dihydro-1H-Indene Type Linker-DM1 Construct (VIIc)

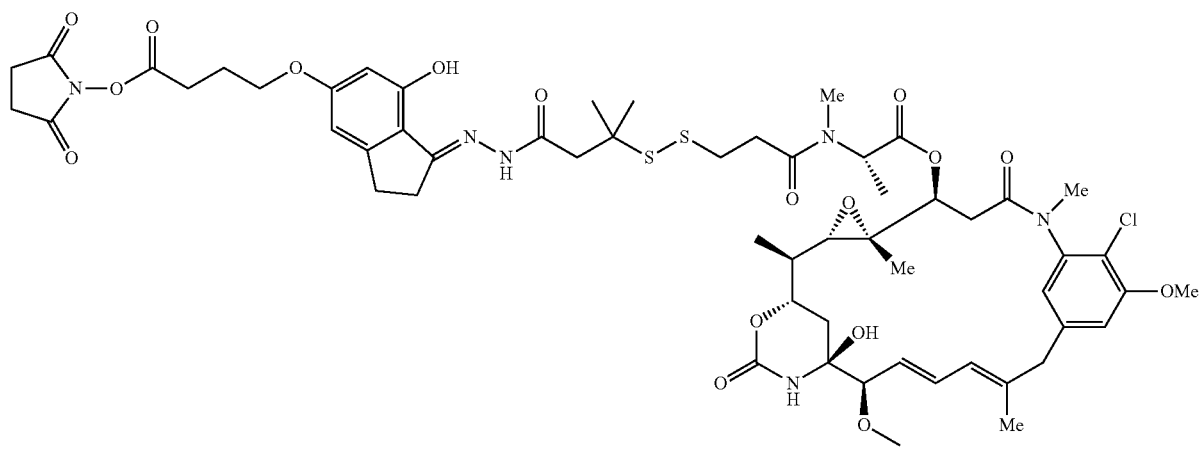

Linker-DM1 construct VIIc was prepared using a similar procedure to VIIa. It was collected as an-off white powder (5.7 mg, 28% yield, single isomer). $^1$H NMR (500 MHz, DMSO-d6) δ=10.50 (br s, 1H), 10.09 (br s, 1H), 7.15 (br s, 1H), 6.89 (br s, 1H), 6.66-6.60 (m, 1H), 6.59-6.48 (m, 3H), 6.33 (br s, 1H), 5.93 (s, 1H), 5.53 (br dd, J=9.2, 14.3 Hz, 1H), 5.31 (br d, J=6.7 Hz, 1H), 4.51 (br d, J=11.7 Hz, 1H), 4.08-4.04 (m, 2H), 3.90 (s, 3H), 3.49 (br d, J=8.8 Hz, 2H), 3.25 (s, 3H), 3.16 (s, 3H), 3.04 (br d, J=3.7 Hz, 2H), 2.83 (br d, J=8.6 Hz, 10H), 2.71 (br s, 3H), 2.09-2.02 (m, 3H), 1.58-1.51 (m, 6H), 1.49-1.40 (m, 4H), 1.23 (br s, 6H), 1.18-1.11 (m, 10H), 0.78 (br s, 3H); LCMS [M+H]$^+$ 1214.

6,7,8,9-Tetrahydro-5H-benzo[7]annulene Type Linker-DM1 Construct (VIIf)

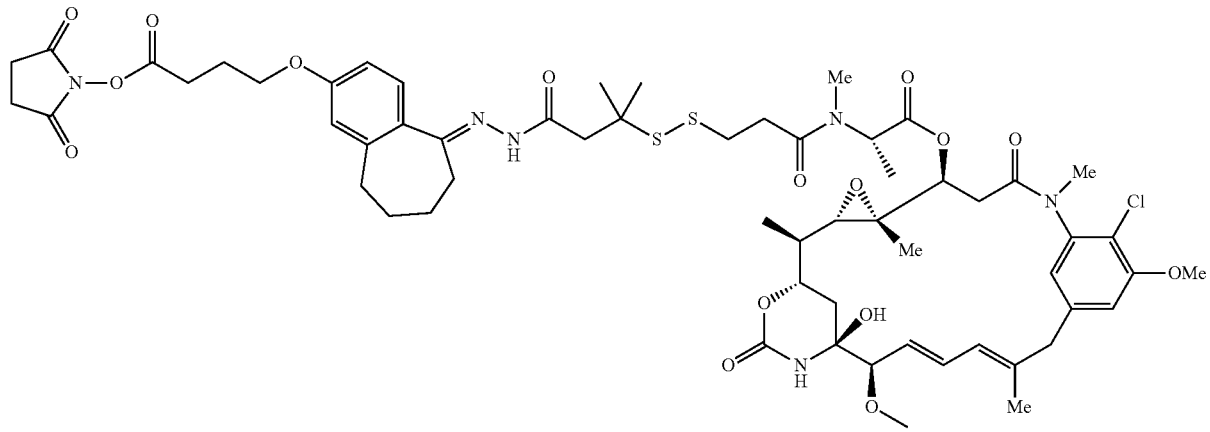

VIIf

Linker-DM1 construct VIIf was prepared using a similar procedure to VIIa. It was collected as a white powder (18 mg, 83% yield, 2 isomers). $^1$H NMR (500 MHz, DMSO-d6) δ=10.24 (s, 1H), 10.07 (s, 1H), 7.35-7.24 (m, 1H), 7.11-7.03 (m, 1H), 6.82 (br d, J=4.3 Hz, 1H), 6.76 (br t, J=8.4 Hz, 1H), 6.70 (br s, 1H), 6.59-6.51 (m, 1H), 6.50-6.44 (m, 2H), 5.85 (br d, J=6.4 Hz, 1H), 5.69 (br s, 1H), 5.51-5.39 (m, 1H), 5.28-5.18 (m, 1H), 4.50-4.39 (m, 1H), 4.04-3.95 (m, 3H), 3.84 (br d, J=5.9 Hz, 3H), 3.45-3.33 (m, 2H), 3.18 (br d, J=4.8 Hz, 3H), 3.09 (s, 2H), 3.05 (s, 2H), 2.82-2.71 (m, 10H), 2.65 (s, 2H), 2.59 (br s, 4H), 2.05-1.93 (m, 4H), 1.67-1.58 (m, 2H), 1.52 (s, 2H), 1.50 (br s, 2H), 1.47 (br s, 2H), 1.42-1.32 (m, 3H), 1.16 (br s, 6H), 1.12-1.08 (m, 3H), 1.05 (br d, J=5.6 Hz, 3H), 0.71 (br d, J=4.0 Hz, 3H); LCMS [M+H]$^+$ 1226.

2,3-Fluoro-dihydro-1H-indene Type Linker-DM1 Construct (VIIg)

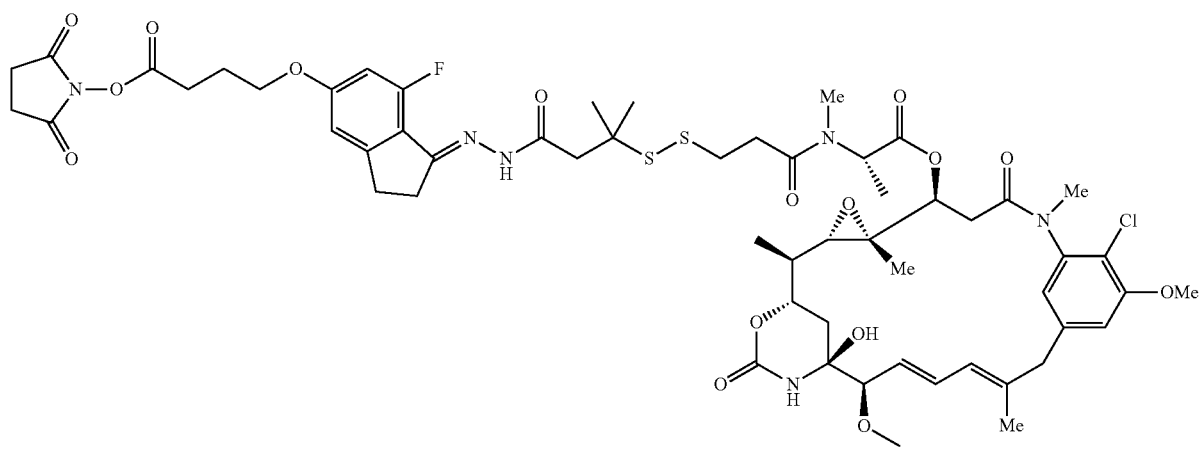

VIIg

Linker-DM1 construct VIIg was prepared using a similar procedure to VIIa. It was collected as a white powder (14.4 mg, 81% yield, 2 isomers). $^1$H NMR (500 MHz, DMSO-d6) δ=10.15 (s, 1H), 9.94 (s, 1H), 7.07 (br d, J=18.0 Hz, 1H), 6.84-6.80 (m, 1H), 6.75 (br d, J=11.6 Hz, 1H), 6.71-6.60 (m, 1H), 6.59-6.50 (m, 1H), 6.46 (br d, J=9.0 Hz, 1H), 5.86 (s, 1H), 5.68 (s, 1H), 5.47 (br dd, J=9.2, 14.8 Hz, 1H), 5.28-5.20 (m, 1H), 4.44 (br d, J=11.9 Hz, 1H), 4.07-3.96 (m, 3H), 3.84

(br d, J=7.8 Hz, 3H), 3.42 (br d, J=11.2 Hz, 2H), 3.18 (s, 2H), 3.08 (br d, J=12.8 Hz, 3H), 2.97 (br s, 2H), 2.93-2.85 (m, 1H), 2.81-2.70 (m, 12H), 2.64 (br d, J=7.0 Hz, 2H), 2.04-1.93 (m, 4H), 1.51 (br d, J=6.1 Hz, 3H), 1.44-1.29 (m, 4H), 1.22 (br d, J=5.6 Hz, 1H), 1.16 (br s, 3H), 1.15 (br s, 3H), 1.10 (br t, J=5.4 Hz, 3H), 1.05 (br d, J=6.0 Hz, 3H), 0.71 (br d, J=4.0 Hz, 3H); LCMS [M+H]$^+$ 1216.

Fluoro-5,6,7,8-tetrahydronaphthalen-1-ol Type Linker-DM1 Construct (VIIh)

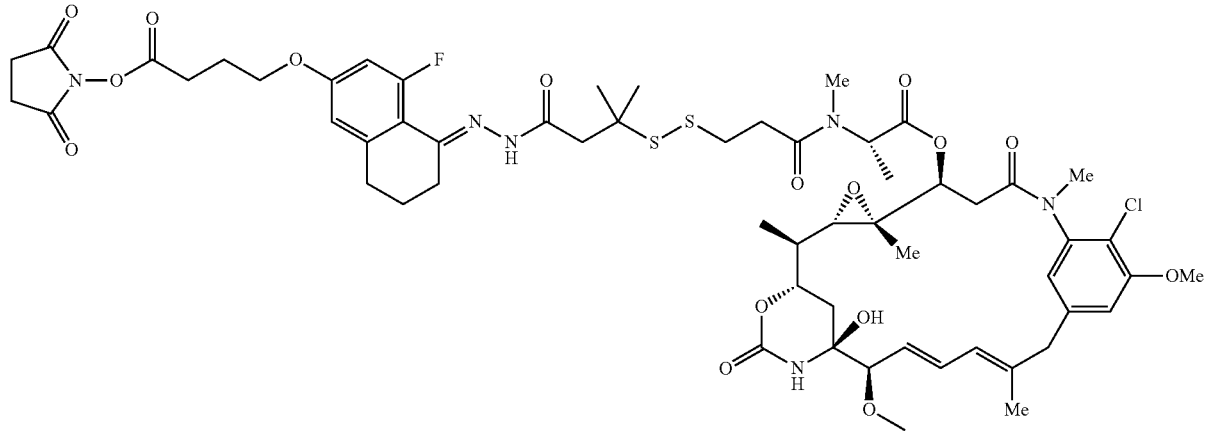

VIIh

Linker-DM1 construct VIIh was prepared using a similar procedure to VIIa. It was collected as a white powder (19 mg, 83% yield, 2 isomers). $^1$H NMR (DMSO-d6, 500 MHz) δ 10.29 (s, 1H), 10.11 (s, 1H), 7.1-7.2 (m, 1H), 6.89 (br s, 1H), 6.7-6.7 (m, 3H), 6.54 (br d, 3H, J=9.7 Hz), 5.9-5.9 (m, 1H), 5.76 (s, 1H), 5.5-5.6 (m, 1H), 5.3-5.4 (m, 1H), 4.52 (br d, 1H, J=10.9 Hz), 4.0-4.1 (m, 5H), 3.9-3.9 (m, 4H), 3.4-3.5 (m, 3H), 3.1-3.2 (m, 4H), 2.8-2.9 (m, 15H), 2.7-2.7 (m, 8H), 2.0-2.1 (m, 5H), 1.75 (br d, 3H, J=1.1 Hz), 1.6-1.6 (m, 4H), 1.4-1.5 (m, 5H), 1.2-1.3 (m, 1H), 1.23 (br s, 6H), 1.21 (s, 2H), 1.16 (br d, 3H, J=6.8 Hz), 1.13 (br d, 3H, J=5.9 Hz), 0.78 (br s, 3H); LCMS [M+H]$^+$ 1230.

Linker-DM1 Construct (VIIj):

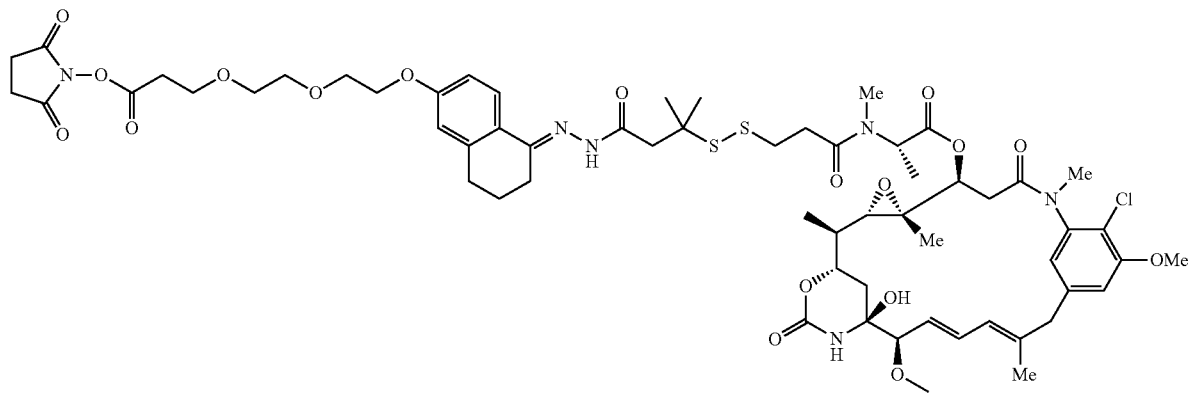

VIIj

Linker-DM1 construct VIIj was prepared using a similar procedure to VIIa. It was collected as a white powder (12.3 mg, 56% yield, 2 isomers). $^1$H NMR (500 MHz, DMSO-d6) δ=10.32 (s, 1H), 10.16 (s, 1H), 7.95 (br dd, J=8.7, 16.9 Hz, 1H), 7.18-7.07 (m, 1H), 6.89 (br d, J=2.9 Hz, 1H), 6.88-6.81 (m, 1H), 6.76 (br s, 1H), 6.61 (br d, J=11.5 Hz, 1H), 6.57-6.50 (m, 1H), 5.93 (br d, J=6.6 Hz, 1H), 5.76 (s, 1H), 5.61-5.47 (m, 1H), 5.38-5.21 (m, 1H), 4.57-4.43 (m, 1H), 4.14-4.04 (m, 3H), 3.91 (br d, J=6.0 Hz, 2H), 3.78-3.71 (m, 4H), 3.59 (br d, J=5.9 Hz, 4H), 3.54-3.46 (m, 2H), 3.25 (br d, J=6.6 Hz, 2H), 3.17 (s, 1H), 3.13 (s, 1H), 2.97 (br d, J=14.2 Hz, 1H), 2.93 (br t, J=5.8 Hz, 2H), 2.86 (br s, 1H), 2.81 (br s, 4H), 2.71 (br d, J=15.0 Hz, 5H), 2.09-2.00 (m, 1H), 1.87-1.74 (m, 2H), 1.58 (br d, J=11.9 Hz, 3H), 1.50-1.42 (m, 3H), 1.23 (br s, 3H), 1.22 (br s, 3H), 1.17 (br t, J=5.6 Hz, 3H), 1.13 (br d, J=6.0 Hz, 2H), 0.79 (br d, J=2.6 Hz, 3H); LCMS [M+H]$^+$ 1286.

Linker-DM1 Construct (VIII):

VIIi

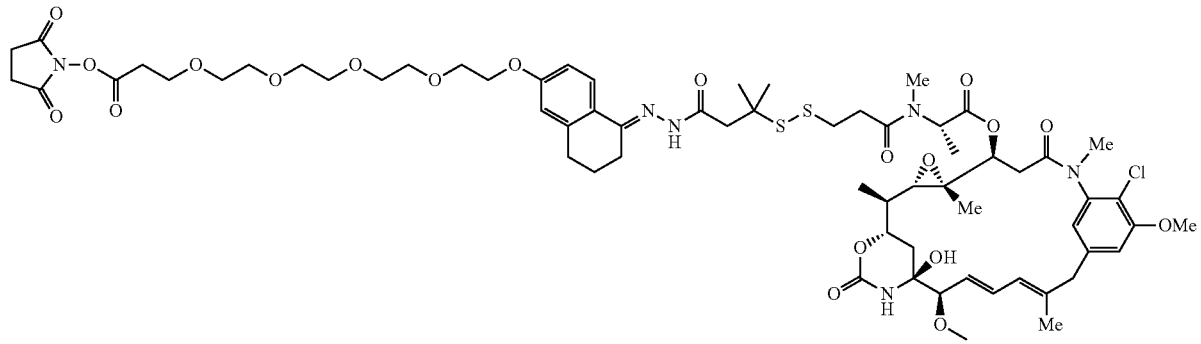

Linker-DM1 construct VIII was prepared using a similar procedure to VIIa. It was collected as a white powder (2.84 mg, 14.3% yield, 2 isomers). $^1$H NMR (500 MHz, DMSO-d6) δ=10.24 (s, 1H), 10.08 (s, 1H), 9.74 (s, 1H), 7.85 (br dd, J=8.7, 16.1 Hz, 1H), 7.10-7.00 (m, 1H), 6.82 (br d, J=4.0 Hz, 1H), 6.80-6.74 (m, 1H), 6.69 (br s, 1H), 6.58-6.51 (m, 1H), 6.49-6.43 (m, 1H), 5.85 (br d, J=7.1 Hz, 1H), 5.68 (br s, 1H), 5.53-5.41 (m, 1H), 5.28-5.16 (m, 1H), 4.48-4.38 (m, 1H), 4.07-3.94 (m, 3H), 3.84 (br d, J=5.7 Hz, 2H), 3.70-3.61 (m, 4H), 3.52 (br s, 2H), 3.48-3.41 (m, 12H), 3.09 (s, 2H), 3.06 (s, 2H), 2.89 (br d, J=13.3 Hz, 1H), 2.85 (br t, J=5.7 Hz, 2H), 2.78 (br d, J=9.2 Hz, 1H), 2.74 (br s, 4H), 2.65 (br s, 2H), 2.62 (br s, 2H), 2.57 (br s, 1H), 2.30 (br s, 1H), 2.01-1.94 (m, 1H), 1.78-1.68 (m, 3H), 1.50 (br d, J=12.0 Hz, 3H), 1.43-1.30 (m, 7H), 1.20-1.18 (m, 1H), 1.16 (br s, 3H), 1.15 (br s, 3H), 1.12-1.08 (m, 3H), 1.05 (br d, J=6.0 Hz, 3H), 0.79 (br dd, J=6.7, 10.7 Hz, 1H), 0.71 (br d, J=3.7 Hz, 3H); LCMS [M+H]$^+$ 1374.

Synthesis of Linker-MonoMethyl Auristatin E (MMAE) Constructs

The representative linkers are conjugated to MMAE via a disulfide bond formation reaction according to the synthetic procedures described in schemes (14) and (15). MMAE intermediate 7-5 was prepared in 4 steps from commercially available (tert-butoxycarbonyl)-L-valyl-L-alanine. It was reacted with 3-((5-nitropyridin-2-yl)disulfaneyl)propanoic acid to form the MMAE-propanoyl-thio(5-nitropyridine) intermediate 7-6. This intermediate was then reacted with thiol of linkers (for example: la-1) to form the disulfide bond between the linker and MMAE intermediate which gave the final linker MMAE constructs (VIIk, VIIb, VIIL and VIIm) that are ready for antibody conjugation.

Scheme 14

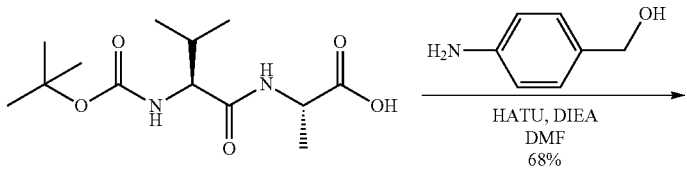

HATU, DIEA
DMF
68%

-continued
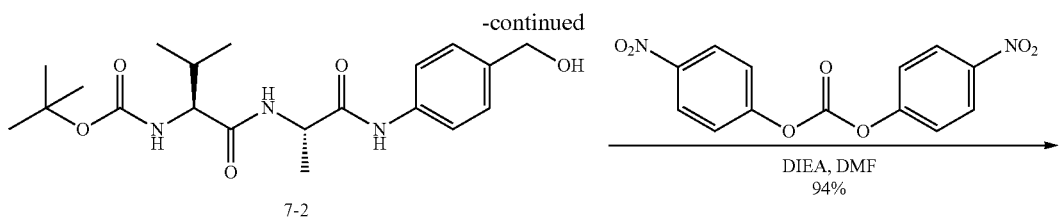
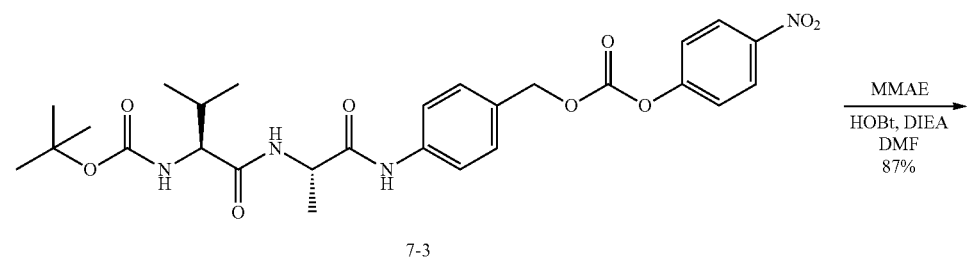
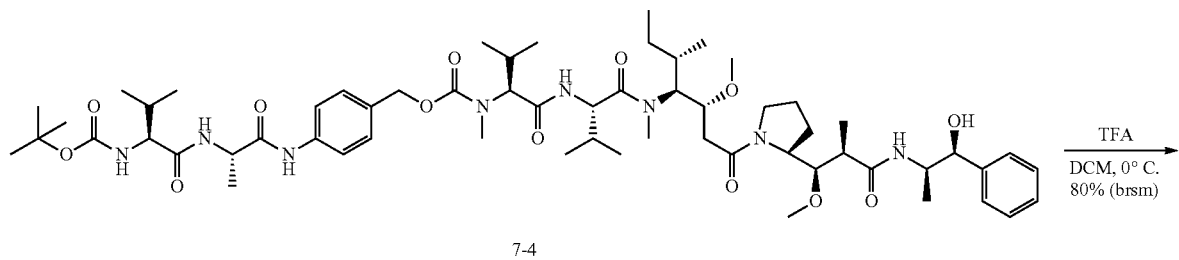
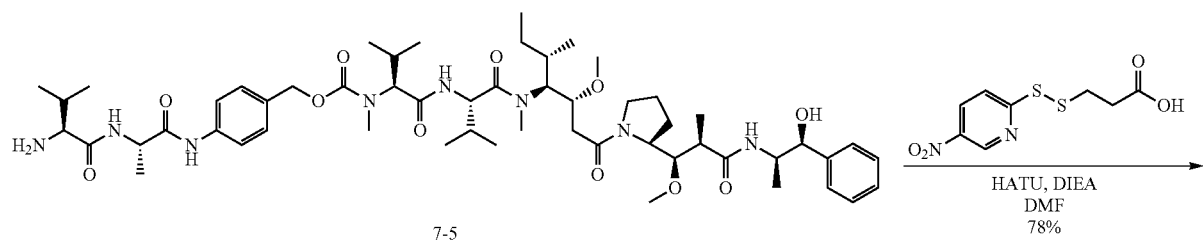
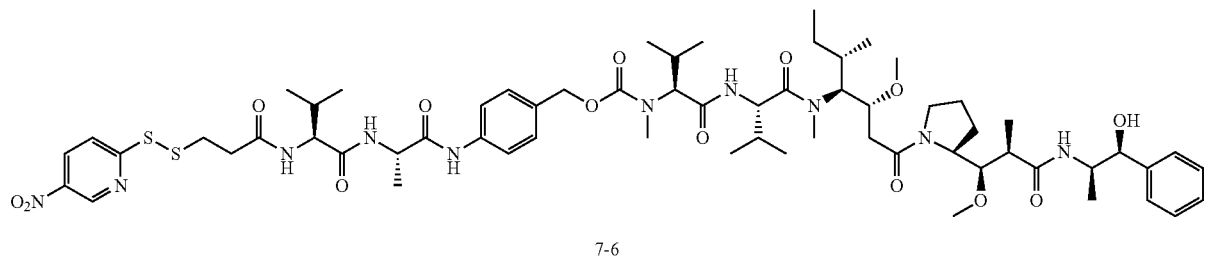

115 tert-Butyl((S)-1-(((S)-1-((4-(hydroxymethyl)phenyl)amino)-1-oxopropan-2-yl)amino)-3-methyl-1-oxobutan-2-yl)carbamate (7-2)

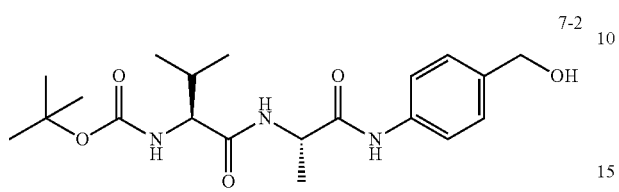

A solution (tert-butoxycarbonyl)-L-valyl-L-alanine (285 mg, 0.988 mmol) and 4-aminobenzyl alcohol (183 mg, 1.483 mmol) in THF (5 ml)) was treated with EEDQ (367 mg, 1.483 mmol) then the solution was stirred at room temperature. After 1 h, no product was observed. DMF (5 ml) and HATU (564 mg, 1.483 mmol) were added. After 5 min, N,N-diisopropylethylamine (0.689 ml, 3.95 mmol) was added after which LCMS showed completion. The mixture was stirred for an additional 1 h. The volatile solvents were removed under reduced pressure. The crude was diluted with EtOAc. The organic layer was washed with water (×3). A small amount of brine was added to break any suspension that has formed. It was washed with brine and dried over $Na_2SO_4$. It was concentrated down, loaded on celite and dried. The crude was purified over Isco (12 g silica column; eluent EtOAc/Hexanes: 0-70% then 70%) to afford the title compound 7-2 as an off-white solid (265 mg, 68% yield). $^1$H NMR (DMSO-d6, 500 MHz) δ 9.93 (br s, 1H), 8.05 (br d, 1H, J=6.7 Hz), 7.53 (br d, 2H, J=8.2 Hz), 7.24 (br d, 2H, J=8.1 Hz), 6.74 (br d, 1H, J=8.7 Hz), 5.10 (t, 1H, J=5.6 Hz), 4.43 (br d, 2H, J=5.3 Hz), 3.84 (br t, 1H, J=7.5 Hz); 1.9-2.0 (m, 1H), 1.39 (s, 9H), 1.30 (br d, 3H, J=6.8 Hz), 0.87 (br d, 3H, J=6.5 Hz), 0.82 (br d, 3H, J=6.4 Hz); LCMS [M+H]$^+$ 394.

116 tert-Butyl((S)-3-methyl-1-(((S)-1-((4-(((((4 nitrophenoxy)carbonyl)oxy)methyl)phenyl)amino)-1-oxopropan-2-yl)amino)-1-oxobutan-2-yl)carbamate (7-3)

To a 100 ml RB flask containing tert-butyl ((S)-1-(((S)-1-((4-(hydroxymethyl)phenyl)amino)-1-oxopropan-2-yl)amino)-3-methyl-1-oxobutan-2-yl)carbamate 7-2 (263 mg, 0.668 mmol) was added bis(4-nitrophenyl) carbonate (244 mg, 0.802 mmol) then DMF (3 ml). N,N-Diisopropylethylamine (0.466 ml, 2.67 mmol) was added to this stirring mixture. After 2 h at rt, LCMS showed almost completion. The solvent was evaporated under high vacuum. The crude was purified over Isco (12 g silica column, eluent: EtOAc/Hexanes; 0%, 0-50% then 50%) to give the title compound 7-3 as an off-white waxy solid (352 mg, 94% yield). $^1$H NMR (DMSO-d6, 500 MHz) δ 10.10 (br s, 1H), 8.32 (br d, 2H, J=8.9 Hz), 8.10 (br d, 1H, J=6.7 Hz), 7.64 (br d, 2H, J=8.2 Hz), 7.58 (br d, 2H, J=8.9 Hz), 7.42 (br d, 2H, J=8.3 Hz), 6.73 (br d, 1H, J=8.7 Hz), 5.25 (s, 2H), 4.44 (br t, 1H, J=6.7 Hz), 3.85 (br t, 1H, J=7.5 Hz), 2.90 (s, 1H), 2.74 (s, 1H), 1.9-2.0 (m, 1H), 1.39 (s, 9H), 1.32 (br d, 3H, J=7.0 Hz), 0.88 (br d, 3H, J=6.7 Hz), 0.83 (br d, 3H, J=6.5 Hz); LCMS [M+H]$^+$ 559.

MMAE Intermediate (7-4):

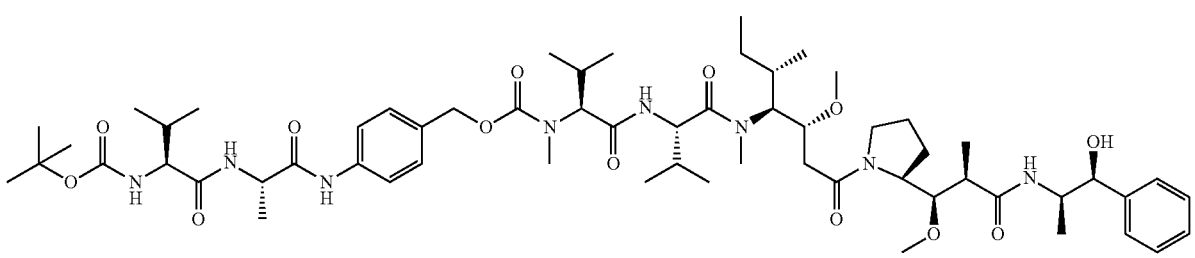

A 100 ml RB flask containing tert-butyl((S)-3-methyl-1-(((S)-1-((4-(((((4nitrophenoxy)carbonyl)oxy)methyl)phenyl)amino)-1-oxopropan-2-yl)amino)-1-oxobutan-2-yl)carbamate 7-3 (349 mg, 0.625 mmol) was charged with monomethyl auristatin E (MMAE) (359 mg, 0.500 mmol) and 1-hydroxybenzotriazole (HOBt) (41.5 mg, 0.307 mmol). DMF (10 ml) was added then the mixture was stirred at rt. N,N-Diisopropylethylamine (0.216 ml, 1.240 mmol) was slowly added via a syringe. After about 24 h at rt, LCMS showed almost completion. The solvent was evaporated under high vacuum. The crude was purified by Isco (12 g column, eluent: EtOAc/Hexanes: 0-100% then 100%) to give the title compound 7-4 as a white foamy solid (493 mg, 87% yield). LCMS [M+H]$^+$1138.

MMAE Intermediate (7-5):

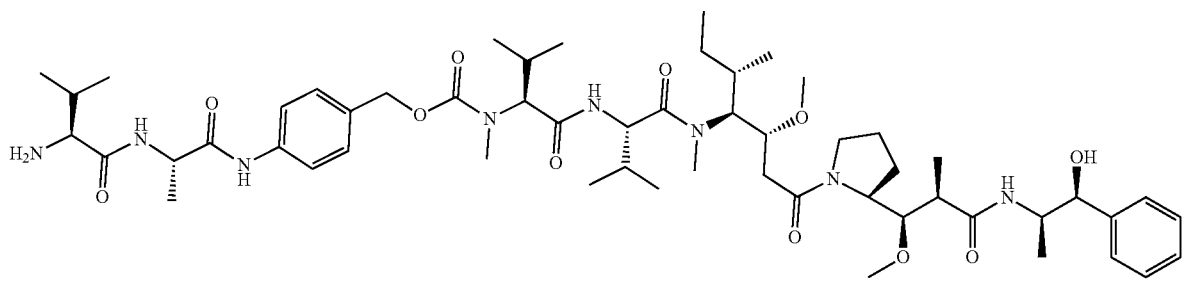

7-5

To a 100 ml RB flask containing MMAE intermediate 7-4 (477 mg, 0.419 mmol) was added dichloromethane (20 ml). The mixture was cooled to 0° C. with an ice bath upon which trifluoroacetic acid (4.00 ml) was added dropwise via a syringe. After 15 min, 2 ml of TFA were added. The mixture was stirred for another 15 min then the solvents were evaporated off. The crude was dissolved in MeOH, loaded on celite and dried. It was purified over Isco (13 g C18 column, eluent: $CH_3CN/H_2O$: 10-100% then 100%). The title compound 7-5 was collected as an off-white solid (307 mg, 80% yield brsm). LCMS $[M+H]^+$ 1038.

MMAE Intermediate (7-6):

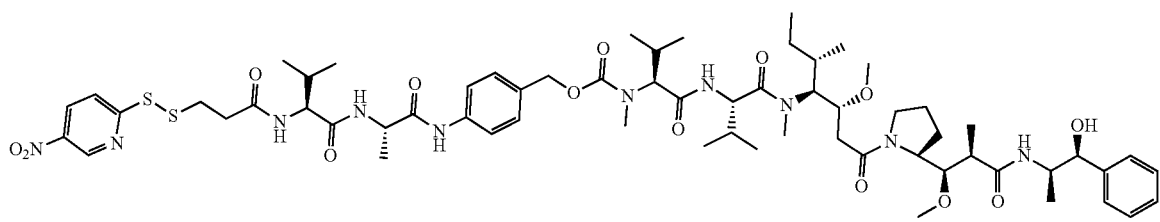

7-6

To a 100 ml RB flask containing MMAE intermediate 7-5 (305 mg, 0.265 mmol), HATU (151 mg, 0.397 mmol) and 3-((5-nitropyridin-2-yl)disulfanyl)propanoic acid (68.9 mg, 0.265 mmol) was added DMF (6 ml). The mixture was stirred for 5 min at rt upon which N,N-diisopropylethylamine (0.231 ml, 1.325 mmol) was added via a syringe. After 30 min at rt, LCMS showed completion. Some celite was added then it was dried for a short time under reduced pressure. The crude was purified over Isco reverse phase (13 g C18 column, eluent: $CH_3CN$/water 10-30%, 30-100% then 100%) to afford the title compound 7-6 as a light orange solid (265 mg, 78% yield). LCMS $[M+H]^+$ 1280.

Synthesis of the Final Linker-MMAE Constructs

The final linker-MMAE constructs were prepared using the same thiol exchange reaction used for the preparation of linker-DM1 constructs as described in Scheme (15).

Scheme 15

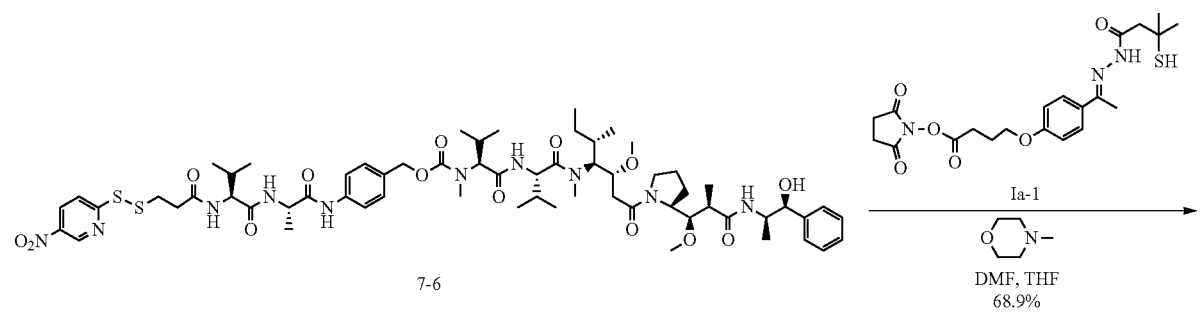

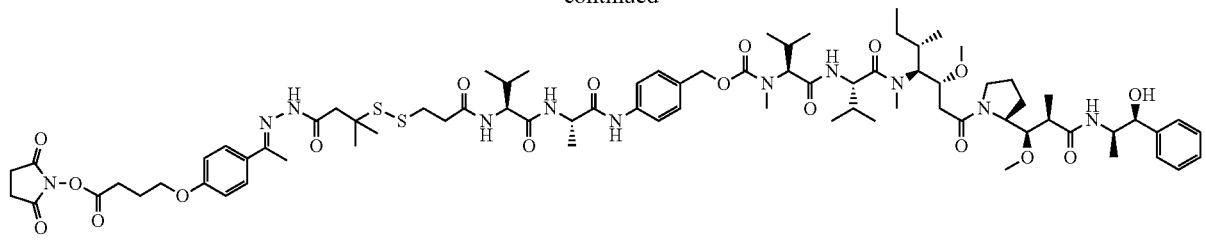

VIIk

Linker-MMAE Construct (VIM):

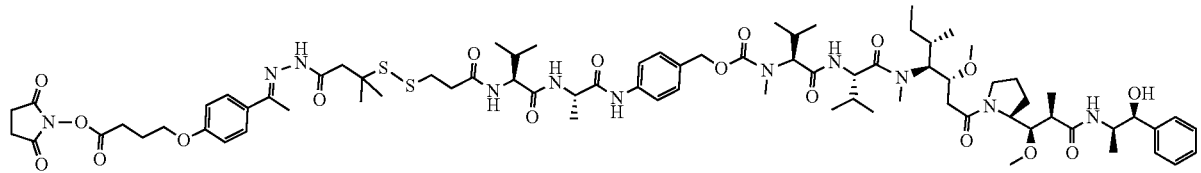

VIIk

MMAE intermediate 7-6 (16.6 mg, 0.013 mmol) was dissolved in DMF (1 ml) then 2,5-dioxopyrrolidin-1-yl-4-(4-(1-(2-(3-mercapto-3-methylbutanoyl)hydrazono)ethyl)phenoxy)butanoate Ia-1 (16.39 mg, 0.036 mmol) in THF (1 ml) was added. 4-Methylmorpholine (0.031 ml, 0.016 mmol) as a (0.5 M) solution in of DMF was added. The mixture was stirred at room temperature for 45 min upon which LCMS showed completion. The crude mixture was separated between water and EtOAc and shaken. The organic layer was washed with water (×3) then brine. It was dried over $Na_2SO_4$ and concentrated down. The crude was purified over Isco (4 g silica column; eluent: EtOAc/Hexanes; 0-100% then 100% EtOAc followed by acetone/EtOAc 0-60% then 60%). The right product was taken in acetonitrile frozen then lyophilized to give the title compound VIIk as a white fluffy powder (14.8 mg, 68.9% yield). LCMS $[M+H]^+$ 1573.

Linker-MMAE Construct (VIIIb):

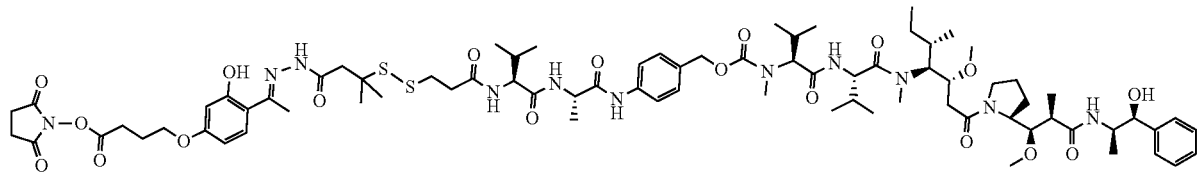

VIIIb

Linker-MMAE construct VIIIb was prepared using a similar procedure to linker-MMAE construct VIIk. It was collected as a white fluffy powder (2.4 mg, 12% yield). LCMS $[M+H]^+$ 1589.

Linker-MMAE Construct (VIIL):

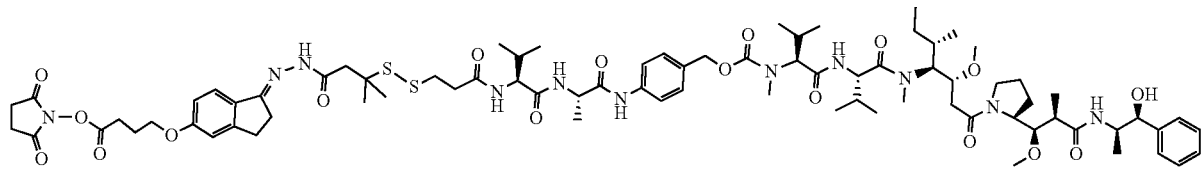

VIIL

Linker-MMAE construct VIIL was prepared using a similar procedure to linker-MMAE construct VIIk. It was collected as a white fluffy powder (7.8 mg, 39.4% yield). LCMS [M+H]+ 1585.

Linker-MMAE Construct (VIIm)

VIIm

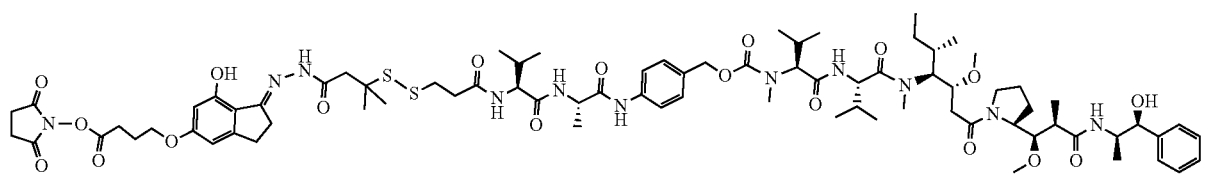

Linker-MMAE construct VIIm was prepared using a similar procedure to linker-MMAE construct VIIk. It was collected as a white fluffy powder (12.8 mg, 63.9% yield). LCMS [M+H]+1601.

Other representative linkers are conjugated to MMAE via a disulfide bond formation reaction according to the synthetic procedures described in scheme (16) and (17). MMAE intermediate 7-8 was prepared in 2 steps from commercially available (9H-fluoren-9-yl)methyl ((S)-3-methyl-1-(((S)-1-((4-((((4-nitrophenoxy)carbonyl)oxy)methyl)phenyl) amino)-1-oxo-5-ureidopentan-2-yl)amino)-1-oxobutan-2-yl)carbamate (Fmoc-Val-Cit-PAB-pnp). It was reacted with 3-((5-nitropyridin-2-yl)disulfaneyl)propanoic acid to form the MMAE-propanoyl-thio(5-nitropyridine) intermediate 7-9. This intermediate was then reacted with thiol of linker type Ia-1 to form the disulfide bond between the linker and MMAE intermediate which gave the final linker MMAE constructs (VIIn, VIIIc, VIIp and VIIq) that are ready for antibody conjugation.

Scheme 16

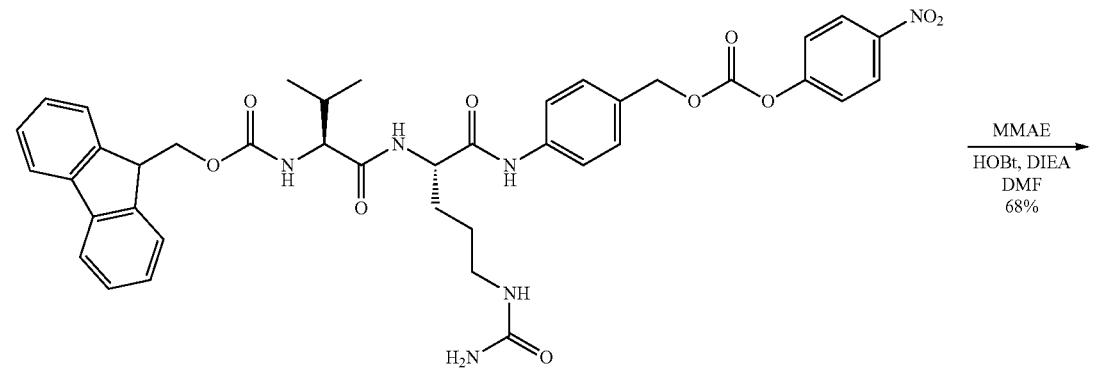

Fmoc-Val-Cit-PAB-pnp

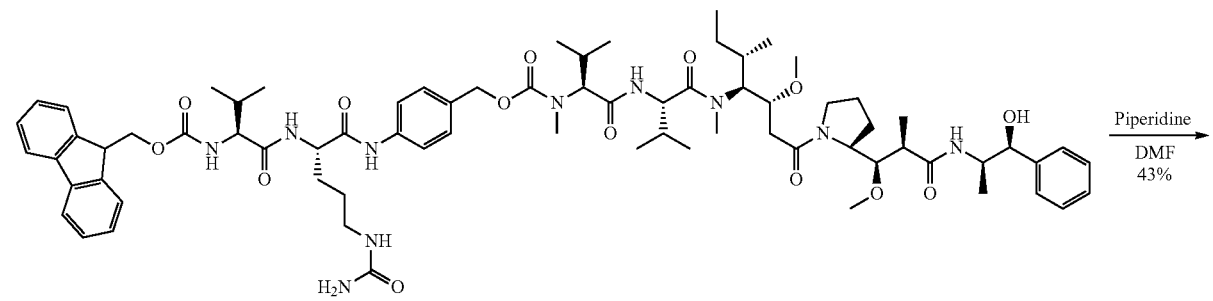

7-7

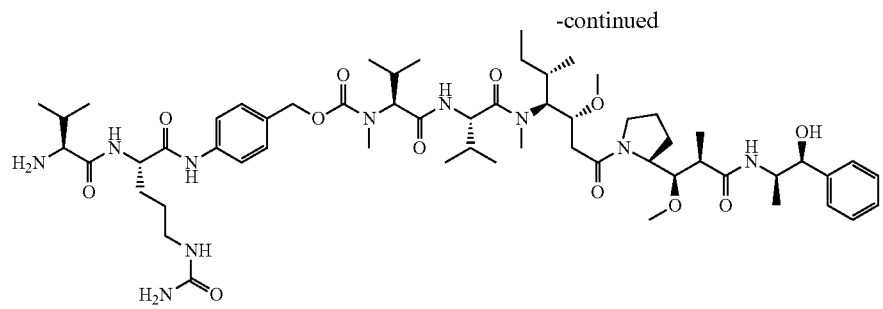 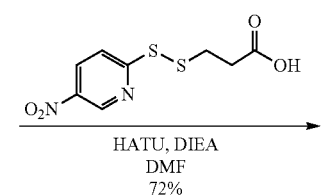

7-8

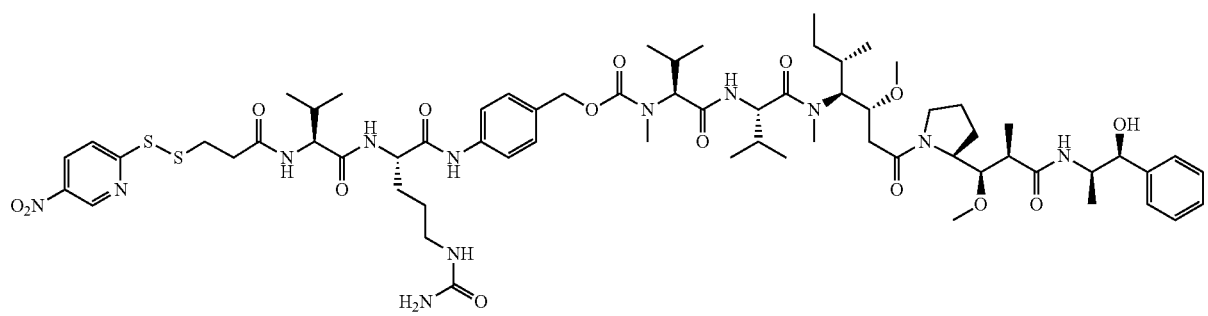

7-9

MMAE Intermediate (7-7):

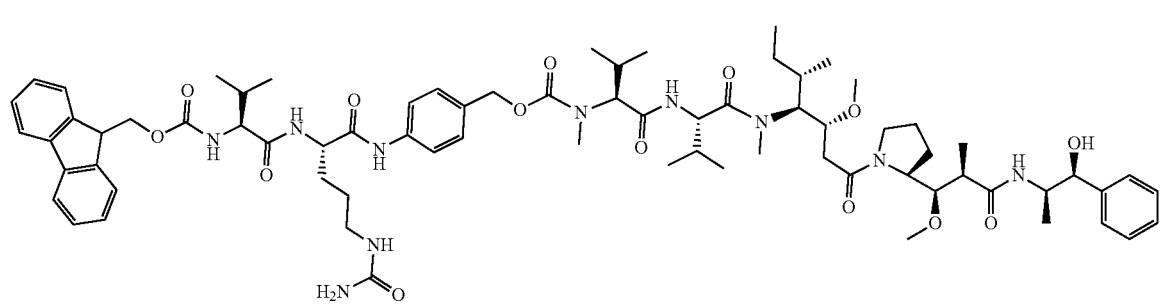

7-7

A 100 ml RB flask was charged with monomethyl auristatin E (MMAE) (200 mg, 0.279 mmol), 1-hydroxybenzotriazole (23.34 mg, 0.173 mmol) and Fmoc-Val-Cit-PAB-pnp (269 mg, 0.351 mmol). N,N-Dimethylformamide (8 ml) was added then the mixture was stirred at rt upon which N,N-diisopropylethylamine (0.121 ml, 0.696 mmol) was slowly added via a syringe. After 1 day at rt, LCMS showed almost completion. The solvent was evaporated under high vacuum. The crude was dissolved in a small volume of DMF, loaded on celite and dried. It was purified by Isco (12 g silica column, eluent: EtOAc/Hexanes: 0-100% then 100% followed by DCM/MeOH: 0-20% then 20%) to give the title compound as an off-white solid (256 mg, 68% yield). LCMS [M+H]$^+$1346.

MMAE Intermediate (7-8):

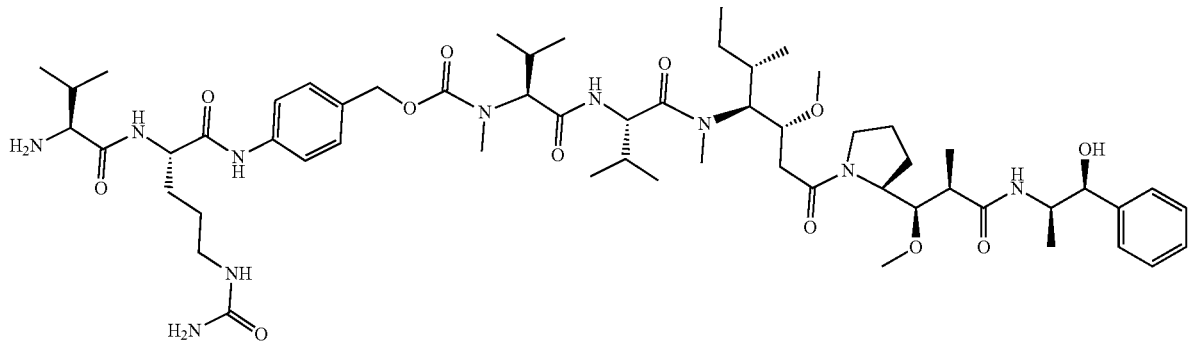

7-8

MMAE intermediate 7-7 (256 mg, 0.190 mmol) was dissolved in N,N-dimethylformamide (4 ml) then piperidine (1.997 mmol, ~1 ml (20% in DMF)) was added. The mixture was stirred at rt for 30 min upon which LCMS showed completion. Celite was added and it was dried. It was purified by Isco reverse phase (13 g C18 column; eluent CH$_3$CN/water: 10-100% then 100%) to afford the title compound 7-8 as an off-white solid (92 mg, 43% yield). LCMS [M+H]$^+$ 1124.

MMAE Intermediate (7-9):

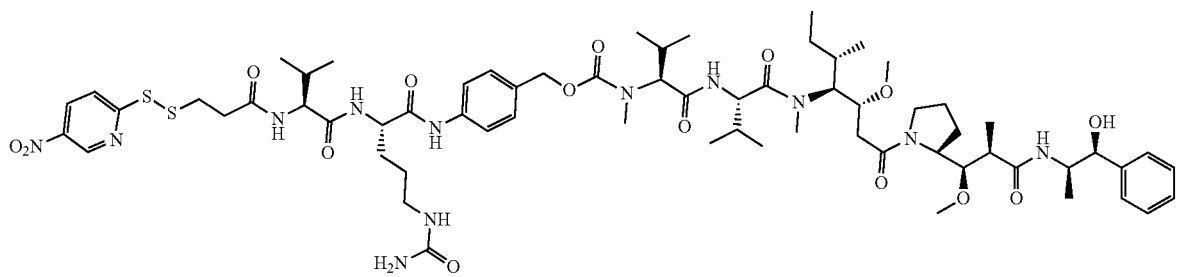

7-9

To a 100 ml RB flask containing MMAE intermediate 7-8 (91 mg, 0.081 mmol), HATU (46.2 mg, 0.122 mmol) and 3-((5-nitropyridin-2-yl)disulfanyl)propanoic acid (21.08 mg, 0.081 mmol) were added. N,N-Dimethylformamide (3 ml) was added and the resulting solution was stirred for 5 min upon which N,N-diisopropylethylamine (0.056 ml, 0.324 mmol) was added. After stirring at room temperature for 30 min, LCMS showed completion. Some celite was added then it was dried for a short time under reduced pressure. It was purified over Isco reverse phase (13 g C18 column; eluent CH$_3$CN/water: 10-100% then 100%). The title compound 7-9 was lyophilized from acetonitrile. It was collected as a very light orange fluffy powder with a partial orange glassy solid (79.6 mg, 72% yield). LCMS [M+H]$^+$ 1366.

Linker-MMAE Constructs

Scheme 17

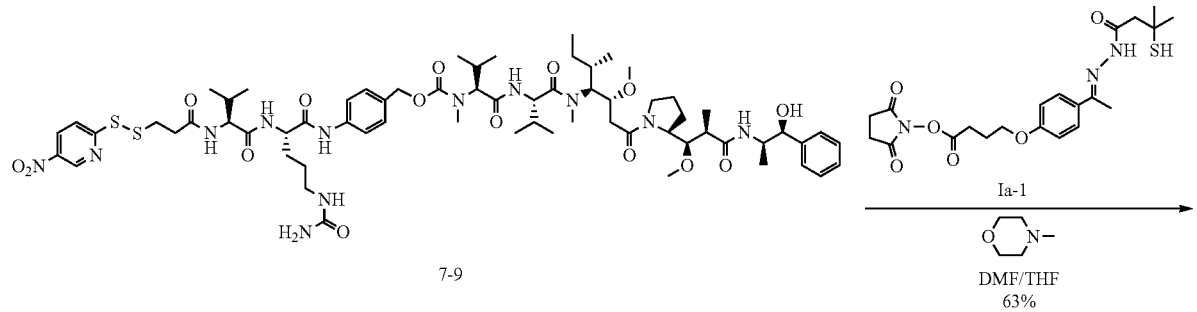

-continued

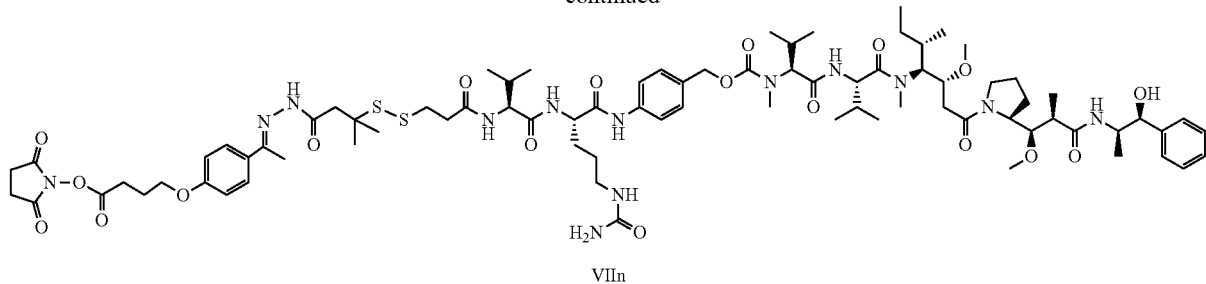

Linker-MMAE Construct (VIIn):

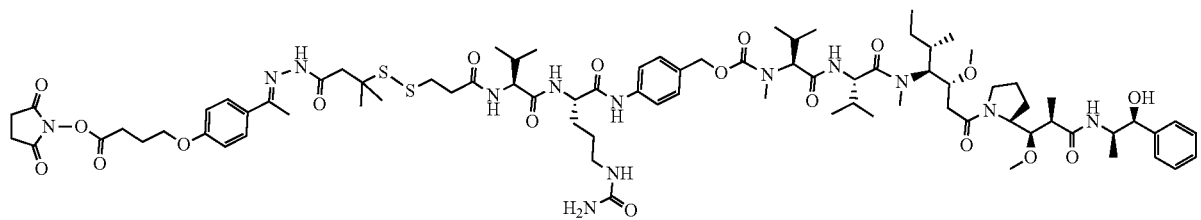

MMAE intermediate 7-9 (18.6 mg, 0.014 mmol) was dissolved in DMF (1 ml) then crude 2,5-dioxopyrrolidin-1-yl-4-(4-(1-(2-(3-mercapto-3-methylbutanoyl)hydrazono)ethyl)phenoxy)butanoate Ia-1 (25.5 mg, 0.057 mmol) in THF (2.6 ml) was added. The mixture was stirred at rt upon which 4-methylmorpholine (0.033 ml, 0.016 mmol) as a (0.5 M) solution in DMF was added. The mixture was stirred at room temperature for 20 min upon which LCMS showed completion. The crude mixture was separated between water and EtOAc then shaken. The organic layer was washed with water (×3) then brine. It was dried over $Na_2SO_4$ and concentrated down. The crude was purified over Isco (4 g silica column; eluent: EtOAc/Hexanes; 0-100% then 100% EtOAc followed by acetone/EtOAc 0-60%, 60%, 60-100% then 100%). The product was taken into acetonitrile frozen then lyophilized. The title compound VIIn was collected as a white fluffy powder (15 mg, 63% yield). LCMS $[M+H]^+$ 1659.

Linker-MMAE Construct (VIIIc):

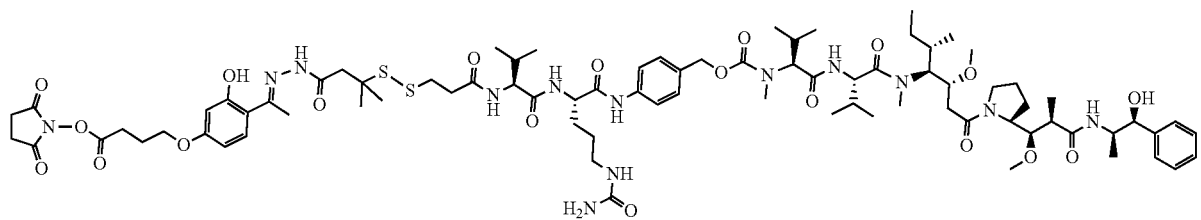

Linker-MMAE construct VIIIc was prepared using a similar procedure to linker-MMAE construct VIIn. It was collected as a white fluffy powder (12.7 mg. 60% yield). LCMS $[M+H]^+$ 1675.

Linker-MMAE Construct (VIIp):

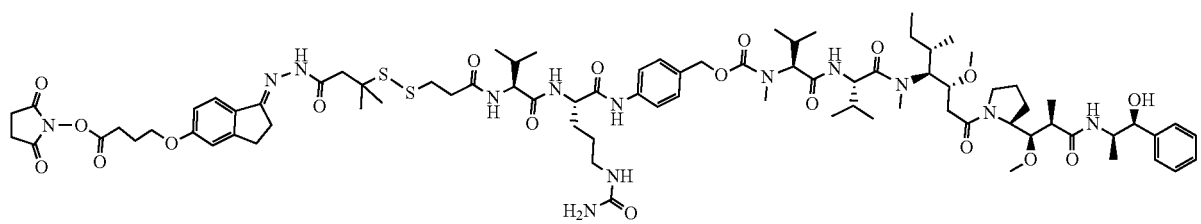

Linker-MMAE construct VIIp was prepared using a similar procedure to linker-MMAE construct VIIn. It was collected as a white fluffy powder (10.5 mg, 55.5% yield). LCMS [M+H]$^+$ 1671.

Linker-MMAE Construct (VIIq):

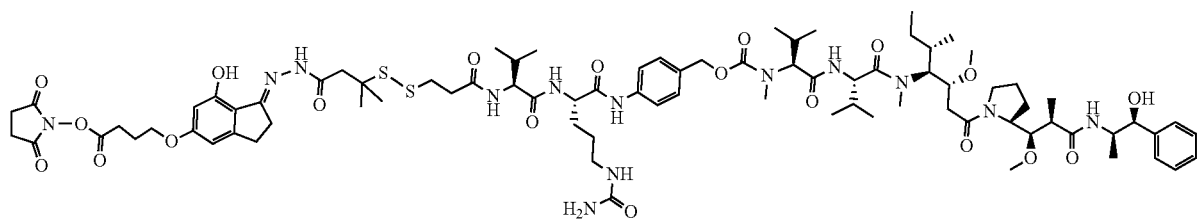

VIIq

Linker-MMAE construct VIIq was prepared using a similar procedure to linker-MMAE construct VIIn. It was collected as a white fluffy powder (5.6 mg, 28% yield). LCMS [M+H]$^+$ 1687.

Synthesis of Linker-DM1 for Cysteine Conjugation

Scheme 18

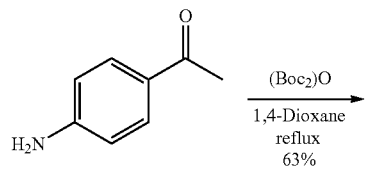

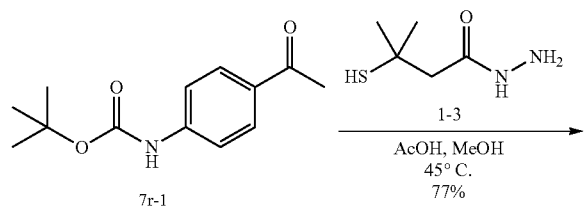

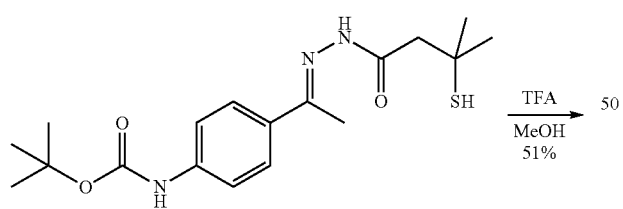

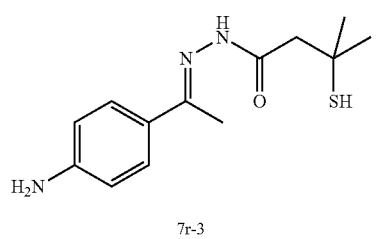

tert-Butyl(4-acetylphenyl)carbamate (7r-1)

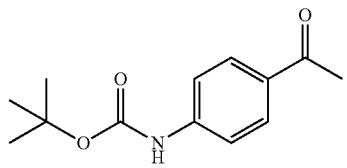

7r-1

To a solution of p-aminoacetophenone (1 g, 7.40 mmol) in 1,4-dioxane (22 ml) was added di tert-butyldicarbonate (2.099 g, 9.62 mmol). The solution was refluxed overnight and then cooled to room temperature. The solvent was removed and the residue was taken in EtOAc and washed with 1M HCl (×3). The organic layer was dried over Na$_2$SO$_4$ and concentrated down. The crude material was purified using Isco (24 g silica column; eluent EtOAc/Hexanes:0-50%) to afford the title compound 7r-1 as a white solid (1.504 g, 63% yield). $^1$H NMR (500 MHz, CDCl$_3$) δ=7.93 (br d, J=8.3 Hz, 2H), 7.47 (br d, J=8.2 Hz, 2H), 6.73 (br s, 1H), 2.58 (s, 3H), 1.55 (s, 9H); LCMS [M+H]$^+$ 236.

tert-Butyl(5-oxo-5,6,7,8-tetrahydronaphthalen-2-yl)carbamate (7s-1)

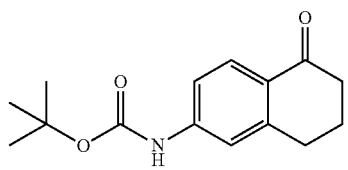

7s-1

The title compound 7s-1 was prepared according to a similar procedure to compound 7r-1. It was obtained as a yellow solid (1.296 g, 40% yield). $^1$H NMR (500 MHz, CDCl$_3$) δ=7.99 (d, J=8.4 Hz, 1H), 7.51 (s, 1H), 7.11 (dd, J=2.1, 8.6 Hz, 1H), 6.66 (br s, 1H), 2.95 (t, J=6.1 Hz, 2H), 2.63 (t, J=1.0 Hz, 2H), 2.13 (quin, J=6.4 Hz, 2H), 1.55 (s, 9H); LCMS [M+H]$^+$ 262.

tert-Butyl(1-oxo-2,3-dihydro-1H-inden-5-yl)carbamate (7t-1)

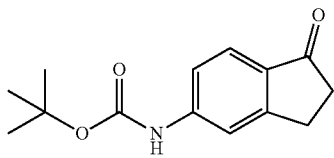

7t-1

The title compound 7t-1 was prepared according to a similar procedure to compound 7r-1. It was obtained as an orange solid (439.35 mg, 87% yield). $^1$H NMR (500 MHz, CDCl$_3$) δ=7.78 (br s, 1H), 7.69 (br d, J=8.3 Hz, 1H), 7.14 (br d, J=8.3 Hz, 1H), 6.76 (br s, 1H), 3.14-3.10 (m, 2H), 2.72-2.68 (m, 2H), 1.56 (s, 9H); LCMS [M+H]$^+$ 248.

tert-Butyl(5-oxo-6,7,8,9-tetrahydro-5H-benzo[7]annulen-2-yl)carbamate (7u-1)

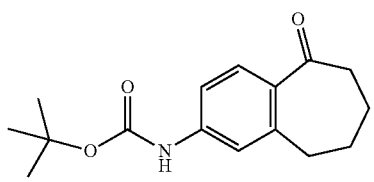

7u-1

The title compound 7u-1 was prepared according to a similar procedure to compound 7r-1. It was obtained as a dark orange oil (460 mg, 97% yield). $^1$H NMR (500 MHz, CDCl$_3$) δ=7.75 (d, J=8.4 Hz, 1H), 7.43 (br s, 1H), 7.15 (br d, J=8.4 Hz, 1H), 6.66 (br s, 1H), 2.93 (br t, J=6.2 Hz, 2H), 2.75-2.71 (m, 2H), 1.92-1.86 (m, 2H), 1.84-1.79 (m, 2H), 1.55 (s, 9H); LCMS [M+H]$^+$ 276.

tert-Butyl-(4-(1-(2-(3-mercapto-3-methylbutanoyl)hydrazineylidene)ethyl) phenyl)carbamate (7r-2)

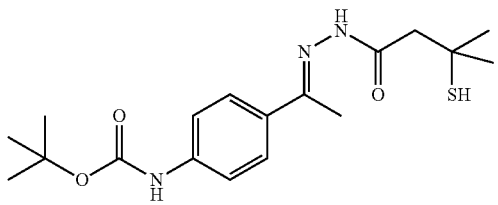

7r-2

To a solution of 3-mercapto-3-methylbutanehydrazide 1-3 (219 mg, 1.479 mmol) in methanol was added 7r-1 (347.95 mg, 1.479 mmol) and AcOH (592 µl, 10.35 mmol). The reaction was heated at 45° C. for 5 h upon which LCMS showed completion. The solvent and acetic acid were evaporated under reduced pressure. The crude residue was purified on using Isco (12 g silica column; eluent EtOAc/Hexanes: 0-100%) to afford the title compound 7r-2 as a yellow solid (414.57 mg, 77% yield, 2 isomers). $^1$H NMR (500 MHz, DMSO-d6) δ=9.51 (br d, J=6.6 Hz, 1H), 7.69 (br dd, J=6.3, 8.5 Hz, 2H), 7.49 (br d, J=7.9 Hz, 2H), 2.52-2.50 (m, 9H), 2.00 (s, 2H), 1.49 (s, 9H); LCMS [M+H]$^+$ 366.

tert-Butyl-(5-(2-(3-mercapto-3-methylbutanoyl)hydrazineylidene)5,6,7,8-tetrahydronaphthalen-2-yl)carbamate (7s-2)

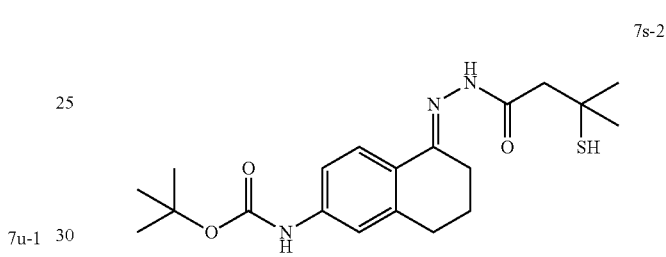

7s-2

The title compound 7s-2 was prepared according to a similar procedure to compound 7r-2. It was obtained as a white solid (166.53 mg, 47% yield, 2 isomers). $^1$H NMR (500 MHz, DMSO-d$_6$) δ=10.32 (s, 1H), 10.18 (br s, 1H), 9.46 (br d, J=7.5 Hz, 1H), 7.89 (t, J=9.5 Hz, 1H), 7.40-7.33 (m, 1H), 7.30-7.23 (m, 1H), 2.71-2.66 (m, 2H), 2.64 (s, 1H), 2.58 (td, J=6.4, 12.5 Hz, 2H), 2.51-2.50 (m, 7H), 1.87-1.74 (m, 2H), 1.48 (s, 9H); LCMS [M+H]$^+$ 392.

tert-Butyl-(1-(2-(3-mercapto-3-methylbutanoyl)hydrazineylidene)2,3-dihydro-1H-inden-5-yl)carbamate (7t-2)

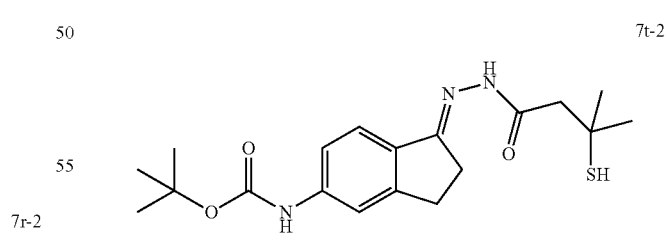

7t-2

The title compound 7t-2 was prepared according to a similar procedure to compound 7r-2. It was obtained as an orange solid (208.16 mg, 81% yield, 2 isomers). $^1$H NMR (500 MHz, CDCl$_3$) δ=9.53 (br s, 1H), 7.65 (br d, J=8.3 Hz, 1H), 7.11 (br d, J=8.2 Hz, 1H), 6.77 (s, 1H), 3.18 (s, 1H), 3.16-0.311 (m, 2H), 2.83-2.78 (m, 2H), 2.60 (s, 1H), 2.57 (s, 1H), 2.12 (s, 6H), 1.55 (s, 9H); LCMS [M+H]$^+$ 378.

tert-Butyl-(5-(2-(3-mercapto-3-methylbutanoyl)hydrazineylidene)6,7,8,9-tetrahydro-5H-benzo[7]annulen-2-yl)carbamate (7u-2)

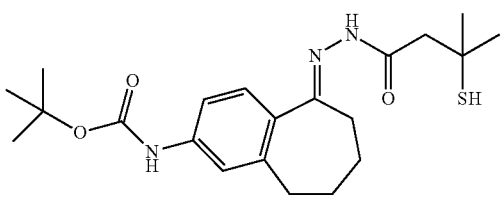

7u-2

The title compound 7u-2 was prepared according to a similar procedure to compound 7r-2. It was obtained as an orange solid (270 mg, 98% yield, 2 isomers). $^1$H NMR (500 MHz, CDCl$_3$) δ=8.86 (br s, 1H), 7.42 (br d, J=8.1 Hz, 1H), 7.15 (br d, J=7.8 Hz, 1H), 6.57 (br s, 1H), 2.73 (br t, J=6.7 Hz, 4H), 2.50-2.46 (m, 3H), 2.12 (s, 4H), 1.84-1.79 (m, 4H), 1.71 (br d, J=5.7 Hz, 3H), 1.58 (s, 9H); LCMS [M+H]$^+$ 406.

N'-(1-(4-Aminophenyl)ethylidene)-3-mercapto-3-methylbutanehydrazide (7r-3)

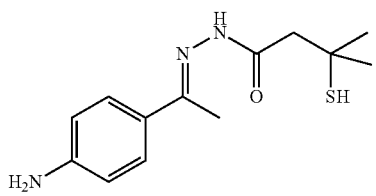

7r-3

A solution of 7r-2 (401 mg, 1.098 mmol) in DCM (0.764 ml) was treated with TFA (0.846 ml, 10.98 mmol) at 0° C. then it was stirred for 1 h. This solution was neutralized with NaHCO$_3$ and the mixture was taken in water and washed with DCM (×4). The combined organic layers were dried over Na$_2$SO$_4$. The solvent was removed under reduced pressure and then residue was purified over Isco (12 g silica column; eluent EtOAc/Hexanes: 0-20%) to give the title compound 7r-3 as a yellow solid (150 mg, 51% yield, 2 isomers). $^1$H NMR (500 MHz, CDCl$_3$) δ=8.36 (br s, 1H), 7.60 (d, J=8.6 Hz, 2H), 6.71 (d, J=8.7 Hz, 2H), 3.17 (s, 2H), 2.17 (s, 3H), 1.60 (s, 5H), 1.57 (s, 4H); LCMS [M+H]$^+$ 266.

N'-(6-Amino-3,4-dihydronaphthalen-1-(2H)-ylidene)-3-mercapto-3-methylbutanehydrazide (7s-3)

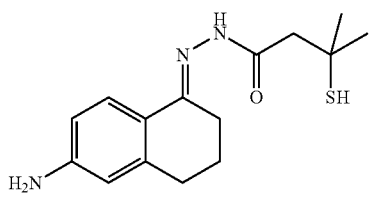

7s-3

The title compound 7s-3 was prepared according to a similar procedure to compound 7r-3. It was obtained as a white solid (60 mg, 50% yield, 2 isomers).

$^1$H NMR (500 MHz, CDCl$_3$) δ=8.36 (br s, 1H), 7.90 (d, J=8.6 Hz, 1H), 6.60 (dd, J=2.3, 8.5 Hz, 1H), 6.45 (d, J=2.0 Hz, 1H), 3.18 (s, 2H), 2.72-2.68 (m, 3H), 2.63 (s, 1H), 2.48 (t, J=6.5 Hz, 2H), 1.99-1.92 (m, 3H), 1.60 (s, 6H); LCMS [M+H]$^+$ 292.

N'-(5-Amino-2,3-dihydronaphthalen-1H-inden-1-ylidene)-3-mercapto-3-methylbutanehydrazide (7t-3)

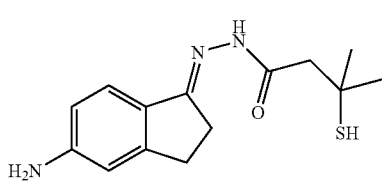

7t-3

The title compound 7t-3 was prepared according to a similar procedure to compound 7r-3. It was obtained as an orange solid (70 mg, 49% yield, 2 isomers). $^1$H NMR (500 MHz, CD$_3$OD) δ=7.68 (br d, J=8.6 Hz, 1H), 6.66 (br d, J=8.8 Hz, 1H), 6.63 (br s, 1H), 5.51 (s, 1H), 3.06-3.00 (m, 2H), 2.89 (br d, J=6.8 Hz, 2H), 2.68 (s, 2H), 1.98 (s, 1H), 1.55 (s, 6H); LCMS [M+H]$^+$ 278.

N'-(2-Amino-6,7,8,9-tetrahydro-5H-benzo[7]annulen-5-ylidene)-3-mercapto-3-methylbutanehydrazide (7u-3)

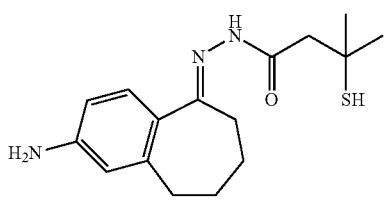

7u-3

The title compound 7u-3 was prepared according to a similar procedure to compound 7r-3. It was obtained as a yellow solid (100 mg, 47% yield, 2 isomers). $^1$H NMR (500 MHz, CDCl$_3$) δ=8.53 (br s, 1H), 7.32 (br d, J=8.1 Hz, 1H), 6.60 (br d, J=7.8 Hz, 1H), 6.55 (s, 1H), 6.46 (s, 1H), 2.65 (br d, J=7.9 Hz, 4H), 2.48-2.41 (m, 3H), 2.07 (s, 4H), 1.82-1.77 (m, 4H), 1.74-1.68 (m, 3H); LCMS [M+H]$^+$ 306.

Synthesis of the Final Linker-DM1 for Cysteine Conjugation
Scheme 19
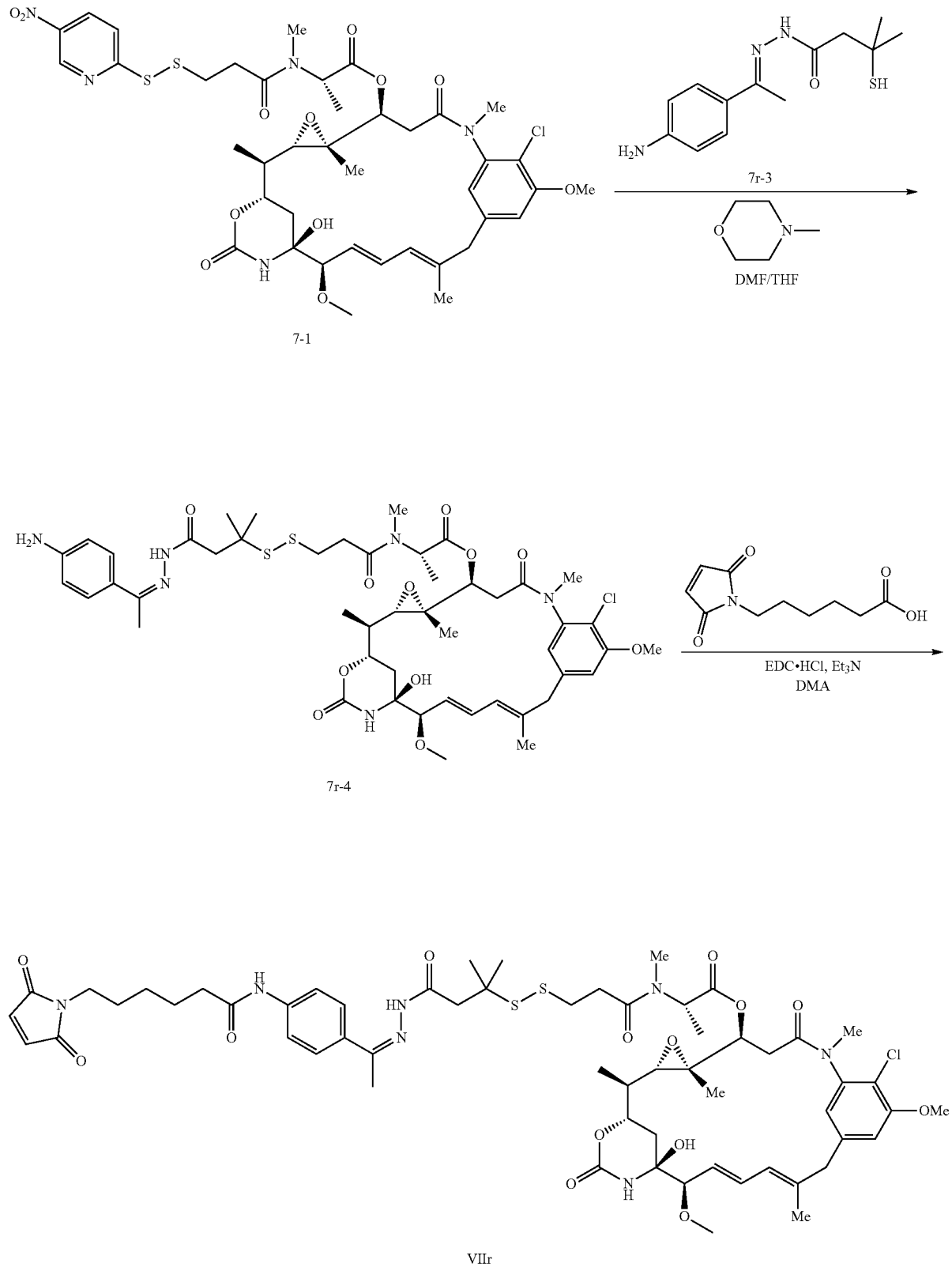

DM1 Intermediate (7r-4):

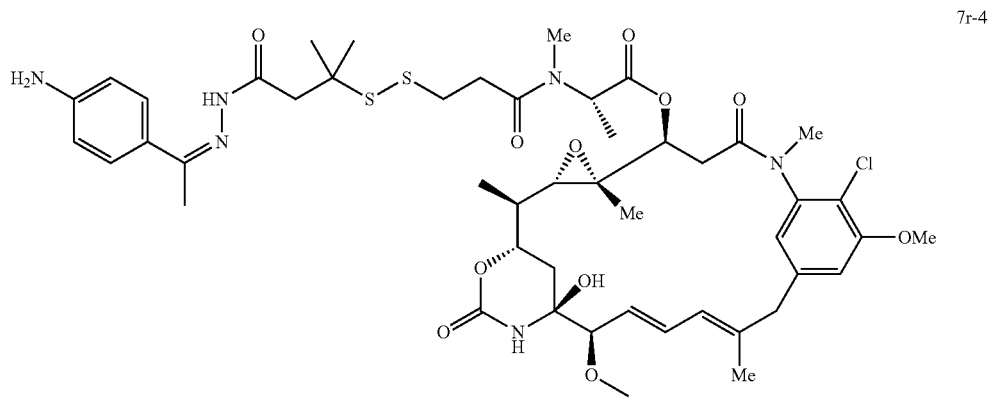 [SMILES: COc1cc2cc(c1Cl)N(C)C(=O)C[C@H](OC(=O)[C@H](C)N(C)C(=O)CCSSC(C)(C)CC(=O)N/N=C(/C)c1ccc(N)cc1)[C@]1(C)O[C@H]1[C@H](C)[C@@H]1C[C@@](O)(NC(=O)O1)[C@H](OC)/C=C/C=C(\C)C2]

To a solution of 7-1 (9 mg, 10.08 µmol) in DMF (0.9 ml) was added 7r-3 (6.96 mg, 0.026 mmol) in THF (0.9 ml). 4-methylmorpholine (20 µl, 10.08 mmol) was added then the mixture was stirred at room temperature overnight upon which LCMS showed completion. The mixture was taken in water and extracted with ethyl acetate. The organic layer was dried over $Na_2SO_4$ and the solvent was removed under reduced pressure. The crude product was purified using Isco (4 g silica column; eluent: EtOAc/Hexanes: 0%, 0-50%, 50%, 50-100% then 100%) to afford the title compound 7r-4 as a yellow solid (11.46 mg, quant. crude, 2 isomers). $^1$H NMR (500 MHz, Acetonitrile-d3) δ=8.86 (s, 1H), 8.68 (s, 1H), 7.62 (br d, J=8.6 Hz, 1H), 7.59 (br d, J=8.7 Hz, 1H), 7.00 (br d, J=1.1 Hz, 1H), 6.70-6.65 (m, 3H), 6.63 (s, 1H), 6.60-6.51 (m, 1H), 6.36 (s, 1H), 5.62 (br dd, J=9.2, 15.3 Hz, 1H), 5.42 (q, J=6.8 Hz, 1H), 4.63-4.59 (m, 1H), 4.43 (br d, J=12.2 Hz, 2H), 4.09 (q, J=7.2 Hz, 2H), 3.94 (s, 3H), 3.64-3.58 (m, 1H), 3.58-3.54 (m, 2H), 3.34 (d, J=4.6 Hz, 3H), 3.25-3.20 (m, 3H), 3.08 (d, J=7.0 Hz, 1H), 3.03-2.97 (m, 2H), 2.92 (d, J=9.7 Hz, 1H), 2.78 (d, J=16.3 Hz, 3H), 2.67-2.65 (m, 1H), 2.64-2.61 (m, 1H), 2.11-2.09 (m, 2H), 2.00 (s, 2H), 1.83 (td, J=2.5, 5.00 Hz, 1H), 1.63 (d, J=8.8 Hz, 3H), 1.55-1.47 (m, 2H), 1.46-1.42 (m, 2H), 1.32 (d, J=4.6 Hz, 4H), 1.30 (s, 1H), 1.25-1.23 (m, 3H), 1.23-1.21 (m, 3H), 1.20 (s, 1H), 0.82 (d, J=3.2 Hz, 3H); LCMS [M+H]$^+$ 1002.

DM1 Intermediate (7s-4):

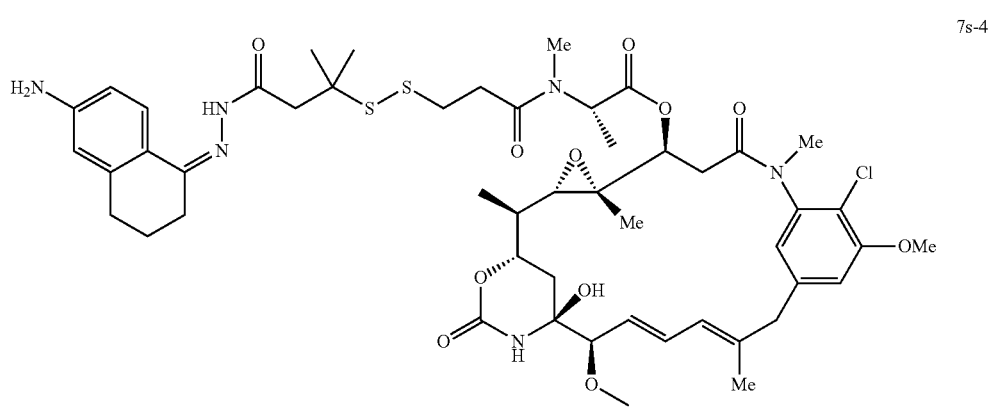 [SMILES: COc1cc2cc(c1Cl)N(C)C(=O)C[C@H](OC(=O)[C@H](C)N(C)C(=O)CCSSC(C)(C)CC(=O)N/N=C1/CCCc3cc(N)ccc31)[C@]1(C)O[C@H]1[C@H](C)[C@@H]1C[C@@](O)(NC(=O)O1)[C@H](OC)/C=C/C=C(\C)C2]

The title compound 7s-4 was prepared using a similar procedure to 7r4. It was obtained as a yellow solid (10.47 mg, 57% yield, 2 isomers). $^1$H NMR (500 MHz, Acetonitrile-d3) δ=8.81 (s, 1H), 8.64 (s, 1H), 7.89 (d, J=8.6 Hz, 1H), 7.83 (d, J=8.8 Hz, 1H), 7.04-7.00 (m, 1H), 6.70 (br d, J=6.1 Hz, 1H), 6.66-6.62 (m, 1H), 6.59-6.51 (m, 2H), 6.42 (s, 1H), 6.36 (s, 1H), 5.66-5.59 (m, 1H), 5.42 (br d, J=6.7 Hz, 1H), 4.61 (br d, J=12.1 Hz, 1H), 4.40 (br d, J=15.3 Hz, 1H), 4.09 (q, J=7.1 Hz, 3H), 3.95 (d, J=2.6 Hz, 3H), 3.62 (br d, J=12.3 Hz, 1H), 3.56 (t, J=4.4 Hz, 1H), 3.34 (d, J=4.5 Hz, 3H), 3.23 (d, J=16.3 Hz, 3H), 3.09 (d, J=4.5 Hz, 1H), 3.04-2.96 (m, 2H), 2.92 (d, J=9.8 Hz, 1H), 2.79 (br d, J=13.7 Hz, 4H), 2.68-2.64 (m, 2H), 2.56-2.48 (m, 2H), 2.00 (s, 3H), 1.84-1.82 (m, 2H), 1.63 (br d, J=7.3 Hz, 3H), 1.31 (br d, J=6.5 Hz, 6H), 1.25 (s, 1H), 1.23 (s, 2H), 1.22 (br s, 3H), 1.20-1.20 (m, 1H), 0.82 (d, J=2.7 Hz, 3H); LCMS [M+H]$^+$ 1028.

DM1 Intermediate (7t-4)

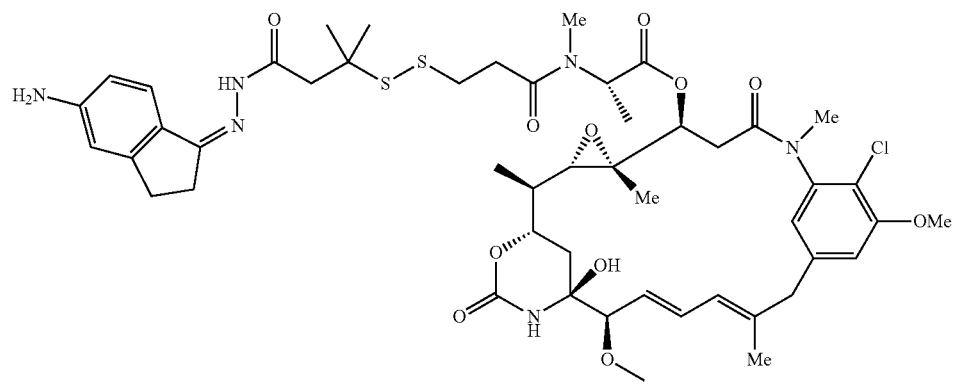

7t-4

The title compound 7t-4 was prepared using a similar procedure to 7r-4. It was obtained as a yellow solid (9 mg, 40% yield, 2 isomers). $^1$H NMR (500 MHz, Acetonitrile-d3) δ=8.61 (s, 1H), 8.38 (s, 1H), 7.49 (d, J=7.9 Hz, 1H), 7.43 (br d, J=8.8 Hz, 1H), 7.02 (br d, J=13.1 Hz, 1H), 6.71 (br d, J=10.9 Hz, 1H), 6.64 (br d, J=5.6 Hz, 1H), 6.61-6.58 (m, 2H), 6.36 (s, 1H), 5.63 (br d, J=6.4 Hz, 1H), 5.44-5.41 (m, 2H), 4.61 (br d, J=12.2 Hz, 1H), 4.52 (br d, J=12.1 Hz, 2H), 4.09 (q, J=7.1 Hz, 3H), 4.04 (br s, 1H), 3.94 (d, J=2.7 Hz, 2H), 3.60 (br s, 1H), 3.56 (br d, J=4.3 Hz, 1H), 3.35 (s, 3H), 3.23 (d, J=9.7 Hz, 3H), 2.99 (br d, J=6.7 Hz, 3H), 2.93 (br d, J=9.7 Hz, 2H), 2.79 (br d, J=9.0 Hz, 5H), 2.75-2.70 (m, 3H), 2.64-2.59 (m, 1H), 2.50-2.46 (m, 1H), 2.11-2.09 (m, 1H), 2.00 (s, 3H), 1.86 (s, 1H), 1.84-1.82 (m, 1H), 1.65 (br s, 1H), 1.62 (br d, J=7.5 Hz, 3H), 1.53-1.47 (m, 3H), 1.44 (br s, 1H), 0.82 (s, 3H); LCMS [M+H]$^+$ 1014.

DM1 Intermediate (7u-4):

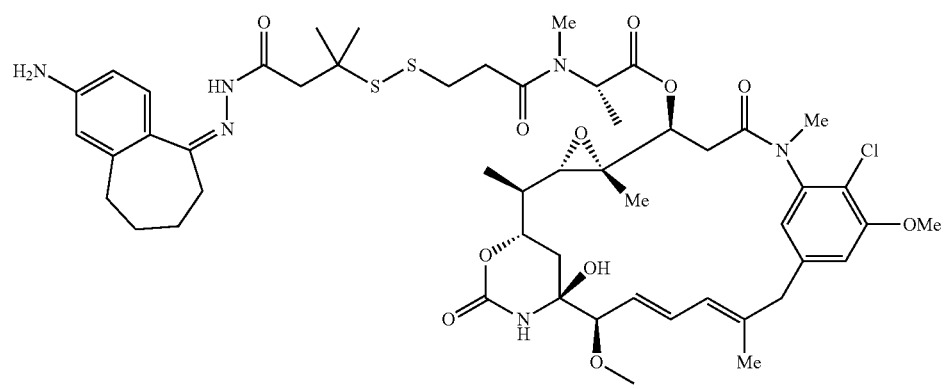

7u-4

The title compound 7u-4 was prepared using a similar procedure to 7r-4. It was obtained as a yellow solid (17.34 mg, 99% yield, 2 isomers). $^1$H NMR (500 MHz, DMSO-d6) δ=10.14 (s, 1H), 10.00 (s, 1H), 7.17 (s, 1H), 7.13 (br s, 1H), 6.89 (br s, 1H), 6.65-6.61 (m, 1H), 6.54 (br d, J=10.9 Hz, 2H), 6.43-6.39 (m, 1H), 6.33 (s, 1H), 5.93 (br s, 1H), 5.57-5.50 (m, 1H), 5.34-5.30 (m, 1H), 5.24 (br d, J=11.1 Hz, 1H), 4.54-4.50 (m, 1H), 4.11-4.07 (m, 1H), 4.04 (br d, J=7.1 Hz, 3H), 3.92 (br d, J=4.9 Hz, 3H), 3.50 (br d, J=9.4 Hz, 2H), 3.26 (d, J=2.6 Hz, 3H), 3.15 (br d, J=15.4 Hz, 3H), 2.86-2.84 (m, 1H), 2.81 (br d, J=10.1 Hz, 2H), 2.72 (s, 2H), 2.67 (s, 1H), 2.65-2.64 (m, 1H), 2.39-2.36 (m, 1H), 2.08-2.02 (m, 1H), 2.00 (s, 3H), 1.80-1.73 (m, 1H), 1.70-1.64 (m, 2H), 1.59 (br d, J=7.9 Hz, 3H), 1.51-1.40 (m, 3H), 1.23 (br s, 4H), 1.18 (br t, J=7.2 Hz, 8H), 1.13 (br d, J=6.4 Hz, 3H), 0.79 (br s, 3H); LCMS [M+H]$^+$ 1042.

Linker-DM1 (VIIr):

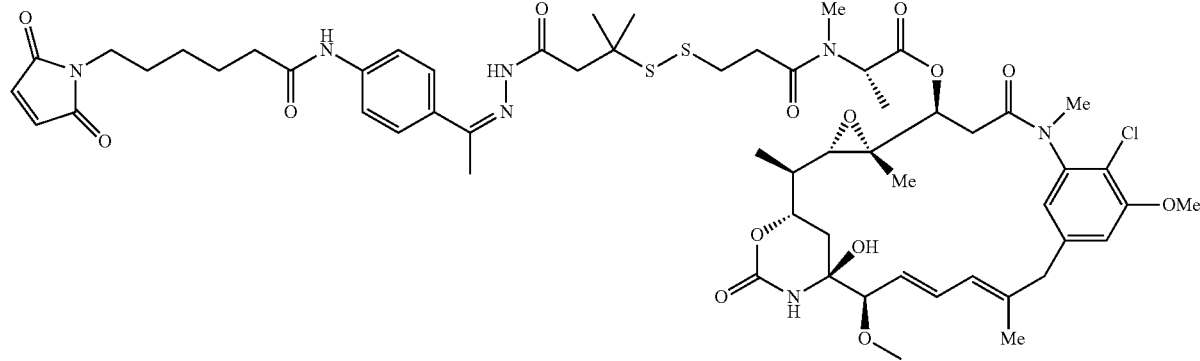

6-maleimidohexanoic acid (32.4 mg, 0.153 mmol) was dissolved in N,N-dimethyl acetamide (1.169 ml) then EDC.HCl (20.98 mg, 0.109 mmol) was added as a solid. The resulting solution was stirred at rt for 10 min upon which 7r-4 (10.96 mg, 10.94 µmol) was added. This yellow solution was stirred for 20 min then DIPEA (23 µl, 0.131 mmol) was added. The progress of the reaction was monitored by LCMS. Upon completion, the mixture was taken in water and extracted with EtOAc (×3). The organic layer was dried over Na$_2$SO$_4$. The solvent was removed under vacuum and the crude residue was purified using Isco (4 g Gold silica column; eluent EtOAc/Hexanes: 0%, 0-50%, 50%, 50-100% then 100%). The right product was taken in acetonitrile and lyophilized to give the title compound VIIr as a white powder (12.45 mg, 95% yield, 2 isomers). $^1$H NMR (500 MHz, Acetonitrile-d3) δ=8.99 (s, 1H), 8.80 (s, 1H), 8.39 (br d, J=7.5 Hz, 1H), 7.81 (br d, J=8.7 Hz, 1H), 7.77 (br d, J=8.6 Hz, 1H), 7.64 (br d, J=8.6 Hz, 2H), 7.04-6.99 (m, 1H), 6.75 (s, 2H), 6.68 (br d, J=12.0 Hz, 1H), 6.63 (s, 1H), 6.60-6.50 (m, 1H), 6.36 (br s, 1H), 5.62 (br dd, J=9.0, 14.9 Hz, 1H), 5.41 (br d, J=6.8 Hz, 1H), 4.63-4.59 (m, 1H), 4.15-4.12 (m, 1H), 4.09 (d, J=7.1 Hz, 1H), 3.57 (s, 1H), 3.55 (br d, J=8.7 Hz, 1H), 3.48 (s, 3H), 3.32 (s, 3H), 3.20 (s, 3H), 3.11-3.07 (m, 1H), 3.04-2.96 (m, 2H), 2.93-2.91 (m, 1H), 2.80 (s, 2H), 2.77 (s, 2H), 2.34 (br t, J=7.4 Hz, 2H), 2.23 (s, 1H), 2.00 (s, 3H), 1.84-1.82 (m, 1H), 1.73-1.66 (m, 3H), 1.64 (s, 1H), 1.61 (br s, 3H), 1.32 (s, 7H), 1.25-1.22 (m, 5H), 1.22-1.19 (m, 5H), 0.82 (br d, J=4.4 Hz, 3H); LCMS [M+H]$^+$ 1195.

Linker-DM1 (VIIs):

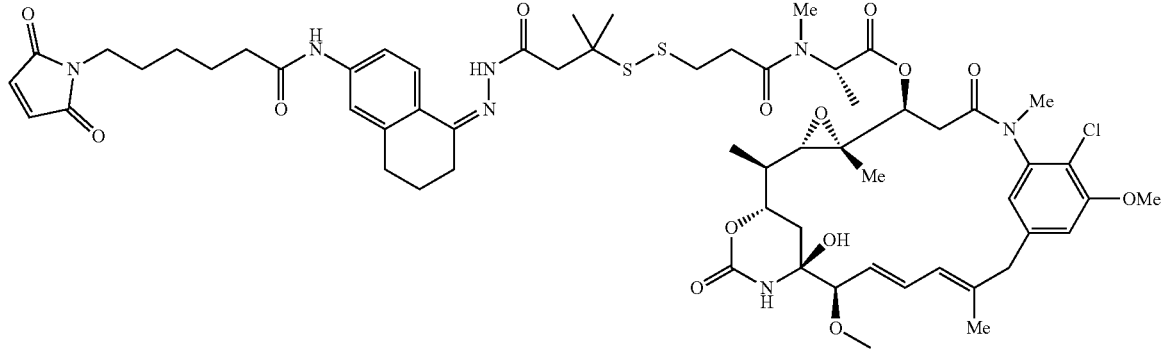

The title compound VIIs was prepared using a similar procedure to VIIr. It was isolated as a white powder (3.9 mg, 33% yield, 2 isomers). $^1$H NMR (500 MHz, Acetonitrile-d3) δ=8.95 (s, 1H), 8.77 (s, 1H), 8.33 (br d, J=8.4 Hz, 1H), 8.08 (d, J=8.7 Hz, 1H), 8.01 (d, J=8.8 Hz, 1H), 7.52-7.46 (m, 1H), 7.44 (br d, J=8.4 Hz, 1H), 7.40-7.37 (m, 1H), 7.04-6.99 (m, 1H), 6.75 (s, 2H), 6.67 (s, 1H), 6.63 (br d, J=1.3 Hz, 1H), 6.59-6.50 (m, 1H), 6.35 (s, 1H), 5.62 (dd, J=9.2, 15.4 Hz, 1H), 5.44-5.39 (m, 1H), 4.61 (br d, J=12.0 Hz, 1H), 4.16-4.10 (m, 1H), 4.08 (s, 1H), 4.05-4.03 (m, 1H), 3.95-3.94 (m, 2H), 3.56 (br d, J=9.3 Hz, 2H), 3.48 (s, 2H), 3.35-3.31 (m, 3H), 3.21 (s, 3H), 3.13-3.06 (m, 1H), 3.05-2.96 (m, 2H), 2.92 (dd, J=2.4, 9.8 Hz, 1H), 2.77 (s, 5H), 2.61-2.53 (m, 2H), 2.33 (s, 1H), 2.12-2.09 (m, 3H), 1.85-1.81 (m, 2H), 1.72-1.65 (m, 3H), 1.63 (br s, 1H), 1.61 (br s, 3H), 1.45-1.42 (m, 2H), 1.32 (br s, 6H), 1.23 (br d, J=6.8 Hz, 3H), 1.20 (br d, J=6.4 Hz, 3H), 0.81 (d, J=4.0 Hz, 3H); LCMS [M+H]$^+$ 1221.

Linker-DM1 (VIIt):

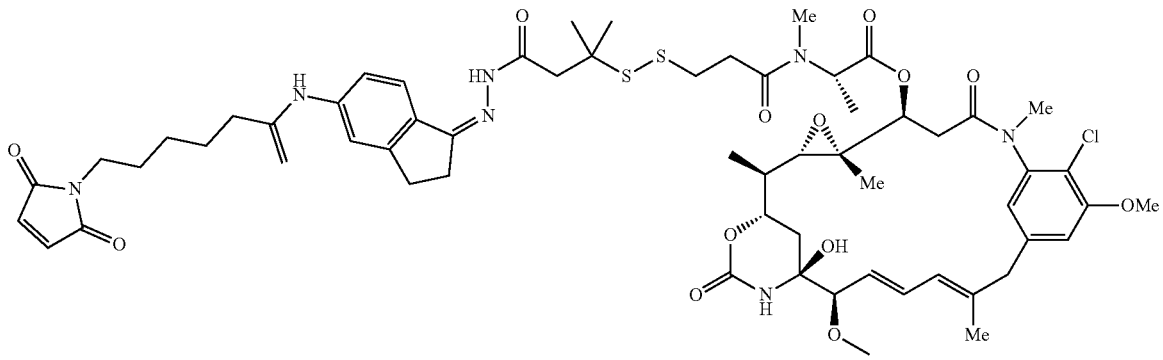

VIIt

The title compound VIIt was prepared using a similar procedure to VIIr. It was isolated as a white powder (2.47 mg, 80% yield, 2 isomers). $^1$H NMR (500 MHz, Acetonitrile-d$_3$) δ=8.77 (s, 1H), 8.54 (s, 1H), 8.42 (br d, J=15.7 Hz, 1H), 7.74 (br d, J=4.5 Hz, 1H), 7.51 (br d, J=7.8 Hz, 1H), 7.39 (br d, J=7.8 Hz, 1H), 7.02 (br d, J=11.0 Hz, 1H), 6.75 (d, J=1.7 Hz, 2H), 6.70 (br t, J=11.2 Hz, 1H), 6.64 (br d, J=2.8 Hz, 1H), 6.55 (br d, J=2.0 Hz, 1H), 6.36 (br d, J=5.9 Hz, 1H), 5.67-5.59 (m, 1H), 5.42 (br dd, J=6.7, 13.4 Hz, 1H), 4.61 (dd, J=2.8, 12.0 Hz, 1H), 4.09 (d, J=7.1 Hz, 1H), 3.94 (d, J=1.5 Hz, 3H), 3.60 (br s, 1H), 3.56 (br d, J=9.0 Hz, 1H), 3.50-3.46 (m, 2H), 3.35 (s, 2H), 3.29 (s, 1H), 3.23 (d, J=10.0 Hz, 3H), 3.16 (br d, J=12.5 Hz, 1H), 3.11 (br d, J=5.7 Hz, 2H), 3.09 (br s, 1H), 3.05 (br dd, J=2.6, 9.4 Hz, 1H), 3.03-3.00 (m, 1H), 2.93 (br d, J=9.5 Hz, 1H), 2.79 (br d, J=6.8 Hz, 4H), 2.66-2.59 (m, 1H), 2.54-2.49 (m, 1H), 2.43-2.37 (m, 1H), 2.37-2.31 (m, 2H), 1.71-1.67 (m, 2H), 1.62 (br d, J=9.4 Hz, 4H), 1.54-1.48 (m, 2H), 1.47-1.42 (m, 2H), 1.35-1.32 (m, 7H), 1.25 (d, J=3.8 Hz, 2H), 1.24 (br d, J=3.7 Hz, 2H), 1.21 (br s, 2H), 1.20 (s, 1H), 0.81 (s, 3H); LCMS [M+H]$^+$1207.

Linker-DM1 (VIIu):

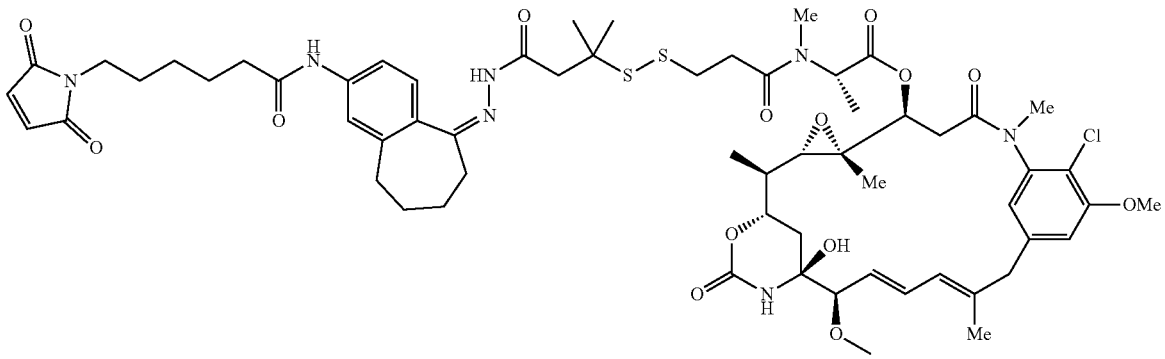

VIIu

The title compound VIIu was prepared using a similar procedure to VIIr. It was isolated as a white powder (5.86 mg, 28% yield, 2 isomers). $^1$H NMR (500 MHz, Acetonitrile-d3) δ=8.99 (s, 1H), 8.78 (s, 1H), 8.32 (br s, 1H), 7.48 (br s, 1H), 7.42 (br d, J=12.7 Hz, 1H), 7.03 (br d, J=16.1 Hz, 1H), 6.75 (s, 2H), 6.70 (br d, J=5.4 Hz, 1H), 6.66 (br d, J=9.4 Hz, 1H), 6.62 (s, 1H), 6.55 (td, J=10.6, 15.2 Hz, 1H), 6.35 (s, 1H), 5.65 (s, 1H), 5.64-5.58 (m, 2H), 5.44-5.38 (m, 1H), 4.64-4.58 (m, 1H), 4.09 (q, J=7.2 Hz, 5H), 3.94 (br s, 3H), 3.59-3.53 (m, 2H), 3.48 (t, J=7.1 Hz, 3H), 3.34-3.32 (m, 3H), 3.25 (s, 1H), 3.20 (s, 1H), 3.10 (br d, J=12.2 Hz, 1H), 3.00 (br s, 1H), 2.95 (br s, 1H), 2.91 (br d, J=4.0 Hz, 1H), 2.80 (s, 1H), 2.73 (s, 3H), 2.53 (br s, 1H), 2.32 (br t, J=7.4 Hz, 3H), 2.10 (td, J=2.5, 4.9 Hz, 2H), 1.84-1.82 (m, 1H), 1.81-1.77 (m, 2H), 1.70-1.67 (m, 3H), 1.64 (br d, J=12.0 Hz, 6H), 1.44 (br s, 1H), 1.32 (br s, 3H), 1.31 (br s, 1H), 1.23 (t, J=7.2 Hz, 10H), 0.82 (br d, J=5.4 Hz, 3H); LCMS [M+H]$^+$ 1235.

Conjugation of Linker-Drug Constructs to Antibody
Conjugation of DM1-Linker Construct VIIa, VIIe and VIIb to Cetuximab Conjugation Reaction—

10 equiv. of VIIa linker-drug conjugate was added in a solution of DMF (30 µL) to ensure that the final DMF concentration was 20% (30 µL, so roughly from a stock solution of 2.5 mg/mL). The solution was stirred at room temperature for 3.5 hours.

a. Four reactions were set up, for 3 hr, 6 hr, 9 hr, and 24 hr.

Purification—

The reaction was transferred to a spin column (10,000 MW cutoff) with 400 µL of PBS (50 mM sodium phosphate, 100 mM NaCl, pH 7.4). The solution was spun down for 5 minutes at 14000×g 5 times with 400 µL of above mentioned pH 7.4 PBS. All flow-through was removed. The column was turned upside down, placed in a clean Epi and spun down for 2 minutes at 1000×g. The flow-through (roughly 75 µL) was collected and another 25 µL of buffer added.

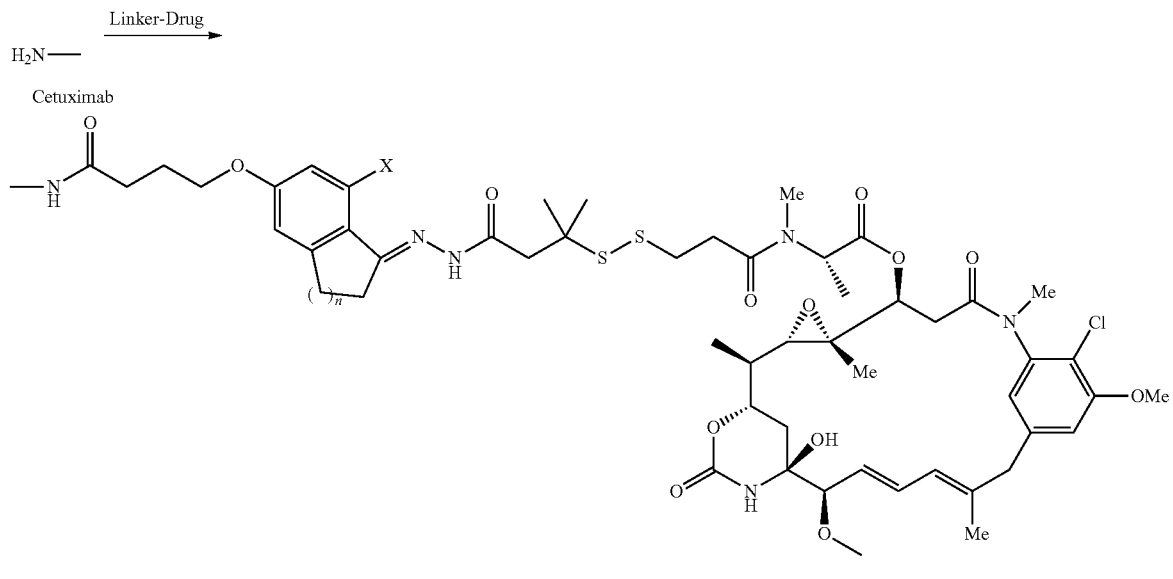

ADCs of Formula III or VI

Synthesis of ADCs IIIa (Mylotarg-Like Linker)
Method A:
Buffer Exchange of Antibody—

100 µL of 5 mg/mL solution of cetuximab (0.5 mg) was loaded onto a spin column (10,000 MW cutoff). 400 µL of PBS was added (50 mM sodium phosphate, 100 mM NaCl, pH 7.8) and the solution spun down for 4 minutes at 14000×g 4 times. All flow-through was then removed. The column was turned upside down, placed in a clean Epi and spun down for 2 minutes at 1000×g. The flow-through (roughly 75 µL) was collected and another 25 µL of buffer was added.

a. Absorbance was read at 280 nm to obtain protein concentration.

b. 4 reactions were prepared (Ab solution 1, 2, 3 and 4, and on average the antibody concentration was between 7.5 to 8 mg/mL.

i. Ab: $\varepsilon_{252}$=87360; $\varepsilon_{280}$=224000
ii. Maytansinoid: $\varepsilon_{252}$=28044; $\varepsilon_{280}$=5700

TABLE 3

ADC Compounds of Formula III or VI from Linker-Drug Compounds of Formula VII

| ADC | Linker Type | Time | Concentration | DAR | Volume |
|---|---|---|---|---|---|
| IIIa-1 | VIIa | 3 hr | 8.3 mg/mL | 0.69 | 100 µL |
| IIIa-2 | VIIa | 6 hr | 6.8 mg/mL | 0.64 | 100 µL |
| IIIa-3 | VIIa | 9 hr | 5.6 mg/mL | 0.74 | 100 µL |
| IIIa-4 | VIIa | 24 hr | 7.8 mg/mL | 0.80 | 100 µL |

Method B:
Buffer Exchange of Antibody—

100 µL of 5 mg/mL solution of cetuximab (0.5 mg) was loaded onto a spin column (10,000 MW cutoff). Note: New batch of antibody used. 400 µL of PBS was added (50 mM sodium phosphate, 100 mM NaCl, pH 7.8). The solution was spun down for 4 minutes at 14000×g 4 times and all flow-through removed. The column was turned upside down, placed in a clean Epi and spun down for 2 minutes at 1000×g. The flow-through (roughly 75 μL) was collected and another 25 μL of buffer added.

a. Read absorbance at 280 nm to obtain protein concentration of 6.5 mg/mL in 100 μL.

Conjugation Reaction—

Solutions of VIIa were prepared with concentrations of 1.8 mg/mL in DMF. 304 were allocated.

a. To the solution of cetuximab was added the 1.8 mg/mL solution of VIIa in a stepwise fashion (6 μL every 15 minutes over 1 hour). 10 equiv. of VIIa was used with respect to cetuximab.

b. The reaction was stirred at room temperature for an additional 2 hours for a total of 3 hours.

Purification—

The reaction was transferred to a spin column (10,000 MW cutoff) with 400 μL of PBS (50 mM sodium phosphate, 100 mM NaCl, pH 7.4). The solution was spun down for 7 minutes at 14000×g 5 times with 4004 of above mentioned pH 7.4 PBS and all flow-through removed. The column was turned upside down, placed in a clean Epi and spun down for 2 minutes at 1000×g. The flow-through (roughly 754) was collected and another 25 μL of buffer added.

iii. Ab: $\varepsilon_{252}$=87360; $\varepsilon_{280}$=224000
iv. Maytansinoid: $\varepsilon_{252}$=28044; $\varepsilon_{280}$=5700

TABLE 4

| ADC Compounds of Formula III or VI from Linker-Drug Compounds of Formula VII | | | | |
|---|---|---|---|---|
| ADC | Linker Type | Volume | Concentration | DAR |
| IIIa-5 | VIIa | 100 μL | 5.2 mg/mL | 1.81 |

(b) Synthesis of ADCs IIIe
(1,2,3,4-Tetrahydronaphthalene Type Linker-DM1)

Method A:

Buffer Exchange of Antibody—

100 μL of 5 mg/mL solution of cetuximab (0.5 mg) was loaded onto a spin column (10,000 MW cutoff). Added 400 μL of PBS (50 mM sodium phosphate, 100 mM NaCl, pH 7.8) and spun down for 4 minutes at 14000×g 4 times. All flow-through was removed. The column was turned upside down, placed in a clean Epi and spun down for 2 minutes at 1000×g. The flow-through (roughly 754) was collected and another 25 μL of buffer was added.

a. Read absorbance at 280 nm to obtain protein concentration.
b. 4 reactions were prepared (Ab solution 1, 2, 3 and 4, and on average the antibody concentration was between 7.5 to 8 mg/mL.

Conjugation Reaction—

10 equiv. of Vile linker was added in a solution of DMF (30 μL) to ensure that the final DMF concentration is 20% (30 μL, so roughly from a stock solution of 2.5 mg/mL). The solution was stirred at room temperature for 3.5 hours.

a. Four reactions were set up, for 3 hr, 6 hr, 9 hr, and 24 hr.

Purification—

The reaction was transferred to a spin column (10,000 MW cutoff) with 400 μL of PBS (50 mM sodium phosphate, 100 mM NaCl, pH 7.4). The solution was spun down for 5 minutes at 14000×g 5 times with 400 μL of above mentioned pH 7.4 PBS. All flow-through was removed. The column was turned upside down, placed in a clean Epi and spun down for 2 minutes at 1000×g. The flow-through (roughly 75 μL) was collected and another 25 μL of buffer was added.

v. Ab: $\varepsilon_{252}$=87360; $\varepsilon_{280}$=224000
vi. Maytansinoid: $\varepsilon_{252}$=28044; $\varepsilon_{280}$=5700

TABLE 5

| ADC Compounds of Formula III or VI from Linker-Drug Compounds of Formula VII | | | | | |
|---|---|---|---|---|---|
| ADC | Linker Type | Time | Concentration | DAR | Volume |
| IIIe-1 | VIIe | 3 hr | 6.5 mg/mL | 1.77 | 100 μL |
| IIIe-2 | VIIe | 6 hr | 6.1 mg/mL | 1.72 | 100 μL |
| IIIe-3 | VIIe | 9 hr | 5.6 mg/mL | 1.67 | 100 μL |
| IIIe-4 | VIIe | 24 hr | 7.8 mg/mL | 1.58 | 100 μL |

Method B:

Buffer Exchange of Antibody—

100 μL of 5 mg/mL solution of cetuximab (0.5 mg) was loaded onto a spin column (10,000 MW cutoff). 400 μL of PBS (50 mM sodium phosphate, 100 mM NaCl, pH 7.8) was added. The solution was spun down for 4 minutes at 14000×g 4 times and all flow-through removed. The column was turned upside down, placed in a clean Epi and spun down for 2 minutes at 1000×g. The flow-through (roughly 754) was collected and another 25 μL of buffer was added.

a. Read absorbance at 280 nm to obtain protein concentration.
b. 2 antibody reactions were prepared (Ab solution 1 and 2, and on average the antibody concentration was between 7.5 to 8 mg/mL.

Conjugation Reaction—

2 solutions of Vile were prepared with concentrations of 5 mg/mL and 2.5 mg/mL respectively. 30 μL were allocated.

a. To Ab solution 1 was added the 2.5 mg/mL solution of Vile in a stepwise fashion (6 mL every 15 minutes over 1 hour). 10 equiv. of Vile was used with respect to cetuximab.
b. To Ab solution 2 was added the 5 mg/mL solution of Vile in a stepwise fashion (6 mL every 15 minutes over 1 hour). 20 equiv. of Vile was used with respect to cetuximab.
c. 11:45 am—first addition for both Ab solution 1 and solution 2 took place.

Purification—

2:45 μm: The reaction was transferred to a spin column (10,000 MW cutoff) with 4004 of PBS (50 mM sodium phosphate, 100 mM NaCl, pH 7.4). The solution was spun down for 7 minutes at 14000×g 5 times with 400 μL of above mentioned pH 7.4 PBS and all flow-through removed. The column was turned upside down, placed in a clean Epi and spun down for 2 minutes at 1000×g. The flow-through (roughly 754) was collected and another 25 μL was added.

vii. Ab: $\varepsilon_{252}$=87360; $\varepsilon_{280}$=224000
viii. Maytansinoid: $\varepsilon_{252}$=28044; $\varepsilon_{280}$=5700

TABLE 6

| ADC Compounds of Formula III or VI from Linker-Drug Compounds of Formula VII | | | | | |
|---|---|---|---|---|---|
| ADC | Linker Type | Time | Concentration | DAR | Volume |
| IIIe-5 | VIIe | 3 hr | 6.9 mg/mL | 2.55 | 100 μL |
| IIIe-6 | VIIe | 3 hr | 6.1 mg/mL | 3.10 | 100 μL |
| IIIe-7 | VIIe | 3 hr | 8.0 mg/mL | 2.02 | 100 μL |

Synthesis of ADC IIIb (5,6,7,8-Tetrahydronaphthalen-1-ol type linker-DM1)

Buffer Exchange of Antibody—

100 μL of 5 mg/mL solution of cetuximab (0.5 mg) was loaded onto a spin column (10,000 MW cutoff). 400 μL of PBS was added (50 mM sodium phosphate, 100 mM NaCl, pH 7.8). The solution was spun down for 4 minutes at 14000×g 4 times and all flow-through removed. The column was turned upside down, placed in a clean Epi and spun down for 2 minutes at 1000×g. All flow-through (roughly 75 μL) was collected and another 25 μL of buffer added.

a. Absorbance was read at 280 nm to obtain protein concentration of 9.6 mg/mL in 100 μL.

Conjugation Reaction—

A solution of VIIb (5,6,7,8-Tetrahydronaphthalen-1-ol type linker-DM1) was prepared with a concentration of 2.67 mg/mL. 30 μL were allocated.

a. To the solution of cetuximab was added the 2.67 mg/mL solution of VIIb in a stepwise fashion (6 mL every 15 minutes over 1 hour). 10 equiv. of VIIb was used with respect to cetuximab.

b. The reaction was stirred at room temperature for an additional 2 hours for a total of 3 hours.

Purification—

The reaction was transferred to a spin column (10,000 MW cutoff) with 400 μL of PBS (50 mM sodium phosphate, 100 mM NaCl, pH 7.4). The solution was spun down for 7 minutes at 14000×g 5 times with 400 μL of above mentioned pH 7.4 PBS and all flow-through removed. The column was turned upside down, placed in a clean Epi and spun down for 2 minutes at 1000×g. The flow-through (roughly 75 μL) was collected and another 25 μL of buffer added.

ix. Ab: $\varepsilon_{252}$=87360; $\varepsilon_{280}$=224000 x. Maytansinoid: $\varepsilon_{252}$=28044; $\varepsilon_{280}$=5700

TABLE 7

ADC Compounds of Formula III or VI from Linker-Drug Compounds of Formula VII

| ADC | Linker Type | Time | Concentration | DAR | Volume |
|---|---|---|---|---|---|
| IIIb-1 | VIIb | 3 hr | 7.9 mg/mL | 2.72 | 100 μL |

Conjugation of DM1-linker constructs of formula VII to Trastuzumab

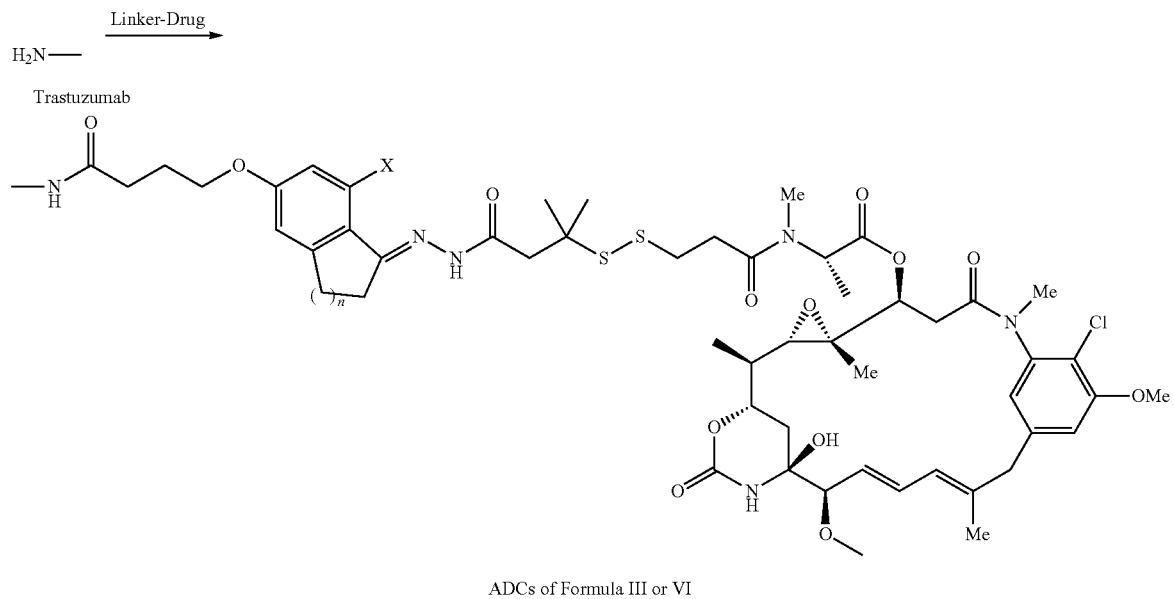

ADCs of Formula III or VI

The goal of this procedure is chemically link the cytotoxin microtubule inhibitor DM1 to surface accessible lysine residues on the human IgG1 antibody Trastuzumab by reaction of DM1-linker constructs (VII) with the antibody.

Concentrated (10 mM) stock solutions of the linker with the attached DM1 payload of formula VII are prepared in dimethylacetamide (DMA) and stored at −20° C. just prior to use. Prior to conjugation the concentrated stock is brought up to the temperature of 25° C. and then used to prepare a working stock in DMA equivalent to 5 times the desired concentration to be used in the reaction. The reaction mixture consists of 13.3 μM of Trastuzumab, 66.5 μM Linker-DM1, 100 mM sodium phosphate, 20 mM NaCl, pH 7.4. Once mixed, the reaction is incubated at 32° C. for 2.5 hours.

The reaction is stopped by buffer exchanging the sample into 20 mM sodium phosphate, 0.02% w/v Polysorbate 20 pH 7.4. Trehalose is then added to 6% w/v prior to storage at −80° C. Buffer exchange can be accomplished via gravity/spin desalting columns or tangential flow filtration methods.

Analysis of Bioconjugates

The absorbance of formulated bioconjugates is measured at 280 nm and one additional wavelength specific for the particular linker used. The extinction coefficient of this second wavelength is determined empirically for each combination of linker and payload used. The corresponding absorbance of the parental antibody is also measured at these two same wavelengths. The drug/antibody ratio is determined using the following equation. The second wavelength shown here is 252 nm, but this will depend on the particular linker-drug combination used;

$$DAR = \frac{\left(\frac{A_{252}}{A_{280} * \varepsilon_{Ab}^{280}}\right) - \varepsilon_{Ab}^{252}}{\varepsilon_{ADC}^{280} - \left(\frac{A_{252}}{A_{280} * \varepsilon_{ADC}^{280}}\right)}$$

ADCO—refers to the free linker-drug prior to conjugation
Ab—refers to the antibody prior t conjugation.

For conjugation with trastuzumab 3 ratios of linker-drug to antibody were tested: 5/1, 10/1 and 15/1. In general, linearity was observed when measuring the DAR of the resulting ADs. A 5/1 ratio gave the lowest DAR whereas a 15/1 ratio gave the highest DAR. As a representative example, the results obtained with a 10/1 ratio are summarized in the table below:

TABLE 8

ADC Compounds of Formula III or VI from Linker-Drug Compounds of Formula VII or VIII

| Trastuzumab ADCs | Linker-Drug | Yield | DAR ratio |
|---|---|---|---|
| IIIa-6 | VIIa | 67.5 | 1.4 |
| IIId | VIId | 61 | 2.4 |
| VIa | VIIIa | 63.8 | 3 |
| IIIc | VIIe | 70 | 2.8 |
| IIIf | VIIf | 71 | 2.9 |
| IIIg | VIIg | 64.3 | 3.3 |
| IIIh | VIIh | 73.6 | 3.9 |
| IIIj | VIIj | 69.5 | 4 |
| IIIi | VIIi | 68 | 3 |

Example: Biological Testing of Antibody-Drug Conjugates

Compounds of the present application display biological activity in the following assay:

(I) Cell Proliferation Assay

The parental U87MG glioblastoma human tumor cell line (ATCC) and the corresponding cell line engineered to over-express wt EGFR (EGFR$^+$ U87) (~2M receptors per cell) were grown in DMEM medium containing 10% fetal bovine serum and 2 mM L-glutamine. Cells were inoculated into 96 well microtiter plates in 100 μL at a plating density of 4000 cells/well After cell inoculation, the microtiter plates were incubated at 37° C., 5% CO$_2$, 95% air and 100% relative humidity. After 24 h incubation, experimental drugs were diluted to 10× the desired final maximum test concentration with complete medium and additional 10-fold or ½ log serial dilutions were made to provide a total of 6 drug concentrations plus control. Aliquots of 10 μl of these different drug dilutions were added to the appropriate microtiter wells already containing 100 μl of medium, resulting in the required final drug concentrations.

Following drug addition, the plates were incubated for an additional 72 h at 37° C., 5% CO$_2$, 95% air, and 100% relative humidity. The assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. The growth was calculated at each of the drug concentrations levels relative to untreated cells (media only control).

Percentage growth inhibition was calculated as:

[(Ti)/(C)]×100

Growth inhibition of 50% (GI50) was calculated using GraphPad software (4 parameter model) to determine the drug concentration resulting in a 50% reduction in the total protein (as measured by SRB staining) relative to control cells during the drug incubation.

The results from this assay are presented in Tables 2 and 3

TABLE 9

Cytotoxic activity of Cetuximab ADCs against glioblastoma U87 parental cell lines

| ADCs and DM1 | Linker Type | DAR | IC$_{50}$ (nM) |
|---|---|---|---|
| IIIe-4 | VIIe | 1.58 | 40.05 |
| IIIe-6 | VIIe | 3.10 | 26.07 |
| IIIe-7 | VIIe | 2.02 | 43.57 |
| EGFR-DM1 | N.A.* | 2.7 | 40.94 |
| DM1 | N.A.* | N.A.* | 12.31 |

*N.A.: non applicable

TABLE 10

Cytotoxic activity of ADCs against glioblastoma EGFR$^+$ U87 cell lines

| ADCs and DM1 | Linker Type | DAR | IC$_{50}$ (nM) |
|---|---|---|---|
| IIIe-4 | VIIe | 1.58 | 1.57 |
| IIIe-6 | VIIe | 3.10 | 0.57 |
| IIIe-7 | VIIe | 0.71 | 43.57 |
| EGFR-DM1 | N.A.* | 2.7 | 1.94 |
| DM1 | N.A.* | N.A.* | 10.27 |

*N.A.: non applicable

DISCUSSION

ADCs IIIe-4, IIIe-6 and IIIe-7 showed low nanomolar or better IC$_{50}$ on EGFR$^+$ U87 cells, and showed a 1-2 order of magnitude enhancement in potency compared to the parental EGFR wild type cells. Here, the DAR (IIIe-4, IIIe-6, IIIe-7) was varied and looked at the effect on cytotoxicity and found that ADCs with a higher DAR (within the same linkage series) showed enhanced cytotoxicity. Interestingly, ADC IIIe-6 (DAR 3.1) showed a three-fold enhancement in cytotoxicity compared with EGFR-DM1.

Cytotoxic Activity of Trastuzumab ADCs Against SKOV3 Ovarian Cell Lines

SKOV3 ovarian cells are incubated with the effectors for a period corresponding to 2 to 3 times their estimated doubling time and the amount of viable cells is determine by measuring ATP content in the wells. ATP has been widely accepted as a valid marker of viable cells. When cells lose membrane integrity, they lose the ability to synthesize ATP and endogenous ATPases rapidly deplete any remaining ATP from the cytoplasm. All ADCs are diluted in DPBS to 6× the highest concentration tested, followed by 10 3-fold serial dilutions in DPBS for a total of 11 concentration points. Each point is added to triplicate wells. DPBS is added in wells to measure the maximum growth. Cells are diluted at their appropriate seeding density (ranging from 150 to 1000 cells per well) in complete media supplemented with glutamine 2 mM, serum and antibiotic cocktail. They are distributed in white, opaque bottom, tissue-culture treated 384 well plates and incubated for 24 hrs at 37° C.+5% $CO_2$. After addition of ADCs, cells are incubated at 37° C.+5% C02 for the appropriate amount of time (3 to 5 days) prior to cell viability count. Total ATP is measured using CellTiter-Glo reagent from Promega as recommended by the supplier. The cells and the reagent are equilibrated at room temp. for 30 min before mixing. Cell lysates are then incubated for 30 min to 1 hr at room temp. protected from light. Signal output is measured on a luminescence plate reader (envision, Perkin Elmer) set at an integration time of 0.1 sec. Integration time is adjusted to minimise signal saturation at high ATP concentration.

Data Analysis

Each concentration point (S) is normalized to the negative control wells (NC) and expressed as % survival (NC–S/NC×100). Potency ($IC_{50}$) and efficacy are calculated from a non-linear curve fit of the points versus log of the concentrations without constrain on the slope. Refined data are analysed using Prism software.

In this study, a positive control ADC (Trastuzumab-SMCC-DM1) and a negative control ADC (Synagis-SMCC-DM1) were used. The cytotoxicity data against SKOV3 ovarian cancer lines is shown in the table below.

TABLE 11

Cytotoxicity against SKOV3 Ovarian cancer cell line

| ADC | DAR | $IC_{50}$ (nM) |
|---|---|---|
| Synagis-SMCC-DM1 | 3.4 | 9.64 |
| Trastuzumab-SMCC-DM1 | 3.5 | 0.038 |
| IIIj | 4.7 | 1.16 |

ADC IIIj showed very potent activity against SKOV3 ovarian cell lines ($IC_{50}$: 1.16 nM). It was about an order of magnitude higher than the negative control Synagis-SMCC-DM1.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION (1) a. In American Cancer Society. "Chemotherapy side effects" 2017. Available at https://www.cancer.org/treatment/treatments-and-side-effects/treatment-types/chemotherapy/chemotherapy-side-effects.html (Accessed Sep. 14, 2017);
b. Beck, A.; Goetsch L.; Dumontet, C. and Corvaia, N. Strategies and challenges of next generation antibody-drug conjugates, Nat. Rev. Drug. Discov. 2017, 16, 315-337.
(2) Chabner, B. A.; Roberts, T. G., Jr. Timeline: Chemotherapy and the war on cancer, Nat. Rev. Cancer 2005, 5, 65-72.
(3) Allen, T. M. Ligand-targeted therapeutics in anticancer therapy, Nat. Rev. Cancer 2002, 2, 750-763.
(4) Helleday, T.; Petermann, E.; Lundin, C.; Hodgson, B.; Sharma, R. A. DNA repair pathways as targets for cancer therapy, Nat. Rev. Cancer 2008, 8, 193-204.
(5) Zhang, J.; Yang, P. L.; Gray, N. S. Targeting cancer with small molecule kinase inhibitors, Nat. Rev. Cancer 2009, 9, 28-39.
(6) Aggarwal, S. Targeted cancer therapies, Nat. Rev. Drug. Discov. 2010, 9, 427-428.
(7) Tennant, D. A.; Duran, R. V.; Gottlieb, E. Targeting metabolic transformation for cancer therapy, Nat. Rev. Cancer 2010, 10, 267-277.
(8) Imai, K.; Takaoka, A. Comparing antibody and small-molecule therapies for cancer, Nat. Rev. Cancer 2006, 6, 714-727.
(9) Weiner, L. M.; Surana, R.; Wang, S. Monoclonal antibodies: versatile platforms for cancer immunotherapy, Nat. Rev. Immunol. 2010, 10, 317-327.
(10) Reichert, J. M. Antibody-based therapeutics to watch in 2011, MAbs 2011, 3, 76-99.
(11) Murphy, K. P.; Travers, P.; Walport, M.; Janeway, C. Janeway's Immunobiology; Garland Science: New York, 2008.
(12) Trail, P. A.; Willner, D.; Lasch, S. J.; Henderson, A. J.; Hofstead, S.; Casazza, A. M.; Firestone, R. A.; Hellstrom, I.; Hellstrom, K. E. Cure of xenografted human carcinomas by BR96-doxorubicin immunoconjugates, Science 1993, 261, 212-215.
(13) Alley, S. C.; Okeley, N. M.; Senter, P. D. Antibody-drug conjugates: targeted drug delivery for cancer, Curr. Opin. Chem. Biol. 2010, 14, 529-537.
(14) Ducry, L.; Stump, B. Antibody-drug conjugates: linking cytotoxic payloads to monoclonal antibodies, Bioconjug. Chem. 2010, 21, 5-13.
(15) Casi, G.; Neri, D. Antibody-drug conjugates: basic concepts, examples and future perspectives, J. Control. Release 2012, 161, 422-428.
(16) Adair, J. R.; Howard, P. W.; Hartley, J. A.; Williams, D. G.; Chester, K. A. Antibody-drug conjugates—a perfect synergy, Expert Opin. Biol. Ther. 2012, 12, 1191-1206.
(17) Carter, P. J. Potent antibody therapeutics by design, Nat. Rev. Immunol. 2006, 6, 343-357.
(18) Teicher, B. A. Antibody-drug conjugate targets, Curr. Cancer Drug Targets 2009, 9, 982-1004.
(19) Doronina, S. O.; Toki, B. E.; Torgov, M. Y.; Mendelsohn, B. A.; Cerveny, C. G.; Chace, D. F.; DeBlanc, R. L.; Gearing, R. P.; Bovee, T. D.; Siegall, C. B.; Francisco, J. A.; Wahl, A. F.; Meyer, D. L.; Senter, P. D. Development of potent monoclonal antibody auristatin conjugates for cancer therapy, Nat. Biotechnol. 2003, 21, 778-784.
(20) Widdison, W. C.; Wilhelm, S. D.; Cavanagh, E. E.; Whiteman, K. R.; Leece, B. A.; Kovtun, Y.; Goldmacher, V. S.; Xie, H.; Steeves, R. M.; Lutz, R. J.; Zhao, R.; Wang, L.; Blattler, W. A.; Chari, R. V. Semisynthetic maytansine analogues for the targeted treatment of cancer, J. Med. Chem. 2006, 49, 4392-4408.
(21) Hartley, J. A. The development of pyrrolobenzodiazepines as antitumour agents, Expert Opin. Investig. Drugs 2011, 20, 733-744.
(22) Doronina, S. O.; Mendelsohn, B. A.; Bovee, T. D.; Cerveny, C. G.; Alley, S. C.; Meyer, D. L.; Oflazoglu, E.; Toki, B. E.; Sanderson, R. J.; Zabinski, R. F.; Wahl, A. F.; Senter, P. D. Enhanced activity of monomethylauristatin F through monoclonal antibody delivery: effects of linker technology on efficacy and toxicity, *Bioconjug. Chem.* 2006, 17, 114-124.
(23) Dosio, F.; Brusa, P.; Cattel, L. Immunotoxins and Anticancer Drug Conjugate Assemblies: The Role of the Linkage between Components, *Toxins (Basel)* 2011, 3, 848-883.
(24) Wu, A. M.; Senter, P. D. Arming antibodies: prospects and challenges for immunoconjugates, *Nat. Biotechnol.* 2005, 23, 1137-1146.
(25) Ansell, S. M. Brentuximab vedotin: delivering an antimitotic drug to activated lymphoma cells, *Expert Opin. Investig. Drugs* 2011, 20, 99-105.
(26) Katz, J.; Janik, J. E.; Younes, A. Brentuximab Vedotin (SGN-35), *Clin. Cancer Res.* 2011, 17, 6428-6436.
(27) Hamann, P. R.; Hinman, L. M.; Hollander, I.; Beyer, C. F.; Lindh, D.; Holcomb, R.; Hallett, W.; Tsou, H. R.; Upeslacis, J.; Shochat, D.; Mountain, A.; Flowers, D. A.; Bernstein, I. Gemtuzumab ozogamicin, a potent and selective anti-CD33 antibody-calicheamicin conjugate for treatment of acute myeloid leukemia, *Bioconjug. Chem.* 2002, 13, 47-58.
(28) Hutter, M. L.; Schlenk, R. F. Gemtuzumab ozogamicin in non-acute promyelocytic acute myeloid leukemia, *Expert Opin. Biol. Ther.* 2011, 11, 1369-1380.
(29) Remillard, S.; Rebhun, L. I.; Howie, G. A.; Kupchan, S. M. Antimitotic activity of the potent tumor inhibitor maytansine, *Science* 1975, 189, 1002-1005.
(30) Goldberg, R. M. Cetuximab, *Nat. Rev. Drug Discov.* 2005, Suppl, S10-11.
(31) Kabolizadeh, P.; Kubicek, G. J.; Heron, D. E.; Ferris, R. L.; Gibson, M. K. The role of cetuximab in the management of head and neck cancers, *Expert Opin. Biol. Ther.* 2012, 12, 517-528.
(32) Broadbridge, V. T.; Karapetis, C. S.; Price, T. J. Cetuximab in metastatic colorectal cancer, *Expert Rev. Anticancer Ther.* 2012, 12, 555-565.
(33) Arteaga, C. L. Overview of epidermal growth factor receptor biology and its role as a therapeutic target in human neoplasia, *Semin. Oncol.* 2002, 29, 3-9.
(34) Mendelsohn, J.; Baselga, J. Status of epidermal growth factor receptor antagonists in the biology and treatment of cancer, *J. Clin. Oncol.* 2003, 21, 2787-2799.
(35) Krause, D. S.; Van Etten, R. A. Tyrosine kinases as targets for cancer therapy, *N. Engl. J. Med.* 2005, 353, 172-187.
(36) Goldstein, N. I.; Prewett, M.; Zuklys, K.; Rockwell, P.; Mendelsohn, J. Biological efficacy of a chimeric antibody to the epidermal growth factor receptor in a human tumor xenograft model, *Clin. Cancer Res.* 1995, 1, 1311-1318.
(37) Hamann, P. R.; Hinman, L. M.; Beyer, C. F.; Lindh, D.; Upeslacis, J.; Flowers, D. A.; Bernstein, I. An anti-CD33 antibody-calicheamicin conjugate for treatment of acute myeloid leukemia. Choice of linker, *Bioconjug. Chem.* 2002, 13, 40-46.
(38) van Der Velden, V. H.; te Marvelde, J. G.; Hoogeveen, P. G.; Bernstein, I. D.; Houtsmuller, A. B.; Berger, M. S.; van Dongen, J. J. Targeting of the CD33-calicheamicin immunoconjugate Mylotarg (CMA-676) in acute myeloid leukemia: in vivo and in vitro saturation and internalization by leukemic and normal myeloid cells, *Blood* 2001, 97, 3197-3204.
(39) Ojima, I.; Geng, X.; Wu, X.; Qu, C.; Borella, C. P.; Xie, H.; Wilhelm, S. D.; Leece, B. A.; Bartle, L. M.; Goldmacher, V. S.; Chari, R. V. Tumor-specific novel taxoid-monoclonal antibody conjugates, *J. Med. Chem.* 2002, 45, 5620-5623.
(40) Erickson, H. K.; Park, P. U.; Widdison, W. C.; Kovtun, Y. V.; Garrett, L. M.; Hoffman, K.; Lutz, R. J.; Goldmacher, V. S.; Blattler, W. A. Antibody-maytansinoid conjugates are activated in targeted cancer cells by lysosomal degradation and linker-dependent intracellular processing, *Cancer Res.* 2006, 66, 4426-4433.
(41) Lewis Phillips, G. D.; Li, G.; Dugger, D. L.; Crocker, L. M.; Parsons, K. L.; Mai, E.; Blattler, W. A.; Lambert, J. M.; Chari, R. V.; Lutz, R. J.; Wong, W. L.; Jacobson, F. S.; Koeppen, H.; Schwall, R. H.; Kenkare-Mitra, S. R.; Spencer, S. D.; Sliwkowski, M. X. Targeting HER2-positive breast cancer with trastuzumab-DM1, an antibody-cytotoxic drug conjugate, *Cancer Res.* 2008, 68, 9280-9290.
(42) Kellogg, B. A.; Garrett, L.; Kovtun, Y.; Lai, K. C.; Leece, B.; Miller, M.; Payne, G.; Steeves, R.; Whiteman, K. R.; Widdison, W.; Xie, H.; Singh, R.; Chari, R. V.; Lambert, J. M.; Lutz, R. J. Disulfide-linked antibody-maytansinoid conjugates: optimization of in vivo activity by varying the steric hindrance at carbon atoms adjacent to the disulfide linkage, *Bioconjug. Chem.* 2011, 22, 717-727.
(43) Dubowchik, G. M.; Mosure, K.; Knipe, J. O.; Firestone, R. A. Cathepsin B-sensitive dipeptide prodrugs. 2. Models of anticancer drugs paclitaxel (Taxol), mitomycin C and doxorubicin, *Bioorg. Med. Chem. Lett.* 1998, 8, 3347-3352.
(44) Francisco, J. A.; Cerveny, C. G.; Meyer, D. L.; Mixan, B. J.; Klussman, K.; Chace, D. F.; Rejniak, S. X.; Gordon, K. A.; DeBlanc, R.; Toki, B. E.; Law, C. L.; Doronina, S. O.; Siegall, C. B.; Senter, P. D.; Wahl, A. F. cAC10-vcMMAE, an anti-CD30-monomethyl auristatin E conjugate with potent and selective antitumor activity, *Blood* 2003, 102, 1458-1465.
(45) Sanderson, R. J.; Hering, M. A.; James, S. F.; Sun, M. M.; Doronina, S. O.; Siadak, A. W.; Senter, P. D.; Wahl, A. F. In vivo drug-linker stability of an anti-CD30 dipeptide-linked auristatin immunoconjugate, *Clin. Cancer Res.* 2005, 11, 843-852.
(46) DiJoseph, J. F.; Dougher, M. M.; Evans, D. Y.; Zhou, B. B.; Damle, N. K. Preclinical anti-tumor activity of antibody-targeted chemotherapy with CMC-544 (inotuzumab ozogamicin), a CD22-specific immunoconjugate of calicheamicin, compared with non-targeted combination chemotherapy with CVP or CHOP, *Cancer Chemother. Pharmacol.* 2011, 67, 741-749.
(47) Toki, B. E.; Cerveny, C. G.; Wahl, A. F.; Senter, P. D. Protease-mediated fragmentation of p-amidobenzyl ethers: a new strategy for the activation of anticancer prodrugs, *J. Org. Chem.* 2002, 67, 1866-1872.
(48) Kovtun, Y. V.; Audette, C. A.; Ye, Y.; Xie, H.; Ruberti, M. F.; Phinney, S. J.; Leece, B. A.; Chittenden, T.; Blattler, W. A.; Goldmacher, V. S. Antibody-drug conjugates designed to eradicate tumors with homogeneous and heterogeneous expression of the target antigen, *Cancer Res.* 2006, 66, 3214-3221.
(49) a. Dugger, R. B.; LeTendre, L. J.; Patel, V. B.; Prashad, A. S. and Zhang, C. Intermediates and methods for synthesizing Calicheamicin derivatives. WO 2015/063680 A1.
b. Moran, J. K. and G, J. Processes for the convergent synthesis of Calicheamicin derivatives. US 2009/0312530 A1.
c. Chiarello, G. A. and Sahli, A. Improved processes for making hydrazides. WO 2008/147765 A1.

The invention claimed is:

1. A compound of Formula (II) or a salt and/or solvate thereof:

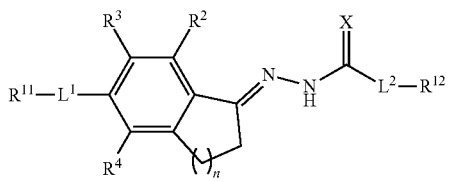

(II)

wherein:
$R^2$ is selected from H, halo, $C_{1-6}$alkyl, $C_{1-6}$fluoroalkyl, $OR^6$, CN, $SR^6$ and $NR^6R^7$;
$R^3$ and $R^4$ are independently selected from H, CN, $NO_2$, halo, $C_{1-6}$alkyl, $C_{1-6}$fluoroalkyl, $OR^8$, $SR^8$ and $NR^8R^9$;
$R^{11}$ and $R^{12}$ are different and are selected from compounds to be linked together;
X is selected from O, S and $NR^{10}$;
$R^6$, $R^7$, $R^8$, $R^9$, and $R^{10}$ are independently selected from H, $C_{1-6}$alkyl and $C_{1-6}$fluoroalkyl;
$L^1$ and $L^2$ are independently a linker moiety; and
n is 0, 1, 2 or 3.

2. The compound of claim 1, wherein $R^{11}$ and $R^{12}$ are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support.

3. The compound of claim 1, wherein $R^{11}$ and $R^{12}$ are independently selected from an antibody and drug.

4. The compound of claim 1, wherein the compound has the following structure:

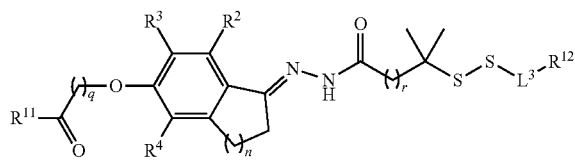

(II)

wherein
$R^2$, $R^3$ and $R^4$ are as defined in claim 1;
$R^{11}$ and $R^{12}$ are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;
$L^3$ is a linker moiety;
n is 0, 1, 2 or 3;
q is 1, 2, 3, 4, 5, 6, 7 or 8; and
r is 1, 2, 3, 4, 5, 6, 7 or 8,
or a pharmaceutically acceptable salt and/or solvate thereof; or
wherein the compound has the following structure:

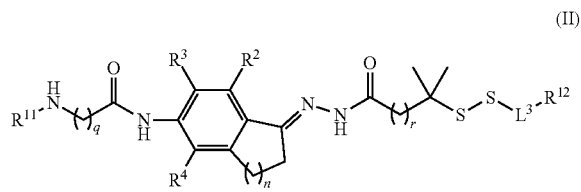

(II)

wherein
$R^2$, $R^3$ and $R^4$ are as defined in claim 1;
$R^{11}$ and $R^{12}$ are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;
$L^3$ is a linker moiety;
n is 0, 1, 2 or 3;
q is 1, 2, 3, 4, 5, 6, 7 or 8; and
r is 1, 2, 3, 4, 5, 6, 7 or 8,
or a pharmaceutically acceptable salt and/or solvate thereof.

5. The compound of claim 1, wherein $R^{11}$ is $R^{13}$, $R^{12}$ is $R^{14}$, $R^{13}$ is an antibody, and the antibody is covalently attached to 1 to 20 of the remaining portion of the compound of Formula II to provide a conjugate having a Formula (III):

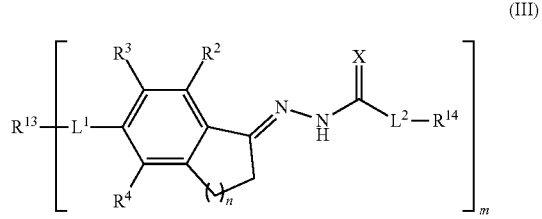

(III)

or a pharmaceutically acceptable salt and/or solvate thereof, wherein
$R^{14}$ is a drug;
$L^1$, $L^2$, $R^2$, $R^3$, $R^4$ and n are as defined in claim 1; and
m is an integer from 1 to 20.

6. The compound of claim 5, wherein the compound is selected from

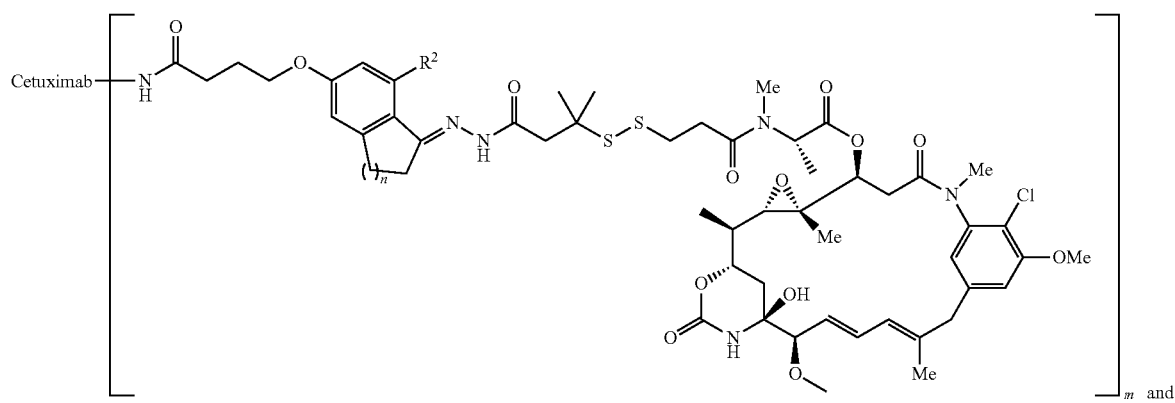

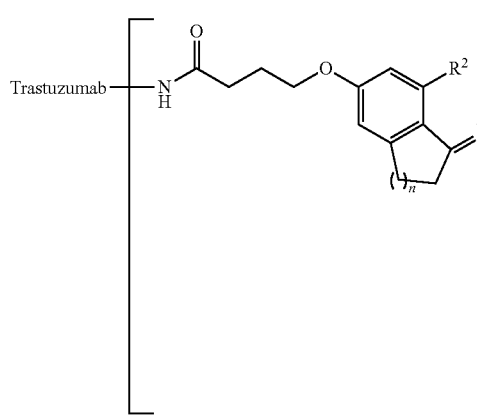
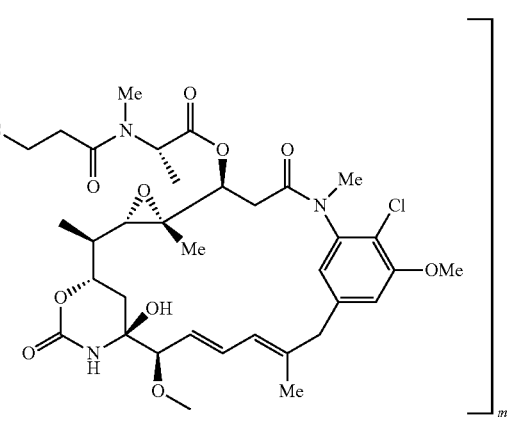

wherein $R^2$ is selected from H, halo, $C_{1-6}$alkly, $C_{1-6}$fluoroalkyl, $OR^6$, CN, $SR^6$ and $NR^6R^7$; n=0, 1, or 2; and m=1 to 20;

or a pharmaceutically acceptable salt and/or solvate thereof.

7. The compound of claim 1, wherein $L^1$ and $L^2$ independently comprise at least one ester, carbonate, carbamate or amide linkage and optionally one or more ether, sulfone, sulfoxide, thioamide, thioester and amine, and optionally one or more $C_1$-$C_{20}$alkylene groups, $C_2$-$C_{20}$alkenylene groups and $C_2$-$C_{20}$alkynylene groups.

8. The compound of claim 1, wherein $L^1$ and $L^2$ are independently selected from a direct bond, Z, $R^a$, Z-$R^a$, $R^a$-Z, $R^a$-Z-$R^b$ and Z-$R^a$-$Z^a$, wherein Z and $Z^a$ are independently selected from O, S, S(O), $SO_2$, NH, N($C_{1-6}$alkyl), C(Q), C(Q)Y, YC(Q), YC(Q)$Y^a$, ($C_{1-6}$alkyleneY)$_p$ and Y-($C_{1-6}$ alkyleneY)$^p$, wherein $R^a$ and $R^b$ are independently selected from $C_{1-10}$alkylene, $C_{2-10}$alkenylene and $C_{2-10}$alkynylene; Q, Y and $Y^a$ are independently selected from O, S, NH and N($C_{1-6}$alkyl); and p is selected from 1, 2, 3, 4, 5 and 6.

9. The compound of claim 8, wherein $R^a$ and $R^b$ are independently selected from $C_{1-6}$alkylene, $C_{2-6}$alkenylene and $C_{2-6}$alkynylene.

10. The compound of claim 8, wherein Q, Y and $Y^a$ are independently selected from O, S, NH and N($CH_3$).

11. The compound of claim 8, wherein Z and $Z^a$ are independently selected from O, S, S(O), $SO_2$, NH, N($CH_3$), C(O), C(O)NH, NHC(O), NHC(O)O, OC(O)O, NHC(O)NH, OC(O)NH, NHC(NH)NH, ($C_{1-6}$alkyleneO)$_p$ and O-($C_{1-6}$alkyleneO)$_p$.

12. The compound of claim 1, wherein $L^1$ is selected from OC(O)$C_{1-10}$alkyleneO, NHC(O)$C_{1-10}$alkyleneO, $C_{1-6}$alkyleneO, OC(O)$C_{1-10}$alkyleneNH, NHC(O)$C_{1-10}$alkyleneNH, $C_{1-6}$alkyleneNH, C(O)$C_{1-10}$alkyleneO and C(O)$C_{1-10}$alkyleneNH.

13. The compound of claim 1, wherein $L^2$ is selected from $C_{1-10}$alkyleneS and $C_{1-10}$alkylene.

14. The compound of claim 1, wherein $R^3$ and $R^4$ are independently selected from H, CN, $NO_2$, halo and $C_{1-6}$alkyl.

15. The compound of claim 14, wherein $R^2$ is selected from H, Cl, F, CN, $CH_3$, $CF_3$ and $OR^6$.

16. The compound of claim 1, wherein X is O.

17. The compound of claim 1, wherein n is 0, 1, or 2.

18. The compound of claim 3, wherein the antibody specifically binds to a receptor encoded by an ErbB gene, or wherein the antibody specifically binds to an ErbB receptor selected from EGFR, HER2, HER3 and HER4, or wherein the antibody binds to one or more tumor-associated antigens or cell-surface ErbB receptor, or wherein the antibody specifically binds to the EGFR receptor, or wherein the antibody is a chimeric antibody, or wherein the antibody is cetuximab or trastuzumab.

19. The compound of claim 3, wherein the drug is a drug for targeting cancer.

20. The compound of claim 3, wherein the drug is DM1 or monomethyl auristatin E (MMAE).

* * * * *